US010988517B2

(12) United States Patent
Schreiber et al.

(10) Patent No.: US 10,988,517 B2
(45) Date of Patent: *Apr. 27, 2021

(54) HETERODIMERIC PROTEINS FOR MODULATING GAMMA DELTA T CELLS

(71) Applicant: Shattuck Labs, Inc., Austin, TX (US)

(72) Inventors: Taylor Schreiber, Austin, TX (US); George Fromm, Austin, TX (US); Suresh De Silva, Austin, TX (US)

(73) Assignee: Shattuck Labs, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/891,672

(22) Filed: Jun. 3, 2020

(65) Prior Publication Data
US 2020/0308238 A1 Oct. 1, 2020

Related U.S. Application Data

(63) Continuation of application No. 16/741,146, filed on Jan. 13, 2020, which is a continuation of application No. PCT/US2020/012589, filed on Jan. 7, 2020.

(60) Provisional application No. 62/941,176, filed on Nov. 27, 2019, provisional application No. 62/876,346, filed on Jul. 19, 2019, provisional application No. 62/789,344, filed on Jan. 7, 2019.

(51) Int. Cl.
C07K 14/47 (2006.01)
C07K 16/28 (2006.01)
A61P 35/00 (2006.01)
A61K 39/00 (2006.01)
A61K 38/00 (2006.01)
C07K 16/30 (2006.01)

(52) U.S. Cl.
CPC .............. C07K 14/47 (2013.01); A61P 35/00 (2018.01); C07K 16/2803 (2013.01); C07K 16/3069 (2013.01); A61K 38/00 (2013.01); A61K 2039/505 (2013.01); C07K 2317/524 (2013.01); C07K 2317/526 (2013.01); C07K 2317/53 (2013.01); C07K 2317/622 (2013.01)

(58) Field of Classification Search
CPC .......... C07K 16/2803; C07K 2317/622; C07K 16/2818; C07K 2319/33; C07K 16/3084; C07K 19/00; C07K 2317/73; C07K 14/47; A61K 2039/505
See application file for complete search history.

(56) References Cited

U.S. PATENT DOCUMENTS

| 9,475,872 | B2 | 10/2016 | Hayday et al. |
| 9,957,319 | B2 | 5/2018 | Hayday et al. |
| 10,081,676 | B2 | 9/2018 | Hayday et al. |
| 10,112,995 | B2 | 10/2018 | Haque et al. |
| 10,131,709 | B2 | 11/2018 | Heyday et al. |
| 10,357,561 | B2 | 7/2019 | Arnett et al. |
| 2004/0053307 | A1 | 3/2004 | Wood et al. |
| 2006/0233819 | A1 | 10/2006 | Wood et al. |
| 2006/0264360 | A1 | 11/2006 | Girardi et al. |
| 2009/0317457 | A1 | 12/2009 | Girardi et al. |
| 2013/0101590 | A1 | 4/2013 | Arnett et al. |
| 2014/0335098 | A1 | 11/2014 | Hayday et al. |
| 2014/0363422 | A1 | 12/2014 | Hayday et al. |
| 2015/0166630 | A1 | 6/2015 | Arnett et al. |
| 2015/0344554 | A1 | 12/2015 | Arnett et al. |
| 2015/0376260 | A1 | 12/2015 | Elhalel et al. |
| 2016/0130552 | A1 | 5/2016 | Henco et al. |
| 2016/0298082 | A1 | 10/2016 | Henco et al. |
| 2016/0368981 | A1 | 12/2016 | Hayday et al. |
| 2016/0376364 | A1 | 12/2016 | Behren et al. |
| 2017/0051053 | A1 | 2/2017 | Hayday et al. |
| 2017/0051055 | A1 | 2/2017 | Haque et al. |
| 2017/0095531 | A1* | 4/2017 | Schreiber ............... C07K 14/00 |
| 2017/0128490 | A1 | 5/2017 | Bauer et al. |
| 2018/0147257 | A1 | 5/2018 | Corey et al. |
| 2018/0296636 | A1 | 10/2018 | Zang et al. |
| 2018/0312808 | A1 | 11/2018 | Hayday et al. |
| 2018/0355035 | A1 | 12/2018 | Yoo et al. |
| 2019/0023779 | A1 | 1/2019 | Hayday et al. |
| 2019/0071499 | A1 | 3/2019 | Haque et al. |
| 2019/0105403 | A1 | 4/2019 | Yoo et al. |
| 2019/0112367 | A1 | 4/2019 | Hayday et al. |
| 2019/0169259 | A1 | 6/2019 | Arnett et al. |
| 2019/0263908 | A1 | 8/2019 | Van Der Vliet et al. |

FOREIGN PATENT DOCUMENTS

| EP | 1499339 A1 | 1/2005 |
| EP | 1536821 A1 | 6/2005 |
| EP | 1499339 A4 | 4/2008 |
| EP | 1536821 A4 | 9/2009 |
| EP | 2556086 A1 | 2/2013 |
| EP | 2797951 A1 | 11/2014 |

(Continued)

OTHER PUBLICATIONS

Rhodes et al .Regulation of Immunity by Butyrophilins.Annu. Rev. Immunol. 2016. 34:151-72.Annual Reviews (Year: 2016).*
Blazquez, et al., "New Insights Into the Regulation of γδ T Cells by BTN3A and Other BTN/BTNL in Tumor Immunity," Frontiers in Immunology, vol. 9, No. 61, Jul. 2018, 11 pages.
Kabelitz, et al., "Immunosurveillance by human γδ T lymphocytes: the emerging role of butyrophilins [version 1; referees: 2 approved]," F1000Research, 6:782, Jun. 5, 2017, 10 pages.

(Continued)

Primary Examiner — Amy E Juedes
Assistant Examiner — Brian Hartnett
(74) Attorney, Agent, or Firm — Morgan, Lewis & Bockius LLP

(57) ABSTRACT

The present technology relates, inter alia, to compositions and methods, including heterodimeric proteins that find use in the treatment of disease, such as immunotherapies for cancer and autoimmunity.

18 Claims, 36 Drawing Sheets
Specification includes a Sequence Listing.

(56) References Cited

FOREIGN PATENT DOCUMENTS

| | | | |
|---|---|---|---|
| EP | 2797952 A1 | 11/2014 | |
| EP | 2556086 B1 | 3/2015 | |
| EP | 2875046 A1 | 5/2015 | |
| EP | 2941438 A1 | 11/2015 | |
| EP | 2941483 A1 | 11/2015 | |
| EP | 2941484 A1 | 11/2015 | |
| EP | 3016977 A1 | 5/2016 | |
| EP | 3016978 A2 | 5/2016 | |
| EP | 3074040 A1 | 10/2016 | |
| EP | 3164142 A1 | 5/2017 | |
| EP | 3173092 A2 | 5/2017 | |
| EP | 3223849 A1 | 10/2017 | |
| EP | 2797951 B1 | 1/2018 | |
| EP | 3368658 A1 | 9/2018 | |
| EP | 3383911 A1 | 10/2018 | |
| EP | 2797952 B1 | 2/2019 | |
| EP | 3436475 A1 | 2/2019 | |
| EP | 3173092 B1 | 6/2019 | |
| WO | WO 03/086449 A1 | 10/2003 | |
| WO | WO 2003/105887 A1 | 12/2003 | |
| WO | WO-2004106381 A1 * | 12/2004 | ............. A61P 29/00 |
| WO | WO 2006/097327 A2 | 9/2006 | |
| WO | WO 2006/097327 A3 | 9/2006 | |
| WO | WO 2008/154516 A2 | 12/2008 | |
| WO | WO 2009/030884 A2 | 3/2009 | |
| WO | WO 2009/030884 A3 | 3/2009 | |
| WO | WO 2011/127418 A1 | 10/2011 | |
| WO | WO 2013/098419 A1 | 7/2013 | |
| WO | WO 2013/098420 A1 | 7/2013 | |
| WO | WO 2014/015148 A1 | 1/2014 | |
| WO | WO 2014/106629 A1 | 7/2014 | |
| WO | WO 2014/106631 A1 | 7/2014 | |
| WO | WO 2014/106839 A1 | 7/2014 | |
| WO | WO 2015/001010 A1 | 1/2015 | |
| WO | WO 2015/001013 A2 | 1/2015 | |
| WO | WO 2015/001013 A3 | 1/2015 | |
| WO | WO 2015/001047 A1 | 1/2015 | |
| WO | WO 2015/077844 A1 | 6/2015 | |
| WO | WO 2016/001405 A1 | 1/2016 | |
| WO | WO 2016/191305 A1 | 12/2016 | |
| WO | WO-2016191305 A1 * | 12/2016 | ........... A61K 38/177 |
| WO | WO 2017/072367 A1 | 5/2017 | |
| WO | WO 2017/096051 A1 | 6/2017 | |
| WO | WO 2018/082590 A1 | 5/2018 | |
| WO | WO 2018/201130 A1 | 11/2018 | |
| WO | WO 2018/222685 A1 | 12/2018 | |
| WO | WO 2018/222689 A1 | 12/2018 | |
| WO | WO 2018/226671 A1 | 12/2018 | |
| WO | WO 2018/229163 A1 | 12/2018 | |
| WO | WO 2019/053272 A1 | 3/2019 | |
| WO | WO 2019/057933 A1 | 3/2019 | |

OTHER PUBLICATIONS

Rigau, et al., "Butyrophilin 2A1 is essential for phosphoantigen reactivity by γδ T cells," Science 10.1126/science.aay5516, 2020, 24 pages.

Vantourout, et al., "Heteromeric interactions regulate butyrophilin (BTN) and BTN-like molecules governing γδ T Cell Biology," PNAS, vol. 115, No. 5, Jan. 30, 2018, pp. 1039-1044.

* cited by examiner

LAG3-Fc-vBTNL3/8

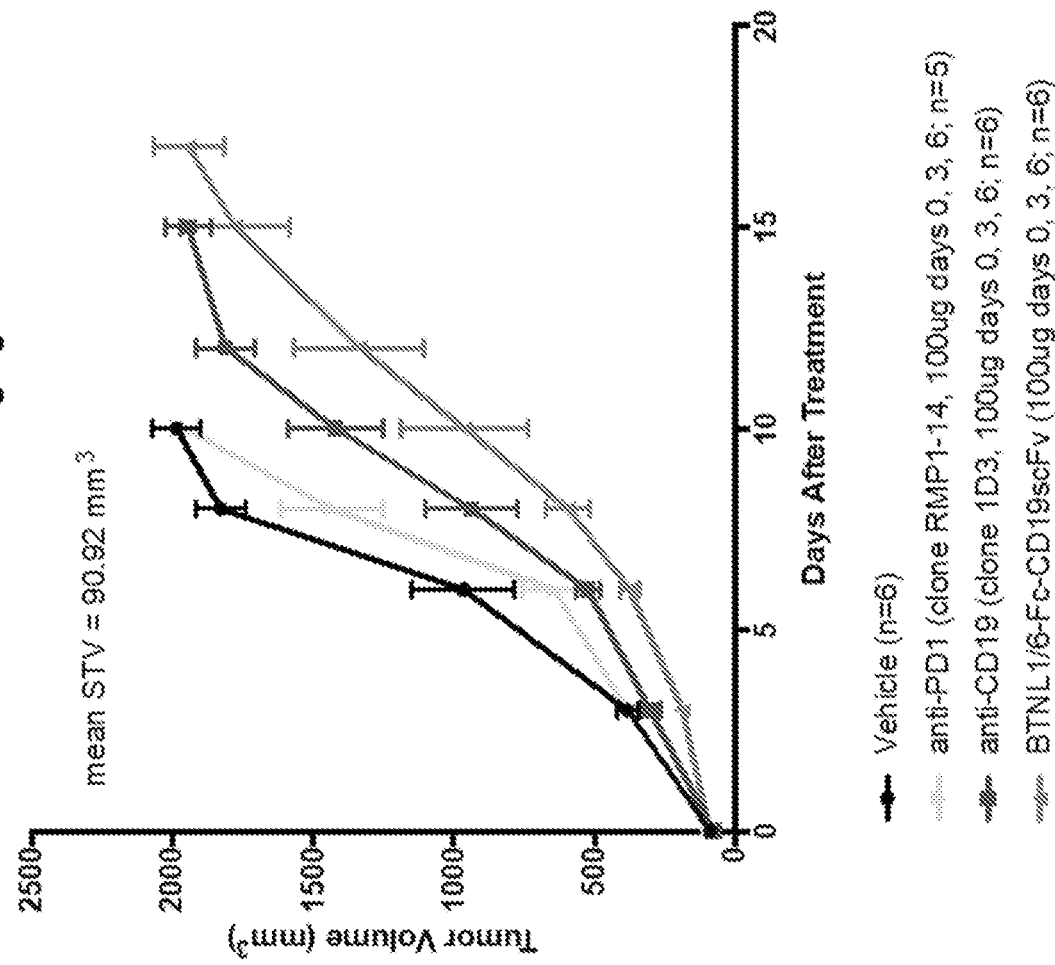

SEQUENCE LISTING

```
<160> NUMBER OF SEQ ID NOS: 111

<210> SEQ ID NO 1
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: REPEAT
<222> LOCATION: (1)..(1)
<223> OTHER INFORMATION: A spacer amino acid such as serine or glycine
<220> FEATURE:
<221> NAME/KEY: REPEAT
<222> LOCATION: (2)..(2)
<223> OTHER INFORMATION: A positively charged amino acid such as
      arginine, histidine or lysine
<220> FEATURE:
<221> NAME/KEY: REPEAT
<222> LOCATION: (3)..(3)
<223> OTHER INFORMATION: A spacer amino acid such as serine or glycine
<220> FEATURE:
<221> NAME/KEY: REPEAT
<222> LOCATION: (4)..(4)
<223> OTHER INFORMATION: A positively charged amino acid such as
      arginine, histidine or lysine
<220> FEATURE:
<221> NAME/KEY: REPEAT
<222> LOCATION: (5)..(5)
<223> OTHER INFORMATION: A spacer amino acid such as serine or glycine

<400> SEQUENCE: 1

Xaa Xaa Xaa Xaa Xaa
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: REPEAT
<222> LOCATION: (1)..(1)
<223> OTHER INFORMATION: A spacer amino acid such as serine or glycine
<220> FEATURE:
<221> NAME/KEY: REPEAT
<222> LOCATION: (2)..(2)
<223> OTHER INFORMATION: A negatively charged amino acid such as
      aspartic acid or glutamic acid
<220> FEATURE:
<221> NAME/KEY: REPEAT
<222> LOCATION: (3)..(3)
<223> OTHER INFORMATION: A spacer amino acid such as serine or glycine
<220> FEATURE:
<221> NAME/KEY: REPEAT
<222> LOCATION: (4)..(4)
<223> OTHER INFORMATION: A negatively charged amino acid such as
      aspartic acid or glutamic acid
```

```
<220> FEATURE:
<221> NAME/KEY: REPEAT
<222> LOCATION: (5)..(5)
<223> OTHER INFORMATION: A spacer amino acid such as serine or glycine

<400> SEQUENCE: 2

Xaa Xaa Xaa Xaa Xaa
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: A spacer amino acid such as serine or glycine
<220> FEATURE:
<221> NAME/KEY: REPEAT
<222> LOCATION: (2)..(2)
<223> OTHER INFORMATION: A spacer amino acid such as serine or glycine
<220> FEATURE:
<221> NAME/KEY: MISC_FEATURE
<222> LOCATION: (3)..(3)
<223> OTHER INFORMATION: A positively charged amino acid such as
      arginine, histidine or lysine
<220> FEATURE:
<221> NAME/KEY: REPEAT
<222> LOCATION: (4)..(4)
<223> OTHER INFORMATION: A positively charged amino acid such as
      arginine, histidine or lysine
<220> FEATURE:
<221> NAME/KEY: MISC_FEATURE
<222> LOCATION: (5)..(5)
<223> OTHER INFORMATION: A spacer amino acid such as serine or glycine
<220> FEATURE:
<221> NAME/KEY: REPEAT
<222> LOCATION: (6)..(6)
<223> OTHER INFORMATION: A spacer amino acid such as serine or glycine
<220> FEATURE:
<221> NAME/KEY: MISC_FEATURE
<222> LOCATION: (7)..(7)
<223> OTHER INFORMATION: A positively charged amino acid such as
      arginine, histidine or lysine
<220> FEATURE:
<221> NAME/KEY: REPEAT
<222> LOCATION: (8)..(8)
<223> OTHER INFORMATION: A positively charged amino acid such as
      arginine, histidine or lysine
<220> FEATURE:
<221> NAME/KEY: MISC_FEATURE
<222> LOCATION: (9)..(9)
<223> OTHER INFORMATION: A spacer amino acid such as serine or glycine
<220> FEATURE:
<221> NAME/KEY: REPEAT
<222> LOCATION: (10)..(10)
<223> OTHER INFORMATION: A spacer amino acid such as serine or glycine

<400> SEQUENCE: 3

Xaa Xaa Xaa Xaa Xaa Xaa Xaa Xaa Xaa Xaa
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: A spacer amino acid such as serine or glycine
<220> FEATURE:
```

-continued

```
<221> NAME/KEY: REPEAT
<222> LOCATION: (2)..(2)
<223> OTHER INFORMATION: A spacer amino acid such as serine or glycine
<220> FEATURE:
<221> NAME/KEY: MISC_FEATURE
<222> LOCATION: (3)..(3)
<223> OTHER INFORMATION: A negatively charged amino acid such as
      aspartic acid or glutamic acid
<220> FEATURE:
<221> NAME/KEY: REPEAT
<222> LOCATION: (4)..(4)
<223> OTHER INFORMATION: A negatively charged amino acid such as
      aspartic acid or glutamic acid
<220> FEATURE:
<221> NAME/KEY: MISC_FEATURE
<222> LOCATION: (5)..(5)
<223> OTHER INFORMATION: A spacer amino acid such as serine or glycine
<220> FEATURE:
<221> NAME/KEY: REPEAT
<222> LOCATION: (6)..(6)
<223> OTHER INFORMATION: A spacer amino acid such as serine or glycine
<220> FEATURE:
<221> NAME/KEY: MISC_FEATURE
<222> LOCATION: (7)..(7)
<223> OTHER INFORMATION: A negatively charged amino acid such as
      aspartic acid or glutamic acid
<220> FEATURE:
<221> NAME/KEY: REPEAT
<222> LOCATION: (8)..(8)
<223> OTHER INFORMATION: A negatively charged amino acid such as
      aspartic acid or glutamic acid
<220> FEATURE:
<221> NAME/KEY: MISC_FEATURE
<222> LOCATION: (9)..(9)
<223> OTHER INFORMATION: A spacer amino acid such as serine or glycine
<220> FEATURE:
<221> NAME/KEY: REPEAT
<222> LOCATION: (10)..(10)
<223> OTHER INFORMATION: A spacer amino acid such as serine or glycine

<400> SEQUENCE: 4

Xaa Xaa Xaa Xaa Xaa Xaa Xaa Xaa Xaa Xaa
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: REPEAT
<222> LOCATION: (1)..(1)
<223> OTHER INFORMATION: A spacer amino acid such as serine or glycine
<220> FEATURE:
<221> NAME/KEY: REPEAT
<222> LOCATION: (2)..(2)
<223> OTHER INFORMATION: A positively charged amino acid such as
      arginine, histidine or lysine
<220> FEATURE:
<221> NAME/KEY: REPEAT
<222> LOCATION: (4)..(4)
<223> OTHER INFORMATION: A spacer amino acid such as serine or glycine
<220> FEATURE:
<221> NAME/KEY: REPEAT
<222> LOCATION: (5)..(5)
<223> OTHER INFORMATION: A positively charged amino acid such as
      arginine, histidine or lysine
<220> FEATURE:
<221> NAME/KEY: REPEAT
<222> LOCATION: (6)..(6)
<223> OTHER INFORMATION: A spacer amino acid such as serine or glycine

<400> SEQUENCE: 5

Xaa Xaa Cys Xaa Xaa Xaa
1               5
```

```
<210> SEQ ID NO 6
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: REPEAT
<222> LOCATION: (1)..(1)
<223> OTHER INFORMATION: A spacer amino acid such as serine or glycine
<220> FEATURE:
<221> NAME/KEY: REPEAT
<222> LOCATION: (2)..(2)
<223> OTHER INFORMATION: A negatively charged amino acid such as
      aspartic acid or glutamic acid
<220> FEATURE:
<221> NAME/KEY: REPEAT
<222> LOCATION: (4)..(4)
<223> OTHER INFORMATION: A spacer amino acid such as serine or glycine
<220> FEATURE:
<221> NAME/KEY: REPEAT
<222> LOCATION: (5)..(5)
<223> OTHER INFORMATION: A negatively charged amino acid such as
      aspartic acid or glutamic acid
<220> FEATURE:
<221> NAME/KEY: REPEAT
<222> LOCATION: (6)..(6)
<223> OTHER INFORMATION: A spacer amino acid such as serine or glycine

<400> SEQUENCE: 6

Xaa Xaa Cys Xaa Xaa Xaa
1               5

<210> SEQ ID NO 7
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 7

Gly Ser Gly Ser Arg Lys Gly Gly Lys Arg Gly Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 8

Gly Ser Gly Ser Arg Lys Cys Gly Lys Arg Gly Ser
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 9

Gly Ser Gly Ser Asp Glu Gly Gly Glu Asp Gly Ser
1               5                   10

<210> SEQ ID NO 10
<211> LENGTH: 12
<212> TYPE: PRT
```

```
<213> ORGANISM: Artificial Sequence
<220> FEATURE:
<223> OTHER INFORMATION: Synthetic Sequence

<400> SEQUENCE: 10

Gly Ser Gly Ser Asp Glu Cys Gly Glu Asp Gly Ser
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 11

Arg Lys Gly Gly Lys Arg
1               5

<210> SEQ ID NO 12
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 12

Gly Ser Gly Ser Arg Lys Gly Gly Lys Arg Gly Ser
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 13

Asp Glu Gly Gly Glu Asp
1               5

<210> SEQ ID NO 14
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 14

Gly Ser Gly Ser Asp Glu Gly Gly Glu Asp Gly Ser
1               5                   10

<210> SEQ ID NO 15
<211> LENGTH: 234
<212> TYPE: PRT
<213> ORGANISM: Artificial Sequence
<220> FEATURE:
<223> OTHER INFORMATION: Synthetic Sequence

<400> SEQUENCE: 15

Ser Lys Tyr Gly Pro Pro Cys Pro Pro Cys Pro Ala Pro Glu Phe Leu
1               5                   10                  15

Gly Gly Pro Ser Val Phe Leu Phe Pro Pro Lys Pro Lys Asp Gln Leu
                20                  25                  30

Met Ile Ser Arg Thr Pro Glu Val Thr Cys Val Val Val Asp Val Ser
            35                  40                  45
```

Gln Glu Asp Pro Glu Val Gln Phe Asn Trp Tyr Val Asp Gly Val Glu
          50                  55                  60

Val His Asn Ala Lys Thr Lys Pro Arg Glu Glu Gln Phe Asn Ser Thr
 65                  70                  75                  80

Tyr Arg Val Val Ser Val Leu Thr Val Leu His Gln Asp Trp Leu Ser
                 85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Leu His Glu Ala Leu His Asn His Tyr Thr Gln Lys Ser Leu Ser Leu
    210                 215                 220

Ser Leu Gly Lys Ile Glu Gly Arg Met Asp
225                 230

<210> SEQ ID NO 16
<211> LENGTH: 249
<212> TYPE: PRT
<213> ORGANISM: Artificial Sequence
<220> FEATURE:
<223> OTHER INFORMATION: Synthetic Sequence

<400> SEQUENCE: 16

Gly Ser Gly Ser Arg Lys Gly Lys Arg Gly Ser Lys Tyr Gly Pro
1               5                   10                  15

Pro Cys Pro Pro Cys Pro Ala Pro Glu Phe Leu Gly Gly Pro Ser Val
            20                  25                  30

Phe Leu Phe Pro Pro Lys Pro Lys Asp Gln Leu Met Ile Ser Arg Thr
        35                  40                  45

Pro Glu Val Thr Cys Val Val Asp Val Ser Gln Glu Asp Pro Glu
    50                  55                  60

Val Gln Phe Asn Trp Tyr Val Asp Gly Val Glu Val His Asn Ala Lys
65                  70                  75                  80

Thr Lys Pro Arg Glu Glu Gln Phe Asn Ser Thr Tyr Arg Val Val Ser
                85                  90                  95

Val Leu Thr Val Leu His Gln Asp Trp Leu Ser Gly Lys Glu Tyr Lys
            100                 105                 110

Cys Lys Val Ser Ser Lys Gly Leu Pro Ser Ser Ile Glu Lys Thr Ile
        115                 120                 125

Ser Asn Ala Thr Gly Gln Pro Arg Glu Pro Gln Val Tyr Thr Leu Pro
    130                 135                 140

Pro Ser Gln Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

```
Gly Gln Pro Glu Asn Asn Tyr Lys Thr Thr Pro Pro Val Leu Asp Ser
            180                 185                 190

Asp Gly Ser Phe Phe Leu Tyr Ser Arg Leu Thr Val Asp Lys Ser Arg
        195                 200                 205

Trp Gln Glu Gly Asn Val Phe Ser Cys Ser Val Leu His Glu Ala Leu
210                 215                 220

His Asn His Tyr Thr Gln Lys Ser Leu Ser Leu Ser Leu Gly Lys Asp
225                 230                 235                 240

Glu Gly Gly Glu Asp Gly Ser Gly Ser
                245

<210> SEQ ID NO 17
<211> LENGTH: 249
<212> TYPE: PRT
<213> ORGANISM: Artificial Sequence
<220> FEATURE:
<223> OTHER INFORMATION: Synthetic Sequence

<400> SEQUENCE: 17

Gly Ser Gly Ser Asp Glu Gly Gly Glu Asp Gly Ser Lys Tyr Gly Pro
1               5                   10                  15

Pro Cys Pro Pro Cys Pro Ala Pro Glu Phe Leu Gly Pro Ser Val
                20                  25                  30

Phe Leu Phe Pro Pro Lys Pro Lys Asp Gln Leu Met Ile Ser Arg Thr
            35                  40                  45

Pro Glu Val Thr Cys Val Val Val Asp Val Ser Gln Glu Asp Pro Glu
        50                  55                  60

Val Gln Phe Asn Trp Tyr Val Asp Gly Val Glu Val His Asn Ala Lys
65                  70                  75                  80

Thr Lys Pro Arg Glu Glu Gln Phe Asn Ser Thr Tyr Arg Val Val Ser
                85                  90                  95

Val Leu Thr Val Leu His Gln Asp Trp Leu Ser Gly Lys Glu Tyr Lys
            100                 105                 110

Cys Lys Val Ser Ser Lys Gly Leu Pro Ser Ser Ile Glu Lys Thr Ile
        115                 120                 125

Ser Asn Ala Thr Gly Gln Pro Arg Glu Pro Gln Val Tyr Thr Leu Pro
130                 135                 140

Pro Ser Gln Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Arg Leu Thr Val Asp Lys Ser Arg
        195                 200                 205

Trp Gln Glu Gly Asn Val Phe Ser Cys Ser Val Leu His Glu Ala Leu
210                 215                 220

His Asn His Tyr Thr Gln Lys Ser Leu Ser Leu Ser Leu Gly Lys Arg
225                 230                 235                 240

Lys Gly Gly Lys Arg Gly Ser Gly Ser
                245

<210> SEQ ID NO 18
<211> LENGTH: 597
<212> TYPE: PRT
<213> ORGANISM: Artificial Sequence
```

<220> FEATURE:
<223> OTHER INFORMATION: Synthetic Sequence

<400> SEQUENCE: 18

```
Glu Leu Leu Asp Pro Cys Gly Tyr Ile Ser Pro Ser Pro Val Val
1               5                   10                  15

Gln Leu His Ser Asn Phe Thr Ala Val Cys Val Leu Lys Glu Lys Cys
            20                  25                  30

Met Asp Tyr Phe His Val Asn Ala Asn Tyr Ile Val Trp Lys Thr Asn
            35                  40                  45

His Phe Thr Ile Pro Lys Glu Gln Tyr Thr Ile Ile Asn Arg Thr Ala
50                  55                  60

Ser Ser Val Thr Phe Thr Asp Ile Ala Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
            115                 120                 125

Glu Thr His Leu Glu Thr Asn Phe Thr Leu Lys Ser Glu Trp Ala Thr
130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
            195                 200                 205

Ile Asn Ser Glu Glu Leu Ser Ser Ile Leu Lys Leu Thr Trp Thr Asn
210                 215                 220

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
            260                 265                 270

Tyr Val Phe Arg Ile Arg Cys Met Lys Glu Asp Gly Lys Gly Tyr Trp
            275                 280                 285

Ser Asp Trp Ser Glu Glu Ala Ser Gly Ile Thr Tyr Glu Asp Arg Pro
290                 295                 300

Ser Lys Ala Pro Ser Phe Trp Tyr Lys Ile Asp Pro Ser His Thr Gln
305                 310                 315                 320

Gly Tyr Arg Thr Val Gln Leu Val Trp Lys Thr Leu Pro Pro Phe Glu
                325                 330                 335

Ala Asn Gly Lys Ile Leu Asp Tyr Glu Val Thr Leu Thr Arg Trp Lys
            340                 345                 350

Ser His Leu Gln Asn Tyr Thr Val Asn Ala Thr Lys Leu Thr Val Asn
            355                 360                 365

Leu Thr Asn Asp Arg Tyr Leu Ala Thr Leu Thr Val Arg Asn Leu Val
370                 375                 380

Gly Lys Ser Asp Ala Ala Val Leu Thr Ile Pro Ala Cys Asp Phe Gln
385                 390                 395                 400
```

```
Ala Thr His Pro Val Met Asp Leu Lys Ala Phe Pro Lys Asp Asn Met
            405                 410                 415

Leu Trp Val Glu Trp Thr Thr Pro Arg Glu Ser Val Lys Lys Tyr Ile
            420                 425                 430

Leu Glu Trp Cys Val Leu Ser Asp Lys Ala Pro Cys Ile Thr Asp Trp
            435                 440                 445

Gln Gln Glu Asp Gly Thr Val His Arg Thr Tyr Leu Arg Gly Asn Leu
            450                 455                 460

Ala Glu Ser Lys Cys Tyr Leu Ile Thr Val Thr Pro Val Tyr Ala Asp
465                 470                 475                 480

Gly Pro Gly Ser Pro Glu Ser Ile Lys Ala Tyr Leu Lys Gln Ala Pro
            485                 490                 495

Pro Ser Lys Gly Pro Thr Val Arg Thr Lys Lys Val Gly Lys Asn Glu
            500                 505                 510

Ala Val Leu Glu Trp Asp Gln Leu Pro Val Asp Val Gln Asn Gly Phe
            515                 520                 525

Ile Arg Asn Tyr Thr Ile Phe Tyr Arg Thr Ile Ile Gly Asn Glu Thr
            530                 535                 540

Ala Val Asn Val Asp Ser Ser His Thr Glu Tyr Thr Leu Ser Ser Leu
545                 550                 555                 560

Thr Ser Asp Thr Leu Tyr Met Val Arg Met Ala Ala Tyr Thr Asp Glu
            565                 570                 575

Gly Gly Lys Asp Gly Pro Glu Phe Thr Phe Thr Thr Pro Lys Phe Ala
            580                 585                 590

Gln Gly Glu Ile Glu
            595

<210> SEQ ID NO 19
<211> LENGTH: 346
<212> TYPE: PRT
<213> ORGANISM: Artificial Sequence
<220> FEATURE:
<223> OTHER INFORMATION: Synthetic Sequence

<400> SEQUENCE: 19

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
            35                  40                  45

Gly Ser His Pro Ser Arg Trp Ala Gly Met Gly Arg Arg Leu Leu Leu
        50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
            85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
            115                 120                 125

Leu Leu Val Arg Lys Phe Gln Asn Ser Pro Ala Glu Asp Phe Gln Glu
            130                 135                 140

Pro Cys Gln Tyr Ser Gln Glu Ser Gln Lys Phe Ser Cys Gln Leu Ala
145                 150                 155                 160
```

```
Val Pro Glu Gly Asp Ser Ser Phe Tyr Ile Val Ser Met Cys Val Ala
            165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
            195                 200                 205

Ala Arg Asn Pro Arg Trp Leu Ser Val Thr Trp Gln Asp Pro His Ser
210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
            245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
            275                 280                 285

Pro Glu Ala Met Gly Thr Pro Trp Thr Glu Ser Arg Ser Pro Pro Ala
            290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
            325                 330                 335

Val Gln Asp Ser Ser Ser Val Pro Leu Pro
            340                 345

<210> SEQ ID NO 20
<211> LENGTH: 197
<212> TYPE: PRT
<213> ORGANISM: Artificial Sequence
<220> FEATURE:
<223> OTHER INFORMATION: Synthetic Sequence

<400> SEQUENCE: 20

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
            35                  40                  45

His Glu Asp Ile Thr Lys Asp Lys Thr Ser Thr Val Glu Ala Cys Leu
        50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175
```

```
Leu His Ala Phe Arg Ile Arg Ala Val Thr Ile Asp Arg Val Met Ser
            180                 185                 190

Tyr Leu Asn Ala Ser
        195

<210> SEQ ID NO 21
<211> LENGTH: 209
<212> TYPE: PRT
<213> ORGANISM: Artificial Sequence
<220> FEATURE:
<223> OTHER INFORMATION: Synthetic Sequence

<400> SEQUENCE: 21

Arg Lys Gly Pro Pro Ala Ala Leu Thr Leu Pro Arg Val Gln Cys Arg
1               5                   10                  15

Ala Ser Arg Tyr Pro Ile Ala Val Asp Cys Ser Trp Thr Leu Pro Pro
            20                  25                  30

Ala Pro Asn Ser Thr Ser Pro Val Ser Phe Ile Ala Thr Tyr Arg Leu
        35                  40                  45

Gly Met Ala Ala Arg Gly His Ser Trp Pro Cys Leu Gln Gln Thr Pro
    50                  55                  60

Thr Ser Thr Ser Cys Thr Ile Thr Asp Val Gln Leu Phe Ser Met Ala
65                  70                  75                  80

Pro Tyr Val Leu Asn Val Thr Ala Val His Pro Trp Gly Ser Ser Ser
                85                  90                  95

Ser Phe Val Pro Phe Ile Thr Glu His Ile Ile Lys Pro Asp Pro Pro
            100                 105                 110

Glu Gly Val Arg Leu Ser Pro Leu Ala Glu Arg Gln Leu Gln Val Gln
        115                 120                 125

Trp Glu Pro Pro Gly Ser Trp Pro Phe Pro Glu Ile Phe Ser Leu Lys
    130                 135                 140

Tyr Trp Ile Arg Tyr Lys Arg Gln Gly Ala Ala Arg Phe His Arg Val
145                 150                 155                 160

Gly Pro Ile Glu Ala Thr Ser Phe Ile Leu Arg Ala Val Arg Pro Arg
                165                 170                 175

Ala Arg Tyr Tyr Val Gln Val Ala Ala Gln Asp Leu Thr Asp Tyr Gly
            180                 185                 190

Glu Leu Ser Asp Trp Ser Leu Pro Ala Thr Ala Thr Met Ser Leu Gly
        195                 200                 205

Lys

<210> SEQ ID NO 22
<211> LENGTH: 1043
<212> TYPE: PRT
<213> ORGANISM: Artificial Sequence
<220> FEATURE:
<223> OTHER INFORMATION: Synthetic Sequence

<400> SEQUENCE: 22

Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
            20                  25                  30

Met Asp Tyr Phe His Val Asn Ala Asn Tyr Ile Val Trp Lys Thr Asn
        35                  40                  45

His Phe Thr Ile Pro Lys Glu Gln Tyr Thr Ile Ile Asn Arg Thr Ala
    50                  55                  60
```

```
Ser Ser Val Thr Phe Thr Asp Ile Ala Ser Leu Asn Ile Gln Leu Thr
 65                  70                  75                  80

Cys Asn Ile Leu Thr Phe Gly Gln Leu Glu Gln Asn Val Tyr Gly Ile
                 85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
            115                 120                 125

Glu Thr His Leu Glu Thr Asn Phe Thr Leu Lys Ser Glu Trp Ala Thr
            130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
            195                 200                 205

Ile Asn Ser Glu Glu Leu Ser Ser Ile Leu Lys Leu Thr Trp Thr Asn
210                 215                 220

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
            260                 265                 270

Tyr Val Phe Arg Ile Arg Cys Met Lys Glu Asp Gly Lys Gly Tyr Trp
            275                 280                 285

Ser Asp Trp Ser Glu Glu Ala Ser Gly Ile Thr Tyr Glu Asp Arg Pro
            290                 295                 300

Ser Lys Ala Pro Ser Phe Trp Tyr Lys Ile Asp Pro Ser His Thr Gln
305                 310                 315                 320

Gly Tyr Arg Thr Val Gln Leu Val Trp Lys Thr Leu Pro Pro Phe Glu
                325                 330                 335

Ala Asn Gly Lys Ile Leu Asp Tyr Glu Val Thr Leu Thr Arg Trp Lys
            340                 345                 350

Ser His Leu Gln Asn Tyr Thr Val Asn Ala Thr Lys Leu Thr Val Asn
            355                 360                 365

Leu Thr Asn Asp Arg Tyr Leu Ala Thr Leu Thr Val Arg Asn Leu Val
            370                 375                 380

Gly Lys Ser Asp Ala Ala Val Leu Thr Ile Pro Ala Cys Asp Phe Gln
385                 390                 395                 400

Ala Thr His Pro Val Met Asp Leu Lys Ala Phe Pro Lys Asp Asn Met
                405                 410                 415

Leu Trp Val Glu Trp Thr Thr Pro Arg Glu Ser Val Lys Lys Tyr Ile
            420                 425                 430

Leu Glu Trp Cys Val Leu Ser Asp Lys Ala Pro Cys Ile Thr Asp Trp
            435                 440                 445

Gln Gln Glu Asp Gly Thr Val His Arg Thr Tyr Leu Arg Gly Asn Leu
            450                 455                 460

Ala Glu Ser Lys Cys Tyr Leu Ile Thr Val Thr Pro Val Tyr Ala Asp
465                 470                 475                 480
```

```
Gly Pro Gly Ser Pro Glu Ser Ile Lys Ala Tyr Leu Lys Gln Ala Pro
                485                 490                 495

Pro Ser Lys Gly Pro Thr Val Arg Thr Lys Lys Val Gly Lys Asn Glu
            500                 505                 510

Ala Val Leu Glu Trp Asp Gln Leu Pro Val Asp Val Gln Asn Gly Phe
        515                 520                 525

Ile Arg Asn Tyr Thr Ile Phe Tyr Arg Thr Ile Ile Gly Asn Glu Thr
    530                 535                 540

Ala Val Asn Val Asp Ser Ser His Thr Glu Tyr Thr Leu Ser Ser Leu
545                 550                 555                 560

Thr Ser Asp Thr Leu Tyr Met Val Arg Met Ala Ala Tyr Thr Asp Glu
                565                 570                 575

Gly Gly Lys Asp Gly Pro Glu Phe Thr Phe Thr Thr Pro Lys Phe Ala
            580                 585                 590

Gln Gly Glu Ile Glu Gly Ser Gly Ser Arg Lys Gly Lys Arg Gly
        595                 600                 605

Ser Lys Tyr Gly Pro Pro Cys Pro Pro Cys Pro Ala Pro Glu Phe Leu
    610                 615                 620

Gly Gly Pro Ser Val Phe Leu Phe Pro Pro Lys Pro Lys Asp Gln Leu
625                 630                 635                 640

Met Ile Ser Arg Thr Pro Glu Val Thr Cys Val Val Val Asp Val Ser
                645                 650                 655

Gln Glu Asp Pro Glu Val Gln Phe Asn Trp Tyr Val Asp Gly Val Glu
            660                 665                 670

Val His Asn Ala Lys Thr Lys Pro Arg Glu Glu Gln Phe Asn Ser Thr
        675                 680                 685

Tyr Arg Val Val Ser Val Leu Thr Val Leu His Gln Asp Trp Leu Ser
    690                 695                 700

Gly Lys Glu Tyr Lys Cys Lys Val Ser Ser Lys Gly Leu Pro Ser Ser
705                 710                 715                 720

Ile Glu Lys Thr Ile Ser Asn Ala Thr Gly Gln Pro Arg Glu Pro Gln
                725                 730                 735

Val Tyr Thr Leu Pro Pro Ser Gln Glu Glu Met Thr Lys Asn Gln Val
            740                 745                 750

Ser Leu Thr Cys Leu Val Lys Gly Phe Tyr Pro Ser Asp Ile Ala Val
        755                 760                 765

Glu Trp Glu Ser Asn Gly Gln Pro Glu Asn Asn Tyr Lys Thr Thr Pro
    770                 775                 780

Pro Val Leu Asp Ser Asp Gly Ser Phe Phe Leu Tyr Ser Arg Leu Thr
785                 790                 795                 800

Val Asp Lys Ser Arg Trp Gln Glu Gly Asn Val Phe Ser Cys Ser Val
                805                 810                 815

Leu His Glu Ala Leu His Asn His Tyr Thr Gln Lys Ser Leu Ser Leu
            820                 825                 830

Ser Leu Gly Lys Asp Glu Gly Glu Asp Gly Ser Gly Ser Arg Asn
        835                 840                 845

Leu Pro Val Ala Thr Pro Asp Pro Gly Met Phe Pro Cys Leu His His
    850                 855                 860

Ser Gln Asn Leu Leu Arg Ala Val Ser Asn Met Leu Gln Lys Ala Arg
865                 870                 875                 880

Gln Thr Leu Glu Phe Tyr Pro Cys Thr Ser Glu Glu Ile Asp His Glu
                885                 890                 895

Asp Ile Thr Lys Asp Lys Thr Ser Thr Val Glu Ala Cys Leu Pro Leu
```

```
                    900              905              910
Glu Leu Thr Lys Asn Glu Ser Cys Leu Asn Ser Arg Glu Thr Ser Phe
            915              920              925

Ile Thr Asn Gly Ser Cys Leu Ala Ser Arg Lys Thr Ser Phe Met Met
            930              935              940

Ala Leu Cys Leu Ser Ser Ile Tyr Glu Asp Leu Lys Met Tyr Gln Val
945              950              955              960

Glu Phe Lys Thr Met Asn Ala Lys Leu Leu Met Asp Pro Lys Arg Gln
            965              970              975

Ile Phe Leu Asp Gln Asn Met Leu Ala Val Ile Asp Glu Leu Met Gln
            980              985              990

Ala Leu Asn Phe Asn Ser Glu Thr Val Pro Gln Lys Ser Ser Leu Glu
            995             1000             1005

Glu Pro Asp Phe Tyr Lys Thr Lys Ile Lys Leu Cys Ile Leu Leu
            1010             1015             1020

His Ala Phe Arg Ile Arg Ala Val Thr Ile Asp Arg Val Met Ser
            1025             1030             1035

Tyr Leu Asn Ala Ser
            1040

<210> SEQ ID NO 23
<211> LENGTH: 804
<212> TYPE: PRT
<213> ORGANISM: Artificial Sequence
<220> FEATURE:
<223> OTHER INFORMATION: Synthetic Sequence

<400> SEQUENCE: 23

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
        35                  40                  45

Gly Ser His Pro Ser Arg Trp Ala Gly Met Gly Arg Arg Leu Leu Leu
    50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
        195                 200                 205

Ala Arg Asn Pro Arg Trp Leu Ser Val Thr Trp Gln Asp Pro His Ser
```

```
                   210                 215                 220
Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                    245                 250                 255

His Cys Val Ile His Asp Ala Trp Ser Gly Leu Arg His Val Val Gln
                260                 265                 270

Leu Arg Ala Gln Glu Glu Phe Gly Gln Gly Glu Trp Ser Glu Trp Ser
            275                 280                 285

Pro Glu Ala Met Gly Thr Pro Trp Thr Glu Ser Arg Ser Pro Pro Ala
290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Gln Asp Ser Ser Ser Val Pro Leu Pro Gly Ser Gly Ser Asp Glu
            340                 345                 350

Gly Gly Glu Asp Gly Ser Lys Tyr Gly Pro Pro Cys Pro Cys Pro
            355                 360                 365

Ala Pro Glu Phe Leu Gly Gly Pro Ser Val Phe Leu Phe Pro Pro Lys
370                 375                 380

Pro Lys Asp Gln Leu Met Ile Ser Arg Thr Pro Glu Val Thr Cys Val
385                 390                 395                 400

Val Val Asp Val Ser Gln Glu Asp Pro Glu Val Gln Phe Asn Trp Tyr
                405                 410                 415

Val Asp Gly Val Glu Val His Asn Ala Lys Thr Lys Pro Arg Glu Glu
                420                 425                 430

Gln Phe Asn Ser Thr Tyr Arg Val Val Ser Val Leu Thr Val Leu His
            435                 440                 445

Gln Asp Trp Leu Ser Gly Lys Glu Tyr Lys Cys Lys Val Ser Ser Lys
450                 455                 460

Gly Leu Pro Ser Ser Ile Glu Lys Thr Ile Ser Asn Ala Thr Gly Gln
465                 470                 475                 480

Pro Arg Glu Pro Gln Val Tyr Thr Leu Pro Pro Ser Gln Glu Glu Met
                485                 490                 495

Thr Lys Asn Gln Val Ser Leu Thr Cys Leu Val Lys Gly Phe Tyr Pro
                500                 505                 510

Ser Asp Ile Ala Val Glu Trp Glu Ser Asn Gly Gln Pro Glu Asn Asn
            515                 520                 525

Tyr Lys Thr Thr Pro Pro Val Leu Asp Ser Asp Gly Ser Phe Phe Leu
530                 535                 540

Tyr Ser Arg Leu Thr Val Asp Lys Ser Arg Trp Gln Glu Gly Asn Val
545                 550                 555                 560

Phe Ser Cys Ser Val Leu His Glu Ala Leu His Asn His Tyr Thr Gln
                565                 570                 575

Lys Ser Leu Ser Leu Ser Leu Gly Lys Arg Lys Gly Gly Lys Arg Gly
            580                 585                 590

Ser Gly Ser Arg Lys Gly Pro Pro Ala Ala Leu Thr Leu Pro Arg Val
            595                 600                 605

Gln Cys Arg Ala Ser Arg Tyr Pro Ile Ala Val Asp Cys Ser Trp Thr
610                 615                 620

Leu Pro Pro Ala Pro Asn Ser Thr Ser Pro Val Ser Phe Ile Ala Thr
625                 630                 635                 640
```

Tyr Arg Leu Gly Met Ala Ala Arg Gly His Ser Trp Pro Cys Leu Gln
                        645                 650                 655

Gln Thr Pro Thr Ser Thr Ser Cys Thr Ile Thr Asp Val Gln Leu Phe
                660                 665                 670

Ser Met Ala Pro Tyr Val Leu Asn Val Thr Ala Val His Pro Trp Gly
            675                 680                 685

Ser Ser Ser Ser Phe Val Pro Phe Ile Thr Glu His Ile Ile Lys Pro
        690                 695                 700

Asp Pro Pro Glu Gly Val Arg Leu Ser Pro Leu Ala Glu Arg Gln Leu
705                 710                 715                 720

Gln Val Gln Trp Glu Pro Pro Gly Ser Trp Pro Phe Pro Glu Ile Phe
                725                 730                 735

Ser Leu Lys Tyr Trp Ile Arg Tyr Lys Arg Gln Gly Ala Ala Arg Phe
                740                 745                 750

His Arg Val Gly Pro Ile Glu Ala Thr Ser Phe Ile Leu Arg Ala Val
            755                 760                 765

Arg Pro Arg Ala Arg Tyr Tyr Val Gln Val Ala Ala Gln Asp Leu Thr
        770                 775                 780

Asp Tyr Gly Glu Leu Ser Asp Trp Ser Leu Pro Ala Thr Ala Thr Met
785                 790                 795                 800

Ser Leu Gly Lys

<210> SEQ ID NO 24
<211> LENGTH: 599
<212> TYPE: PRT
<213> ORGANISM: Artificial Sequence
<220> FEATURE:
<223> OTHER INFORMATION: Synthetic Sequence

<400> SEQUENCE: 24

Cys Cys Gly Cys Cys Ala Cys Cys Met Glu Phe Gly Leu Ser Trp Val
1               5                   10                  15

Phe Leu Val Ala Ile Ile Lys Gly Val Gln Cys Gln Trp Gln Val Thr
                20                  25                  30

Gly Pro Gly Lys Phe Val Gln Ala Leu Val Gly Glu Asp Ala Val Phe
            35                  40                  45

Ser Cys Ser Leu Phe Pro Glu Thr Ser Ala Glu Ala Met Glu Val Arg
        50                  55                  60

Phe Phe Arg Asn Gln Phe His Ala Val His Leu Tyr Arg Asp Gly
65                  70                  75                  80

Glu Asp Trp Glu Ser Lys Gln Met Pro Gln Tyr Arg Gly Arg Thr Glu
                85                  90                  95

Phe Val Lys Asp Ser Ile Ala Gly Gly Arg Val Ser Leu Arg Leu Lys
            100                 105                 110

Asn Ile Thr Pro Ser Asp Ile Gly Leu Tyr Gly Cys Trp Phe Ser Ser
        115                 120                 125

Gln Ile Tyr Asp Glu Glu Ala Thr Trp Glu Leu Arg Val Ala Ala Leu
    130                 135                 140

Gly Ser Leu Pro Leu Ile Ser Ile Val Gly Tyr Val Asp Gly Gly Ile
145                 150                 155                 160

Gln Leu Leu Cys Leu Ser Ser Gly Trp Phe Pro Gln Pro Thr Ala Lys
                165                 170                 175

Trp Lys Gly Pro Gln Gly Gln Asp Leu Ser Ser Asp Ser Arg Ala Asn
            180                 185                 190

```
Ala Asp Gly Tyr Ser Leu Tyr Asp Val Glu Ile Ser Ile Val Gln
            195                 200                 205

Glu Asn Ala Gly Ser Ile Leu Cys Ser Ile His Leu Ala Glu Gln Ser
        210                 215                 220

His Glu Val Glu Ser Lys Val Leu Ile Gly Glu Thr Phe Phe Gln Pro
225                 230                 235                 240

Ser Pro Trp Arg Leu Ala Ser Gly Ser Arg Lys Gly Gly Lys
                245                 250                 255

Arg Gly Ser Lys Tyr Gly Pro Pro Cys Pro Cys Pro Ala Pro Glu
            260                 265                 270

Phe Leu Gly Gly Pro Ser Val Phe Leu Phe Pro Pro Lys Pro Lys Asp
        275                 280                 285

Gln Leu Met Ile Ser Arg Thr Pro Glu Val Thr Cys Val Val Asp
            290                 295                 300

Val Ser Gln Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
                325                 330                 335

Ser Thr Tyr Arg Val Val Ser Val Leu Thr Val Leu His Gln Asp Trp
            340                 345                 350

Leu Ser Gly Lys Glu Tyr Lys Cys Lys Val Ser Ser Lys Gly Leu Pro
        355                 360                 365

Ser Ser Ile Glu Lys Thr Ile Ser Asn Ala Thr Gly Gln Pro Arg Glu
    370                 375                 380

Pro Gln Val Tyr Thr Leu Pro Pro Ser Gln Glu Glu Met Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Arg
        435                 440                 445

Leu Thr Val Asp Lys Ser Arg Trp Gln Glu Gly Asn Val Phe Ser Cys
    450                 455                 460

Ser Val Leu His Glu Ala Leu His Asn His Tyr Thr Gln Lys Ser Leu
465                 470                 475                 480

Ser Leu Ser Leu Gly Lys Asp Glu Gly Glu Asp Gly Ser Gly Ser
                485                 490                 495

Met Met Thr Gly Thr Ile Glu Thr Thr Gly Asn Ile Ser Ala Glu Lys
            500                 505                 510

Gly Gly Ser Ile Ile Leu Gln Cys His Leu Ser Ser Thr Thr Ala Gln
        515                 520                 525

Val Thr Gln Val Asn Trp Glu Gln Gln Asp Gln Leu Leu Ala Ile Cys
    530                 535                 540

Asn Ala Asp Leu Gly Trp His Ile Ser Pro Ser Phe Lys Asp Arg Val
545                 550                 555                 560

Ala Pro Gly Pro Gly Leu Gly Leu Thr Leu Gln Ser Leu Thr Val Asn
                565                 570                 575

Asp Thr Gly Glu Tyr Phe Cys Ile Tyr His Thr Tyr Pro Asp Gly Thr
            580                 585                 590

Tyr Thr Gly Arg Ile Phe Leu
        595
```

<210> SEQ ID NO 25
<211> LENGTH: 573
<212> TYPE: PRT
<213> ORGANISM: Artificial Sequence
<220> FEATURE:
<223> OTHER INFORMATION: Synthetic Sequence

<400> SEQUENCE: 25

```
Gln Trp Gln Val Phe Gly Pro Asp Lys Pro Val Gln Ala Leu Val Gly
1               5                   10                  15

Glu Asp Ala Ala Phe Ser Cys Phe Leu Ser Pro Lys Thr Asn Ala Glu
            20                  25                  30

Ala Met Glu Val Arg Phe Phe Arg Gly Gln Phe Ser Ser Val Val His
        35                  40                  45

Leu Tyr Arg Asp Gly Lys Asp Gln Pro Phe Met Gln Met Pro Gln Tyr
    50                  55                  60

Gln Gly Arg Thr Lys Leu Val Lys Asp Ser Ile Ala Glu Gly Arg Ile
65                  70                  75                  80

Ser Leu Arg Leu Glu Asn Ile Thr Val Leu Asp Ala Gly Leu Tyr Gly
                85                  90                  95

Cys Arg Ile Ser Ser Gln Ser Tyr Tyr Gln Lys Ala Ile Trp Glu Leu
            100                 105                 110

Gln Val Ser Ala Leu Gly Ser Val Pro Leu Ile Ser Ile Thr Gly Tyr
        115                 120                 125

Val Asp Arg Asp Ile Gln Leu Leu Cys Gln Ser Ser Gly Trp Phe Pro
    130                 135                 140

Arg Pro Thr Ala Lys Trp Lys Gly Pro Gln Gly Gln Asp Leu Ser Thr
145                 150                 155                 160

Asp Ser Arg Thr Asn Arg Asp Met His Gly Leu Phe Asp Val Glu Ile
                165                 170                 175

Ser Leu Thr Val Gln Glu Asn Ala Gly Ser Ile Ser Cys Ser Met Arg
            180                 185                 190

His Ala His Leu Ser Arg Glu Val Glu Ser Arg Val Gln Ile Gly Asp
        195                 200                 205

Thr Phe Phe Glu Pro Ile Ser Trp His Leu Ala Thr Lys Gly Ser Gly
    210                 215                 220

Ser Asp Glu Gly Gly Glu Asp Gly Ser Lys Tyr Gly Pro Pro Cys Pro
225                 230                 235                 240

Pro Cys Pro Ala Pro Glu Phe Leu Gly Gly Pro Ser Val Phe Leu Phe
                245                 250                 255

Pro Pro Lys Pro Lys Asp Gln Leu Met Ile Ser Arg Thr Pro Glu Val
            260                 265                 270

Thr Cys Val Val Val Asp Val Ser Gln Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu His Gln Asp Trp Leu Ser Gly Lys Glu Tyr Lys Cys Lys Val
                325                 330                 335

Ser Ser Lys Gly Leu Pro Ser Ser Ile Glu Lys Thr Ile Ser Asn Ala
            340                 345                 350

Thr Gly Gln Pro Arg Glu Pro Gln Val Tyr Thr Leu Pro Pro Ser Gln
        355                 360                 365

Glu Glu Met Thr Lys Asn Gln Val Ser Leu Thr Cys Leu Val Lys Gly
```

-continued

```
                370                 375                 380
Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Arg Leu Thr Val Asp Lys Ser Arg Trp Gln Glu
                420                 425                 430

Gly Asn Val Phe Ser Cys Ser Val Leu His Glu Ala Leu His Asn His
                435                 440                 445

Tyr Thr Gln Lys Ser Leu Ser Leu Ser Leu Gly Lys Arg Lys Gly Gly
                450                 455                 460

Lys Arg Gly Ser Gly Ser Met Met Thr Gly Thr Ile Glu Thr Thr Gly
465                 470                 475                 480

Asn Ile Ser Ala Glu Lys Gly Gly Ser Ile Ile Leu Gln Cys His Leu
                485                 490                 495

Ser Ser Thr Thr Ala Gln Val Thr Gln Val Asn Trp Glu Gln Gln Asp
                500                 505                 510

Gln Leu Leu Ala Ile Cys Asn Ala Asp Leu Gly Trp His Ile Ser Pro
                515                 520                 525

Ser Phe Lys Asp Arg Val Ala Pro Gly Pro Gly Leu Gly Leu Thr Leu
                530                 535                 540

Gln Ser Leu Thr Val Asn Asp Thr Gly Glu Tyr Phe Cys Ile Tyr His
545                 550                 555                 560

Thr Tyr Pro Asp Gly Thr Tyr Thr Gly Arg Ile Phe Leu
                565                 570

<210> SEQ ID NO 26
<211> LENGTH: 600
<212> TYPE: PRT
<213> ORGANISM: Artificial Sequence
<220> FEATURE:
<223> OTHER INFORMATION: Synthetic Sequence

<400> SEQUENCE: 26

Gln Trp Gln Val Thr Gly Pro Gly Lys Phe Val Gln Ala Leu Val Gly
1               5                   10                  15

Glu Asp Ala Val Phe Ser Cys Ser Leu Phe Pro Glu Thr Ser Ala Glu
                20                  25                  30

Ala Met Glu Val Arg Phe Phe Arg Asn Gln Phe His Ala Val Val His
                35                  40                  45

Leu Tyr Arg Asp Gly Glu Asp Trp Glu Ser Lys Gln Met Pro Gln Tyr
    50                  55                  60

Arg Gly Arg Thr Glu Phe Val Lys Asp Ser Ile Ala Gly Gly Arg Val
65                  70                  75                  80

Ser Leu Arg Leu Lys Asn Ile Thr Pro Ser Asp Ile Gly Leu Tyr Gly
                85                  90                  95

Cys Trp Phe Ser Ser Gln Ile Tyr Asp Glu Ala Thr Trp Glu Leu
                100                 105                 110

Arg Val Ala Ala Leu Gly Ser Leu Pro Leu Ile Ser Ile Val Gly Tyr
                115                 120                 125

Val Asp Gly Gly Ile Gln Leu Leu Cys Leu Ser Ser Gly Trp Phe Pro
                130                 135                 140

Gln Pro Thr Ala Lys Trp Lys Gly Pro Gln Gly Gln Asp Leu Ser Ser
145                 150                 155                 160

Asp Ser Arg Ala Asn Ala Asp Gly Tyr Ser Leu Tyr Asp Val Glu Ile
```

-continued

```
                165                 170                 175
Ser Ile Ile Val Gln Glu Asn Ala Gly Ser Ile Leu Cys Ser Ile His
            180                 185                 190

Leu Ala Glu Gln Ser His Glu Val Glu Ser Lys Val Leu Ile Gly Glu
            195                 200                 205

Thr Phe Phe Gln Pro Ser Pro Trp Arg Leu Ala Ser Gly Ser Gly Ser
            210                 215                 220

Arg Lys Gly Gly Lys Arg Gly Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Gln Leu Met Ile Ser Arg Thr Pro Glu Val Thr
            260                 265                 270

Cys Val Val Val Asp Val Ser Gln Glu Asp Pro Glu Val Gln Phe Asn
            275                 280                 285

Trp Tyr Val Asp Gly Val Glu Val His Asn Ala Lys Thr Lys Pro Arg
            290                 295                 300

Glu Glu Gln Phe Asn Ser Thr Tyr Arg Val Val Ser Val Leu Thr Val
305                 310                 315                 320

Leu His Gln Asp Trp Leu Ser Gly Lys Glu Tyr Lys Cys Lys Val Ser
                325                 330                 335

Ser Lys Gly Leu Pro Ser Ser Ile Glu Lys Thr Ile Ser Asn Ala Thr
            340                 345                 350

Gly Gln Pro Arg Glu Pro Gln Val Tyr Thr Leu Pro Pro Ser Gln Glu
            355                 360                 365

Glu Met Thr Lys Asn Gln Val Ser Leu Thr Cys Leu Val Lys Gly Phe
            370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Leu His Glu Ala Leu His Asn His Tyr
            435                 440                 445

Thr Gln Lys Ser Leu Ser Leu Ser Leu Gly Lys Asp Glu Gly Gly Glu
            450                 455                 460

Asp Gly Ser Gly Ser Gly Ala Pro Ala Gln Leu Pro Cys Ser Pro Thr
465                 470                 475                 480

Ile Pro Leu Gln Asp Leu Ser Leu Leu Arg Arg Ala Gly Val Thr Trp
                485                 490                 495

Gln His Gln Pro Asp Ser Gly Pro Pro Ala Ala Ala Pro Gly His Pro
            500                 505                 510

Leu Ala Pro Gly Pro His Pro Ala Ala Pro Ser Ser Trp Gly Pro Arg
            515                 520                 525

Pro Arg Arg Tyr Thr Val Leu Ser Val Gly Pro Gly Gly Leu Arg Ser
            530                 535                 540

Gly Arg Leu Pro Leu Gln Pro Arg Val Gln Leu Asp Glu Arg Gly Arg
545                 550                 555                 560

Gln Arg Gly Asp Phe Ser Leu Trp Leu Arg Pro Ala Arg Arg Ala Asp
                565                 570                 575

Ala Gly Glu Tyr Arg Ala Ala Val His Leu Arg Asp Arg Ala Leu Ser
            580                 585                 590
```

```
Cys Arg Leu Arg Leu Arg Leu Gly
        595                 600

<210> SEQ ID NO 27
<211> LENGTH: 601
<212> TYPE: PRT
<213> ORGANISM: Artificial Sequence
<220> FEATURE:
<223> OTHER INFORMATION: Synthetic Sequence

<400> SEQUENCE: 27

Gln Trp Gln Val Phe Gly Pro Asp Lys Pro Val Gln Ala Leu Val Gly
1               5                   10                  15

Glu Asp Ala Ala Phe Ser Cys Phe Leu Ser Pro Lys Thr Asn Ala Glu
            20                  25                  30

Ala Met Glu Val Arg Phe Phe Arg Gly Gln Phe Ser Ser Val Val His
        35                  40                  45

Leu Tyr Arg Asp Gly Lys Asp Gln Pro Phe Met Gln Met Pro Gln Tyr
    50                  55                  60

Gln Gly Arg Thr Lys Leu Val Lys Asp Ser Ile Ala Glu Gly Arg Ile
65                  70                  75                  80

Ser Leu Arg Leu Glu Asn Ile Thr Val Leu Asp Ala Gly Leu Tyr Gly
                85                  90                  95

Cys Arg Ile Ser Ser Gln Ser Tyr Tyr Gln Lys Ala Ile Trp Glu Leu
            100                 105                 110

Gln Val Ser Ala Leu Gly Ser Val Pro Leu Ile Ser Ile Thr Gly Tyr
        115                 120                 125

Val Asp Arg Asp Ile Gln Leu Leu Cys Gln Ser Ser Gly Trp Phe Pro
    130                 135                 140

Arg Pro Thr Ala Lys Trp Lys Gly Pro Gln Gly Gln Asp Leu Ser Thr
145                 150                 155                 160

Asp Ser Arg Thr Asn Arg Asp Met His Gly Leu Phe Asp Val Glu Ile
                165                 170                 175

Ser Leu Thr Val Gln Glu Asn Ala Gly Ser Ile Ser Cys Ser Met Arg
            180                 185                 190

His Ala His Leu Ser Arg Glu Val Glu Ser Arg Val Gln Ile Gly Asp
        195                 200                 205

Thr Phe Phe Glu Pro Ile Ser Trp His Leu Ala Thr Lys Gly Ser Gly
    210                 215                 220

Ser Asp Glu Gly Gly Glu Asp Gly Ser Lys Tyr Gly Pro Pro Cys Pro
225                 230                 235                 240

Pro Cys Pro Ala Pro Glu Phe Leu Gly Gly Pro Ser Val Phe Leu Phe
                245                 250                 255

Pro Pro Lys Pro Lys Asp Gln Leu Met Ile Ser Arg Thr Pro Glu Val
            260                 265                 270

Thr Cys Val Val Val Asp Val Ser Gln Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu His Gln Asp Trp Leu Ser Gly Lys Glu Tyr Lys Cys Lys Val
                325                 330                 335

Ser Ser Lys Gly Leu Pro Ser Ser Ile Glu Lys Thr Ile Ser Asn Ala
            340                 345                 350
```

```
Thr Gly Gln Pro Arg Glu Pro Gln Val Tyr Thr Leu Pro Pro Ser Gln
            355                 360                 365

Glu Glu Met Thr Lys Asn Gln Val Ser Leu Thr Cys Leu Val Lys Gly
        370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Arg Leu Thr Val Asp Lys Ser Arg Trp Gln Glu
            420                 425                 430

Gly Asn Val Phe Ser Cys Ser Val Leu His Glu Ala Leu His Asn His
            435                 440                 445

Tyr Thr Gln Lys Ser Leu Ser Leu Ser Leu Gly Lys Arg Lys Gly Gly
        450                 455                 460

Lys Arg Gly Ser Gly Ser Gly Ala Pro Ala Gln Leu Pro Cys Ser Pro
465                 470                 475                 480

Thr Ile Pro Leu Gln Asp Leu Ser Leu Leu Arg Arg Ala Gly Val Thr
                485                 490                 495

Trp Gln His Gln Pro Asp Ser Gly Pro Pro Ala Ala Ala Pro Gly His
            500                 505                 510

Pro Leu Ala Pro Gly Pro His Pro Ala Ala Pro Ser Ser Trp Gly Pro
        515                 520                 525

Arg Pro Arg Arg Tyr Thr Val Leu Ser Val Gly Pro Gly Gly Leu Arg
530                 535                 540

Ser Gly Arg Leu Pro Leu Gln Pro Arg Val Gln Leu Asp Glu Arg Gly
545                 550                 555                 560

Arg Gln Arg Gly Asp Phe Ser Leu Trp Leu Arg Pro Ala Arg Arg Ala
                565                 570                 575

Asp Ala Gly Glu Tyr Arg Ala Ala Val His Leu Arg Asp Arg Ala Leu
            580                 585                 590

Ser Cys Arg Leu Arg Leu Arg Leu Gly
            595                 600

<210> SEQ ID NO 28
<211> LENGTH: 450
<212> TYPE: PRT
<213> ORGANISM: Artificial Sequence
<220> FEATURE:
<223> OTHER INFORMATION: Synthetic Sequence

<400> SEQUENCE: 28

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
                20                  25                  30

Val Thr Gln Val Asn Trp Glu Gln Gln Asp Gln Leu Leu Ala Ile Cys
            35                  40                  45

Asn Ala Asp Leu Gly Trp His Ile Ser Pro Ser Phe Lys Asp Arg Val
        50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
                100                 105                 110
```

His Gly Ala Arg Phe Gln Ile Pro Gly Ser Gly Ser Arg Lys Gly Gly
        115                 120                 125

Lys Arg Gly Ser Lys Tyr Gly Pro Pro Cys Pro Cys Pro Ala Pro
    130                 135                 140

Glu Phe Leu Gly Gly Pro Ser Val Phe Leu Phe Pro Pro Lys Pro Lys
145                 150                 155                 160

Asp Gln Leu Met Ile Ser Arg Thr Pro Glu Val Thr Cys Val Val Val
                165                 170                 175

Asp Val Ser Gln Glu Asp Pro Glu Val Gln Phe Asn Trp Tyr Val Asp
            180                 185                 190

Gly Val Glu Val His Asn Ala Lys Thr Lys Pro Arg Glu Glu Gln Phe
        195                 200                 205

Asn Ser Thr Tyr Arg Val Val Ser Val Leu Thr Val Leu His Gln Asp
    210                 215                 220

Trp Leu Ser Gly Lys Glu Tyr Lys Cys Lys Val Ser Ser Lys Gly Leu
225                 230                 235                 240

Pro Ser Ser Ile Glu Lys Thr Ile Ser Asn Ala Thr Gly Gln Pro Arg
                245                 250                 255

Glu Pro Gln Val Tyr Thr Leu Pro Pro Ser Gln Glu Glu Met Thr Lys
            260                 265                 270

Asn Gln Val Ser Leu Thr Cys Leu Val Lys Gly Phe Tyr Pro Ser Asp
    275                 280                 285

Ile Ala Val Glu Trp Glu Ser Asn Gly Gln Pro Glu Asn Asn Tyr Lys
290                 295                 300

Thr Thr Pro Pro Val Leu Asp Ser Asp Gly Ser Phe Phe Leu Tyr Ser
305                 310                 315                 320

Arg Leu Thr Val Asp Lys Ser Arg Trp Gln Glu Gly Asn Val Phe Ser
                325                 330                 335

Cys Ser Val Leu His Glu Ala Leu His Asn His Tyr Thr Gln Lys Ser
            340                 345                 350

Leu Ser Leu Ser Leu Gly Lys Asp Glu Gly Gly Glu Asp Gly Ser Gly
    355                 360                 365

Ser Pro Leu Ile Ser Ile Val Gly Tyr Val Asp Gly Gly Ile Gln Leu
370                 375                 380

Leu Cys Leu Ser Ser Gly Trp Phe Pro Gln Pro Thr Ala Lys Trp Lys
385                 390                 395                 400

Gly Pro Gln Gly Gln Asp Leu Ser Ser Asp Ser Arg Ala Asn Ala Asp
                405                 410                 415

Gly Tyr Ser Leu Tyr Asp Val Glu Ile Ser Ile Ile Val Gln Glu Asn
            420                 425                 430

Ala Gly Ser Ile Leu Cys Ser Ile His Leu Ala Glu Gln Ser His Glu
    435                 440                 445

Val Glu
    450

<210> SEQ ID NO 29
<211> LENGTH: 459
<212> TYPE: PRT
<213> ORGANISM: Artificial Sequence
<220> FEATURE:
<223> OTHER INFORMATION: Synthetic Sequence

<400> SEQUENCE: 29

Met Met Thr Gly Thr Ile Glu Thr Gly Asn Ile Ser Ala Glu Lys
1               5                   10                  15

```
Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
50                      55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Ser Ser Val Ala Glu
                100                 105                 110

His Gly Ala Arg Phe Gln Ile Pro Gly Ser Gly Ser Asp Glu Gly Gly
            115                 120                 125

Glu Asp Gly Ser Lys Tyr Gly Pro Pro Cys Pro Pro Cys Pro Ala Pro
130                 135                 140

Glu Phe Leu Gly Gly Pro Ser Val Phe Leu Phe Pro Pro Lys Pro Lys
145                 150                 155                 160

Asp Gln Leu Met Ile Ser Arg Thr Pro Glu Val Thr Cys Val Val Val
                165                 170                 175

Asp Val Ser Gln Glu Asp Pro Glu Val Gln Phe Asn Trp Tyr Val Asp
            180                 185                 190

Gly Val Glu Val His Asn Ala Lys Thr Lys Pro Arg Glu Glu Gln Phe
        195                 200                 205

Asn Ser Thr Tyr Arg Val Val Ser Val Leu Thr Val Leu His Gln Asp
    210                 215                 220

Trp Leu Ser Gly Lys Glu Tyr Lys Cys Lys Val Ser Ser Lys Gly Leu
225                 230                 235                 240

Pro Ser Ser Ile Glu Lys Thr Ile Ser Asn Ala Thr Gly Gln Pro Arg
                245                 250                 255

Glu Pro Gln Val Tyr Thr Leu Pro Pro Ser Gln Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Arg Leu Thr Val Asp Lys Ser Arg Trp Gln Glu Gly Asn Val Phe Ser
                325                 330                 335

Cys Ser Val Leu His Glu Ala Leu His Asn His Tyr Thr Gln Lys Ser
            340                 345                 350

Leu Ser Leu Ser Leu Gly Lys Arg Lys Gly Gly Lys Arg Gly Ser Gly
        355                 360                 365

Ser Ala Leu Gly Ser Val Pro Leu Ile Ser Ile Thr Gly Tyr Val Asp
    370                 375                 380

Arg Asp Ile Gln Leu Leu Cys Gln Ser Ser Gly Trp Phe Pro Arg Pro
385                 390                 395                 400

Thr Ala Lys Trp Lys Gly Pro Gln Gly Gln Asp Leu Ser Thr Asp Ser
                405                 410                 415

Arg Thr Asn Arg Asp Met His Gly Leu Phe Asp Val Glu Ile Ser Leu
            420                 425                 430
```

```
Thr Val Gln Glu Asn Ala Gly Ser Ile Ser Cys Ser Met Arg His Ala
            435                 440                 445

His Leu Ser Arg Glu Val Glu Ser Arg Val Gln
    450                 455

<210> SEQ ID NO 30
<211> LENGTH: 752
<212> TYPE: PRT
<213> ORGANISM: Artificial Sequence
<220> FEATURE:
<223> OTHER INFORMATION: Synthetic Sequence

<400> SEQUENCE: 30

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
    130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
    210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
            260                 265                 270

Pro Gly Gly Gly Pro Asp Leu Leu Val Thr Gly Asp Asn Gly Asp Phe
        275                 280                 285

Thr Leu Arg Leu Glu Asp Val Ser Gln Ala Gln Ala Gly Thr Tyr Thr
    290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335
```

```
Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
            355                 360                 365

Trp Leu Glu Ala Gln Glu Ala Gln Leu Leu Ser Gln Pro Trp Gln Cys
            370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
            405                 410                 415

Leu Pro Ala Gly His Leu Gly Ser Gly Ser Arg Lys Gly Gly Lys Arg
            420                 425                 430

Gly Ser Lys Tyr Gly Pro Pro Cys Pro Pro Cys Pro Ala Pro Glu Phe
            435                 440                 445

Leu Gly Gly Pro Ser Val Phe Leu Phe Pro Pro Lys Pro Lys Asp Gln
            450                 455                 460

Leu Met Ile Ser Arg Thr Pro Glu Val Thr Cys Val Val Val Asp Val
465                 470                 475                 480

Ser Gln Glu Asp Pro Glu Val Gln Phe Asn Trp Tyr Val Asp Gly Val
            485                 490                 495

Glu Val His Asn Ala Lys Thr Lys Pro Arg Glu Glu Gln Phe Asn Ser
            500                 505                 510

Thr Tyr Arg Val Val Ser Val Leu Thr Val Leu His Gln Asp Trp Leu
            515                 520                 525

Ser Gly Lys Glu Tyr Lys Cys Lys Val Ser Ser Lys Gly Leu Pro Ser
            530                 535                 540

Ser Ile Glu Lys Thr Ile Ser Asn Ala Thr Gly Gln Pro Arg Glu Pro
545                 550                 555                 560

Gln Val Tyr Thr Leu Pro Pro Ser Gln Glu Glu Met Thr Lys Asn Gln
            565                 570                 575

Val Ser Leu Thr Cys Leu Val Lys Gly Phe Tyr Pro Ser Asp Ile Ala
            580                 585                 590

Val Glu Trp Glu Ser Asn Gly Gln Pro Glu Asn Asn Tyr Lys Thr Thr
            595                 600                 605

Pro Pro Val Leu Asp Ser Asp Gly Ser Phe Phe Leu Tyr Ser Arg Leu
            610                 615                 620

Thr Val Asp Lys Ser Arg Trp Gln Glu Gly Asn Val Phe Ser Cys Ser
625                 630                 635                 640

Val Leu His Glu Ala Leu His Asn His Tyr Thr Gln Lys Ser Leu Ser
            645                 650                 655

Leu Ser Leu Gly Lys Asp Glu Gly Glu Asp Gly Ser Gly Ser Pro
            660                 665                 670

Leu Ile Ser Ile Val Gly Tyr Val Asp Gly Ile Gln Leu Leu Cys
            675                 680                 685

Leu Ser Ser Gly Trp Phe Pro Gln Pro Thr Ala Lys Trp Lys Gly Pro
            690                 695                 700

Gln Gly Gln Asp Leu Ser Ser Asp Ser Arg Ala Asn Ala Asp Gly Tyr
705                 710                 715                 720

Ser Leu Tyr Asp Val Glu Ile Ser Ile Val Gln Glu Asn Ala Gly
            725                 730                 735

Ser Ile Leu Cys Ser Ile His Leu Ala Glu Gln Ser His Glu Val Glu
            740                 745                 750
```

-continued

```
<210> SEQ ID NO 31
<211> LENGTH: 761
<212> TYPE: PRT
<213> ORGANISM: Artificial Sequence
<220> FEATURE:
<223> OTHER INFORMATION: Synthetic Sequence

<400> SEQUENCE: 31

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
    130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
    210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
            260                 265                 270

Pro Gly Gly Gly Pro Asp Leu Leu Val Thr Gly Asp Asn Gly Asp Phe
        275                 280                 285

Thr Leu Arg Leu Glu Asp Val Ser Gln Ala Gln Ala Gly Thr Tyr Thr
    290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
        355                 360                 365

Trp Leu Glu Ala Gln Glu Ala Gln Leu Leu Ser Gln Pro Trp Gln Cys
```

```
                370                 375                 380
Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
            405                 410                 415

Leu Pro Ala Gly His Leu Gly Ser Gly Ser Asp Glu Gly Gly Glu Asp
            420                 425                 430

Gly Ser Lys Tyr Gly Pro Pro Cys Pro Pro Cys Pro Ala Pro Glu Phe
            435                 440                 445

Leu Gly Gly Pro Ser Val Phe Leu Phe Pro Pro Lys Pro Lys Asp Gln
450                 455                 460

Leu Met Ile Ser Arg Thr Pro Glu Val Thr Cys Val Val Val Asp Val
465                 470                 475                 480

Ser Gln Glu Asp Pro Glu Val Gln Phe Asn Trp Tyr Val Asp Gly Val
            485                 490                 495

Glu Val His Asn Ala Lys Thr Lys Pro Arg Glu Glu Gln Phe Asn Ser
            500                 505                 510

Thr Tyr Arg Val Val Ser Val Leu Thr Val Leu His Gln Asp Trp Leu
            515                 520                 525

Ser Gly Lys Glu Tyr Lys Cys Lys Val Ser Ser Lys Gly Leu Pro Ser
            530                 535                 540

Ser Ile Glu Lys Thr Ile Ser Asn Ala Thr Gly Gln Pro Arg Glu Pro
545                 550                 555                 560

Gln Val Tyr Thr Leu Pro Pro Ser Gln Glu Glu Met Thr Lys Asn Gln
            565                 570                 575

Val Ser Leu Thr Cys Leu Val Lys Gly Phe Tyr Pro Ser Asp Ile Ala
            580                 585                 590

Val Glu Trp Glu Ser Asn Gly Gln Pro Glu Asn Asn Tyr Lys Thr Thr
            595                 600                 605

Pro Pro Val Leu Asp Ser Asp Gly Ser Phe Phe Leu Tyr Ser Arg Leu
            610                 615                 620

Thr Val Asp Lys Ser Arg Trp Gln Glu Gly Asn Val Phe Ser Cys Ser
625                 630                 635                 640

Val Leu His Glu Ala Leu His Asn His Tyr Thr Gln Lys Ser Leu Ser
            645                 650                 655

Leu Ser Leu Gly Lys Arg Lys Gly Gly Lys Arg Gly Ser Gly Ser Ala
            660                 665                 670

Leu Gly Ser Val Pro Leu Ile Ser Ile Thr Gly Tyr Val Asp Arg Asp
            675                 680                 685

Ile Gln Leu Leu Cys Gln Ser Ser Gly Trp Phe Pro Arg Pro Thr Ala
            690                 695                 700

Lys Trp Lys Gly Pro Gln Gly Gln Asp Leu Ser Thr Asp Ser Arg Thr
705                 710                 715                 720

Asn Arg Asp Met His Gly Leu Phe Asp Val Glu Ile Ser Leu Thr Val
            725                 730                 735

Gln Glu Asn Ala Gly Ser Ile Ser Cys Ser Met Arg His Ala His Leu
            740                 745                 750

Ser Arg Glu Val Glu Ser Arg Val Gln
            755                 760

<210> SEQ ID NO 32
<211> LENGTH: 480
<212> TYPE: PRT
<213> ORGANISM: Artificial Sequence
```

<220> FEATURE:
<223> OTHER INFORMATION: Synthetic Sequence

<400> SEQUENCE: 32

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Gly Ser Gly Ser Arg Lys Gly Gly Lys Arg
145                 150                 155                 160

Gly Ser Lys Tyr Gly Pro Pro Cys Pro Pro Cys Pro Ala Pro Glu Phe
                165                 170                 175

Leu Gly Gly Pro Ser Val Phe Leu Phe Pro Pro Lys Pro Lys Asp Gln
            180                 185                 190

Leu Met Ile Ser Arg Thr Pro Glu Val Thr Cys Val Val Val Asp Val
        195                 200                 205

Ser Gln Glu Asp Pro Glu Val Gln Phe Asn Trp Tyr Val Asp Gly Val
210                 215                 220

Glu Val His Asn Ala Lys Thr Lys Pro Arg Glu Glu Gln Phe Asn Ser
225                 230                 235                 240

Thr Tyr Arg Val Val Ser Val Leu Thr Val Leu His Gln Asp Trp Leu
                245                 250                 255

Ser Gly Lys Glu Tyr Lys Cys Lys Val Ser Ser Lys Gly Leu Pro Ser
            260                 265                 270

Ser Ile Glu Lys Thr Ile Ser Asn Ala Thr Gly Gln Pro Arg Glu Pro
        275                 280                 285

Gln Val Tyr Thr Leu Pro Pro Ser Gln Glu Glu Met Thr Lys Asn Gln
290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Val Leu Asp Ser Asp Gly Ser Phe Phe Leu Tyr Ser Arg Leu
            340                 345                 350

Thr Val Asp Lys Ser Arg Trp Gln Glu Gly Asn Val Phe Ser Cys Ser
        355                 360                 365

Val Leu His Glu Ala Leu His Asn His Tyr Thr Gln Lys Ser Leu Ser
370                 375                 380

Leu Ser Leu Gly Lys Asp Glu Gly Gly Glu Asp Gly Ser Gly Ser Pro
385                 390                 395                 400
```

```
Leu Ile Ser Ile Val Gly Tyr Val Asp Gly Ile Gln Leu Leu Cys
            405                 410                 415

Leu Ser Ser Gly Trp Phe Pro Gln Pro Thr Ala Lys Trp Lys Gly Pro
        420                 425                 430

Gln Gly Gln Asp Leu Ser Ser Asp Ser Arg Ala Asn Ala Asp Gly Tyr
        435                 440                 445

Ser Leu Tyr Asp Val Glu Ile Ser Ile Val Gln Glu Asn Ala Gly
    450                 455                 460

Ser Ile Leu Cys Ser Ile His Leu Ala Glu Gln Ser His Glu Val Glu
465                 470                 475                 480

<210> SEQ ID NO 33
<211> LENGTH: 489
<212> TYPE: PRT
<213> ORGANISM: Artificial Sequence
<220> FEATURE:
<223> OTHER INFORMATION: Synthetic Sequence

<400> SEQUENCE: 33

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Ser Gly Ser Asp Glu Gly Gly Glu Asp
145                 150                 155                 160

Gly Ser Lys Tyr Gly Pro Pro Cys Pro Pro Cys Pro Ala Pro Glu Phe
                165                 170                 175

Leu Gly Gly Pro Ser Val Phe Leu Phe Pro Pro Lys Pro Lys Asp Gln
            180                 185                 190

Leu Met Ile Ser Arg Thr Pro Glu Val Thr Cys Val Val Val Asp Val
        195                 200                 205

Ser Gln Glu Asp Pro Glu Val Gln Phe Asn Trp Tyr Val Asp Gly Val
    210                 215                 220

Glu Val His Asn Ala Lys Thr Lys Pro Arg Glu Glu Gln Phe Asn Ser
225                 230                 235                 240

Thr Tyr Arg Val Val Ser Val Leu Thr Val Leu His Gln Asp Trp Leu
                245                 250                 255

Ser Gly Lys Glu Tyr Lys Cys Lys Val Ser Ser Lys Gly Leu Pro Ser
            260                 265                 270

Ser Ile Glu Lys Thr Ile Ser Asn Ala Thr Gly Gln Pro Arg Glu Pro
        275                 280                 285
```

```
Gln Val Tyr Thr Leu Pro Pro Ser Gln Glu Glu Met Thr Lys Asn Gln
            290                 295                 300
Val Ser Leu Thr Cys Leu Val Lys Gly Phe Tyr Pro Ser Asp Ile Ala
305                 310                 315                 320
Val Glu Trp Glu Ser Asn Gly Gln Pro Glu Asn Asn Tyr Lys Thr Thr
            325                 330                 335
Pro Pro Val Leu Asp Ser Asp Gly Ser Phe Phe Leu Tyr Ser Arg Leu
            340                 345                 350
Thr Val Asp Lys Ser Arg Trp Gln Glu Gly Asn Val Phe Ser Cys Ser
            355                 360                 365
Val Leu His Glu Ala Leu His Asn His Tyr Thr Gln Lys Ser Leu Ser
370                 375                 380
Leu Ser Leu Gly Lys Arg Lys Gly Gly Lys Arg Gly Ser Gly Ser Ala
385                 390                 395                 400
Leu Gly Ser Val Pro Leu Ile Ser Ile Thr Gly Tyr Val Asp Arg Asp
                405                 410                 415
Ile Gln Leu Leu Cys Gln Ser Ser Gly Trp Phe Pro Arg Pro Thr Ala
                420                 425                 430
Lys Trp Lys Gly Pro Gln Gly Gln Asp Leu Ser Thr Ser Ser Arg Thr
            435                 440                 445
Asn Arg Asp Met His Gly Leu Phe Asp Val Glu Ile Ser Leu Thr Val
450                 455                 460
Gln Glu Asn Ala Gly Ser Ile Ser Cys Ser Met Arg His Ala His Leu
465                 470                 475                 480
Ser Arg Glu Val Glu Ser Arg Val Gln
                485

<210> SEQ ID NO 34
<211> LENGTH: 228
<212> TYPE: PRT
<213> ORGANISM: Artificial Sequence
<220> FEATURE:
<223> OTHER INFORMATION: Synthetic Sequence

<400> SEQUENCE: 34

Ser Lys Tyr Gly Pro Pro Cys Pro Pro Cys Pro Ala Pro Glu Phe Leu
1               5                   10                  15
Gly Gly Pro Ser Val Phe Leu Phe Pro Pro Lys Pro Lys Asp Gln Leu
            20                  25                  30
Met Ile Ser Arg Thr Pro Glu Val Thr Cys Val Val Val Asp Val Ser
        35                  40                  45
Gln Glu Asp Pro Glu Val Gln Phe Asn Trp Tyr Val Asp Gly Val Glu
50                  55                  60
Val His Asn Ala Lys Thr Lys Pro Arg Glu Glu Gln Phe Asn Ser Thr
65                  70                  75                  80
Tyr Arg Val Val Ser Val Leu Thr Val Leu His Gln Asp Trp Leu Ser
                85                  90                  95
Gly Lys Glu Tyr Lys Cys Lys Val Ser Ser Lys Gly Leu Pro Ser Ser
            100                 105                 110
Ile Glu Lys Thr Ile Ser Asn Ala Thr Gly Gln Pro Arg Glu Pro Gln
        115                 120                 125
Val Tyr Thr Leu Pro Pro Ser Gln Glu Glu Met Thr Lys Asn Gln Val
    130                 135                 140
Ser Leu Thr Cys Leu Val Lys Gly Phe Tyr Pro Ser Asp Ile Ala Val
145                 150                 155                 160
```

```
Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Leu His Glu Ala Leu His Asn His Tyr Thr Gln Lys Ser Leu Ser Leu
    210                 215                 220

Ser Leu Gly Lys
225

<210> SEQ ID NO 35
<211> LENGTH: 580
<212> TYPE: PRT
<213> ORGANISM: Artificial Sequence
<220> FEATURE:
<223> OTHER INFORMATION: Synthetic Sequence

<400> SEQUENCE: 35

Gln Trp Gln Val Thr Gly Pro Gly Lys Phe Val Gln Ala Leu Val Gly
1               5                   10                  15

Glu Asp Ala Val Phe Ser Cys Ser Leu Phe Pro Glu Thr Ser Ala Glu
            20                  25                  30

Ala Met Glu Val Arg Phe Phe Arg Asn Gln Phe His Ala Val Val His
        35                  40                  45

Leu Tyr Arg Asp Gly Glu Asp Trp Glu Ser Lys Gln Met Pro Gln Tyr
    50                  55                  60

Arg Gly Arg Thr Glu Phe Val Lys Asp Ser Ile Ala Gly Gly Arg Val
65                  70                  75                  80

Ser Leu Arg Leu Lys Asn Ile Thr Pro Ser Asp Ile Gly Leu Tyr Gly
                85                  90                  95

Cys Trp Phe Ser Ser Gln Ile Tyr Asp Glu Glu Ala Thr Trp Glu Leu
            100                 105                 110

Arg Val Ala Ala Leu Gly Ser Leu Pro Leu Ile Ser Ile Val Gly Tyr
        115                 120                 125

Val Asp Gly Gly Ile Gln Leu Leu Cys Leu Ser Ser Gly Trp Phe Pro
    130                 135                 140

Gln Pro Thr Ala Lys Trp Lys Gly Pro Gln Gly Gln Asp Leu Ser Ser
145                 150                 155                 160

Asp Ser Arg Ala Asn Ala Asp Gly Tyr Ser Leu Tyr Asp Val Glu Ile
                165                 170                 175

Ser Ile Ile Val Gln Glu Asn Ala Gly Ser Ile Leu Cys Ser Ile His
            180                 185                 190

Leu Ala Glu Gln Ser His Glu Val Glu Ser Lys Val Leu Ile Gly Glu
        195                 200                 205

Thr Phe Phe Gln Pro Ser Pro Trp Arg Leu Ala Ser Gly Ser Gly Ser
    210                 215                 220

Arg Lys Gly Gly Lys Arg Gly Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Gln Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285
```

```
Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Ser Gly Lys Glu Tyr Lys Cys Lys Val Ser
                325                 330                 335

Ser Lys Gly Leu Pro Ser Ser Ile Glu Lys Thr Ile Ser Asn Ala Thr
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Leu His Glu Ala Leu His Asn His Tyr
        435                 440                 445

Thr Gln Lys Ser Leu Ser Leu Ser Leu Gly Lys Asp Glu Gly Gly Glu
    450                 455                 460

Asp Gly Ser Gly Ser Asp Ile Gln Leu Thr Gln Ser Pro Ala Ser Leu
465                 470                 475                 480

Ala Val Ser Leu Gly Gln Arg Ala Thr Ile Ser Cys Lys Ala Ser Gln
                485                 490                 495

Ser Val Asp Tyr Asp Gly Asp Ser Tyr Leu Asn Trp Tyr Gln Gln Ile
            500                 505                 510

Pro Gly Gln Pro Pro Lys Leu Leu Ile Tyr Asp Ala Ser Asn Leu Val
        515                 520                 525

Ser Gly Ile Pro Pro Arg Phe Ser Gly Ser Gly Ser Gly Thr Asp Phe
    530                 535                 540

Thr Leu Asn Ile His Pro Val Glu Lys Val Asp Ala Ala Thr Tyr His
545                 550                 555                 560

Cys Gln Gln Ser Thr Glu Asp Pro Trp Thr Phe Gly Gly Gly Thr Lys
                565                 570                 575

Leu Glu Ile Lys
        580

<210> SEQ ID NO 36
<211> LENGTH: 575
<212> TYPE: PRT
<213> ORGANISM: Artificial Sequence
<220> FEATURE:
<223> OTHER INFORMATION: Synthetic Sequence

<400> SEQUENCE: 36

Gln Trp Gln Val Phe Gly Pro Asp Lys Pro Val Gln Ala Leu Val Gly
1               5                   10                  15

Glu Asp Ala Ala Phe Ser Cys Phe Leu Ser Pro Lys Thr Asn Ala Glu
                20                  25                  30

Ala Met Glu Val Arg Phe Phe Arg Gly Gln Phe Ser Ser Val Val His
            35                  40                  45

Leu Tyr Arg Asp Gly Lys Asp Gln Pro Phe Met Gln Met Pro Gln Tyr
        50                  55                  60
```

```
Gln Gly Arg Thr Lys Leu Val Lys Asp Ser Ile Ala Glu Gly Arg Ile
 65                  70                  75                  80

Ser Leu Arg Leu Glu Asn Ile Thr Val Leu Asp Ala Gly Leu Tyr Gly
                 85                  90                  95

Cys Arg Ile Ser Ser Gln Ser Tyr Tyr Gln Lys Ala Ile Trp Glu Leu
            100                 105                 110

Gln Val Ser Ala Leu Gly Ser Val Pro Leu Ile Ser Ile Thr Gly Tyr
        115                 120                 125

Val Asp Arg Asp Ile Gln Leu Leu Cys Gln Ser Ser Gly Trp Phe Pro
    130                 135                 140

Arg Pro Thr Ala Lys Trp Lys Gly Pro Gln Gly Gln Asp Leu Ser Thr
145                 150                 155                 160

Asp Ser Arg Thr Asn Arg Asp Met His Gly Leu Phe Asp Val Glu Ile
                165                 170                 175

Ser Leu Thr Val Gln Glu Asn Ala Gly Ser Ile Ser Cys Ser Met Arg
            180                 185                 190

His Ala His Leu Ser Arg Glu Val Glu Ser Arg Val Gln Ile Gly Asp
        195                 200                 205

Thr Phe Phe Glu Pro Ile Ser Trp His Leu Ala Thr Lys Gly Ser Gly
    210                 215                 220

Ser Asp Glu Gly Gly Glu Asp Gly Ser Lys Tyr Gly Pro Pro Cys Pro
225                 230                 235                 240

Pro Cys Pro Ala Pro Glu Phe Leu Gly Gly Pro Ser Val Phe Leu Phe
                245                 250                 255

Pro Pro Lys Pro Lys Asp Gln Leu Met Ile Ser Arg Thr Pro Glu Val
            260                 265                 270

Thr Cys Val Val Val Asp Val Ser Gln Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu His Gln Asp Trp Leu Ser Gly Lys Glu Tyr Lys Cys Lys Val
                325                 330                 335

Ser Ser Lys Gly Leu Pro Ser Ser Ile Glu Lys Thr Ile Ser Asn Ala
            340                 345                 350

Thr Gly Gln Pro Arg Glu Pro Gln Val Tyr Thr Leu Pro Pro Ser Gln
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Arg Leu Thr Val Asp Lys Ser Arg Trp Gln Glu
            420                 425                 430

Gly Asn Val Phe Ser Cys Ser Val Leu His Glu Ala Leu His Asn His
        435                 440                 445

Tyr Thr Gln Lys Ser Leu Ser Leu Ser Leu Gly Lys Arg Lys Gly Gly
    450                 455                 460

Lys Arg Gly Ser Gly Ser Ile Gln Leu Thr Gln Ser Pro Ala Ile Met
465                 470                 475                 480
```

```
Ser Ala Ser Pro Gly Glu Lys Val Thr Met Thr Cys Arg Ala Ser Ser
            485                 490                 495
Ser Val Ser Tyr Met Asn Trp Tyr Gln Gln Lys Ser Gly Thr Ser Pro
        500                 505                 510
Lys Arg Trp Ile Tyr Asp Thr Ser Lys Val Ala Ser Gly Val Pro Tyr
            515                 520                 525
Arg Phe Ser Gly Ser Gly Ser Gly Thr Ser Tyr Ser Leu Thr Ile Ser
        530                 535                 540
Ser Met Glu Ala Glu Asp Ala Ala Thr Tyr Tyr Cys Gln Gln Trp Ser
545                 550                 555                 560
Ser Asn Pro Leu Thr Phe Gly Ala Gly Thr Lys Leu Glu Leu Lys
            565                 570                 575

<210> SEQ ID NO 37
<211> LENGTH: 579
<212> TYPE: PRT
<213> ORGANISM: Artificial Sequence
<220> FEATURE:
<223> OTHER INFORMATION: Synthetic Sequence

<400> SEQUENCE: 37

Gln Trp Gln Val Thr Gly Pro Gly Lys Phe Val Gln Ala Leu Val Gly
1               5                   10                  15
Glu Asp Ala Val Phe Ser Cys Ser Leu Phe Pro Glu Thr Ser Ala Glu
            20                  25                  30
Ala Met Glu Val Arg Phe Phe Arg Asn Gln Phe His Ala Val Val His
        35                  40                  45
Leu Tyr Arg Asp Gly Glu Asp Trp Glu Ser Lys Gln Met Pro Gln Tyr
    50                  55                  60
Arg Gly Arg Thr Glu Phe Val Lys Asp Ser Ile Ala Gly Gly Arg Val
65                  70                  75                  80
Ser Leu Arg Leu Lys Asn Ile Thr Pro Ser Asp Ile Gly Leu Tyr Gly
                85                  90                  95
Cys Trp Phe Ser Ser Gln Ile Tyr Asp Glu Glu Ala Thr Trp Glu Leu
            100                 105                 110
Arg Val Ala Ala Leu Gly Ser Leu Pro Leu Ile Ser Ile Val Gly Tyr
        115                 120                 125
Val Asp Gly Gly Ile Gln Leu Leu Cys Leu Ser Ser Gly Trp Phe Pro
    130                 135                 140
Gln Pro Thr Ala Lys Trp Lys Gly Pro Gln Gly Gln Asp Leu Ser Ser
145                 150                 155                 160
Asp Ser Arg Ala Asn Ala Asp Gly Tyr Ser Leu Tyr Asp Val Glu Ile
                165                 170                 175
Ser Ile Ile Val Gln Glu Asn Ala Gly Ser Ile Leu Cys Ser Ile His
            180                 185                 190
Leu Ala Glu Gln Ser His Glu Val Gly Ser Lys Val Leu Ile Gly Glu
        195                 200                 205
Thr Phe Phe Gln Pro Ser Pro Trp Arg Leu Ala Ser Gly Ser Gly Ser
    210                 215                 220
Arg Lys Gly Gly Lys Arg Gly Ser Lys Tyr Gly Pro Pro Cys Pro Pro
225                 230                 235                 240
Cys Pro Ala Pro Glu Phe Leu Gly Gly Pro Ser Val Phe Leu Phe Pro
                245                 250                 255
Pro Lys Pro Lys Asp Gln Leu Met Ile Ser Arg Thr Pro Glu Val Thr
            260                 265                 270
```

```
Cys Val Val Asp Val Ser Gln Glu Asp Pro Glu Val Gln Phe Asn
            275                 280                 285

Trp Tyr Val Asp Gly Val Glu Val His Asn Ala Lys Thr Lys Pro Arg
290                 295                 300

Glu Glu Gln Phe Asn Ser Thr Tyr Arg Val Val Ser Val Leu Thr Val
305                 310                 315                 320

Leu His Gln Asp Trp Leu Ser Gly Lys Glu Tyr Lys Cys Lys Val Ser
                325                 330                 335

Ser Lys Gly Leu Pro Ser Ser Ile Glu Lys Thr Ile Ser Asn Ala Thr
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Leu His Glu Ala Leu His Asn His Tyr
        435                 440                 445

Thr Gln Lys Ser Leu Ser Leu Ser Leu Gly Lys Asp Glu Gly Gly Glu
    450                 455                 460

Asp Gly Ser Gly Ser Gly Glu Val Gln Leu Val Glu Ser Gly Gly Gly
465                 470                 475                 480

Leu Val Gln Pro Gly Gly Ser Leu Thr Leu Ser Cys Ala Ala Ser Arg
                485                 490                 495

Phe Met Ile Ser Glu Tyr His Met His Trp Val Arg Gln Ala Pro Gly
            500                 505                 510

Lys Gly Leu Glu Trp Val Ser Thr Ile Asn Pro Ala Gly Thr Thr Asp
        515                 520                 525

Tyr Ala Glu Ser Val Lys Gly Arg Phe Thr Ile Ser Arg Asp Asn Ala
530                 535                 540

Lys Asn Thr Leu Tyr Leu Gln Met Asn Ser Leu Lys Pro Glu Asp Thr
545                 550                 555                 560

Ala Val Tyr Tyr Cys Asp Ser Tyr Gly Tyr Arg Gly Gln Gly Thr Gln
                565                 570                 575

Val Thr Val

<210> SEQ ID NO 38
<211> LENGTH: 580
<212> TYPE: PRT
<213> ORGANISM: Artificial Sequence
<220> FEATURE:
<223> OTHER INFORMATION: Synthetic Sequence

<400> SEQUENCE: 38

Gln Trp Gln Val Phe Gly Pro Asp Lys Pro Val Gln Ala Leu Val Gly
1               5                   10                  15

Glu Asp Ala Ala Phe Ser Cys Phe Leu Ser Pro Lys Thr Asn Ala Glu
            20                  25                  30

Ala Met Glu Val Arg Phe Phe Arg Gly Gln Phe Ser Ser Val Val His
        35                  40                  45

Leu Tyr Arg Asp Gly Lys Asp Gln Pro Phe Met Gln Met Pro Gln Tyr
```

-continued

```
            50                  55                  60
Gln Gly Arg Thr Lys Leu Val Lys Asp Ser Ile Ala Glu Gly Arg Ile
 65                  70                  75                  80
Ser Leu Arg Leu Glu Asn Ile Thr Val Leu Asp Ala Gly Leu Tyr Gly
                     85                  90                  95
Cys Arg Ile Ser Ser Gln Ser Tyr Tyr Gln Lys Ala Ile Trp Glu Leu
                100                 105                 110
Gln Val Ser Ala Leu Gly Ser Val Pro Leu Ile Ser Ile Thr Gly Tyr
                115                 120                 125
Val Asp Arg Asp Ile Gln Leu Leu Cys Gln Ser Ser Gly Trp Phe Pro
            130                 135                 140
Arg Pro Thr Ala Lys Trp Lys Gly Pro Gln Gly Gln Asp Leu Ser Thr
145                 150                 155                 160
Asp Ser Arg Thr Asn Arg Asp Met His Gly Leu Phe Asp Val Glu Ile
                165                 170                 175
Ser Leu Thr Val Gln Glu Asn Ala Gly Ser Ile Ser Cys Ser Met Arg
                180                 185                 190
His Ala His Leu Ser Arg Glu Val Glu Ser Arg Val Gln Ile Gly Asp
                195                 200                 205
Thr Phe Phe Glu Pro Ile Ser Trp His Leu Ala Thr Lys Gly Ser Gly
            210                 215                 220
Ser Asp Glu Gly Gly Asp Gly Ser Lys Tyr Gly Pro Pro Cys Pro
225                 230                 235                 240
Pro Cys Pro Ala Pro Glu Phe Leu Gly Gly Pro Ser Val Phe Leu Phe
                245                 250                 255
Pro Pro Lys Pro Lys Asp Gln Leu Met Ile Ser Arg Thr Pro Glu Val
                260                 265                 270
Thr Cys Val Val Val Asp Val Ser Gln Glu Asp Pro Glu Val Gln Phe
                275                 280                 285
Asn Trp Tyr Val Asp Gly Val Glu Val His Asn Ala Lys Thr Lys Pro
            290                 295                 300
Arg Glu Glu Gln Phe Asn Ser Thr Tyr Arg Val Val Ser Val Leu Thr
305                 310                 315                 320
Val Leu His Gln Asp Trp Leu Ser Gly Lys Glu Tyr Lys Cys Lys Val
                325                 330                 335
Ser Ser Lys Gly Leu Pro Ser Ser Ile Glu Lys Thr Ile Ser Asn Ala
                340                 345                 350
Thr Gly Gln Pro Arg Glu Pro Gln Val Tyr Thr Leu Pro Pro Ser Gln
                355                 360                 365
Glu Glu Met Thr Lys Asn Gln Val Ser Leu Thr Cys Leu Val Lys Gly
            370                 375                 380
Phe Tyr Pro Ser Asp Ile Ala Val Glu Trp Ser Asn Gly Gln Pro
385                 390                 395                 400
Glu Asn Asn Tyr Lys Thr Thr Pro Pro Val Leu Asp Ser Asp Gly Ser
                405                 410                 415
Phe Phe Leu Tyr Ser Arg Leu Thr Val Asp Lys Ser Arg Trp Gln Glu
                420                 425                 430
Gly Asn Val Phe Ser Cys Ser Val Leu His Glu Ala Leu His Asn His
            435                 440                 445
Tyr Thr Gln Lys Ser Leu Ser Leu Ser Leu Gly Lys Arg Lys Gly Gly
                450                 455                 460
Lys Arg Gly Ser Gly Ser Gly Gln Thr Val Val Thr Gln Glu Pro Ser
465                 470                 475                 480
```

```
Leu Thr Val Ser Pro Gly Gly Thr Val Thr Leu Thr Cys Ala Ser Ser
                485                 490                 495

Thr Gly Ala Val Thr Ser Gly Asn Tyr Pro Asn Trp Val Gln Gln Lys
            500                 505                 510

Pro Gly Gln Ala Pro Arg Gly Leu Ile Gly Gly Thr Lys Phe Leu Val
            515                 520                 525

Pro Gly Thr Pro Ala Arg Phe Ser Gly Ser Leu Leu Gly Gly Lys Ala
            530                 535                 540

Ala Leu Thr Leu Ser Gly Val Gln Pro Glu Asp Glu Ala Glu Tyr Tyr
545                 550                 555                 560

Cys Thr Leu Trp Tyr Ser Asn Arg Trp Val Phe Gly Gly Gly Thr Lys
                565                 570                 575

Leu Thr Val Leu
            580

<210> SEQ ID NO 39
<211> LENGTH: 744
<212> TYPE: PRT
<213> ORGANISM: Artificial Sequence
<220> FEATURE:
<223> OTHER INFORMATION: Synthetic Sequence

<400> SEQUENCE: 39

Cys Cys Gly Cys Ala Cys Cys Met Glu Phe Gly Leu Ser Trp Val
1               5                   10                  15

Phe Leu Val Ala Ile Ile Lys Gly Val Gln Cys Gln Trp Gln Val Thr
                20                  25                  30

Gly Pro Gly Lys Phe Val Gln Ala Leu Val Gly Glu Asp Ala Val Phe
            35                  40                  45

Ser Cys Ser Leu Phe Pro Glu Thr Ser Ala Glu Ala Met Glu Val Arg
    50                  55                  60

Phe Phe Arg Asn Gln Phe His Ala Val Val His Leu Tyr Arg Asp Gly
65                  70                  75                  80

Glu Asp Trp Glu Ser Lys Gln Met Pro Gln Tyr Arg Gly Arg Thr Glu
                85                  90                  95

Phe Val Lys Asp Ser Ile Ala Gly Gly Arg Val Ser Leu Arg Leu Lys
                100                 105                 110

Asn Ile Thr Pro Ser Asp Ile Gly Leu Tyr Gly Cys Trp Phe Ser Ser
            115                 120                 125

Gln Ile Tyr Asp Glu Glu Ala Thr Trp Glu Leu Arg Val Ala Ala Leu
        130                 135                 140

Gly Ser Leu Pro Leu Ile Ser Ile Val Gly Tyr Val Asp Gly Gly Ile
145                 150                 155                 160

Gln Leu Leu Cys Leu Ser Ser Gly Trp Phe Pro Gln Pro Thr Ala Lys
                165                 170                 175

Trp Lys Gly Pro Gln Gly Gln Asp Leu Ser Ser Asp Ser Arg Ala Asn
            180                 185                 190

Ala Asp Gly Tyr Ser Leu Tyr Asp Val Glu Ile Ser Ile Ile Val Gln
        195                 200                 205

Glu Asn Ala Gly Ser Ile Leu Cys Ser Ile His Leu Ala Glu Gln Ser
    210                 215                 220

His Glu Val Glu Ser Lys Val Leu Ile Gly Glu Thr Phe Phe Gln Pro
225                 230                 235                 240

Ser Pro Trp Arg Leu Ala Ser Gly Ser Gly Ser Arg Lys Gly Gly Lys
                245                 250                 255
```

```
Arg Gly Ser Lys Tyr Gly Pro Pro Cys Pro Pro Cys Pro Ala Pro Glu
            260                 265                 270

Phe Leu Gly Gly Pro Ser Val Phe Leu Phe Pro Pro Lys Pro Lys Asp
            275                 280                 285

Gln Leu Met Ile Ser Arg Thr Pro Glu Val Thr Cys Val Val Val Asp
290                 295                 300

Val Ser Gln Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
            325                 330                 335

Ser Thr Tyr Arg Val Val Ser Val Leu Thr Val Leu His Gln Asp Trp
            340                 345                 350

Leu Ser Gly Lys Glu Tyr Lys Cys Lys Val Ser Ser Lys Gly Leu Pro
            355                 360                 365

Ser Ser Ile Glu Lys Thr Ile Ser Asn Ala Thr Gly Gln Pro Arg Glu
370                 375                 380

Pro Gln Val Tyr Thr Leu Pro Pro Ser Gln Glu Glu Met Thr Lys Asn
385                 390                 395                 400

Gln Val Ser Leu Thr Cys Leu Val Lys Gly Phe Tyr Pro Ser Asp Ile
            405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Arg
            435                 440                 445

Leu Thr Val Asp Lys Ser Arg Trp Gln Glu Gly Asn Val Phe Ser Cys
450                 455                 460

Ser Val Leu His Glu Ala Leu His Asn His Tyr Thr Gln Lys Ser Leu
465                 470                 475                 480

Ser Leu Ser Leu Gly Lys Asp Glu Gly Gly Glu Asp Gly Ser Gln Val
            485                 490                 495

Gln Leu Gln Gln Ser Gly Ala Glu Leu Val Arg Pro Gly Ser Ser Val
            500                 505                 510

Lys Ile Ser Cys Lys Ala Ser Gly Tyr Ala Phe Ser Ser Tyr Trp Met
            515                 520                 525

Asn Trp Val Lys Gln Arg Pro Gly Gln Gly Leu Glu Trp Ile Gly Gln
530                 535                 540

Ile Trp Pro Gly Asp Gly Asp Thr Asn Tyr Asn Gly Lys Phe Lys Gly
545                 550                 555                 560

Lys Ala Thr Leu Thr Ala Asp Glu Ser Ser Ser Thr Ala Tyr Met Gln
            565                 570                 575

Leu Ser Ser Leu Ala Ser Glu Asp Ser Ala Val Tyr Phe Cys Ala Arg
            580                 585                 590

Arg Glu Thr Thr Thr Val Gly Arg Tyr Tyr Tyr Ala Met Asp Tyr Trp
            595                 600                 605

Gly Gln Gly Thr Thr Val Thr Val Ser Ser Gly Gly Gly Gly Ser Gly
            610                 615                 620

Gly Gly Gly Ser Gly Gly Gly Gly Ser Asp Ile Gln Leu Thr Gln Ser
625                 630                 635                 640

Pro Ala Ser Leu Ala Val Ser Leu Gly Gln Arg Ala Thr Ile Ser Cys
            645                 650                 655

Lys Ala Ser Gln Ser Val Asp Tyr Asp Gly Asp Ser Tyr Leu Asn Trp
            660                 665                 670
```

```
Tyr Gln Gln Ile Pro Gly Gln Pro Lys Leu Leu Ile Tyr Asp Ala
            675                 680                 685

Ser Asn Leu Val Ser Gly Ile Pro Pro Arg Phe Ser Gly Ser Gly
690                 695                 700

Gly Thr Asp Phe Thr Leu Asn Ile His Pro Val Glu Lys Val Asp Ala
705                 710                 715                 720

Ala Thr Tyr His Cys Gln Gln Ser Thr Glu Asp Pro Trp Thr Phe Gly
                725                 730                 735

Gly Gly Thr Lys Leu Glu Ile Lys
            740
```

<210> SEQ ID NO 40
<211> LENGTH: 747
<212> TYPE: PRT
<213> ORGANISM: Artificial Sequence
<220> FEATURE:
<223> OTHER INFORMATION: Synthetic Sequence

<400> SEQUENCE: 40

```
Cys Cys Gly Cys Cys Ala Cys Cys Met Glu Phe Gly Leu Ser Trp Val
1               5                   10                  15

Phe Leu Val Ala Ile Ile Lys Gly Val Gln Cys Gln Trp Gln Val Phe
            20                  25                  30

Gly Pro Asp Lys Pro Val Gln Ala Leu Val Gly Glu Asp Ala Ala Phe
        35                  40                  45

Ser Cys Phe Leu Ser Pro Lys Thr Asn Ala Glu Ala Met Glu Val Arg
    50                  55                  60

Phe Phe Arg Gly Gln Phe Ser Ser Val Val His Leu Tyr Arg Asp Gly
65                  70                  75                  80

Lys Asp Gln Pro Phe Met Gln Met Pro Gln Tyr Gln Gly Arg Thr Lys
                85                  90                  95

Leu Val Lys Asp Ser Ile Ala Glu Gly Arg Ile Ser Leu Arg Leu Glu
            100                 105                 110

Asn Ile Thr Val Leu Asp Ala Gly Leu Tyr Gly Cys Arg Ile Ser Ser
        115                 120                 125

Gln Ser Tyr Tyr Gln Lys Ala Ile Trp Glu Leu Gln Val Ser Ala Leu
    130                 135                 140

Gly Ser Val Pro Leu Ile Ser Ile Thr Gly Tyr Val Asp Arg Asp Ile
145                 150                 155                 160

Gln Leu Leu Cys Gln Ser Ser Gly Trp Phe Pro Arg Pro Thr Ala Lys
                165                 170                 175

Trp Lys Gly Pro Gln Gly Gln Asp Leu Ser Thr Asp Ser Arg Thr Asn
            180                 185                 190

Arg Asp Met His Gly Leu Phe Asp Val Glu Ile Ser Leu Thr Val Gln
        195                 200                 205

Glu Asn Ala Gly Ser Ile Ser Cys Ser Met Arg His Ala His Leu Ser
    210                 215                 220

Arg Glu Val Glu Ser Arg Val Gln Ile Gly Asp Thr Phe Phe Glu Pro
225                 230                 235                 240

Ile Ser Trp His Leu Ala Thr Lys Gly Ser Gly Ser Asp Glu Gly Gly
                245                 250                 255

Glu Asp Gly Ser Lys Tyr Gly Pro Pro Cys Pro Pro Cys Pro Ala Pro
            260                 265                 270

Glu Phe Leu Gly Gly Pro Ser Val Phe Leu Phe Pro Pro Lys Pro Lys
        275                 280                 285
```

```
Asp Gln Leu Met Ile Ser Arg Thr Pro Glu Val Thr Cys Val Val Val
    290                 295                 300
Asp Val Ser Gln Glu Asp Pro Glu Val Gln Phe Asn Trp Tyr Val Asp
305                 310                 315                 320
Gly Val Glu Val His Asn Ala Lys Thr Lys Pro Arg Glu Gln Phe
                325                 330                 335
Asn Ser Thr Tyr Arg Val Val Ser Val Leu Thr Val Leu His Gln Asp
                340                 345                 350
Trp Leu Ser Gly Lys Glu Tyr Lys Cys Lys Val Ser Ser Lys Gly Leu
            355                 360                 365
Pro Ser Ser Ile Glu Lys Thr Ile Ser Asn Ala Thr Gly Gln Pro Arg
370                 375                 380
Glu Pro Gln Val Tyr Thr Leu Pro Pro Ser Gln Glu Glu Met Thr Lys
385                 390                 395                 400
Asn Gln Val Ser Leu Thr Cys Leu Val Lys Gly Phe Tyr Pro Ser Asp
                405                 410                 415
Ile Ala Val Glu Trp Glu Ser Asn Gly Gln Pro Glu Asn Asn Tyr Lys
                420                 425                 430
Thr Thr Pro Pro Val Leu Asp Ser Asp Gly Ser Phe Phe Leu Tyr Ser
                435                 440                 445
Arg Leu Thr Val Asp Lys Ser Arg Trp Gln Glu Gly Asn Val Phe Ser
450                 455                 460
Cys Ser Val Leu His Glu Ala Leu His Asn His Tyr Thr Gln Lys Ser
465                 470                 475                 480
Leu Ser Leu Ser Leu Gly Lys Arg Lys Gly Gly Lys Arg Gly Ser Gly
                485                 490                 495
Ser Gln Val Gln Leu Gln Gln Ser Gly Ala Glu Leu Val Arg Pro Gly
                500                 505                 510
Ser Ser Val Lys Ile Ser Cys Lys Ala Ser Gly Tyr Ala Phe Ser Ser
            515                 520                 525
Tyr Trp Met Asn Trp Val Lys Gln Arg Pro Gly Gln Gly Leu Glu Trp
            530                 535                 540
Ile Gly Gln Ile Trp Pro Gly Asp Gly Asp Thr Asn Tyr Asn Gly Lys
545                 550                 555                 560
Phe Lys Gly Lys Ala Thr Leu Thr Ala Asp Glu Ser Ser Ser Thr Ala
                565                 570                 575
Tyr Met Gln Leu Ser Ser Leu Ala Ser Glu Asp Ser Ala Val Tyr Phe
                580                 585                 590
Cys Ala Arg Arg Glu Thr Thr Thr Val Gly Arg Tyr Tyr Tyr Ala Met
            595                 600                 605
Asp Tyr Trp Gly Gln Gly Thr Thr Val Thr Val Ser Ser Gly Gly Gly
            610                 615                 620
Gly Ser Gly Gly Gly Gly Ser Gly Gly Gly Gly Ser Asp Ile Gln Leu
625                 630                 635                 640
Thr Gln Ser Pro Ala Ser Leu Ala Val Ser Leu Gly Gln Arg Ala Thr
                645                 650                 655
Ile Ser Cys Lys Ala Ser Gln Ser Val Asp Tyr Asp Gly Asp Ser Tyr
                660                 665                 670
Leu Asn Trp Tyr Gln Gln Ile Pro Gly Gln Pro Lys Leu Leu Ile
            675                 680                 685
Tyr Asp Ala Ser Asn Leu Val Ser Gly Ile Pro Pro Arg Phe Ser Gly
690                 695                 700
Ser Gly Ser Gly Thr Asp Phe Thr Leu Asn Ile His Pro Val Glu Lys
```

```
                   705                 710                 715                 720

Val Asp Ala Ala Thr Tyr His Cys Gln Gln Ser Thr Glu Asp Pro Trp
                725                 730                 735

Thr Phe Gly Gly Gly Thr Lys Leu Glu Ile Lys
                740                 745

<210> SEQ ID NO 41
<211> LENGTH: 733
<212> TYPE: PRT
<213> ORGANISM: Artificial Sequence
<220> FEATURE:
<223> OTHER INFORMATION: Synthetic Sequence

<400> SEQUENCE: 41

Cys Cys Gly Cys Cys Ala Cys Cys Met Glu Phe Gly Leu Ser Trp Val
1               5                   10                  15

Phe Leu Val Ala Ile Ile Lys Gly Val Gln Cys Gln Trp Gln Val Thr
                20                  25                  30

Gly Pro Gly Lys Phe Val Gln Ala Leu Val Gly Glu Asp Ala Val Phe
            35                  40                  45

Ser Cys Ser Leu Phe Pro Glu Thr Ser Ala Glu Ala Met Glu Val Arg
    50                  55                  60

Phe Phe Arg Asn Gln Phe His Ala Val Val His Leu Tyr Arg Asp Gly
65                  70                  75                  80

Glu Asp Trp Glu Ser Lys Gln Met Pro Gln Tyr Arg Gly Arg Thr Glu
                85                  90                  95

Phe Val Lys Asp Ser Ile Ala Gly Gly Arg Val Ser Leu Arg Leu Lys
            100                 105                 110

Asn Ile Thr Pro Ser Asp Ile Gly Leu Tyr Gly Cys Trp Phe Ser Ser
        115                 120                 125

Gln Ile Tyr Asp Glu Glu Ala Thr Trp Glu Leu Arg Val Ala Ala Leu
    130                 135                 140

Gly Ser Leu Pro Leu Ile Ser Ile Val Gly Tyr Val Asp Gly Gly Ile
145                 150                 155                 160

Gln Leu Leu Cys Leu Ser Ser Gly Trp Phe Pro Gln Pro Thr Ala Lys
                165                 170                 175

Trp Lys Gly Pro Gln Gly Gln Asp Leu Ser Ser Asp Ser Arg Ala Asn
            180                 185                 190

Ala Asp Gly Tyr Ser Leu Tyr Asp Val Glu Ile Ser Ile Ile Val Gln
        195                 200                 205

Glu Asn Ala Gly Ser Ile Leu Cys Ser Ile His Leu Ala Glu Gln Ser
    210                 215                 220

His Glu Val Glu Ser Lys Val Leu Ile Gly Glu Thr Phe Phe Gln Pro
225                 230                 235                 240

Ser Pro Trp Arg Leu Ala Ser Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
```

```
            325                 330                 335
Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
370                 375                 380

Pro Ser Arg Asp Glu Leu Thr Lys Asn Gln Val Ser Leu Tyr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Val Leu Asp Ser
                420                 425                 430

Asp Gly Ser Phe Phe Leu Tyr Ser Lys Leu Thr Val Asp Lys Ser Arg
                435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Lys Gly
465                 470                 475                 480

Gly Gly Ser Gln Val Gln Leu Gln Gln Ser Gly Ala Glu Leu Val Arg
                485                 490                 495

Pro Gly Ser Ser Val Lys Ile Ser Cys Lys Ala Ser Gly Tyr Ala Phe
                500                 505                 510

Ser Ser Tyr Trp Met Asn Trp Val Lys Gln Arg Pro Gly Gln Gly Leu
                515                 520                 525

Glu Trp Ile Gly Gln Ile Trp Pro Gly Asp Gly Asp Thr Asn Tyr Asn
530                 535                 540

Gly Lys Phe Lys Gly Lys Ala Thr Leu Thr Ala Asp Glu Ser Ser Ser
545                 550                 555                 560

Thr Ala Tyr Met Gln Leu Ser Ser Leu Ala Ser Glu Asp Ser Ala Val
                565                 570                 575

Tyr Phe Cys Ala Arg Arg Glu Thr Thr Thr Val Gly Arg Tyr Tyr Tyr
                580                 585                 590

Ala Met Asp Tyr Trp Gly Gln Gly Thr Thr Val Thr Val Ser Ser Gly
                595                 600                 605

Gly Gly Gly Ser Gly Gly Gly Ser Gly Gly Gly Ser Asp Ile
                610                 615                 620

Gln Leu Thr Gln Ser Pro Ala Ser Leu Ala Val Ser Leu Gly Gln Arg
625                 630                 635                 640

Ala Thr Ile Ser Cys Lys Ala Ser Gln Ser Val Asp Tyr Asp Gly Asp
                645                 650                 655

Ser Tyr Leu Asn Trp Tyr Gln Gln Ile Pro Gly Gln Pro Pro Lys Leu
                660                 665                 670

Leu Ile Tyr Asp Ala Ser Asn Leu Val Ser Gly Ile Pro Pro Arg Phe
                675                 680                 685

Ser Gly Ser Gly Ser Gly Thr Asp Phe Thr Leu Asn Ile His Pro Val
                690                 695                 700

Glu Lys Val Asp Ala Ala Thr Tyr His Cys Gln Gln Ser Thr Glu Asp
705                 710                 715                 720

Pro Trp Thr Phe Gly Gly Gly Thr Lys Leu Glu Ile Lys
                725                 730

<210> SEQ ID NO 42
```

<211> LENGTH: 734
<212> TYPE: PRT
<213> ORGANISM: Artificial Sequence
<220> FEATURE:
<223> OTHER INFORMATION: Synthetic Sequence

<400> SEQUENCE: 42

Cys Cys Gly Cys Cys Ala Cys Cys Met Glu Phe Gly Leu Ser Trp Val
1               5                   10                  15

Phe Leu Val Ala Ile Ile Lys Gly Val Gln Cys Gln Trp Gln Val Phe
            20                  25                  30

Gly Pro Asp Lys Pro Val Gln Ala Leu Val Gly Glu Asp Ala Ala Phe
        35                  40                  45

Ser Cys Phe Leu Ser Pro Lys Thr Asn Ala Glu Ala Met Glu Val Arg
    50                  55                  60

Phe Phe Arg Gly Gln Phe Ser Ser Val Val His Leu Tyr Arg Asp Gly
65                  70                  75                  80

Lys Asp Gln Pro Phe Met Gln Met Pro Gln Tyr Gln Gly Arg Thr Lys
                85                  90                  95

Leu Val Lys Asp Ser Ile Ala Glu Gly Arg Ile Ser Leu Arg Leu Glu
            100                 105                 110

Asn Ile Thr Val Leu Asp Ala Gly Leu Tyr Gly Cys Arg Ile Ser Ser
        115                 120                 125

Gln Ser Tyr Tyr Gln Lys Ala Ile Trp Glu Leu Gln Val Ser Ala Leu
    130                 135                 140

Gly Ser Val Pro Leu Ile Ser Ile Thr Gly Tyr Val Asp Arg Asp Ile
145                 150                 155                 160

Gln Leu Leu Cys Gln Ser Ser Gly Trp Phe Pro Arg Pro Thr Ala Lys
                165                 170                 175

Trp Lys Gly Pro Gln Gly Gln Asp Leu Ser Thr Asp Ser Arg Thr Asn
            180                 185                 190

Arg Asp Met His Gly Leu Phe Asp Val Glu Ile Ser Leu Thr Val Gln
        195                 200                 205

Glu Asn Ala Gly Ser Ile Ser Cys Ser Met Arg His Ala His Leu Ser
    210                 215                 220

Arg Glu Val Glu Ser Arg Val Gln Ile Gly Asp Thr Phe Phe Glu Pro
225                 230                 235                 240

Ile Ser Trp His Leu Ala Thr Lys Glu Pro Lys Ser Cys Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Asp Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
    370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
            405                 410                 415

Asn Gly Gln Pro Glu Asn Asn Tyr Lys Thr Thr Pro Pro Val Leu Asp
        420                 425                 430

Ser Asp Gly Ser Phe Phe Leu Thr Ser Lys Leu Thr Val Asp Lys Ser
        435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480

Gly Gly Gly Ser Gln Val Gln Leu Gln Gln Ser Gly Ala Glu Leu Val
            485                 490                 495

Arg Pro Gly Ser Ser Val Lys Ile Ser Cys Lys Ala Ser Gly Tyr Ala
            500                 505                 510

Phe Ser Ser Tyr Trp Met Asn Trp Val Lys Gln Arg Pro Gly Gln Gly
        515                 520                 525

Leu Glu Trp Ile Gly Gln Ile Trp Pro Gly Asp Gly Asp Thr Asn Tyr
    530                 535                 540

Asn Gly Lys Phe Lys Gly Lys Ala Thr Leu Thr Ala Asp Glu Ser Ser
545                 550                 555                 560

Ser Thr Ala Tyr Met Gln Leu Ser Ser Leu Ala Ser Glu Asp Ser Ala
            565                 570                 575

Val Tyr Phe Cys Ala Arg Arg Glu Thr Thr Thr Val Gly Arg Tyr Tyr
            580                 585                 590

Tyr Ala Met Asp Tyr Trp Gly Gln Gly Thr Thr Val Thr Val Ser Ser
        595                 600                 605

Gly Gly Gly Gly Ser Gly Gly Gly Ser Gly Gly Gly Gly Ser Gly Asp
        610                 615                 620

Ile Gln Leu Thr Gln Ser Pro Ala Ser Leu Ala Val Ser Leu Gly Gln
625                 630                 635                 640

Arg Ala Thr Ile Ser Cys Lys Ala Ser Gln Ser Val Asp Tyr Asp Gly
            645                 650                 655

Asp Ser Tyr Leu Asn Trp Tyr Gln Gln Ile Pro Gly Gln Pro Pro Lys
            660                 665                 670

Leu Leu Ile Tyr Asp Ala Ser Asn Leu Val Ser Gly Ile Pro Pro Arg
        675                 680                 685

Phe Ser Gly Ser Gly Ser Gly Thr Asp Phe Thr Leu Asn Ile His Pro
        690                 695                 700

Val Glu Lys Val Asp Ala Ala Thr Tyr His Cys Gln Gln Ser Thr Glu
705                 710                 715                 720

Asp Pro Trp Thr Phe Gly Gly Gly Thr Lys Leu Glu Ile Lys
            725                 730

<210> SEQ ID NO 43
<211> LENGTH: 736
<212> TYPE: PRT
<213> ORGANISM: Artificial Sequence
<220> FEATURE:
<223> OTHER INFORMATION: Synthetic Sequence

<400> SEQUENCE: 43

Cys Cys Gly Cys Cys Ala Cys Cys Met Glu Phe Gly Leu Ser Trp Val
1               5                   10                  15

```
Phe Leu Val Ala Ile Ile Lys Gly Val Gln Cys Glu Val Ser Trp Phe
             20                  25                  30

Ser Val Lys Gly Pro Ala Glu Pro Ile Thr Val Leu Leu Gly Thr Glu
         35                  40                  45

Ala Thr Leu Pro Cys Gln Leu Ser Pro Glu Gln Ser Ala Ala Arg Met
 50                  55                  60

His Ile Arg Trp Tyr Arg Ala Gln Pro Thr Pro Ala Val Leu Val Phe
 65                  70                  75                  80

His Asn Gly Gln Glu Gln Gly Glu Val Gln Met Pro Glu Tyr Arg Gly
             85                  90                  95

Arg Thr Gln Met Val Arg Gln Ala Ile Asp Met Gly Ser Val Ala Leu
            100                 105                 110

Gln Ile Gln Gln Val Gln Ala Ser Asp Asp Gly Leu Tyr His Cys Gln
            115                 120                 125

Phe Thr Asp Gly Phe Thr Ser Gln Glu Val Ser Met Glu Leu Arg Val
130                 135                 140

Ile Gly Leu Gly Ser Ala Pro Leu Val His Met Thr Gly Pro Glu Asn
145                 150                 155                 160

Asp Gly Ile Arg Val Leu Cys Ser Ser Ser Gly Trp Phe Pro Lys Pro
            165                 170                 175

Lys Val Gln Trp Arg Asp Thr Ser Gly Asn Met Leu Leu Ser Ser Ser
            180                 185                 190

Glu Leu Gln Thr Gln Asp Arg Glu Gly Leu Phe Gln Val Glu Val Ser
            195                 200                 205

Leu Leu Val Thr Asp Arg Ala Ile Gly Asn Val Ile Cys Ser Ile Gln
            210                 215                 220

Asn Pro Met Tyr Asp Gln Glu Lys Ser Lys Ala Ile Leu Leu Pro Glu
225                 230                 235                 240

Pro Phe Phe Pro Lys Thr Cys Pro Trp Lys Gly Ser Gly Ser Asp Glu
            245                 250                 255

Gly Gly Glu Asp Gly Val Pro Arg Asp Cys Gly Cys Lys Pro Cys Ile
            260                 265                 270

Cys Thr Val Pro Glu Val Ser Ser Val Phe Ile Phe Pro Pro Lys Pro
            275                 280                 285

Lys Asp Val Leu Thr Ile Thr Leu Thr Pro Lys Val Thr Cys Val Val
290                 295                 300

Val Asp Ile Ser Lys Asp Asp Pro Glu Val Gln Phe Ser Trp Phe Val
305                 310                 315                 320

Asp Asp Val Glu Val His Thr Ala Gln Thr Gln Pro Arg Glu Glu Gln
            325                 330                 335

Phe Asn Ser Thr Phe Arg Ser Val Ser Glu Leu Pro Ile Met His Gln
            340                 345                 350

Asp Trp Leu Asn Gly Lys Glu Phe Lys Cys Arg Val Asn Ser Ala Ala
            355                 360                 365

Phe Pro Ala Pro Ile Glu Lys Thr Ile Ser Lys Thr Lys Gly Arg Pro
            370                 375                 380

Lys Ala Pro Gln Val Tyr Thr Ile Pro Pro Lys Glu Gln Met Ala
385                 390                 395                 400

Lys Asp Lys Val Ser Leu Thr Cys Met Ile Thr Asp Phe Phe Pro Glu
            405                 410                 415

Asp Ile Thr Val Glu Trp Gln Trp Asn Gly Gln Pro Ala Glu Asn Tyr
            420                 425                 430
```

-continued

```
Lys Asn Thr Gln Pro Ile Met Asp Thr Asp Gly Ser Tyr Phe Val Tyr
            435                 440                 445

Ser Lys Leu Asn Val Gln Lys Ser Asn Trp Glu Ala Gly Asn Thr Phe
    450                 455                 460

Thr Cys Ser Val Leu His Glu Gly Leu His Asn His Thr Glu Lys
465                 470                 475                 480

Ser Leu Ser His Ser Pro Gly Ile Arg Lys Gly Gly Lys Arg Gly Ser
                485                 490                 495

Gly Ser Glu Val Gln Leu Gln Gln Ser Gly Ala Glu Leu Val Arg Pro
            500                 505                 510

Gly Thr Ser Val Lys Leu Ser Cys Lys Val Ser Gly Asp Thr Ile Thr
            515                 520                 525

Phe Tyr Tyr Met His Phe Val Lys Gln Arg Pro Gly Gln Gly Leu Glu
            530                 535                 540

Trp Ile Gly Arg Ile Asp Pro Glu Asp Glu Ser Thr Lys Tyr Ser Glu
545                 550                 555                 560

Lys Phe Lys Asn Lys Ala Thr Leu Thr Ala Asp Thr Ser Ser Asn Thr
                565                 570                 575

Ala Tyr Leu Lys Leu Ser Ser Leu Thr Ser Glu Asp Thr Ala Thr Tyr
            580                 585                 590

Phe Cys Ile Tyr Gly Gly Tyr Tyr Phe Asp Tyr Trp Gly Gln Gly Val
            595                 600                 605

Met Val Thr Val Ser Ser Gly Gly Gly Ser Gly Gly Gly Gly Ser
            610                 615                 620

Gly Gly Gly Gly Ser Asp Ile Gln Met Thr Gln Ser Pro Ala Ser Leu
625                 630                 635                 640

Ser Thr Ser Leu Gly Glu Thr Val Thr Ile Gln Cys Gln Ala Ser Glu
                645                 650                 655

Asp Ile Tyr Ser Gly Leu Ala Trp Tyr Gln Gln Lys Pro Gly Lys Ser
            660                 665                 670

Pro Gln Leu Leu Ile Tyr Gly Ala Ser Asp Leu Gln Asp Gly Val Pro
            675                 680                 685

Ser Arg Phe Ser Gly Ser Gly Ser Gly Thr Gln Tyr Ser Leu Lys Ile
            690                 695                 700

Thr Ser Met Gln Thr Glu Asp Glu Gly Val Tyr Phe Cys Gln Gln Gly
705                 710                 715                 720

Leu Thr Tyr Pro Arg Thr Phe Gly Gly Gly Thr Lys Leu Glu Leu Lys
                725                 730                 735

<210> SEQ ID NO 44
<211> LENGTH: 676
<212> TYPE: PRT
<213> ORGANISM: Artificial Sequence
<220> FEATURE:
<223> OTHER INFORMATION: Synthetic Sequence

<400> SEQUENCE: 44

Cys Cys Gly Cys Cys Ala Cys Cys Met Glu Phe Gly Leu Ser Trp Val
1               5                   10                  15

Phe Leu Val Ala Ile Ile Lys Gly Val Gln Cys Glu Gln Leu Pro Glu
                20                  25                  30

Tyr Ser Gln Arg Thr Ser Leu Val Lys Glu Gln Phe His Gln Gly Thr
            35                  40                  45

Ala Ala Val Arg Ile Leu Asn Val Gln Ala Pro Asp Ser Gly Ile Tyr
        50                  55                  60
```

```
Ile Cys His Phe Lys Gln Gly Val Phe Tyr Glu Ala Ile Leu Glu
 65                  70                  75                  80

Leu Lys Val Ala Ala Met Gly Ser Val Pro Glu Val Tyr Ile Lys Gly
                 85                  90                  95

Pro Glu Asp Gly Gly Val Cys Val Val Cys Ile Thr Ser Gly Trp Tyr
                100                 105                 110

Pro Glu Pro Gln Val His Trp Lys Asp Ser Arg Gly Glu Lys Leu Thr
                115                 120                 125

Ala Ser Leu Glu Ile His Ser Glu Asp Ala Gln Gly Leu Phe Arg Thr
            130                 135                 140

Glu Thr Ser Leu Val Val Arg Asp Ser Val Arg Asn Val Thr Cys
145                 150                 155                 160

Ser Thr Phe Asn Pro Ile Leu Gly Gln Glu Lys Ala Met Ala Met Phe
                165                 170                 175

Leu Pro Glu Pro Phe Phe Pro Lys Val Ser Pro Trp Lys Pro Gly Ser
            180                 185                 190

Gly Ser Asp Glu Gly Gly Glu Asp Gly Val Pro Arg Asp Cys Gly Cys
            195                 200                 205

Lys Pro Cys Ile Cys Thr Val Pro Glu Val Ser Ser Val Phe Ile Phe
            210                 215                 220

Pro Pro Lys Pro Lys Asp Val Leu Thr Ile Thr Leu Thr Pro Lys Val
225                 230                 235                 240

Thr Cys Val Val Val Asp Ile Ser Lys Asp Asp Pro Glu Val Gln Phe
                245                 250                 255

Ser Trp Phe Val Asp Asp Val Glu Val His Thr Ala Gln Thr Gln Pro
                260                 265                 270

Arg Glu Glu Gln Phe Asn Ser Thr Phe Arg Ser Val Ser Glu Leu Pro
            275                 280                 285

Ile Met His Gln Asp Trp Leu Asn Gly Lys Glu Phe Lys Cys Arg Val
            290                 295                 300

Asn Ser Ala Ala Phe Pro Ala Pro Ile Glu Lys Thr Ile Ser Lys Thr
305                 310                 315                 320

Lys Gly Arg Pro Lys Ala Pro Gln Val Tyr Thr Ile Pro Pro Pro Lys
                325                 330                 335

Glu Gln Met Ala Lys Asp Lys Val Ser Leu Thr Cys Met Ile Thr Asp
                340                 345                 350

Phe Phe Pro Glu Asp Ile Thr Val Glu Trp Gln Trp Asn Gly Gln Pro
            355                 360                 365

Ala Glu Asn Tyr Lys Asn Thr Gln Pro Ile Met Asp Thr Asp Gly Ser
            370                 375                 380

Tyr Phe Val Tyr Ser Lys Leu Asn Val Gln Lys Ser Asn Trp Glu Ala
385                 390                 395                 400

Gly Asn Thr Phe Thr Cys Ser Val Leu His Glu Gly Leu His Asn His
                405                 410                 415

His Thr Glu Lys Ser Leu Ser His Ser Pro Gly Ile Lys Gly Gly
                420                 425                 430

Lys Arg Gly Ser Gly Ser Glu Val Gln Leu Gln Gln Ser Gly Ala Glu
            435                 440                 445

Leu Val Arg Pro Gly Thr Ser Val Lys Leu Ser Cys Lys Val Ser Gly
            450                 455                 460

Asp Thr Ile Thr Phe Tyr Tyr Met His Phe Val Lys Gln Arg Pro Gly
465                 470                 475                 480

Gln Gly Leu Glu Trp Ile Gly Arg Ile Asp Pro Glu Asp Glu Ser Thr
```

```
                    485                 490                 495
Lys Tyr Ser Glu Lys Phe Lys Asn Lys Ala Thr Leu Thr Ala Asp Thr
                500                 505                 510

Ser Ser Asn Thr Ala Tyr Leu Lys Leu Ser Ser Leu Thr Ser Glu Asp
            515                 520                 525

Thr Ala Thr Tyr Phe Cys Ile Tyr Gly Gly Tyr Tyr Phe Asp Tyr Trp
        530                 535                 540

Gly Gln Gly Val Met Val Thr Val Ser Gly Gly Gly Ser Gly
545                 550                 555                 560

Gly Gly Gly Ser Gly Gly Gly Ser Asp Ile Gln Met Thr Gln Ser
                565                 570                 575

Pro Ala Ser Leu Ser Thr Ser Leu Gly Glu Thr Val Thr Ile Gln Cys
            580                 585                 590

Gln Ala Ser Glu Asp Ile Tyr Ser Gly Leu Ala Trp Tyr Gln Gln Lys
        595                 600                 605

Pro Gly Lys Ser Pro Gln Leu Leu Ile Tyr Gly Ala Ser Asp Leu Gln
610                 615                 620

Asp Gly Val Pro Ser Arg Phe Ser Gly Ser Gly Ser Gly Thr Gln Tyr
625                 630                 635                 640

Ser Leu Lys Ile Thr Ser Met Gln Thr Glu Asp Glu Gly Val Tyr Phe
                645                 650                 655

Cys Gln Gln Gly Leu Thr Tyr Pro Arg Thr Phe Gly Gly Gly Thr Lys
            660                 665                 670

Leu Glu Leu Lys
        675

<210> SEQ ID NO 45
<211> LENGTH: 736
<212> TYPE: PRT
<213> ORGANISM: Artificial Sequence
<220> FEATURE:
<223> OTHER INFORMATION: Synthetic Sequence

<400> SEQUENCE: 45

Cys Cys Gly Cys Cys Ala Cys Cys Met Glu Phe Gly Leu Ser Trp Val
1               5                   10                  15

Phe Leu Val Ala Ile Ile Lys Gly Val Gln Cys Glu Val Ser Trp Phe
                20                  25                  30

Ser Val Lys Gly Pro Ala Glu Pro Ile Thr Val Leu Leu Gly Thr Glu
            35                  40                  45

Ala Thr Leu Pro Cys Gln Leu Ser Pro Glu Gln Ser Ala Ala Arg Met
        50                  55                  60

His Ile Arg Trp Tyr Arg Ala Gln Pro Thr Pro Ala Val Leu Val Phe
65                  70                  75                  80

His Asn Gly Gln Glu Gln Gly Glu Val Gln Met Pro Glu Tyr Arg Gly
                85                  90                  95

Arg Thr Gln Met Val Arg Gln Ala Ile Asp Met Gly Ser Val Ala Leu
            100                 105                 110

Gln Ile Gln Gln Val Gln Ala Ser Asp Asp Gly Leu Tyr His Cys Gln
        115                 120                 125

Phe Thr Asp Gly Phe Thr Ser Gln Glu Val Ser Met Glu Leu Arg Val
    130                 135                 140

Ile Gly Leu Gly Ser Ala Pro Leu Val His Met Thr Gly Pro Glu Asn
145                 150                 155                 160

Asp Gly Ile Arg Val Leu Cys Ser Ser Ser Gly Trp Phe Pro Lys Pro
```

```
                165                 170                 175
Lys Val Gln Trp Arg Asp Thr Ser Gly Asn Met Leu Leu Ser Ser Ser
            180                 185                 190

Glu Leu Gln Thr Gln Asp Arg Glu Gly Leu Phe Gln Val Glu Val Ser
            195                 200                 205

Leu Leu Val Thr Asp Arg Ala Ile Gly Asn Val Ile Cys Ser Ile Gln
            210                 215                 220

Asn Pro Met Tyr Asp Gln Glu Lys Ser Lys Ala Ile Leu Leu Pro Glu
225                 230                 235                 240

Pro Phe Phe Pro Lys Thr Cys Pro Trp Lys Gly Ser Gly Ser Asp Glu
            245                 250                 255

Gly Gly Glu Asp Gly Val Pro Arg Asp Cys Gly Cys Lys Pro Cys Ile
            260                 265                 270

Cys Thr Val Pro Glu Val Ser Ser Val Phe Ile Phe Pro Pro Lys Pro
            275                 280                 285

Lys Asp Val Leu Thr Ile Thr Leu Thr Pro Lys Val Thr Cys Val Val
            290                 295                 300

Val Asp Ile Ser Lys Asp Asp Pro Glu Val Gln Phe Ser Trp Phe Val
305                 310                 315                 320

Asp Asp Val Glu Val His Thr Ala Gln Thr Gln Pro Arg Glu Glu Gln
            325                 330                 335

Phe Asn Ser Thr Phe Arg Ser Val Ser Glu Leu Pro Ile Met His Gln
            340                 345                 350

Asp Trp Leu Asn Gly Lys Glu Phe Lys Cys Arg Val Asn Ser Ala Ala
            355                 360                 365

Phe Pro Ala Pro Ile Glu Lys Thr Ile Ser Lys Thr Lys Gly Arg Pro
370                 375                 380

Lys Ala Pro Gln Val Tyr Thr Ile Pro Pro Lys Glu Gln Met Ala
385                 390                 395                 400

Lys Asp Lys Val Ser Leu Thr Cys Met Ile Thr Asp Phe Phe Pro Glu
            405                 410                 415

Asp Ile Thr Val Glu Trp Gln Trp Asn Gly Gln Pro Ala Glu Asn Tyr
            420                 425                 430

Lys Asn Thr Gln Pro Ile Met Asp Thr Asp Gly Ser Tyr Phe Val Tyr
            435                 440                 445

Ser Lys Leu Asn Val Gln Lys Ser Asn Trp Glu Ala Gly Asn Thr Phe
450                 455                 460

Thr Cys Ser Val Leu His Glu Gly Leu His Asn His His Thr Glu Lys
465                 470                 475                 480

Ser Leu Ser His Ser Pro Gly Ile Arg Lys Gly Gly Lys Arg Gly Ser
            485                 490                 495

Gly Ser Asp Ile Gln Met Thr Gln Ser Pro Ala Ser Leu Ser Thr Ser
            500                 505                 510

Leu Gly Glu Thr Val Thr Ile Gln Cys Gln Ala Ser Glu Asp Ile Tyr
            515                 520                 525

Ser Gly Leu Ala Trp Tyr Gln Gln Lys Pro Gly Lys Ser Pro Gln Leu
            530                 535                 540

Leu Ile Tyr Gly Ala Ser Asp Leu Gln Asp Gly Val Pro Ser Arg Phe
545                 550                 555                 560

Ser Gly Ser Gly Ser Gly Thr Gln Tyr Ser Leu Lys Ile Thr Ser Met
            565                 570                 575

Gln Thr Glu Asp Glu Gly Val Tyr Phe Cys Gln Gln Gly Leu Thr Tyr
            580                 585                 590
```

```
Pro Arg Thr Phe Gly Gly Gly Thr Lys Leu Glu Leu Lys Gly Gly
            595                 600                 605

Gly Ser Gly Gly Gly Ser Gly Gly Gly Ser Glu Val Gln Leu
    610                 615                 620

Gln Gln Ser Gly Ala Glu Leu Val Arg Pro Gly Thr Ser Val Lys Leu
625                 630                 635                 640

Ser Cys Lys Val Ser Gly Asp Thr Ile Thr Phe Tyr Tyr Met His Phe
                645                 650                 655

Val Lys Gln Arg Pro Gly Gln Gly Leu Glu Trp Ile Gly Arg Ile Asp
                660                 665                 670

Pro Glu Asp Glu Ser Thr Lys Tyr Ser Glu Lys Phe Lys Asn Lys Ala
                675                 680                 685

Thr Leu Thr Ala Asp Thr Ser Ser Asn Thr Ala Tyr Leu Lys Leu Ser
            690                 695                 700

Ser Leu Thr Ser Glu Asp Thr Ala Thr Tyr Phe Cys Ile Tyr Gly Gly
705                 710                 715                 720

Tyr Tyr Phe Asp Tyr Trp Gly Gln Gly Val Met Val Thr Val Ser Ser
                725                 730                 735

<210> SEQ ID NO 46
<211> LENGTH: 676
<212> TYPE: PRT
<213> ORGANISM: Artificial Sequence
<220> FEATURE:
<223> OTHER INFORMATION: Synthetic Sequence

<400> SEQUENCE: 46

Cys Cys Gly Cys Cys Ala Cys Cys Met Glu Phe Gly Leu Ser Trp Val
1               5                   10                  15

Phe Leu Val Ala Ile Ile Lys Gly Val Gln Cys Glu Gln Leu Pro Glu
                20                  25                  30

Tyr Ser Gln Arg Thr Ser Leu Val Lys Glu Gln Phe His Gln Gly Thr
            35                  40                  45

Ala Ala Val Arg Ile Leu Asn Val Gln Ala Pro Asp Ser Gly Ile Tyr
        50                  55                  60

Ile Cys His Phe Lys Gln Gly Val Phe Tyr Glu Ala Ile Leu Glu
65              70                  75                  80

Leu Lys Val Ala Ala Met Gly Ser Val Pro Glu Val Tyr Ile Lys Gly
                85                  90                  95

Pro Glu Asp Gly Gly Val Cys Val Cys Ile Thr Ser Gly Trp Tyr
            100                 105                 110

Pro Glu Pro Gln Val His Trp Lys Asp Ser Arg Gly Glu Lys Leu Thr
        115                 120                 125

Ala Ser Leu Glu Ile His Ser Glu Asp Ala Gln Gly Leu Phe Arg Thr
    130                 135                 140

Glu Thr Ser Leu Val Val Arg Asp Ser Ser Val Arg Asn Val Thr Cys
145                 150                 155                 160

Ser Thr Phe Asn Pro Ile Leu Gly Gln Glu Lys Ala Met Ala Met Phe
                165                 170                 175

Leu Pro Glu Pro Phe Phe Pro Lys Val Ser Pro Trp Lys Pro Gly Ser
            180                 185                 190

Gly Ser Asp Glu Gly Gly Glu Asp Gly Val Pro Arg Asp Cys Gly Cys
        195                 200                 205

Lys Pro Cys Ile Cys Thr Val Pro Glu Val Ser Ser Val Phe Ile Phe
    210                 215                 220
```

-continued

```
Pro Pro Lys Pro Lys Asp Val Leu Thr Ile Thr Leu Thr Pro Lys Val
225                 230                 235                 240

Thr Cys Val Val Val Asp Ile Ser Lys Asp Asp Pro Glu Val Gln Phe
                245                 250                 255

Ser Trp Phe Val Asp Asp Val Glu Val His Thr Ala Gln Thr Gln Pro
                260                 265                 270

Arg Glu Glu Gln Phe Asn Ser Thr Phe Arg Ser Val Ser Glu Leu Pro
                275                 280                 285

Ile Met His Gln Asp Trp Leu Asn Gly Lys Glu Phe Lys Cys Arg Val
290                 295                 300

Asn Ser Ala Ala Phe Pro Ala Pro Ile Glu Lys Thr Ile Ser Lys Thr
305                 310                 315                 320

Lys Gly Arg Pro Lys Ala Pro Gln Val Tyr Thr Ile Pro Pro Pro Lys
                325                 330                 335

Glu Gln Met Ala Lys Asp Lys Val Ser Leu Thr Cys Met Ile Thr Asp
                340                 345                 350

Phe Phe Pro Glu Asp Ile Thr Val Glu Trp Gln Trp Asn Gly Gln Pro
                355                 360                 365

Ala Glu Asn Tyr Lys Asn Thr Gln Pro Ile Met Asp Thr Asp Gly Ser
370                 375                 380

Tyr Phe Val Tyr Ser Lys Leu Asn Val Gln Lys Ser Asn Trp Glu Ala
385                 390                 395                 400

Gly Asn Thr Phe Thr Cys Ser Val Leu His Glu Gly Leu His Asn His
                405                 410                 415

His Thr Glu Lys Ser Leu Ser His Ser Pro Gly Ile Arg Lys Gly Gly
                420                 425                 430

Lys Arg Gly Ser Gly Ser Asp Ile Gln Met Thr Gln Ser Pro Ala Ser
                435                 440                 445

Leu Ser Thr Ser Leu Gly Glu Thr Val Thr Ile Gln Cys Gln Ala Ser
                450                 455                 460

Glu Asp Ile Tyr Ser Gly Leu Ala Trp Tyr Gln Gln Lys Pro Gly Lys
465                 470                 475                 480

Ser Pro Gln Leu Leu Ile Tyr Gly Ala Ser Asp Leu Gln Asp Gly Val
                485                 490                 495

Pro Ser Arg Phe Ser Gly Ser Gly Ser Gly Thr Gln Tyr Ser Leu Lys
                500                 505                 510

Ile Thr Ser Met Gln Thr Glu Asp Glu Gly Val Tyr Phe Cys Gln Gln
                515                 520                 525

Gly Leu Thr Tyr Pro Arg Thr Phe Gly Gly Gly Thr Lys Leu Glu Leu
                530                 535                 540

Lys Gly Gly Gly Gly Ser Gly Gly Gly Gly Ser Gly Gly Gly Gly Ser
545                 550                 555                 560

Glu Val Gln Leu Gln Gln Ser Gly Ala Glu Leu Val Arg Pro Gly Thr
                565                 570                 575

Ser Val Lys Leu Ser Cys Lys Val Ser Gly Asp Thr Ile Thr Phe Tyr
                580                 585                 590

Tyr Met His Phe Val Lys Gln Arg Pro Gly Gln Gly Leu Glu Trp Ile
                595                 600                 605

Gly Arg Ile Asp Pro Glu Asp Glu Ser Thr Lys Tyr Ser Glu Lys Phe
                610                 615                 620

Lys Asn Lys Ala Thr Leu Thr Ala Asp Thr Ser Ser Asn Thr Ala Tyr
625                 630                 635                 640
```

```
Leu Lys Leu Ser Ser Leu Thr Ser Glu Asp Thr Ala Thr Tyr Phe Cys
            645                 650                 655

Ile Tyr Gly Gly Tyr Tyr Phe Asp Tyr Trp Gly Gln Gly Val Met Val
        660                 665                 670

Thr Val Ser Ser
        675

<210> SEQ ID NO 47
<211> LENGTH: 223
<212> TYPE: PRT
<213> ORGANISM: Mus musculus

<400> SEQUENCE: 47

Glu Val Ser Trp Phe Ser Val Lys Gly Pro Ala Glu Pro Ile Thr Val
1               5                   10                  15

Leu Leu Gly Thr Glu Ala Thr Leu Pro Cys Gln Leu Ser Pro Glu Gln
            20                  25                  30

Ser Ala Ala Arg Met His Ile Arg Trp Tyr Arg Ala Gln Pro Thr Pro
        35                  40                  45

Ala Val Leu Val Phe His Asn Gly Gln Glu Gln Gly Glu Val Gln Met
    50                  55                  60

Pro Glu Tyr Arg Gly Arg Thr Gln Met Val Arg Gln Ala Ile Asp Met
65                  70                  75                  80

Gly Ser Val Ala Leu Gln Ile Gln Gln Val Gln Ala Ser Asp Asp Gly
                85                  90                  95

Leu Tyr His Cys Gln Phe Thr Asp Gly Phe Thr Ser Gln Glu Val Ser
            100                 105                 110

Met Glu Leu Arg Val Ile Gly Leu Gly Ser Ala Pro Leu Val His Met
        115                 120                 125

Thr Gly Pro Glu Asn Asp Gly Ile Arg Val Leu Cys Ser Ser Ser Gly
    130                 135                 140

Trp Phe Pro Lys Pro Lys Val Gln Trp Arg Asp Thr Ser Gly Asn Met
145                 150                 155                 160

Leu Leu Ser Ser Ser Glu Leu Gln Thr Gln Asp Arg Glu Gly Leu Phe
                165                 170                 175

Gln Val Glu Val Ser Leu Leu Val Thr Asp Arg Ala Ile Gly Asn Val
            180                 185                 190

Ile Cys Ser Ile Gln Asn Pro Met Tyr Asp Gln Glu Lys Ser Lys Ala
        195                 200                 205

Ile Leu Leu Pro Glu Pro Phe Phe Pro Lys Thr Cys Pro Trp Lys
    210                 215                 220

<210> SEQ ID NO 48
<211> LENGTH: 163
<212> TYPE: PRT
<213> ORGANISM: Mus musculus

<400> SEQUENCE: 48

Glu Gln Leu Pro Glu Tyr Ser Gln Arg Thr Ser Leu Val Lys Glu Gln
1               5                   10                  15

Phe His Gln Gly Thr Ala Ala Val Arg Ile Leu Asn Val Gln Ala Pro
            20                  25                  30

Asp Ser Gly Ile Tyr Ile Cys His Phe Lys Gln Gly Val Phe Tyr Glu
        35                  40                  45

Glu Ala Ile Leu Glu Leu Lys Val Ala Ala Met Gly Ser Val Pro Glu
    50                  55                  60
```

Val Tyr Ile Lys Gly Pro Glu Asp Gly Gly Val Cys Val Val Cys Ile
65                  70                  75                  80

Thr Ser Gly Trp Tyr Pro Glu Pro Gln Val His Trp Lys Asp Ser Arg
                85                  90                  95

Gly Glu Lys Leu Thr Ala Ser Leu Glu Ile His Ser Glu Asp Ala Gln
            100                 105                 110

Gly Leu Phe Arg Thr Glu Thr Ser Leu Val Val Arg Asp Ser Ser Val
            115                 120                 125

Arg Asn Val Thr Cys Ser Thr Phe Asn Pro Ile Leu Gly Gln Glu Lys
130                 135                 140

Ala Met Ala Met Phe Leu Pro Glu Pro Phe Phe Pro Lys Val Ser Pro
145                 150                 155                 160

Trp Lys Pro

<210> SEQ ID NO 49
<211> LENGTH: 220
<212> TYPE: PRT
<213> ORGANISM: Homo sapiens

<400> SEQUENCE: 49

Gln Trp Gln Val Thr Gly Pro Gly Lys Phe Val Gln Ala Leu Val Gly
1               5                   10                  15

Glu Asp Ala Val Phe Ser Cys Ser Leu Phe Pro Glu Thr Ser Ala Glu
                20                  25                  30

Ala Met Glu Val Arg Phe Phe Arg Asn Gln Phe His Ala Val Val His
            35                  40                  45

Leu Tyr Arg Asp Gly Glu Asp Trp Glu Ser Lys Gln Met Pro Gln Tyr
50                  55                  60

Arg Gly Arg Thr Glu Phe Val Lys Asp Ser Ile Ala Gly Gly Arg Val
65                  70                  75                  80

Ser Leu Arg Leu Lys Asn Ile Thr Pro Ser Asp Ile Gly Leu Tyr Gly
                85                  90                  95

Cys Trp Phe Ser Ser Gln Ile Tyr Asp Glu Glu Ala Thr Trp Glu Leu
            100                 105                 110

Arg Val Ala Ala Leu Gly Ser Leu Pro Leu Ile Ser Ile Val Gly Tyr
            115                 120                 125

Val Asp Gly Gly Ile Gln Leu Leu Cys Leu Ser Ser Gly Trp Phe Pro
130                 135                 140

Gln Pro Thr Ala Lys Trp Lys Gly Pro Gln Gly Gln Asp Leu Ser Ser
145                 150                 155                 160

Asp Ser Arg Ala Asn Ala Asp Gly Tyr Ser Leu Tyr Asp Val Glu Ile
                165                 170                 175

Ser Ile Ile Val Gln Glu Asn Ala Gly Ser Ile Leu Cys Ser Ile His
            180                 185                 190

Leu Ala Glu Gln Ser His Glu Val Gly Ser Lys Val Leu Ile Gly Glu
            195                 200                 205

Thr Phe Phe Gln Pro Ser Pro Trp Arg Leu Ala Ser
210                 215                 220

<210> SEQ ID NO 50
<211> LENGTH: 225
<212> TYPE: PRT
<213> ORGANISM: Homo sapiens

<400> SEQUENCE: 50

Gln Phe Ser Val Leu Gly Pro Ser Gly Pro Ile Leu Ala Met Val Gly

```
  1               5                  10                  15
Glu Asp Ala Asp Leu Pro Cys His Leu Phe Pro Thr Met Ser Ala Glu
                20                  25                  30

Thr Met Glu Leu Lys Trp Val Ser Ser Leu Arg Gln Val Val Asn
            35                  40                  45

Val Tyr Ala Asp Gly Lys Glu Val Glu Asp Arg Gln Ser Ala Pro Tyr
        50                  55                  60

Arg Gly Arg Thr Ser Ile Leu Arg Asp Gly Ile Thr Ala Gly Lys Ala
 65                  70                  75                  80

Ala Leu Arg Ile His Asn Val Thr Ala Ser Asp Ser Gly Lys Tyr Leu
                85                  90                  95

Cys Tyr Phe Gln Asp Gly Asp Phe Tyr Glu Lys Ala Leu Val Glu Leu
                100                 105                 110

Lys Val Ala Ala Leu Gly Ser Asp Leu His Val Asp Val Lys Gly Tyr
            115                 120                 125

Lys Asp Gly Gly Ile His Leu Glu Cys Arg Ser Thr Gly Trp Tyr Pro
 130                 135                 140

Gln Pro Gln Ile Gln Trp Ser Asn Asn Lys Gly Glu Asn Ile Pro Thr
145                 150                 155                 160

Val Glu Ala Pro Val Val Ala Asp Gly Val Gly Leu Tyr Ala Val Ala
                165                 170                 175

Ala Ser Val Ile Met Arg Gly Ser Ser Gly Glu Gly Val Ser Cys Thr
                180                 185                 190

Ile Arg Ser Ser Leu Leu Gly Leu Glu Lys Thr Ala Ser Ile Ser Ile
            195                 200                 205

Ala Asp Pro Phe Phe Arg Ser Ala Gln Arg Trp Ile Ala Ala Leu Ala
        210                 215                 220

Gly
225

<210> SEQ ID NO 51
<211> LENGTH: 219
<212> TYPE: PRT
<213> ORGANISM: Homo sapiens

<400> SEQUENCE: 51

Gln Phe Ser Val Leu Gly Pro Ser Gly Pro Ile Leu Ala Met Val Gly
 1               5                  10                  15

Glu Asp Ala Asp Leu Pro Cys His Leu Phe Pro Thr Met Ser Ala Glu
                20                  25                  30

Thr Met Glu Leu Lys Trp Val Ser Ser Leu Arg Gln Val Val Asn
            35                  40                  45

Val Tyr Ala Asp Gly Lys Glu Val Glu Asp Arg Gln Ser Ala Pro Tyr
        50                  55                  60

Arg Gly Arg Thr Ser Ile Leu Arg Asp Gly Ile Thr Ala Gly Lys Ala
 65                  70                  75                  80

Ala Leu Arg Ile His Asn Val Thr Ala Ser Asp Ser Gly Lys Tyr Leu
                85                  90                  95

Cys Tyr Phe Gln Asp Gly Asp Phe Tyr Glu Lys Ala Leu Val Glu Leu
                100                 105                 110

Lys Val Ala Ala Leu Gly Ser Asn Leu His Val Glu Val Lys Gly Tyr
            115                 120                 125

Glu Asp Gly Gly Ile His Leu Glu Cys Arg Ser Thr Gly Trp Tyr Pro
 130                 135                 140
```

Gln Pro Gln Ile Gln Trp Ser Asn Ala Lys Gly Glu Asn Ile Pro Ala
145                 150                 155                 160

Val Glu Ala Pro Val Val Ala Asp Gly Val Gly Leu Tyr Arg Val Ala
                165                 170                 175

Ala Ser Val Ile Met Arg Gly Gly Ser Gly Glu Gly Val Ser Cys Ile
            180                 185                 190

Ile Arg Asn Ser Leu Leu Gly Leu Glu Lys Thr Ala Ser Ile Ser Ile
        195                 200                 205

Ala Asp Pro Phe Phe Arg Ser Ala Gln Pro Trp
    210                 215

<210> SEQ ID NO 52
<211> LENGTH: 221
<212> TYPE: PRT
<213> ORGANISM: Homo sapiens

<400> SEQUENCE: 52

Gln Trp Gln Val Phe Gly Pro Asp Lys Pro Val Gln Ala Leu Val Gly
1               5                   10                  15

Glu Asp Ala Ala Phe Ser Cys Phe Leu Ser Pro Lys Thr Asn Ala Glu
            20                  25                  30

Ala Met Glu Val Arg Phe Phe Arg Gly Gln Phe Ser Ser Val Val His
        35                  40                  45

Leu Tyr Arg Asp Gly Lys Asp Gln Pro Phe Met Gln Met Pro Gln Tyr
    50                  55                  60

Gln Gly Arg Thr Lys Leu Val Lys Asp Ser Ile Ala Glu Gly Arg Ile
65                  70                  75                  80

Ser Leu Arg Leu Glu Asn Ile Thr Val Leu Asp Ala Gly Leu Tyr Gly
                85                  90                  95

Cys Arg Ile Ser Ser Gln Ser Tyr Tyr Gln Lys Ala Ile Trp Glu Leu
            100                 105                 110

Gln Val Ser Ala Leu Gly Ser Val Pro Leu Ile Ser Ile Thr Gly Tyr
        115                 120                 125

Val Asp Arg Asp Ile Gln Leu Leu Cys Gln Ser Ser Gly Trp Phe Pro
    130                 135                 140

Arg Pro Thr Ala Lys Trp Lys Gly Pro Gln Gly Gln Asp Leu Ser Thr
145                 150                 155                 160

Asp Ser Arg Thr Asn Arg Asp Met His Gly Leu Phe Asp Val Glu Ile
                165                 170                 175

Ser Leu Thr Val Gln Glu Asn Ala Gly Ser Ile Ser Cys Ser Met Arg
            180                 185                 190

His Ala His Leu Ser Arg Glu Val Glu Ser Arg Val Gln Ile Gly Asp
        195                 200                 205

Thr Phe Phe Glu Pro Ile Ser Trp His Leu Ala Thr Lys
    210                 215                 220

<210> SEQ ID NO 53
<211> LENGTH: 111
<212> TYPE: PRT
<213> ORGANISM: Artificial Sequence
<220> FEATURE:
<223> OTHER INFORMATION: Synthetic Sequence_scFVh19

<400> SEQUENCE: 53

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp

```
                20                  25                  30
Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 54
<211> LENGTH: 109
<212> TYPE: PRT
<213> ORGANISM: Artificial Sequence
<220> FEATURE:
<223> OTHER INFORMATION: Synthetic Sequence_scFVlh19

<400> SEQUENCE: 54

Glu Val Gln Leu Val Glu Ser Gly Gly Gly Leu Val Gln Pro Gly Gly
 1               5                  10                  15

Ser Leu Thr Leu Ser Cys Ala Ala Ser Arg Phe Met Ile Ser Glu Tyr
                20                  25                  30

His Met His Trp Val Arg Gln Ala Pro Gly Lys Gly Leu Glu Trp Val
            35                  40                  45

Ser Thr Ile Asn Pro Ala Gly Thr Thr Asp Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Lys Pro Glu Asp Thr Ala Val Tyr Tyr Cys Asp
                85                  90                  95

Ser Tyr Gly Tyr Arg Gly Gln Gly Thr Gln Val Thr Val
            100                 105

<210> SEQ ID NO 55
<211> LENGTH: 120
<212> TYPE: PRT
<213> ORGANISM: Artificial Sequence
<220> FEATURE:
<223> OTHER INFORMATION: Synthetic Sequence_scFVlPSMA

<400> SEQUENCE: 55

Arg Lys Gly Gly Lys Arg Gly Ser Gly Gly Gln Thr Val Val Thr
 1               5                  10                  15

Gln Glu Pro Ser Leu Thr Val Ser Pro Gly Gly Thr Val Thr Leu Thr
                20                  25                  30

Cys Ala Ser Ser Thr Gly Ala Val Thr Ser Gly Asn Tyr Pro Asn Trp
            35                  40                  45

Val Gln Gln Lys Pro Gly Gln Ala Pro Arg Gly Leu Ile Gly Gly Thr
 50                  55                  60

Lys Phe Leu Val Pro Gly Thr Pro Ala Arg Phe Ser Gly Ser Leu Leu
 65                  70                  75                  80

Gly Gly Lys Ala Ala Leu Thr Leu Ser Gly Val Gln Pro Glu Asp Glu
                85                  90                  95

Ala Glu Tyr Tyr Cys Thr Leu Tyr Ser Asn Arg Trp Val Phe Gly
            100                 105                 110
```

Gly Gly Thr Lys Leu Thr Val Leu
         115                 120

<210> SEQ ID NO 56
<211> LENGTH: 250
<212> TYPE: PRT
<213> ORGANISM: Artificial Sequence
<220> FEATURE:
<223> OTHER INFORMATION: Synthetic Sequence_scFvCD19

<400> SEQUENCE: 56

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Gly Gly Gly Gly
        115                 120                 125

Ser Gly Gly Gly Gly Ser Gly Gly Gly Ser Asp Ile Gln Leu Thr
    130                 135                 140

Gln Ser Pro Ala Ser Leu Ala Val Ser Leu Gly Gln Arg Ala Thr Ile
145                 150                 155                 160

Ser Cys Lys Ala Ser Gln Ser Val Asp Tyr Asp Gly Asp Ser Tyr Leu
                165                 170                 175

Asn Trp Tyr Gln Gln Ile Pro Gly Gln Pro Pro Lys Leu Leu Ile Tyr
            180                 185                 190

Asp Ala Ser Asn Leu Val Ser Gly Ile Pro Pro Arg Phe Ser Gly Ser
        195                 200                 205

Gly Ser Gly Thr Asp Phe Thr Leu Asn Ile His Pro Val Glu Lys Val
    210                 215                 220

Asp Ala Ala Thr Tyr His Cys Gln Gln Ser Thr Glu Asp Pro Trp Thr
225                 230                 235                 240

Phe Gly Gly Gly Thr Lys Leu Glu Ile Lys
                245                 250

<210> SEQ ID NO 57
<211> LENGTH: 238
<212> TYPE: PRT
<213> ORGANISM: Artificial Sequence
<220> FEATURE:
<223> OTHER INFORMATION: Synthetic Sequence

<400> SEQUENCE: 57

Glu Val Gln Leu Gln Gln Ser Gly Ala Glu Leu Val Arg Pro Gly Thr
1               5                   10                  15

Ser Val Lys Leu Ser Cys Lys Val Ser Gly Asp Thr Ile Thr Phe Tyr
            20                  25                  30

Tyr Met His Phe Val Lys Gln Arg Pro Gly Gln Gly Leu Glu Trp Ile
        35                  40                  45

Gly Arg Ile Asp Pro Glu Asp Glu Ser Thr Lys Tyr Ser Glu Lys Phe
                50                  55                  60

Lys Asn Lys Ala Thr Leu Thr Ala Asp Thr Ser Asn Thr Ala Tyr
 65                  70                  75                  80

Leu Lys Leu Ser Ser Leu Thr Ser Glu Asp Thr Ala Thr Tyr Phe Cys
                    85                  90                  95

Ile Tyr Gly Gly Tyr Tyr Phe Asp Tyr Trp Gly Gln Gly Val Met Val
                100                 105                 110

Thr Val Ser Ser Gly Gly Gly Ser Gly Gly Gly Ser Gly Gly
            115                 120                 125

Gly Gly Ser Asp Ile Gln Met Thr Gln Ser Pro Ala Ser Leu Ser Thr
130                 135                 140

Ser Leu Gly Glu Thr Val Thr Ile Gln Cys Gln Ala Ser Glu Asp Ile
145                 150                 155                 160

Tyr Ser Gly Leu Ala Trp Tyr Gln Gln Lys Pro Gly Lys Ser Pro Gln
                165                 170                 175

Leu Leu Ile Tyr Gly Ala Ser Asp Leu Gln Asp Gly Val Pro Ser Arg
                180                 185                 190

Phe Ser Gly Ser Gly Ser Gly Thr Gln Tyr Ser Leu Lys Ile Thr Ser
                195                 200                 205

Met Gln Thr Glu Asp Glu Gly Val Tyr Phe Cys Gln Gln Gly Leu Thr
210                 215                 220

Tyr Pro Arg Thr Phe Gly Gly Gly Thr Lys Leu Glu Leu Lys
225                 230                 235

<210> SEQ ID NO 58
<211> LENGTH: 238
<212> TYPE: PRT
<213> ORGANISM: Artificial Sequence
<220> FEATURE:
<223> OTHER INFORMATION: Synthetic Sequence_scFvCD19VLVH

<400> SEQUENCE: 58

Asp Ile Gln Met Thr Gln Ser Pro Ala Ser Leu Ser Thr Ser Leu Gly
1               5                   10                  15

Glu Thr Val Thr Ile Gln Cys Gln Ala Ser Glu Asp Ile Tyr Ser Gly
                20                  25                  30

Leu Ala Trp Tyr Gln Gln Lys Pro Gly Lys Ser Pro Gln Leu Leu Ile
            35                  40                  45

Tyr Gly Ala Ser Asp Leu Gln Asp Gly Val Pro Ser Arg Phe Ser Gly
 50                  55                  60

Ser Gly Ser Gly Thr Gln Tyr Ser Leu Lys Ile Thr Ser Met Gln Thr
 65                  70                  75                  80

Glu Asp Glu Gly Val Tyr Phe Cys Gln Gln Gly Leu Thr Tyr Pro Arg
                 85                  90                  95

Thr Phe Gly Gly Gly Thr Lys Leu Glu Leu Lys Gly Gly Gly Gly Ser
            100                 105                 110

Gly Gly Gly Gly Ser Gly Gly Gly Ser Glu Val Gln Leu Gln Gln
            115                 120                 125

Ser Gly Ala Glu Leu Val Arg Pro Gly Thr Ser Val Lys Leu Ser Cys
130                 135                 140

Lys Val Ser Gly Asp Thr Ile Thr Phe Tyr Tyr Met His Phe Val Lys
145                 150                 155                 160

Gln Arg Pro Gly Gln Gly Leu Glu Trp Ile Gly Arg Ile Asp Pro Glu
                165                 170                 175

Asp Glu Ser Thr Lys Tyr Ser Glu Lys Phe Lys Asn Lys Ala Thr Leu
            180                 185                 190

Thr Ala Asp Thr Ser Ser Asn Thr Ala Tyr Leu Lys Leu Ser Ser Leu
            195                 200                 205

Thr Ser Glu Asp Thr Ala Thr Tyr Phe Cys Ile Tyr Gly Gly Tyr Tyr
            210                 215                 220

Phe Asp Tyr Trp Gly Gln Gly Val Met Val Thr Val Ser Ser
225                 230                 235

<210> SEQ ID NO 59
<211> LENGTH: 239
<212> TYPE: PRT
<213> ORGANISM: Artificial Sequence
<220> FEATURE:
<223> OTHER INFORMATION: Synthetic Sequence_19scFv3

<400> SEQUENCE: 59

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Ser Gly
            100                 105                 110

Gly Gly Ser Gly Gly Gly Ser Glu Val Lys Leu Gln Glu Ser Gly Pro
        115                 120                 125

Gly Leu Val Ala Pro Ser Gln Ser Leu Ser Val Thr Cys Thr Val Ser
130                 135                 140

Gly Val Ser Leu Pro Asp Tyr Gly Val Ser Trp Ile Arg Gln Pro Pro
145                 150                 155                 160

Arg Lys Gly Leu Glu Trp Leu Gly Val Ile Trp Gly Ser Glu Thr Thr
                165                 170                 175

Tyr Tyr Asn Ser Ala Leu Lys Ser Arg Leu Thr Ile Ile Lys Asp Asn
            180                 185                 190

Ser Lys Ser Gln Val Phe Leu Lys Met Asn Ser Leu Gln Thr Asp Asp
            195                 200                 205

Thr Ala Ile Tyr Tyr Cys Ala Lys His Tyr Tyr Tyr Gly Gly Ser Tyr
            210                 215                 220

Ala Met Asp Tyr Trp Gly Gln Gly Thr Ser Val Thr Val Ser Ser
225                 230                 235

<210> SEQ ID NO 60
<211> LENGTH: 166
<212> TYPE: PRT
<213> ORGANISM: Artificial Sequence
<220> FEATURE:
<223> OTHER INFORMATION: Synthetic Sequence_GD2scFv3

<400> SEQUENCE: 60

Gly Thr Asp Phe Thr Leu Lys Ile Ser Arg Val Glu Ala Glu Asp Leu

```
1               5                   10                  15
Gly Val Tyr Phe Cys Ser Gln Ser Thr His Val Pro Pro Leu Thr Phe
                20                  25                  30
Gly Ala Gly Thr Lys Leu Glu Leu Lys Gly Gly Ser Gly Gly Gly
        35                  40                  45
Ser Gly Gly Gly Ser Glu Val Gln Leu Leu Gln Ser Gly Pro Glu Leu
50                  55                  60
Glu Lys Pro Gly Ala Ser Val Met Ile Ser Cys Lys Ala Ser Gly Ser
65                  70                  75                  80
Ser Phe Thr Gly Tyr Asn Met Asn Trp Val Arg Gln Asn Ile Gly Lys
                85                  90                  95
Ser Leu Glu Trp Ile Gly Ala Ile Asp Pro Tyr Tyr Gly Gly Thr Ser
                100                 105                 110
Tyr Asn Gln Lys Phe Lys Gly Arg Ala Thr Leu Thr Val Asp Lys Ser
                115                 120                 125
Ser Ser Thr Ala Tyr Met His Leu Lys Ser Leu Thr Ser Glu Asp Ser
        130                 135                 140
Ala Val Tyr Tyr Cys Val Ser Gly Met Lys Tyr Trp Gly Gln Gly Thr
145                 150                 155                 160
Ser Val Thr Val Ser Ser
                165

<210> SEQ ID NO 61
<211> LENGTH: 222
<212> TYPE: PRT
<213> ORGANISM: Artificial Sequence
<220> FEATURE:
<223> OTHER INFORMATION: Synthetic Sequence_core domain

<400> SEQUENCE: 61

Cys Pro Pro Cys Pro Ala Pro Glu Phe Leu Gly Gly Pro Ser Val Phe
1               5                   10                  15
Leu Phe Pro Pro Lys Pro Lys Asp Gln Leu Met Ile Ser Arg Thr Pro
                20                  25                  30
Glu Val Thr Cys Val Val Val Asp Val Ser Gln Glu Asp Pro Glu Val
            35                  40                  45
Gln Phe Asn Trp Tyr Val Asp Gly Val Glu Val His Asn Ala Lys Thr
        50                  55                  60
Lys Pro Arg Glu Glu Gln Phe Asn Ser Thr Tyr Arg Val Val Ser Val
65                  70                  75                  80
Leu Thr Val Leu His Gln Asp Trp Leu Ser Gly Lys Glu Tyr Lys Cys
                85                  90                  95
Lys Val Ser Ser Lys Gly Leu Pro Ser Ser Ile Glu Lys Thr Ile Ser
                100                 105                 110
Asn Ala Thr Gly Gln Pro Arg Glu Pro Gln Val Tyr Thr Leu Pro Pro
        115                 120                 125
Ser Gln Glu Glu Met Thr Lys Asn Gln Val Ser Leu Thr Cys Leu Val
        130                 135                 140
Lys Gly Phe Tyr Pro Ser Asp Ile Ala Val Glu Trp Glu Ser Asn Gly
145                 150                 155                 160
Gln Pro Glu Asn Asn Tyr Lys Thr Thr Pro Pro Val Leu Asp Ser Asp
                165                 170                 175
Gly Ser Phe Phe Leu Tyr Ser Arg Leu Thr Val Asp Lys Ser Arg Trp
                180                 185                 190
Gln Glu Gly Asn Val Phe Ser Cys Ser Val Leu His Glu Ala Leu His
```

```
                195                 200                 205
Asn His Tyr Thr Gln Lys Ser Leu Ser Leu Ser Leu Gly Lys
    210                 215                 220
```

<210> SEQ ID NO 62
<211> LENGTH: 232
<212> TYPE: PRT
<213> ORGANISM: Artificial Sequence
<220> FEATURE:
<223> OTHER INFORMATION: Synthetic Sequence_a KIHT22Y protein

<400> SEQUENCE: 62

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Tyr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 63
<211> LENGTH: 232
<212> TYPE: PRT
<213> ORGANISM: Artificial Sequence
<220> FEATURE:
<223> OTHER INFORMATION: Synthetic Sequence_a KIHY86T protein

<400> SEQUENCE: 63

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45
```

```
Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Thr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 64
<211> LENGTH: 227
<212> TYPE: PRT
<213> ORGANISM: Artificial Sequence
<220> FEATURE:
<223> OTHER INFORMATION: Synthetic Sequence_a KIHY86T protein

<400> SEQUENCE: 64

Val Pro Arg Asp Cys Gly Cys Lys Pro Cys Ile Cys Thr Val Pro Glu
 1               5                  10                  15

Val Ser Ser Val Phe Ile Phe Pro Pro Lys Pro Lys Asp Val Leu Thr
                 20                  25                  30

Ile Thr Leu Thr Pro Lys Val Thr Cys Val Val Val Asp Ile Ser Lys
                 35                  40                  45

Asp Asp Pro Glu Val Gln Phe Ser Trp Phe Val Asp Asp Val Glu Val
 50                  55                  60

His Thr Ala Gln Thr Gln Pro Arg Glu Glu Gln Phe Asn Ser Thr Phe
 65                  70                  75                  80

Arg Ser Val Ser Glu Leu Pro Ile Met His Gln Asp Trp Leu Asn Gly
                 85                  90                  95

Lys Glu Phe Lys Cys Arg Val Asn Ser Ala Ala Phe Pro Ala Pro Ile
                100                 105                 110

Glu Lys Thr Ile Ser Lys Thr Lys Gly Arg Pro Lys Ala Pro Gln Val
                115                 120                 125

Tyr Thr Ile Pro Pro Pro Lys Glu Gln Met Ala Lys Asp Lys Val Ser
                130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175
```

```
Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His His Thr Glu Lys Ser Leu Ser His Ser
    210                 215                 220

Pro Gly Ile
225

<210> SEQ ID NO 65
<211> LENGTH: 222
<212> TYPE: PRT
<213> ORGANISM: Artificial Sequence
<220> FEATURE:
<223> OTHER INFORMATION: Synthetic Sequence

<400> SEQUENCE: 65

Cys Pro Pro Cys Pro Ala Pro Glu Phe Leu Gly Gly Pro Ser Val Phe
1               5                   10                  15

Leu Phe Pro Pro Lys Pro Lys Asp Gln Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Ser Gly Lys Glu Tyr Lys Cys
                85                  90                  95

Lys Val Ser Ser Lys Gly Leu Pro Ser Ser Ile Glu Lys Thr Ile Ser
            100                 105                 110

Asn Ala Thr Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Leu His Glu Ala Leu His
        195                 200                 205

Asn His Tyr Thr Gln Lys Ser Leu Ser Leu Ser Leu Gly Lys
    210                 215                 220

<210> SEQ ID NO 66

<400> SEQUENCE: 66

000

<210> SEQ ID NO 67
<211> LENGTH: 594
<212> TYPE: PRT
<213> ORGANISM: Homo sapiens

<400> SEQUENCE: 67
```

```
Met Glu Phe Gly Leu Ser Trp Val Phe Leu Val Ala Ile Ile Lys Gly
1               5                   10                  15

Val Gln Cys Gln Trp Gln Val Phe Gly Pro Asp Lys Pro Val Gln Ala
            20                  25                  30

Leu Val Gly Glu Asp Ala Ala Phe Ser Cys Phe Leu Ser Pro Lys Thr
        35                  40                  45

Asn Ala Glu Ala Met Glu Val Arg Phe Phe Arg Gly Gln Phe Ser Ser
    50                  55                  60

Val Val His Leu Tyr Arg Asp Gly Lys Asp Gln Pro Phe Met Gln Met
65                  70                  75                  80

Pro Gln Tyr Gln Gly Arg Thr Lys Leu Val Lys Asp Ser Ile Ala Glu
            85                  90                  95

Gly Arg Ile Ser Leu Arg Leu Glu Asn Ile Thr Val Leu Asp Ala Gly
            100                 105                 110

Leu Tyr Gly Cys Arg Ile Ser Ser Gln Ser Tyr Tyr Gln Lys Ala Ile
        115                 120                 125

Trp Glu Leu Gln Val Ser Ala Leu Gly Ser Val Pro Leu Ile Ser Ile
        130                 135                 140

Thr Gly Tyr Val Asp Arg Asp Ile Gln Leu Leu Cys Gln Ser Ser Gly
145                 150                 155                 160

Trp Phe Pro Arg Pro Thr Ala Lys Trp Lys Gly Pro Gln Gly Gln Asp
            165                 170                 175

Leu Ser Thr Asp Ser Arg Thr Asn Arg Asp Met His Gly Leu Phe Asp
            180                 185                 190

Val Glu Ile Ser Leu Thr Val Gln Glu Asn Ala Gly Ser Ile Ser Cys
            195                 200                 205

Ser Met Arg His Ala His Leu Ser Arg Glu Val Glu Ser Arg Val Gln
    210                 215                 220

Ile Gly Asp Thr Phe Phe Glu Pro Ile Ser Trp His Leu Ala Thr Lys
225                 230                 235                 240

Gly Ser Gly Ser Asp Glu Gly Gly Glu Asp Gly Ser Lys Tyr Gly Pro
            245                 250                 255

Pro Cys Pro Pro Cys Pro Ala Pro Glu Phe Leu Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
        290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
            325                 330                 335

Val Leu Thr Val Leu His Gln Asp Trp Leu Ser Gly Lys Glu Tyr Lys
            340                 345                 350

Cys Lys Val Ser Ser Lys Gly Leu Pro Ser Ser Ile Glu Lys Thr Ile
        355                 360                 365

Ser Asn Ala Thr Gly Gln Pro Arg Glu Pro Gln Val Tyr Thr Leu Pro
    370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
            405                 410                 415

Gly Gln Pro Glu Asn Asn Tyr Lys Thr Thr Pro Pro Val Leu Asp Ser
```

```
            420             425             430
Asp Gly Ser Phe Phe Leu Tyr Ser Arg Leu Thr Val Asp Lys Ser Arg
            435             440             445

Trp Gln Glu Gly Asn Val Phe Ser Cys Ser Val Leu His Glu Ala Leu
450             455             460

His Asn His Tyr Thr Gln Lys Ser Leu Ser Leu Ser Leu Gly Lys Arg
465             470             475             480

Lys Gly Gly Lys Arg Gly Ser Gly Ser Ile Gln Leu Thr Gln Ser Pro
            485             490             495

Ala Ile Met Ser Ala Ser Pro Gly Glu Lys Val Thr Met Thr Cys Arg
            500             505             510

Ala Ser Ser Ser Val Ser Tyr Met Asn Trp Tyr Gln Gln Lys Ser Gly
            515             520             525

Thr Ser Pro Lys Arg Trp Ile Tyr Asp Thr Ser Lys Val Ala Ser Gly
            530             535             540

Val Pro Tyr Arg Phe Ser Gly Ser Gly Ser Gly Thr Ser Tyr Ser Leu
545             550             555             560

Thr Ile Ser Ser Met Glu Ala Glu Asp Ala Ala Thr Tyr Tyr Cys Gln
            565             570             575

Gln Trp Ser Ser Asn Pro Leu Thr Phe Gly Ala Gly Thr Lys Leu Glu
            580             585             590

Leu Lys

<210> SEQ ID NO 68
<211> LENGTH: 598
<212> TYPE: PRT
<213> ORGANISM: Homo sapiens

<400> SEQUENCE: 68

Met Glu Phe Gly Leu Ser Trp Val Phe Leu Val Ala Ile Ile Lys Gly
1               5                   10                  15

Val Gln Cys Gln Trp Gln Val Thr Gly Pro Gly Lys Phe Val Gln Ala
            20                  25                  30

Leu Val Gly Glu Asp Ala Val Phe Ser Cys Ser Leu Phe Pro Glu Thr
        35                  40                  45

Ser Ala Glu Ala Met Glu Val Arg Phe Phe Arg Asn Gln Phe His Ala
    50                  55                  60

Val Val His Leu Tyr Arg Asp Gly Glu Asp Trp Glu Ser Lys Gln Met
65                  70                  75                  80

Pro Gln Tyr Arg Gly Arg Thr Glu Phe Val Lys Asp Ser Ile Ala Gly
                85                  90                  95

Gly Arg Val Ser Leu Arg Leu Lys Asn Ile Thr Pro Ser Asp Ile Gly
            100                 105                 110

Leu Tyr Gly Cys Trp Phe Ser Ser Gln Ile Tyr Asp Glu Glu Ala Thr
        115                 120                 125

Trp Glu Leu Arg Val Ala Ala Leu Gly Ser Leu Pro Leu Ile Ser Ile
    130                 135                 140

Val Gly Tyr Val Asp Gly Gly Ile Gln Leu Leu Cys Leu Ser Ser Gly
145                 150                 155                 160

Trp Phe Pro Gln Pro Thr Ala Lys Trp Lys Gly Pro Gln Gly Gln Asp
                165                 170                 175

Leu Ser Ser Asp Ser Arg Ala Asn Ala Asp Gly Tyr Ser Leu Tyr Asp
            180                 185                 190

Val Glu Ile Ser Ile Ile Val Gln Glu Asn Ala Gly Ser Ile Leu Cys
```

```
              195                 200                 205
Ser Ile His Leu Ala Glu Gln Ser His Glu Val Glu Ser Lys Val Leu
            210                 215                 220
Ile Gly Glu Thr Phe Phe Gln Pro Ser Pro Trp Arg Leu Ala Ser Gly
225                 230                 235                 240
Ser Gly Ser Arg Lys Gly Lys Arg Gly Ser Lys Tyr Gly Pro Pro
                245                 250                 255
Cys Pro Pro Cys Pro Ala Pro Glu Phe Leu Gly Gly Pro Ser Val Phe
                260                 265                 270
Leu Phe Pro Pro Lys Pro Lys Asp Gln Leu Met Ile Ser Arg Thr Pro
                275                 280                 285
Glu Val Thr Cys Val Val Val Asp Val Ser Gln Glu Asp Pro Glu Val
            290                 295                 300
Gln Phe Asn Trp Tyr Val Asp Gly Val Glu Val His Asn Ala Lys Thr
305                 310                 315                 320
Lys Pro Arg Glu Glu Gln Phe Asn Ser Thr Tyr Arg Val Val Ser Val
                325                 330                 335
Leu Thr Val Leu His Gln Asp Trp Leu Ser Gly Lys Glu Tyr Lys Cys
            340                 345                 350
Lys Val Ser Ser Lys Gly Leu Pro Ser Ser Ile Glu Lys Thr Ile Ser
                355                 360                 365
Asn Ala Thr Gly Gln Pro Arg Glu Pro Gln Val Tyr Thr Leu Pro Pro
            370                 375                 380
Ser Gln Glu Glu Met Thr Lys Asn Gln Val Ser Leu Thr Cys Leu Val
385                 390                 395                 400
Lys Gly Phe Tyr Pro Ser Asp Ile Ala Val Glu Trp Glu Ser Asn Gly
                405                 410                 415
Gln Pro Glu Asn Asn Tyr Lys Thr Thr Pro Pro Val Leu Asp Ser Asp
            420                 425                 430
Gly Ser Phe Phe Leu Tyr Ser Arg Leu Thr Val Asp Lys Ser Arg Trp
            435                 440                 445
Gln Glu Gly Asn Val Phe Ser Cys Ser Val Leu His Glu Ala Leu His
            450                 455                 460
Asn His Tyr Thr Gln Lys Ser Leu Ser Leu Ser Leu Gly Lys Asp Glu
465                 470                 475                 480
Gly Gly Glu Asp Gly Ser Gly Ser Gly Glu Val Gln Leu Val Glu Ser
                485                 490                 495
Gly Gly Gly Leu Val Gln Pro Gly Gly Ser Leu Thr Leu Ser Cys Ala
            500                 505                 510
Ala Ser Arg Phe Met Ile Ser Glu Tyr His Met His Trp Val Arg Gln
            515                 520                 525
Ala Pro Gly Lys Gly Leu Glu Trp Val Ser Thr Ile Asn Pro Ala Gly
            530                 535                 540
Thr Thr Asp Tyr Ala Glu Ser Val Lys Gly Arg Phe Thr Ile Ser Arg
545                 550                 555                 560
Asp Asn Ala Lys Asn Thr Leu Tyr Leu Gln Met Asn Ser Leu Lys Pro
                565                 570                 575
Glu Asp Thr Ala Val Tyr Tyr Cys Asp Ser Tyr Gly Tyr Arg Gly Gln
                580                 585                 590
Gly Thr Gln Val Thr Val
            595

<210> SEQ ID NO 69
```

```
<211> LENGTH: 599
<212> TYPE: PRT
<213> ORGANISM: Homo sapiens

<400> SEQUENCE: 69

Met Glu Phe Gly Leu Ser Trp Val Phe Leu Val Ala Ile Ile Lys Gly
1               5                   10                  15

Val Gln Cys Gln Trp Gln Val Phe Gly Pro Asp Lys Pro Val Gln Ala
            20                  25                  30

Leu Val Gly Glu Asp Ala Ala Phe Ser Cys Phe Leu Ser Pro Lys Thr
        35                  40                  45

Asn Ala Glu Ala Met Glu Val Arg Phe Phe Arg Gly Gln Phe Ser Ser
    50                  55                  60

Val Val His Leu Tyr Arg Asp Gly Lys Asp Gln Pro Phe Met Gln Met
65                  70                  75                  80

Pro Gln Tyr Gln Gly Arg Thr Lys Leu Val Lys Asp Ser Ile Ala Glu
                85                  90                  95

Gly Arg Ile Ser Leu Arg Leu Glu Asn Ile Thr Val Leu Asp Ala Gly
            100                 105                 110

Leu Tyr Gly Cys Arg Ile Ser Ser Gln Ser Tyr Tyr Gln Lys Ala Ile
        115                 120                 125

Trp Glu Leu Gln Val Ser Ala Leu Gly Ser Val Pro Leu Ile Ser Ile
    130                 135                 140

Thr Gly Tyr Val Asp Arg Asp Ile Gln Leu Leu Cys Gln Ser Ser Gly
145                 150                 155                 160

Trp Phe Pro Arg Pro Thr Ala Lys Trp Lys Gly Pro Gln Gly Gln Asp
                165                 170                 175

Leu Ser Thr Asp Ser Arg Thr Asn Arg Asp Met His Gly Leu Phe Asp
            180                 185                 190

Val Glu Ile Ser Leu Thr Val Gln Glu Asn Ala Gly Ser Ile Ser Cys
        195                 200                 205

Ser Met Arg His Ala His Leu Ser Arg Glu Val Glu Ser Arg Val Gln
    210                 215                 220

Ile Gly Asp Thr Phe Phe Glu Pro Ile Ser Trp His Leu Ala Thr Lys
225                 230                 235                 240

Gly Ser Gly Ser Asp Glu Gly Glu Asp Gly Ser Lys Tyr Gly Pro
                245                 250                 255

Pro Cys Pro Pro Cys Pro Ala Pro Glu Phe Leu Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Ser Gly Lys Glu Tyr Lys
            340                 345                 350

Cys Lys Val Ser Ser Lys Gly Leu Pro Ser Ser Ile Glu Lys Thr Ile
        355                 360                 365

Ser Asn Ala Thr Gly Gln Pro Arg Glu Pro Gln Val Tyr Thr Leu Pro
    370                 375                 380

Pro Ser Gln Glu Glu Met Thr Lys Asn Gln Val Ser Leu Thr Cys Leu
```

```
                385                 390                 395                 400
Val Lys Gly Phe Tyr Pro Ser Asp Ile Ala Val Glu Trp Glu Ser Asn
                    405                 410                 415

Gly Gln Pro Glu Asn Asn Tyr Lys Thr Thr Pro Pro Val Leu Asp Ser
                420                 425                 430

Asp Gly Ser Phe Phe Leu Tyr Ser Arg Leu Thr Val Asp Lys Ser Arg
            435                 440                 445

Trp Gln Glu Gly Asn Val Phe Ser Cys Ser Val Leu His Glu Ala Leu
        450                 455                 460

His Asn His Tyr Thr Gln Lys Ser Leu Ser Leu Ser Leu Gly Lys Arg
465                 470                 475                 480

Lys Gly Gly Lys Arg Gly Ser Gly Ser Gly Gln Thr Val Val Thr Gln
                    485                 490                 495

Glu Pro Ser Leu Thr Val Ser Pro Gly Gly Thr Val Thr Leu Thr Cys
                500                 505                 510

Ala Ser Ser Thr Gly Ala Val Thr Ser Gly Asn Tyr Pro Asn Trp Val
            515                 520                 525

Gln Gln Lys Pro Gly Gln Ala Pro Arg Gly Leu Ile Gly Gly Thr Lys
        530                 535                 540

Phe Leu Val Pro Gly Thr Pro Ala Arg Phe Ser Gly Ser Leu Leu Gly
545                 550                 555                 560

Gly Lys Ala Ala Leu Thr Leu Ser Gly Val Gln Pro Glu Asp Glu Ala
                    565                 570                 575

Glu Tyr Tyr Cys Thr Leu Trp Tyr Ser Asn Arg Trp Val Phe Gly Gly
                580                 585                 590

Gly Thr Lys Leu Thr Val Leu
            595

<210> SEQ ID NO 70
<211> LENGTH: 741
<212> TYPE: PRT
<213> ORGANISM: Homo sapiens

<400> SEQUENCE: 70

Met Glu Phe Gly Leu Ser Trp Val Phe Leu Val Ala Ile Ile Lys Gly
1               5                   10                  15

Val Gln Cys Gln Phe Ser Val Leu Gly Pro Ser Gly Pro Ile Leu Ala
            20                  25                  30

Met Val Gly Glu Asp Ala Asp Leu Pro Cys His Leu Phe Pro Thr Met
        35                  40                  45

Ser Ala Glu Thr Met Glu Leu Lys Trp Val Ser Ser Ser Leu Arg Gln
    50                  55                  60

Val Val Asn Val Tyr Ala Asp Gly Lys Glu Val Glu Asp Arg Gln Ser
65                  70                  75                  80

Ala Pro Tyr Arg Gly Arg Thr Ser Ile Leu Arg Asp Gly Ile Thr Ala
                85                  90                  95

Gly Lys Ala Ala Leu Arg Ile His Asn Val Thr Ala Ser Asp Ser Gly
            100                 105                 110

Lys Tyr Leu Cys Tyr Phe Gln Asp Gly Asp Phe Tyr Glu Lys Ala Leu
        115                 120                 125

Val Glu Leu Lys Val Ala Ala Leu Gly Ser Asp Leu His Val Asp Val
    130                 135                 140

Lys Gly Tyr Lys Asp Gly Gly Ile His Leu Glu Cys Arg Ser Thr Gly
145                 150                 155                 160
```

Trp Tyr Pro Gln Pro Gln Ile Gln Trp Ser Asn Asn Lys Gly Glu Asn
                165                 170                 175

Ile Pro Thr Val Glu Ala Pro Val Val Ala Asp Gly Val Gly Leu Tyr
            180                 185                 190

Ala Val Ala Ala Ser Val Ile Met Arg Gly Ser Ser Gly Glu Gly Val
        195                 200                 205

Ser Cys Thr Ile Arg Ser Ser Leu Leu Gly Leu Glu Lys Thr Ala Ser
    210                 215                 220

Ile Ser Ile Ala Asp Pro Phe Phe Arg Ser Ala Gln Arg Trp Ile Ala
225                 230                 235                 240

Ala Leu Ala Gly Gly Ser Gly Ser Arg Lys Gly Gly Lys Arg Gly Ser
                245                 250                 255

Lys Tyr Gly Pro Pro Cys Pro Pro Cys Pro Ala Pro Glu Phe Leu Gly
            260                 265                 270

Gly Pro Ser Val Phe Leu Phe Pro Pro Lys Pro Lys Asp Gln Leu Met
        275                 280                 285

Ile Ser Arg Thr Pro Glu Val Thr Cys Val Val Val Asp Val Ser Gln
    290                 295                 300

Glu Asp Pro Glu Val Gln Phe Asn Trp Tyr Val Asp Gly Val Glu Val
305                 310                 315                 320

His Asn Ala Lys Thr Lys Pro Arg Glu Glu Gln Phe Asn Ser Thr Tyr
                325                 330                 335

Arg Val Val Ser Val Leu Thr Val Leu His Gln Asp Trp Leu Ser Gly
            340                 345                 350

Lys Glu Tyr Lys Cys Lys Val Ser Ser Lys Gly Leu Pro Ser Ser Ile
        355                 360                 365

Glu Lys Thr Ile Ser Asn Ala Thr Gly Gln Pro Arg Glu Pro Gln Val
    370                 375                 380

Tyr Thr Leu Pro Pro Ser Gln Glu Glu Met Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Arg Leu Thr Val
        435                 440                 445

Asp Lys Ser Arg Trp Gln Glu Gly Asn Val Phe Ser Cys Ser Val Leu
    450                 455                 460

His Glu Ala Leu His Asn His Tyr Thr Gln Lys Ser Leu Ser Leu Ser
465                 470                 475                 480

Leu Gly Lys Asp Glu Gly Gly Glu Asp Gly Ser Gln Val Gln Leu Gln
                485                 490                 495

Gln Ser Gly Ala Glu Leu Val Arg Pro Gly Ser Ser Val Lys Ile Ser
            500                 505                 510

Cys Lys Ala Ser Gly Tyr Ala Phe Ser Ser Tyr Trp Met Asn Trp Val
        515                 520                 525

Lys Gln Arg Pro Gly Gln Gly Leu Glu Trp Ile Gly Gln Ile Trp Pro
    530                 535                 540

Gly Asp Gly Asp Thr Asn Tyr Asn Gly Lys Phe Lys Gly Lys Ala Thr
545                 550                 555                 560

Leu Thr Ala Asp Glu Ser Ser Ser Thr Ala Tyr Met Gln Leu Ser Ser
                565                 570                 575

Leu Ala Ser Glu Asp Ser Ala Val Tyr Phe Cys Ala Arg Arg Glu Thr

```
                    580              585              590
Thr Thr Val Gly Arg Tyr Tyr Tyr Ala Met Asp Tyr Trp Gly Gln Gly
            595              600              605

Thr Thr Val Thr Val Ser Ser Gly Gly Gly Ser Gly Gly Gly Gly
            610              615              620

Ser Gly Gly Gly Ser Asp Ile Gln Leu Thr Gln Ser Pro Ala Ser
625              630              635              640

Leu Ala Val Ser Leu Gly Gln Arg Ala Thr Ile Ser Cys Lys Ala Ser
                    645              650              655

Gln Ser Val Asp Tyr Asp Gly Asp Ser Tyr Leu Asn Trp Tyr Gln Gln
            660              665              670

Ile Pro Gly Gln Pro Pro Lys Leu Leu Ile Tyr Asp Ala Ser Asn Leu
            675              680              685

Val Ser Gly Ile Pro Pro Arg Phe Ser Gly Ser Gly Ser Gly Thr Asp
            690              695              700

Phe Thr Leu Asn Ile His Pro Val Glu Lys Val Asp Ala Ala Thr Tyr
705              710              715              720

His Cys Gln Gln Ser Thr Glu Asp Pro Trp Thr Phe Gly Gly Gly Thr
                    725              730              735

Lys Leu Glu Ile Lys
            740

<210> SEQ ID NO 71
<211> LENGTH: 737
<212> TYPE: PRT
<213> ORGANISM: Homo sapiens

<400> SEQUENCE: 71

Met Glu Phe Gly Leu Ser Trp Val Phe Leu Val Ala Ile Ile Lys Gly
1               5                   10                  15

Val Gln Cys Gln Phe Ser Val Leu Gly Pro Ser Gly Pro Ile Leu Ala
            20                  25                  30

Met Val Gly Glu Asp Ala Asp Leu Pro Cys His Leu Phe Pro Thr Met
        35                  40                  45

Ser Ala Glu Thr Met Glu Leu Lys Trp Val Ser Ser Ser Leu Arg Gln
    50                  55                  60

Val Val Asn Val Tyr Ala Asp Gly Lys Glu Val Glu Asp Arg Gln Ser
65                  70                  75                  80

Ala Pro Tyr Arg Gly Arg Thr Ser Ile Leu Arg Asp Gly Ile Thr Ala
                85                  90                  95

Gly Lys Ala Ala Leu Arg Ile His Asn Val Thr Ala Ser Asp Ser Gly
            100                 105                 110

Lys Tyr Leu Cys Tyr Phe Gln Asp Gly Asp Phe Tyr Glu Lys Ala Leu
        115                 120                 125

Val Glu Leu Lys Val Ala Ala Leu Gly Ser Asn Leu His Val Glu Val
    130                 135                 140

Lys Gly Tyr Glu Asp Gly Gly Ile His Leu Glu Cys Arg Ser Thr Gly
145                 150                 155                 160

Trp Tyr Pro Gln Pro Gln Ile Gln Trp Ser Asn Ala Lys Gly Glu Asn
                165                 170                 175

Ile Pro Ala Val Glu Ala Pro Val Val Ala Asp Gly Val Gly Leu Tyr
            180                 185                 190

Glu Val Ala Ala Ser Val Ile Met Arg Gly Gly Ser Gly Glu Gly Val
        195                 200                 205
```

-continued

```
Ser Cys Ile Ile Arg Asn Ser Leu Leu Gly Leu Glu Lys Thr Ala Ser
    210                 215                 220
Ile Ser Ile Ala Asp Pro Phe Phe Arg Ser Ala Gln Pro Trp Gly Ser
225                 230                 235                 240
Gly Ser Asp Glu Gly Gly Glu Asp Gly Ser Lys Tyr Gly Pro Pro Cys
                245                 250                 255
Pro Pro Cys Pro Ala Pro Glu Phe Leu Gly Gly Pro Ser Val Phe Leu
            260                 265                 270
Phe Pro Pro Lys Pro Lys Asp Gln Leu Met Ile Ser Arg Thr Pro Glu
        275                 280                 285
Val Thr Cys Val Val Val Asp Val Ser Gln Glu Asp Pro Glu Val Gln
    290                 295                 300
Phe Asn Trp Tyr Val Asp Gly Val Glu Val His Asn Ala Lys Thr Lys
305                 310                 315                 320
Pro Arg Glu Glu Gln Phe Asn Ser Thr Tyr Arg Val Val Ser Val Leu
                325                 330                 335
Thr Val Leu His Gln Asp Trp Leu Ser Gly Lys Glu Tyr Lys Cys Lys
            340                 345                 350
Val Ser Ser Lys Gly Leu Pro Ser Ser Ile Glu Lys Thr Ile Ser Asn
        355                 360                 365
Ala Thr Gly Gln Pro Arg Glu Pro Gln Val Tyr Thr Leu Pro Pro Ser
    370                 375                 380
Gln Glu Glu Met Thr Lys Asn Gln Val Ser Leu Thr Cys Leu Val Lys
385                 390                 395                 400
Gly Phe Tyr Pro Ser Asp Ile Ala Val Glu Trp Glu Ser Asn Gly Gln
                405                 410                 415
Pro Glu Asn Asn Tyr Lys Thr Thr Pro Pro Val Leu Asp Ser Asp Gly
            420                 425                 430
Ser Phe Phe Leu Tyr Ser Arg Leu Thr Val Asp Lys Ser Arg Trp Gln
        435                 440                 445
Glu Gly Asn Val Phe Ser Cys Ser Val Leu His Glu Ala Leu His Asn
    450                 455                 460
His Tyr Thr Gln Lys Ser Leu Ser Leu Ser Leu Gly Lys Arg Lys Gly
465                 470                 475                 480
Gly Lys Arg Gly Ser Gly Ser Gln Val Gln Leu Gln Gln Ser Gly Ala
                485                 490                 495
Glu Leu Val Arg Pro Gly Ser Ser Val Lys Ile Ser Cys Lys Ala Ser
            500                 505                 510
Gly Tyr Ala Phe Ser Ser Tyr Trp Met Asn Trp Val Lys Gln Arg Pro
        515                 520                 525
Gly Gln Gly Leu Glu Trp Ile Gly Gln Ile Trp Pro Gly Asp Gly Asp
    530                 535                 540
Thr Asn Tyr Asn Gly Lys Phe Lys Gly Lys Ala Thr Leu Thr Ala Asp
545                 550                 555                 560
Glu Ser Ser Ser Thr Ala Tyr Met Gln Leu Ser Ser Leu Ala Ser Glu
                565                 570                 575
Asp Ser Ala Val Tyr Phe Cys Ala Arg Arg Glu Thr Thr Thr Val Gly
            580                 585                 590
Arg Tyr Tyr Tyr Ala Met Asp Tyr Trp Gly Gln Gly Thr Thr Val Thr
        595                 600                 605
Val Ser Ser Gly Gly Gly Gly Ser Gly Gly Gly Gly Ser Gly Gly Gly
    610                 615                 620
Gly Ser Asp Ile Gln Leu Thr Gln Ser Pro Ala Ser Leu Ala Val Ser
```

```
                625                 630                 635                 640
Leu Gly Gln Arg Ala Thr Ile Ser Cys Lys Ala Ser Gln Ser Val Asp
                    645                 650                 655

Tyr Asp Gly Asp Ser Tyr Leu Asn Trp Tyr Gln Gln Ile Pro Gly Gln
                660                 665                 670

Pro Pro Lys Leu Leu Ile Tyr Asp Ala Ser Asn Leu Val Ser Gly Ile
            675                 680                 685

Pro Pro Arg Phe Ser Gly Ser Gly Ser Gly Thr Asp Phe Thr Leu Asn
        690                 695                 700

Ile His Pro Val Glu Lys Val Asp Ala Ala Thr Tyr His Cys Gln Gln
705                 710                 715                 720

Ser Thr Glu Asp Pro Trp Thr Phe Gly Gly Gly Thr Lys Leu Glu Ile
                    725                 730                 735

Lys

<210> SEQ ID NO 72
<211> LENGTH: 736
<212> TYPE: PRT
<213> ORGANISM: Homo sapiens

<400> SEQUENCE: 72

Met Glu Phe Gly Leu Ser Trp Val Phe Leu Val Ala Ile Ile Lys Gly
1               5                   10                  15

Val Gln Cys Gln Trp Gln Val Thr Gly Pro Gly Lys Phe Val Gln Ala
                20                  25                  30

Leu Val Gly Glu Asp Ala Val Phe Ser Cys Ser Leu Phe Pro Glu Thr
            35                  40                  45

Ser Ala Glu Ala Met Glu Val Arg Phe Phe Arg Asn Gln Phe His Ala
        50                  55                  60

Val Val His Leu Tyr Arg Asp Gly Glu Asp Trp Glu Ser Lys Gln Met
65                  70                  75                  80

Pro Gln Tyr Arg Gly Arg Thr Glu Phe Val Lys Asp Ser Ile Ala Gly
                85                  90                  95

Gly Arg Val Ser Leu Arg Leu Lys Asn Ile Thr Pro Ser Asp Ile Gly
            100                 105                 110

Leu Tyr Gly Cys Trp Phe Ser Ser Gln Ile Tyr Asp Glu Glu Ala Thr
        115                 120                 125

Trp Glu Leu Arg Val Ala Ala Leu Gly Ser Leu Pro Leu Ile Ser Ile
    130                 135                 140

Val Gly Tyr Val Asp Gly Gly Ile Gln Leu Leu Cys Leu Ser Ser Gly
145                 150                 155                 160

Trp Phe Pro Gln Pro Thr Ala Lys Trp Lys Gly Pro Gln Gly Gln Asp
                165                 170                 175

Leu Ser Ser Asp Ser Arg Ala Asn Ala Asp Gly Tyr Ser Leu Tyr Asp
            180                 185                 190

Val Glu Ile Ser Ile Val Gln Glu Asn Ala Gly Ser Ile Leu Cys
        195                 200                 205

Ser Ile His Leu Ala Glu Gln Ser His Glu Val Glu Ser Lys Val Leu
    210                 215                 220

Ile Gly Glu Thr Phe Phe Gln Pro Ser Pro Trp Arg Leu Ala Ser Gly
225                 230                 235                 240

Ser Gly Ser Arg Lys Gly Gly Lys Arg Gly Ser Lys Tyr Gly Pro Pro
                245                 250                 255

Cys Pro Pro Cys Pro Ala Pro Glu Phe Leu Gly Gly Pro Ser Val Phe
```

```
              260                 265                 270
Leu Phe Pro Pro Lys Pro Lys Asp Gln Leu Met Ile Ser Arg Thr Pro
            275                 280                 285

Glu Val Thr Cys Val Val Val Asp Val Ser Gln Glu Asp Pro Glu Val
290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Tyr Arg Val Val Ser Val
                325                 330                 335

Leu Thr Val Leu His Gln Asp Trp Leu Ser Gly Lys Glu Tyr Lys Cys
            340                 345                 350

Lys Val Ser Ser Lys Gly Leu Pro Ser Ser Ile Glu Lys Thr Ile Ser
        355                 360                 365

Asn Ala Thr Gly Gln Pro Arg Glu Pro Gln Val Tyr Thr Leu Pro Pro
    370                 375                 380

Ser Gln Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Arg Leu Thr Val Asp Lys Ser Arg Trp
        435                 440                 445

Gln Glu Gly Asn Val Phe Ser Cys Ser Val Leu His Glu Ala Leu His
    450                 455                 460

Asn His Tyr Thr Gln Lys Ser Leu Ser Leu Ser Leu Gly Lys Asp Glu
465                 470                 475                 480

Gly Gly Glu Asp Gly Ser Gln Val Gln Leu Gln Gln Ser Gly Ala Glu
                485                 490                 495

Leu Val Arg Pro Gly Ser Ser Val Lys Ile Ser Cys Lys Ala Ser Gly
            500                 505                 510

Tyr Ala Phe Ser Ser Tyr Trp Met Asn Trp Val Lys Gln Arg Pro Gly
        515                 520                 525

Gln Gly Leu Glu Trp Ile Gly Gln Ile Trp Pro Gly Asp Gly Asp Thr
    530                 535                 540

Asn Tyr Asn Gly Lys Phe Lys Gly Lys Ala Thr Leu Thr Ala Asp Glu
545                 550                 555                 560

Ser Ser Ser Thr Ala Tyr Met Gln Leu Ser Ser Leu Ala Ser Glu Asp
                565                 570                 575

Ser Ala Val Tyr Phe Cys Ala Arg Arg Glu Thr Thr Thr Val Gly Arg
            580                 585                 590

Tyr Tyr Tyr Ala Met Asp Tyr Trp Gly Gln Gly Thr Thr Val Thr Val
        595                 600                 605

Ser Ser Gly Gly Gly Gly Ser Gly Gly Gly Gly Ser Gly Gly Gly Gly
    610                 615                 620

Ser Asp Ile Gln Leu Thr Gln Ser Pro Ala Ser Leu Ala Val Ser Leu
625                 630                 635                 640

Gly Gln Arg Ala Thr Ile Ser Cys Lys Ala Ser Gln Ser Val Asp Tyr
                645                 650                 655

Asp Gly Asp Ser Tyr Leu Asn Trp Tyr Gln Gln Ile Pro Gly Gln Pro
            660                 665                 670

Pro Lys Leu Leu Ile Tyr Asp Ala Ser Asn Leu Val Ser Gly Ile Pro
        675                 680                 685
```

```
Pro Arg Phe Ser Gly Ser Gly Ser Gly Thr Asp Phe Thr Leu Asn Ile
    690                 695                 700

His Pro Val Glu Lys Val Asp Ala Ala Thr Tyr His Cys Gln Gln Ser
705                 710                 715                 720

Thr Glu Asp Pro Trp Thr Phe Gly Gly Gly Thr Lys Leu Glu Ile Lys
                725                 730                 735
```

<210> SEQ ID NO 73
<211> LENGTH: 739
<212> TYPE: PRT
<213> ORGANISM: Homo sapiens

<400> SEQUENCE: 73

```
Met Glu Phe Gly Leu Ser Trp Val Phe Leu Val Ala Ile Ile Lys Gly
1               5                   10                  15

Val Gln Cys Gln Trp Gln Val Phe Gly Pro Asp Lys Pro Val Gln Ala
                20                  25                  30

Leu Val Gly Glu Asp Ala Ala Phe Ser Cys Phe Leu Ser Pro Lys Thr
            35                  40                  45

Asn Ala Glu Ala Met Glu Val Arg Phe Phe Arg Gly Gln Phe Ser Ser
        50                  55                  60

Val Val His Leu Tyr Arg Asp Gly Lys Asp Gln Pro Phe Met Gln Met
65                  70                  75                  80

Pro Gln Tyr Gln Gly Arg Thr Lys Leu Val Lys Asp Ser Ile Ala Glu
                85                  90                  95

Gly Arg Ile Ser Leu Arg Leu Glu Asn Ile Thr Val Leu Asp Ala Gly
            100                 105                 110

Leu Tyr Gly Cys Arg Ile Ser Ser Gln Ser Tyr Tyr Gln Lys Ala Ile
        115                 120                 125

Trp Glu Leu Gln Val Ser Ala Leu Gly Ser Val Pro Leu Ile Ser Ile
130                 135                 140

Thr Gly Tyr Val Asp Arg Asp Ile Gln Leu Leu Cys Gln Ser Ser Gly
145                 150                 155                 160

Trp Phe Pro Arg Pro Thr Ala Lys Trp Lys Gly Pro Gln Gly Gln Asp
                165                 170                 175

Leu Ser Thr Asp Ser Arg Thr Asn Arg Asp Met His Gly Leu Phe Asp
            180                 185                 190

Val Glu Ile Ser Leu Thr Val Gln Glu Asn Ala Gly Ser Ile Ser Cys
        195                 200                 205

Ser Met Arg His Ala His Leu Ser Arg Glu Val Glu Ser Arg Val Gln
210                 215                 220

Ile Gly Asp Thr Phe Phe Glu Pro Ile Ser Trp His Leu Ala Thr Lys
225                 230                 235                 240

Gly Ser Gly Ser Asp Glu Gly Glu Asp Gly Ser Lys Tyr Gly Pro
                245                 250                 255

Pro Cys Pro Pro Cys Pro Ala Pro Glu Phe Leu Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Asp Val Ser Gln Glu Asp Pro Glu
290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
```

```
                325                 330                 335
Val Leu Thr Val Leu His Gln Asp Trp Leu Ser Gly Lys Glu Tyr Lys
            340                 345                 350
Cys Lys Val Ser Ser Lys Gly Leu Pro Ser Ser Ile Glu Lys Thr Ile
            355                 360                 365
Ser Asn Ala Thr Gly Gln Pro Arg Glu Pro Gln Val Tyr Thr Leu Pro
            370                 375                 380
Pro Ser Gln Glu Glu Met Thr Lys Asn Gln Val Ser Leu Thr Cys Leu
385                 390                 395                 400
Val Lys Gly Phe Tyr Pro Ser Asp Ile Ala Val Glu Trp Glu Ser Asn
                405                 410                 415
Gly Gln Pro Glu Asn Asn Tyr Lys Thr Thr Pro Pro Val Leu Asp Ser
            420                 425                 430
Asp Gly Ser Phe Phe Leu Tyr Ser Arg Leu Thr Val Asp Lys Ser Arg
            435                 440                 445
Trp Gln Glu Gly Asn Val Phe Ser Cys Ser Val Leu His Glu Ala Leu
            450                 455                 460
His Asn His Tyr Thr Gln Lys Ser Leu Ser Leu Ser Leu Gly Lys Arg
465                 470                 475                 480
Lys Gly Gly Lys Arg Gly Ser Gly Ser Gln Val Gln Leu Gln Gln Ser
                485                 490                 495
Gly Ala Glu Leu Val Arg Pro Gly Ser Ser Val Lys Ile Ser Cys Lys
            500                 505                 510
Ala Ser Gly Tyr Ala Phe Ser Ser Tyr Trp Met Asn Trp Val Lys Gln
            515                 520                 525
Arg Pro Gly Gln Gly Leu Glu Trp Ile Gly Gln Ile Trp Pro Gly Asp
            530                 535                 540
Gly Asp Thr Asn Tyr Asn Gly Lys Phe Lys Gly Lys Ala Thr Leu Thr
545                 550                 555                 560
Ala Asp Glu Ser Ser Ser Thr Ala Tyr Met Gln Leu Ser Ser Leu Ala
                565                 570                 575
Ser Glu Asp Ser Ala Val Tyr Phe Cys Ala Arg Arg Glu Thr Thr Thr
            580                 585                 590
Val Gly Arg Tyr Tyr Tyr Ala Met Asp Tyr Trp Gly Gln Gly Thr Thr
            595                 600                 605
Val Thr Val Ser Ser Gly Gly Gly Gly Ser Gly Gly Gly Gly Ser Gly
            610                 615                 620
Gly Gly Gly Ser Asp Ile Gln Leu Thr Gln Ser Pro Ala Ser Leu Ala
625                 630                 635                 640
Val Ser Leu Gly Gln Arg Ala Thr Ile Ser Cys Lys Ala Ser Gln Ser
                645                 650                 655
Val Asp Tyr Asp Gly Asp Ser Tyr Leu Asn Trp Tyr Gln Gln Ile Pro
            660                 665                 670
Gly Gln Pro Pro Lys Leu Leu Ile Tyr Asp Ala Ser Asn Leu Val Ser
            675                 680                 685
Gly Ile Pro Pro Arg Phe Ser Gly Ser Gly Ser Gly Thr Asp Phe Thr
            690                 695                 700
Leu Asn Ile His Pro Val Glu Lys Val Asp Ala Ala Thr Tyr His Cys
705                 710                 715                 720
Gln Gln Ser Thr Glu Asp Pro Trp Thr Phe Gly Gly Gly Thr Lys Leu
                725                 730                 735
Glu Ile Lys
```

<210> SEQ ID NO 74
<211> LENGTH: 725
<212> TYPE: PRT
<213> ORGANISM: Homo sapiens

<400> SEQUENCE: 74

```
Met Glu Phe Gly Leu Ser Trp Val Phe Leu Val Ala Ile Ile Lys Gly
  1               5                  10                  15

Val Gln Cys Gln Trp Gln Val Thr Gly Pro Gly Lys Pro Phe Gln Ala
             20                  25                  30

Leu Val Gly Glu Asp Ala Val Phe Ser Cys Ser Leu Phe Pro Glu Thr
         35                  40                  45

Ser Ala Glu Ala Met Glu Val Arg Phe Phe Arg Asn Gln Phe His Ala
     50                  55                  60

Val Val His Leu Tyr Arg Asp Gly Glu Asp Trp Glu Ser Lys Gln Met
 65                  70                  75                  80

Pro Gln Tyr Arg Gly Arg Thr Glu Phe Val Lys Asp Ser Ile Ala Gly
                 85                  90                  95

Gly Arg Val Ser Leu Arg Leu Lys Asn Ile Thr Pro Ser Asp Ile Gly
            100                 105                 110

Leu Tyr Gly Cys Trp Phe Ser Ser Gln Ile Tyr Asp Glu Glu Ala Thr
        115                 120                 125

Trp Glu Leu Arg Val Ala Ala Leu Gly Ser Leu Pro Leu Ile Ser Ile
    130                 135                 140

Val Gly Tyr Val Asp Gly Gly Ile Gln Leu Leu Cys Leu Ser Ser Gly
145                 150                 155                 160

Trp Phe Pro Gln Pro Thr Ala Lys Trp Lys Gly Pro Gln Gly Gln Asp
                165                 170                 175

Leu Ser Ser Asp Ser Arg Ala Asn Ala Asp Gly Tyr Ser Leu Tyr Asp
            180                 185                 190

Val Glu Ile Ser Ile Ile Val Gln Glu Asn Ala Gly Ser Ile Leu Cys
        195                 200                 205

Ser Ile His Leu Ala Glu Gln Ser His Glu Val Glu Ser Lys Val Leu
    210                 215                 220

Ile Gly Glu Thr Phe Phe Gln Pro Ser Pro Trp Arg Leu Ala Ser Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380
```

```
Asn Gln Val Ser Leu Tyr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys Gly Gly Ser Gln Val Gln Leu Gln
465                 470                 475                 480

Gln Ser Gly Ala Glu Leu Val Arg Pro Gly Ser Ser Val Lys Ile Ser
                485                 490                 495

Cys Lys Ala Ser Gly Tyr Ala Phe Ser Ser Tyr Trp Met Asn Trp Val
            500                 505                 510

Lys Gln Arg Pro Gly Gln Gly Leu Glu Trp Ile Gly Gln Ile Trp Pro
        515                 520                 525

Gly Asp Gly Asp Thr Asn Tyr Asn Gly Lys Phe Lys Gly Lys Ala Thr
    530                 535                 540

Leu Thr Ala Asp Glu Ser Ser Ser Thr Ala Tyr Met Gln Leu Ser Ser
545                 550                 555                 560

Leu Ala Ser Glu Asp Ser Ala Val Tyr Phe Cys Ala Arg Arg Glu Thr
                565                 570                 575

Thr Thr Val Gly Arg Tyr Tyr Ala Met Asp Tyr Trp Gly Gln Gly
            580                 585                 590

Thr Thr Val Thr Val Ser Ser Gly Gly Gly Ser Gly Gly Gly Gly
        595                 600                 605

Ser Gly Gly Gly Gly Ser Asp Ile Gln Leu Thr Gln Ser Pro Ala Ser
    610                 615                 620

Leu Ala Val Ser Leu Gly Gln Arg Ala Thr Ile Ser Cys Lys Ala Ser
625                 630                 635                 640

Gln Ser Val Asp Tyr Asp Gly Asp Ser Tyr Leu Asn Trp Tyr Gln Gln
                645                 650                 655

Ile Pro Gly Gln Pro Pro Lys Leu Leu Ile Tyr Asp Ala Ser Asn Leu
            660                 665                 670

Val Ser Gly Ile Pro Pro Arg Phe Ser Gly Ser Gly Ser Gly Thr Asp
        675                 680                 685

Phe Thr Leu Asn Ile His Pro Val Glu Lys Val Asp Ala Ala Thr Tyr
    690                 695                 700

His Cys Gln Gln Ser Thr Glu Asp Pro Trp Thr Phe Gly Gly Gly Thr
705                 710                 715                 720

Lys Leu Glu Ile Lys
                725

<210> SEQ ID NO 75
<211> LENGTH: 726
<212> TYPE: PRT
<213> ORGANISM: Homo sapiens

<400> SEQUENCE: 75

Met Glu Phe Gly Leu Ser Trp Val Phe Leu Val Ala Ile Ile Lys Gly
1               5                   10                  15

Val Gln Cys Gln Trp Gln Val Phe Gly Pro Asp Lys Pro Val Gln Ala
```

```
            20                  25                  30
Leu Val Gly Glu Asp Ala Ala Phe Ser Cys Phe Leu Ser Pro Lys Thr
            35                  40                  45

Asn Ala Glu Ala Met Glu Val Arg Phe Phe Arg Gly Gln Phe Ser Ser
            50                  55                  60

Val Val His Leu Tyr Arg Asp Gly Lys Asp Gln Pro Phe Met Gln Met
65                  70                  75                  80

Pro Gln Tyr Gln Gly Arg Thr Lys Leu Val Lys Asp Ser Ile Ala Glu
                    85                  90                  95

Gly Arg Ile Ser Leu Arg Leu Glu Asn Ile Thr Val Leu Asp Ala Gly
                100                 105                 110

Leu Tyr Gly Cys Arg Ile Ser Ser Gln Ser Tyr Tyr Gln Lys Ala Ile
            115                 120                 125

Trp Glu Leu Gln Val Ser Ala Leu Gly Ser Val Pro Leu Ile Ser Ile
            130                 135                 140

Thr Gly Tyr Val Asp Arg Asp Ile Gln Leu Leu Cys Gln Ser Ser Gly
145                 150                 155                 160

Trp Phe Pro Arg Pro Thr Ala Lys Trp Lys Gly Pro Gln Gly Gln Asp
                165                 170                 175

Leu Ser Thr Asp Ser Arg Thr Asn Arg Asp Met His Gly Leu Phe Asp
                180                 185                 190

Val Glu Ile Ser Leu Thr Val Gln Glu Asn Ala Gly Ser Ile Ser Cys
            195                 200                 205

Ser Met Arg His Ala His Leu Ser Arg Glu Val Glu Ser Arg Val Gln
            210                 215                 220

Ile Gly Asp Thr Phe Phe Glu Pro Ile Ser Trp His Leu Ala Thr Lys
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
            290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
            370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Thr
                420                 425                 430

Ser Lys Leu Thr Val Asp Lys Ser Arg Trp Gln Gln Gly Asn Val Phe
            435                 440                 445
```

```
Ser Cys Ser Val Met His Glu Ala Leu His Asn His Tyr Thr Gln Lys
    450                 455                 460
Ser Leu Ser Leu Ser Pro Gly Lys Gly Gly Ser Gln Val Gln Leu
465                 470                 475                 480
Gln Gln Ser Gly Ala Glu Leu Val Arg Pro Gly Ser Ser Val Lys Ile
                485                 490                 495
Ser Cys Lys Ala Ser Gly Tyr Ala Phe Ser Ser Tyr Trp Met Asn Trp
            500                 505                 510
Val Lys Gln Arg Pro Gly Gln Gly Leu Glu Trp Ile Gly Gln Ile Trp
        515                 520                 525
Pro Gly Asp Gly Asp Thr Asn Tyr Asn Gly Lys Phe Lys Gly Lys Ala
    530                 535                 540
Thr Leu Thr Ala Asp Glu Ser Ser Ser Thr Ala Tyr Met Gln Leu Ser
545                 550                 555                 560
Ser Leu Ala Ser Glu Asp Ser Ala Val Tyr Phe Cys Ala Arg Arg Glu
                565                 570                 575
Thr Thr Thr Val Gly Arg Tyr Tyr Tyr Ala Met Asp Tyr Trp Gly Gln
            580                 585                 590
Gly Thr Thr Val Thr Val Ser Ser Gly Gly Gly Ser Gly Gly Gly
        595                 600                 605
Gly Ser Gly Gly Gly Ser Asp Ile Gln Leu Thr Gln Ser Pro Ala
    610                 615                 620
Ser Leu Ala Val Ser Leu Gly Gln Arg Ala Thr Ile Ser Cys Lys Ala
625                 630                 635                 640
Ser Gln Ser Val Asp Tyr Asp Gly Asp Ser Tyr Leu Asn Trp Tyr Gln
                645                 650                 655
Gln Ile Pro Gly Gln Pro Pro Lys Leu Leu Ile Tyr Asp Ala Ser Asn
            660                 665                 670
Leu Val Ser Gly Ile Pro Pro Arg Phe Ser Gly Ser Gly Ser Gly Thr
        675                 680                 685
Asp Phe Thr Leu Asn Ile His Pro Val Glu Lys Val Asp Ala Ala Thr
    690                 695                 700
Tyr His Cys Gln Gln Ser Thr Glu Asp Pro Trp Thr Phe Gly Gly Gly
705                 710                 715                 720
Thr Lys Leu Glu Ile Lys
                725

<210> SEQ ID NO 76
<211> LENGTH: 728
<212> TYPE: PRT
<213> ORGANISM: Mus musculus

<400> SEQUENCE: 76

Met Glu Phe Gly Leu Ser Trp Val Phe Leu Val Ala Ile Ile Lys Gly
1               5                   10                  15
Val Gln Cys Glu Val Ser Trp Phe Ser Val Lys Gly Pro Ala Glu Pro
            20                  25                  30
Ile Thr Val Leu Leu Gly Thr Glu Ala Thr Leu Pro Cys Gln Leu Ser
        35                  40                  45
Pro Glu Gln Ser Ala Ala Arg Met His Ile Arg Trp Tyr Arg Ala Gln
    50                  55                  60
Pro Thr Pro Ala Val Leu Val Phe His Asn Gly Gln Glu Gln Gly Glu
65                  70                  75                  80
Val Gln Met Pro Glu Tyr Arg Gly Arg Thr Gln Met Val Arg Gln Ala
```

```
                        85                  90                  95
Ile Asp Met Gly Ser Val Ala Leu Gln Ile Gln Gln Val Gln Ala Ser
            100                 105                 110

Asp Asp Gly Leu Tyr His Cys Gln Phe Thr Asp Gly Phe Thr Ser Gln
            115                 120                 125

Glu Val Ser Met Glu Leu Arg Val Ile Gly Leu Gly Ser Ala Pro Leu
    130                 135                 140

Val His Met Thr Gly Pro Glu Asn Asp Gly Ile Arg Val Leu Cys Ser
145                 150                 155                 160

Ser Ser Gly Trp Phe Pro Lys Pro Lys Val Gln Trp Arg Asp Thr Ser
                165                 170                 175

Gly Asn Met Leu Leu Ser Ser Glu Leu Gln Thr Gln Asp Arg Glu
            180                 185                 190

Gly Leu Phe Gln Val Glu Val Ser Leu Leu Val Thr Asp Arg Ala Ile
        195                 200                 205

Gly Asn Val Ile Cys Ser Ile Gln Asn Pro Met Tyr Asp Gln Glu Lys
    210                 215                 220

Ser Lys Ala Ile Leu Leu Pro Glu Pro Phe Phe Pro Lys Thr Cys Pro
225                 230                 235                 240

Trp Lys Gly Ser Gly Ser Asp Glu Gly Gly Glu Asp Gly Val Pro Arg
                245                 250                 255

Asp Cys Gly Cys Lys Pro Cys Ile Cys Thr Val Pro Glu Val Ser Ser
            260                 265                 270

Val Phe Ile Phe Pro Pro Lys Pro Lys Asp Val Leu Thr Ile Thr Leu
        275                 280                 285

Thr Pro Lys Val Thr Cys Val Val Asp Ile Ser Lys Asp Asp Pro
    290                 295                 300

Glu Val Gln Phe Ser Trp Phe Val Asp Asp Val Glu Val His Thr Ala
305                 310                 315                 320

Gln Thr Gln Pro Arg Glu Glu Gln Phe Asn Ser Thr Phe Arg Ser Val
                325                 330                 335

Ser Glu Leu Pro Ile Met His Gln Asp Trp Leu Asn Gly Lys Glu Phe
            340                 345                 350

Lys Cys Arg Val Asn Ser Ala Ala Phe Pro Ala Pro Ile Glu Lys Thr
        355                 360                 365

Ile Ser Lys Thr Lys Gly Arg Pro Lys Ala Pro Gln Val Tyr Thr Ile
    370                 375                 380

Pro Pro Pro Lys Glu Gln Met Ala Lys Asp Lys Val Ser Leu Thr Cys
385                 390                 395                 400

Met Ile Thr Asp Phe Phe Pro Glu Asp Ile Thr Val Glu Trp Gln Trp
                405                 410                 415

Asn Gly Gln Pro Ala Glu Asn Tyr Lys Asn Thr Gln Pro Ile Met Asp
            420                 425                 430

Thr Asp Gly Ser Tyr Phe Val Tyr Ser Lys Leu Asn Val Gln Lys Ser
        435                 440                 445

Asn Trp Glu Ala Gly Asn Thr Phe Thr Cys Ser Val Leu His Glu Gly
    450                 455                 460

Leu His Asn His His Thr Glu Lys Ser Leu Ser His Ser Pro Gly Ile
465                 470                 475                 480

Arg Lys Gly Gly Lys Arg Gly Ser Gly Ser Glu Val Gln Leu Gln Gln
                485                 490                 495

Ser Gly Ala Glu Leu Val Arg Pro Gly Thr Ser Val Lys Leu Ser Cys
            500                 505                 510
```

Lys Val Ser Gly Asp Thr Ile Thr Phe Tyr Tyr Met His Phe Val Lys
            515                 520                 525

Gln Arg Pro Gly Gln Gly Leu Glu Trp Ile Gly Arg Ile Asp Pro Glu
        530                 535                 540

Asp Glu Ser Thr Lys Tyr Ser Glu Lys Phe Lys Asn Lys Ala Thr Leu
545                 550                 555                 560

Thr Ala Asp Thr Ser Ser Asn Thr Ala Tyr Leu Lys Leu Ser Ser Leu
                565                 570                 575

Thr Ser Glu Asp Thr Ala Thr Tyr Phe Cys Ile Tyr Gly Gly Tyr Tyr
            580                 585                 590

Phe Asp Tyr Trp Gly Gln Gly Val Met Val Thr Val Ser Ser Gly Gly
        595                 600                 605

Gly Gly Ser Gly Gly Gly Gly Ser Gly Gly Gly Gly Ser Asp Ile Gln
            610                 615                 620

Met Thr Gln Ser Pro Ala Ser Leu Ser Thr Ser Leu Gly Glu Thr Val
625                 630                 635                 640

Thr Ile Gln Cys Gln Ala Ser Glu Asp Ile Tyr Ser Gly Leu Ala Trp
                645                 650                 655

Tyr Gln Gln Lys Pro Gly Lys Ser Pro Gln Leu Leu Ile Tyr Gly Ala
            660                 665                 670

Ser Asp Leu Gln Asp Gly Val Pro Ser Arg Phe Ser Gly Ser Gly Ser
        675                 680                 685

Gly Thr Gln Tyr Ser Leu Lys Ile Thr Ser Met Gln Thr Glu Asp Glu
            690                 695                 700

Gly Val Tyr Phe Cys Gln Gln Gly Leu Thr Tyr Pro Arg Thr Phe Gly
705                 710                 715                 720

Gly Gly Thr Lys Leu Glu Leu Lys
                725

<210> SEQ ID NO 77
<211> LENGTH: 668
<212> TYPE: PRT
<213> ORGANISM: Mus musculus

<400> SEQUENCE: 77

Met Glu Phe Gly Leu Ser Trp Val Phe Leu Val Ala Ile Ile Lys Gly
1               5                   10                  15

Val Gln Cys Glu Gln Leu Pro Glu Tyr Ser Gln Arg Thr Ser Leu Val
                20                  25                  30

Lys Glu Gln Phe His Gln Gly Thr Ala Ala Val Arg Ile Leu Asn Val
            35                  40                  45

Gln Ala Pro Asp Ser Gly Ile Tyr Ile Cys His Phe Lys Gln Gly Val
        50                  55                  60

Phe Tyr Glu Glu Ala Ile Leu Glu Leu Lys Val Ala Ala Met Gly Ser
65                  70                  75                  80

Val Pro Glu Val Tyr Ile Lys Gly Pro Glu Asp Gly Gly Val Cys Val
                85                  90                  95

Val Cys Ile Thr Ser Gly Trp Tyr Pro Glu Pro Gln Val His Trp Lys
            100                 105                 110

Asp Ser Arg Gly Glu Lys Leu Thr Ala Ser Leu Glu Ile His Ser Glu
        115                 120                 125

Asp Ala Gln Gly Leu Phe Arg Thr Glu Thr Ser Leu Val Val Arg Asp
    130                 135                 140

Ser Ser Val Arg Asn Val Thr Cys Ser Thr Phe Asn Pro Ile Leu Gly

```
            145                 150                 155                 160
        Gln Glu Lys Ala Met Ala Met Phe Leu Pro Glu Pro Phe Pro Lys
                            165                 170                 175

Val Ser Pro Trp Lys Pro Gly Ser Gly Ser Asp Glu Gly Gly Glu Asp
                        180                 185                 190

Gly Val Pro Arg Asp Cys Gly Cys Lys Pro Cys Ile Cys Thr Val Pro
                    195                 200                 205

Glu Val Ser Ser Val Phe Ile Phe Pro Pro Lys Pro Lys Asp Val Leu
                210                 215                 220

Thr Ile Thr Leu Thr Pro Lys Val Thr Cys Val Val Asp Ile Ser
        225                 230                 235                 240

Lys Asp Asp Pro Glu Val Gln Phe Ser Trp Phe Val Asp Asp Val Glu
                        245                 250                 255

Val His Thr Ala Gln Thr Gln Pro Arg Glu Glu Gln Phe Asn Ser Thr
                    260                 265                 270

Phe Arg Ser Val Ser Glu Leu Pro Ile Met His Gln Asp Trp Leu Asn
                275                 280                 285

Gly Lys Glu Phe Lys Cys Arg Val Asn Ser Ala Ala Phe Pro Ala Pro
        290                 295                 300

Ile Glu Lys Thr Ile Ser Lys Thr Lys Gly Arg Pro Lys Ala Pro Gln
        305                 310                 315                 320

Val Tyr Thr Ile Pro Pro Pro Lys Glu Gln Met Ala Lys Asp Lys Val
                        325                 330                 335

Ser Leu Thr Cys Met Ile Thr Asp Phe Phe Pro Glu Asp Ile Thr Val
                    340                 345                 350

Glu Trp Gln Trp Asn Gly Gln Pro Ala Glu Asn Tyr Lys Asn Thr Gln
                355                 360                 365

Pro Ile Met Asp Thr Asp Gly Ser Tyr Phe Val Tyr Ser Lys Leu Asn
                370                 375                 380

Val Gln Lys Ser Asn Trp Glu Ala Gly Asn Thr Phe Thr Cys Ser Val
        385                 390                 395                 400

Leu His Glu Gly Leu His Asn His His Thr Glu Lys Ser Leu Ser His
                        405                 410                 415

Ser Pro Gly Ile Arg Lys Gly Lys Arg Gly Ser Gly Ser Glu Val
                    420                 425                 430

Gln Leu Gln Gln Ser Gly Ala Glu Leu Val Arg Pro Gly Thr Ser Val
                435                 440                 445

Lys Leu Ser Cys Lys Val Ser Gly Asp Thr Ile Thr Phe Tyr Tyr Met
                450                 455                 460

His Phe Val Lys Gln Arg Pro Gly Gln Gly Leu Glu Trp Ile Gly Arg
        465                 470                 475                 480

Ile Asp Pro Glu Asp Glu Ser Thr Lys Tyr Ser Glu Lys Phe Lys Asn
                        485                 490                 495

Lys Ala Thr Leu Thr Ala Asp Thr Ser Ser Asn Thr Ala Tyr Leu Lys
                    500                 505                 510

Leu Ser Ser Leu Thr Ser Glu Asp Thr Ala Thr Tyr Phe Cys Ile Tyr
                515                 520                 525

Gly Gly Tyr Tyr Phe Asp Tyr Trp Gly Gln Gly Val Met Val Thr Val
                530                 535                 540

Ser Ser Gly Gly Gly Gly Ser Gly Gly Gly Gly Ser Gly Gly Gly Gly
        545                 550                 555                 560

Ser Asp Ile Gln Met Thr Gln Ser Pro Ala Ser Leu Ser Thr Ser Leu
                        565                 570                 575
```

```
Gly Glu Thr Val Thr Ile Gln Cys Gln Ala Ser Glu Asp Ile Tyr Ser
            580                 585                 590

Gly Leu Ala Trp Tyr Gln Gln Lys Pro Gly Lys Ser Pro Gln Leu Leu
            595                 600                 605

Ile Tyr Gly Ala Ser Asp Leu Gln Asp Gly Val Pro Ser Arg Phe Ser
            610                 615                 620

Gly Ser Gly Ser Gly Thr Gln Tyr Ser Leu Lys Ile Thr Ser Met Gln
625                 630                 635                 640

Thr Glu Asp Glu Gly Val Tyr Phe Cys Gln Gln Gly Leu Thr Tyr Pro
                645                 650                 655

Arg Thr Phe Gly Gly Gly Thr Lys Leu Glu Leu Lys
            660                 665

<210> SEQ ID NO 78
<211> LENGTH: 728
<212> TYPE: PRT
<213> ORGANISM: Mus musculus

<400> SEQUENCE: 78

Met Glu Phe Gly Leu Ser Trp Val Phe Leu Val Ala Ile Ile Lys Gly
1               5                   10                  15

Val Gln Cys Glu Val Ser Trp Phe Ser Val Lys Gly Pro Ala Glu Pro
            20                  25                  30

Ile Thr Val Leu Leu Gly Thr Glu Ala Thr Leu Pro Cys Gln Leu Ser
            35                  40                  45

Pro Glu Gln Ser Ala Ala Arg Met His Ile Arg Trp Tyr Arg Ala Gln
50                  55                  60

Pro Thr Pro Ala Val Leu Val Phe His Asn Gly Gln Glu Gln Gly Glu
65                  70                  75                  80

Val Gln Met Pro Glu Tyr Arg Gly Arg Thr Gln Met Val Arg Gln Ala
                85                  90                  95

Ile Asp Met Gly Ser Val Ala Leu Gln Ile Gln Asn Val Gln Ala Ser
            100                 105                 110

Asp Asp Gly Leu Tyr His Cys Gln Phe Thr Asp Gly Phe Thr Ser Gln
            115                 120                 125

Glu Val Ser Met Glu Leu Arg Val Ile Gly Leu Gly Ser Ala Pro Leu
            130                 135                 140

Val His Met Thr Gly Pro Glu Asn Asp Gly Ile Arg Val Leu Cys Ser
145                 150                 155                 160

Ser Ser Gly Trp Phe Pro Lys Pro Lys Val Gln Trp Arg Asp Thr Ser
                165                 170                 175

Gly Asn Met Leu Leu Ser Ser Ser Glu Leu Gln Thr Gln Asp Arg Glu
            180                 185                 190

Gly Leu Phe Gln Val Glu Val Ser Leu Leu Val Thr Asp Arg Ala Ile
            195                 200                 205

Gly Asn Val Ile Cys Ser Ile Gln Asn Pro Met Tyr Asp Gln Glu Lys
            210                 215                 220

Ser Lys Ala Ile Leu Leu Pro Glu Pro Phe Phe Pro Lys Thr Cys Pro
225                 230                 235                 240

Trp Lys Gly Ser Gly Ser Asp Glu Gly Gly Glu Asp Gly Val Pro Arg
                245                 250                 255

Asp Cys Gly Cys Lys Pro Cys Ile Cys Thr Val Pro Glu Val Ser Ser
            260                 265                 270

Val Phe Ile Phe Pro Pro Lys Pro Lys Asp Val Leu Thr Ile Thr Leu
```

-continued

```
            275                 280                 285
Thr Pro Lys Val Thr Cys Val Val Asp Ile Ser Lys Asp Asp Pro
        290                 295                 300
Glu Val Gln Phe Ser Trp Phe Val Asp Asp Val Glu Val His Thr Ala
305                 310                 315                 320
Gln Thr Gln Pro Arg Glu Glu Gln Phe Asn Ser Thr Phe Arg Ser Val
                325                 330                 335
Ser Glu Leu Pro Ile Met His Gln Asp Trp Leu Asn Gly Lys Glu Phe
            340                 345                 350
Lys Cys Arg Val Asn Ser Ala Ala Phe Pro Ala Pro Ile Glu Lys Thr
        355                 360                 365
Ile Ser Lys Thr Lys Gly Arg Pro Lys Ala Pro Gln Val Tyr Thr Ile
    370                 375                 380
Pro Pro Pro Lys Glu Gln Met Ala Lys Asp Lys Val Ser Leu Thr Cys
385                 390                 395                 400
Met Ile Thr Asp Phe Phe Pro Glu Asp Ile Thr Val Glu Trp Gln Trp
                405                 410                 415
Asn Gly Gln Pro Ala Glu Asn Tyr Lys Asn Thr Gln Pro Ile Met Asp
            420                 425                 430
Thr Asp Gly Ser Tyr Phe Val Tyr Ser Lys Leu Asn Val Gln Lys Ser
        435                 440                 445
Asn Trp Glu Ala Gly Asn Thr Phe Thr Cys Ser Val Leu His Glu Gly
    450                 455                 460
Leu His Asn His His Thr Glu Lys Ser Leu Ser His Ser Pro Gly Ile
465                 470                 475                 480
Arg Lys Gly Gly Lys Arg Gly Ser Gly Ser Asp Ile Gln Met Thr Gln
                485                 490                 495
Ser Pro Ala Ser Leu Ser Thr Ser Leu Gly Glu Thr Val Thr Ile Gln
            500                 505                 510
Cys Gln Ala Ser Glu Asp Ile Tyr Ser Gly Leu Ala Trp Tyr Gln Gln
        515                 520                 525
Lys Pro Gly Lys Ser Pro Gln Leu Leu Ile Tyr Gly Ala Ser Asp Leu
    530                 535                 540
Gln Asp Gly Val Pro Ser Arg Phe Ser Gly Ser Gly Ser Gly Thr Gln
545                 550                 555                 560
Tyr Ser Leu Lys Ile Thr Ser Met Gln Thr Glu Asp Glu Gly Val Tyr
                565                 570                 575
Phe Cys Gln Gln Gly Leu Thr Tyr Pro Arg Thr Phe Gly Gly Gly Thr
            580                 585                 590
Lys Leu Glu Leu Lys Gly Gly Gly Ser Gly Gly Gly Gly Ser Gly
        595                 600                 605
Gly Gly Gly Ser Glu Val Gln Leu Gln Gln Ser Gly Ala Glu Leu Val
    610                 615                 620
Arg Pro Gly Thr Ser Val Lys Leu Ser Cys Lys Val Ser Gly Asp Thr
625                 630                 635                 640
Ile Thr Phe Tyr Tyr Met His Phe Val Lys Gln Arg Pro Gly Gln Gly
                645                 650                 655
Leu Glu Trp Ile Gly Arg Ile Asp Pro Glu Asp Glu Ser Thr Lys Tyr
            660                 665                 670
Ser Glu Lys Phe Lys Asn Lys Ala Thr Leu Thr Ala Asp Thr Ser Ser
        675                 680                 685
Asn Thr Ala Tyr Leu Lys Leu Ser Ser Leu Thr Ser Glu Asp Thr Ala
    690                 695                 700
```

```
Thr Tyr Phe Cys Ile Tyr Gly Gly Tyr Tyr Phe Asp Tyr Trp Gly Gln
705                 710                 715                 720

Gly Val Met Val Thr Val Ser Ser
                725
```

<210> SEQ ID NO 79
<211> LENGTH: 668
<212> TYPE: PRT
<213> ORGANISM: Mus musculus

<400> SEQUENCE: 79

```
Met Glu Phe Gly Leu Ser Trp Val Phe Leu Val Ala Ile Ile Lys Gly
1               5                   10                  15

Val Gln Cys Glu Gln Leu Pro Glu Tyr Ser Gln Arg Thr Ser Leu Val
                20                  25                  30

Lys Glu Gln Phe His Gln Gly Thr Ala Ala Val Arg Ile Leu Asn Val
            35                  40                  45

Gln Ala Pro Asp Ser Gly Ile Tyr Ile Cys His Phe Lys Gln Gly Val
        50                  55                  60

Phe Tyr Glu Glu Ala Ile Leu Glu Leu Lys Val Ala Ala Met Gly Ser
65                  70                  75                  80

Val Pro Glu Val Tyr Ile Lys Gly Pro Glu Asp Gly Gly Val Cys Val
                85                  90                  95

Val Cys Ile Thr Ser Gly Trp Tyr Pro Glu Pro Gln Val His Trp Lys
                100                 105                 110

Asp Ser Arg Gly Glu Lys Leu Thr Ala Ser Leu Glu Ile His Ser Glu
            115                 120                 125

Asp Ala Gln Gly Leu Phe Arg Thr Glu Thr Ser Leu Val Val Arg Asp
        130                 135                 140

Ser Ser Val Arg Asn Val Thr Cys Ser Thr Phe Asn Pro Ile Leu Gly
145                 150                 155                 160

Gln Glu Lys Ala Met Ala Met Phe Leu Pro Glu Pro Phe Phe Pro Lys
                165                 170                 175

Val Ser Pro Trp Lys Pro Gly Ser Gly Ser Asp Glu Gly Gly Glu Asp
                180                 185                 190

Gly Val Pro Arg Asp Cys Gly Cys Lys Pro Cys Ile Cys Thr Val Pro
            195                 200                 205

Glu Val Ser Ser Val Phe Ile Phe Pro Pro Lys Pro Lys Asp Val Leu
        210                 215                 220

Thr Ile Thr Leu Thr Pro Lys Val Thr Cys Val Val Val Asp Ile Ser
225                 230                 235                 240

Lys Asp Asp Pro Glu Val Gln Phe Ser Trp Phe Val Asp Asp Val Glu
                245                 250                 255

Val His Thr Ala Gln Thr Gln Pro Arg Glu Glu Gln Phe Asn Ser Thr
                260                 265                 270

Phe Arg Ser Val Ser Glu Leu Pro Ile Met His Gln Asp Trp Leu Asn
            275                 280                 285

Gly Lys Glu Phe Lys Cys Arg Val Asn Ser Ala Ala Phe Pro Ala Pro
        290                 295                 300

Ile Glu Lys Thr Ile Ser Lys Thr Lys Gly Arg Pro Lys Ala Pro Gln
305                 310                 315                 320

Val Tyr Thr Ile Pro Pro Pro Lys Glu Gln Met Ala Lys Asp Lys Val
                325                 330                 335

Ser Leu Thr Cys Met Ile Thr Asp Phe Phe Pro Glu Asp Ile Thr Val
```

```
                    340                 345                 350
Glu Trp Gln Trp Asn Gly Gln Pro Ala Glu Asn Tyr Lys Asn Thr Gln
            355                 360                 365
Pro Ile Met Asp Thr Asp Gly Ser Tyr Phe Val Tyr Ser Lys Leu Asn
        370                 375                 380
Val Gln Lys Ser Asn Trp Glu Ala Gly Asn Thr Phe Thr Cys Ser Val
385                 390                 395                 400
Leu His Glu Gly Leu His Asn His Thr Glu Lys Ser Leu Ser His
                405                 410                 415
Ser Pro Gly Ile Arg Lys Gly Lys Arg Gly Ser Gly Ser Asp Ile
                420                 425                 430
Gln Met Thr Gln Ser Pro Ala Ser Leu Ser Thr Ser Leu Gly Glu Thr
            435                 440                 445
Val Thr Ile Gln Cys Gln Ala Ser Glu Asp Ile Tyr Ser Gly Leu Ala
        450                 455                 460
Trp Tyr Gln Gln Lys Pro Gly Lys Ser Pro Gln Leu Leu Ile Tyr Gly
465                 470                 475                 480
Ala Ser Asp Leu Gln Asp Gly Val Pro Ser Arg Phe Ser Gly Ser Gly
                485                 490                 495
Ser Gly Thr Gln Tyr Ser Leu Lys Ile Thr Ser Met Gln Thr Glu Asp
                500                 505                 510
Glu Gly Val Tyr Phe Cys Gln Gln Gly Leu Thr Tyr Pro Arg Thr Phe
            515                 520                 525
Gly Gly Gly Thr Lys Leu Glu Leu Lys Gly Gly Gly Ser Gly Gly
        530                 535                 540
Gly Gly Ser Gly Gly Gly Ser Glu Val Gln Leu Gln Gln Ser Gly
545                 550                 555                 560
Ala Glu Leu Val Arg Pro Gly Thr Ser Val Lys Leu Ser Cys Lys Val
                565                 570                 575
Ser Gly Asp Thr Ile Thr Phe Tyr Tyr Met His Phe Val Lys Gln Arg
                580                 585                 590
Pro Gly Gln Gly Leu Glu Trp Ile Gly Arg Ile Asp Pro Glu Asp Glu
            595                 600                 605
Ser Thr Lys Tyr Ser Glu Lys Phe Lys Asn Lys Ala Thr Leu Thr Ala
        610                 615                 620
Asp Thr Ser Ser Asn Thr Ala Tyr Leu Lys Leu Ser Ser Leu Thr Ser
625                 630                 635                 640
Glu Asp Thr Ala Thr Tyr Phe Cys Ile Tyr Gly Gly Tyr Tyr Phe Asp
                645                 650                 655
Tyr Trp Gly Gln Gly Val Met Val Thr Val Ser Ser
                660                 665

<210> SEQ ID NO 80
<211> LENGTH: 725
<212> TYPE: PRT
<213> ORGANISM: Homo sapiens

<400> SEQUENCE: 80

Met Glu Phe Gly Leu Ser Trp Val Phe Leu Val Ala Ile Ile Lys Gly
1               5                   10                  15
Val Gln Cys Gln Trp Gln Val Thr Gly Pro Gly Lys Phe Val Gln Ala
            20                  25                  30
Leu Val Gly Glu Asp Ala Val Phe Ser Cys Ser Leu Phe Pro Glu Thr
        35                  40                  45
```

Ser Ala Glu Ala Met Glu Val Arg Phe Phe Arg Asn Gln Phe His Ala
    50                  55                  60

Val Val His Leu Tyr Arg Asp Gly Glu Asp Trp Glu Ser Lys Gln Met
65                  70                  75                  80

Pro Gln Tyr Arg Gly Arg Thr Glu Phe Val Lys Asp Ser Ile Ala Gly
                85                  90                  95

Gly Arg Val Ser Leu Arg Leu Lys Asn Ile Thr Pro Ser Asp Ile Gly
                100                 105                 110

Leu Tyr Gly Cys Trp Phe Ser Gln Ile Tyr Asp Glu Glu Ala Thr
                115                 120                 125

Trp Glu Leu Arg Val Ala Ala Leu Gly Ser Leu Pro Leu Ile Ser Ile
    130                 135                 140

Val Gly Tyr Val Asp Gly Gly Ile Gln Leu Leu Cys Leu Ser Ser Gly
145                 150                 155                 160

Trp Phe Pro Gln Pro Thr Ala Lys Trp Lys Gly Pro Gln Gly Gln Asp
                165                 170                 175

Leu Ser Ser Asp Ser Arg Ala Asn Ala Asp Gly Tyr Ser Leu Tyr Asp
                180                 185                 190

Val Glu Ile Ser Ile Ile Val Gln Glu Asn Ala Gly Ser Ile Leu Cys
    195                 200                 205

Ser Ile His Leu Ala Glu Gln Ser His Glu Val Glu Ser Lys Val Leu
    210                 215                 220

Ile Gly Glu Thr Phe Phe Gln Pro Ser Pro Trp Arg Leu Ala Ser Gly
225                 230                 235                 240

Ser Gly Ser Arg Lys Gly Gly Lys Arg Gly Ser Lys Tyr Gly Pro Pro
                245                 250                 255

Cys Pro Pro Cys Pro Ala Pro Glu Phe Leu Gly Gly Pro Ser Val Phe
                260                 265                 270

Leu Phe Pro Pro Lys Pro Lys Asp Gln Leu Met Ile Ser Arg Thr Pro
                275                 280                 285

Glu Val Thr Cys Val Val Val Asp Val Ser Gln Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Tyr Arg Val Val Ser Val
                325                 330                 335

Leu Thr Val Leu His Gln Asp Trp Leu Ser Gly Lys Glu Tyr Lys Cys
                340                 345                 350

Lys Val Ser Ser Lys Gly Leu Pro Ser Ser Ile Glu Lys Thr Ile Ser
    355                 360                 365

Asn Ala Thr Gly Gln Pro Arg Glu Pro Gln Val Tyr Thr Leu Pro Pro
    370                 375                 380

Ser Gln Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
                420                 425                 430

Gly Ser Phe Phe Leu Tyr Ser Arg Leu Thr Val Asp Lys Ser Arg Trp
                435                 440                 445

Gln Glu Gly Asn Val Phe Ser Cys Ser Val Leu His Glu Ala Leu His
    450                 455                 460

Asn His Tyr Thr Gln Lys Ser Leu Ser Leu Ser Leu Gly Lys Asp Glu

```
                  465                 470                 475                 480
        Gly Gly Glu Asp Gly Ser Asp Ile Gln Met Thr Gln Thr Thr Ser Ser
                        485                 490                 495

Leu Ser Ala Ser Leu Gly Asp Arg Val Thr Ile Ser Cys Arg Ala Ser
                        500                 505                 510

Gln Asp Ile Ser Lys Tyr Leu Asn Trp Tyr Gln Gln Lys Pro Asp Gly
                        515                 520                 525

Thr Val Lys Leu Leu Ile Tyr His Thr Ser Arg Leu His Ser Gly Val
                        530                 535                 540

Pro Ser Arg Phe Ser Gly Ser Gly Ser Gly Thr Asp Tyr Ser Leu Thr
        545                 550                 555                 560

Ile Ser Asn Leu Glu Gln Glu Asp Ile Ala Thr Tyr Phe Cys Gln Gln
                        565                 570                 575

Gly Asn Thr Leu Pro Tyr Thr Phe Gly Gly Gly Thr Lys Leu Glu Ile
                        580                 585                 590

Thr Gly Gly Gly Ser Gly Gly Gly Ser Gly Gly Gly Ser Glu Val Lys
                        595                 600                 605

Leu Gln Glu Ser Gly Pro Gly Leu Val Ala Pro Ser Gln Ser Leu Ser
                        610                 615                 620

Val Thr Cys Thr Val Ser Gly Val Ser Leu Pro Asp Tyr Gly Val Ser
        625                 630                 635                 640

Trp Ile Arg Gln Pro Pro Arg Lys Gly Leu Glu Trp Leu Gly Val Ile
                        645                 650                 655

Trp Gly Ser Glu Thr Thr Tyr Tyr Asn Ser Ala Leu Lys Ser Arg Leu
                        660                 665                 670

Thr Ile Ile Lys Asp Asn Ser Lys Ser Gln Val Phe Leu Lys Met Asn
                        675                 680                 685

Ser Leu Gln Thr Asp Asp Thr Ala Ile Tyr Tyr Cys Ala Lys His Tyr
                        690                 695                 700

Tyr Tyr Gly Gly Ser Tyr Ala Met Asp Tyr Trp Gly Gln Gly Thr Ser
        705                 710                 715                 720

Val Thr Val Ser Ser
                        725

<210> SEQ ID NO 81
<211> LENGTH: 728
<212> TYPE: PRT
<213> ORGANISM: Homo sapiens

<400> SEQUENCE: 81

Met Glu Phe Gly Leu Ser Trp Val Phe Leu Val Ala Ile Ile Lys Gly
1               5                   10                  15

Val Gln Cys Gln Trp Gln Val Phe Gly Pro Asp Lys Pro Val Gln Ala
                20                  25                  30

Leu Val Gly Glu Asp Ala Ala Phe Ser Cys Phe Leu Ser Pro Lys Thr
            35                  40                  45

Asn Ala Glu Ala Met Glu Val Arg Phe Phe Arg Gly Gln Phe Ser Ser
        50                  55                  60

Val Val His Leu Tyr Arg Asp Gly Lys Asp Gln Pro Phe Met Gln Met
65                  70                  75                  80

Pro Gln Tyr Gln Gly Arg Thr Lys Leu Val Lys Asp Ser Ile Ala Glu
                85                  90                  95

Gly Arg Ile Ser Leu Arg Leu Glu Asn Ile Thr Val Leu Asp Ala Gly
                100                 105                 110
```

```
Leu Tyr Gly Cys Arg Ile Ser Ser Gln Ser Tyr Gln Lys Ala Ile
            115                 120                 125
Trp Glu Leu Gln Val Ser Ala Leu Gly Ser Val Pro Leu Ile Ser Ile
130                 135                 140
Thr Gly Tyr Val Asp Arg Asp Ile Gln Leu Leu Cys Gln Ser Ser Gly
145                 150                 155                 160
Trp Phe Pro Arg Pro Thr Ala Lys Trp Lys Gly Pro Gln Gly Gln Asp
                165                 170                 175
Leu Ser Thr Asp Ser Arg Thr Asn Arg Asp Met His Gly Leu Phe Asp
                180                 185                 190
Val Glu Ile Ser Leu Thr Val Gln Glu Asn Ala Gly Ser Ile Ser Cys
            195                 200                 205
Ser Met Arg His Ala His Leu Ser Arg Glu Val Glu Ser Arg Val Gln
210                 215                 220
Ile Gly Asp Thr Phe Phe Glu Pro Ile Ser Trp His Leu Ala Thr Lys
225                 230                 235                 240
Gly Ser Gly Ser Asp Glu Gly Glu Asp Gly Ser Lys Tyr Gly Pro
                245                 250                 255
Pro Cys Pro Pro Cys Pro Ala Pro Glu Phe Leu Gly Gly Pro Ser Val
                260                 265                 270
Phe Leu Phe Pro Pro Lys Pro Lys Asp Gln Leu Met Ile Ser Arg Thr
            275                 280                 285
Pro Glu Val Thr Cys Val Val Val Asp Val Ser Gln Glu Asp Pro Glu
            290                 295                 300
Val Gln Phe Asn Trp Tyr Val Asp Gly Val Glu Val His Asn Ala Lys
305                 310                 315                 320
Thr Lys Pro Arg Glu Glu Gln Phe Asn Ser Thr Tyr Arg Val Val Ser
                325                 330                 335
Val Leu Thr Val Leu His Gln Asp Trp Leu Ser Gly Lys Glu Tyr Lys
                340                 345                 350
Cys Lys Val Ser Ser Lys Gly Leu Pro Ser Ser Ile Glu Lys Thr Ile
            355                 360                 365
Ser Asn Ala Thr Gly Gln Pro Arg Glu Pro Gln Val Tyr Thr Leu Pro
370                 375                 380
Pro Ser Gln Glu Glu Met Thr Lys Asn Gln Val Ser Leu Thr Cys Leu
385                 390                 395                 400
Val Lys Gly Phe Tyr Pro Ser Asp Ile Ala Val Glu Trp Glu Ser Asn
                405                 410                 415
Gly Gln Pro Glu Asn Asn Tyr Lys Thr Thr Pro Pro Val Leu Asp Ser
                420                 425                 430
Asp Gly Ser Phe Phe Leu Tyr Ser Arg Leu Thr Val Asp Lys Ser Arg
            435                 440                 445
Trp Gln Glu Gly Asn Val Phe Ser Cys Ser Val Leu His Glu Ala Leu
            450                 455                 460
His Asn His Tyr Thr Gln Lys Ser Leu Ser Leu Ser Leu Gly Lys Arg
465                 470                 475                 480
Lys Gly Gly Lys Arg Gly Ser Gly Ser Asp Ile Gln Met Thr Gln Thr
                485                 490                 495
Thr Ser Ser Leu Ser Ala Ser Leu Gly Asp Arg Val Thr Ile Ser Cys
                500                 505                 510
Arg Ala Ser Gln Asp Ile Ser Lys Tyr Leu Asn Trp Tyr Gln Gln Lys
            515                 520                 525
Pro Asp Gly Thr Val Lys Leu Leu Ile Tyr His Thr Ser Arg Leu His
```

```
              530                 535                 540
Ser Gly Val Pro Ser Arg Phe Ser Gly Ser Gly Ser Gly Thr Asp Tyr
545                 550                 555                 560

Ser Leu Thr Ile Ser Asn Leu Glu Gln Glu Asp Ile Ala Thr Tyr Phe
                565                 570                 575

Cys Gln Gln Gly Asn Thr Leu Pro Tyr Thr Phe Gly Gly Gly Thr Lys
                580                 585                 590

Leu Glu Ile Thr Gly Gly Gly Gly Ser Gly Gly Gly Gly Ser Gly Gly Gly Ser
                595                 600                 605

Glu Val Lys Leu Gln Glu Ser Gly Pro Gly Leu Val Ala Pro Ser Gln
                610                 615                 620

Ser Leu Ser Val Thr Cys Thr Val Ser Gly Val Ser Leu Pro Asp Tyr
625                 630                 635                 640

Gly Val Ser Trp Ile Arg Gln Pro Pro Arg Lys Gly Leu Glu Trp Leu
                645                 650                 655

Gly Val Ile Trp Gly Ser Glu Thr Thr Tyr Tyr Asn Ser Ala Leu Lys
                660                 665                 670

Ser Arg Leu Thr Ile Ile Lys Asp Asn Ser Lys Ser Gln Val Phe Leu
                675                 680                 685

Lys Met Asn Ser Leu Gln Thr Asp Asp Thr Ala Ile Tyr Tyr Cys Ala
                690                 695                 700

Lys His Tyr Tyr Tyr Gly Gly Ser Tyr Ala Met Asp Tyr Trp Gly Gln
705                 710                 715                 720

Gly Thr Ser Val Thr Val Ser Ser
                725

<210> SEQ ID NO 82
<211> LENGTH: 730
<212> TYPE: PRT
<213> ORGANISM: Homo sapiens

<400> SEQUENCE: 82

Met Glu Phe Gly Leu Ser Trp Val Phe Leu Val Ala Ile Ile Lys Gly
1               5                   10                  15

Val Gln Cys Gln Phe Ser Val Leu Gly Pro Ser Gly Pro Ile Leu Ala
                20                  25                  30

Met Val Gly Glu Asp Ala Asp Leu Pro Cys His Leu Phe Pro Thr Met
                35                  40                  45

Ser Ala Glu Thr Met Glu Leu Lys Trp Val Ser Ser Ser Leu Arg Gln
50                  55                  60

Val Val Asn Val Tyr Ala Asp Gly Lys Glu Val Glu Asp Arg Gln Ser
65                  70                  75                  80

Ala Pro Tyr Arg Gly Arg Thr Ser Ile Leu Arg Asp Gly Ile Thr Ala
                85                  90                  95

Gly Lys Ala Ala Leu Arg Ile His Asn Val Thr Ala Ser Asp Ser Gly
                100                 105                 110

Lys Tyr Leu Cys Tyr Phe Gln Asp Gly Asp Phe Tyr Glu Lys Ala Leu
                115                 120                 125

Val Glu Leu Lys Val Ala Ala Leu Gly Ser Asp Leu His Val Asp Val
                130                 135                 140

Lys Gly Tyr Lys Asp Gly Gly Ile His Leu Glu Cys Arg Ser Thr Gly
145                 150                 155                 160

Trp Tyr Pro Gln Pro Gln Ile Gln Trp Ser Asn Asn Lys Gly Glu Asn
                165                 170                 175
```

```
Ile Pro Thr Val Glu Ala Pro Val Val Ala Asp Gly Val Gly Leu Tyr
                180                 185                 190
Ala Val Ala Ala Ser Val Ile Met Arg Gly Ser Ser Glu Gly Val
            195                 200                 205
Ser Cys Thr Ile Arg Ser Ser Leu Leu Gly Leu Glu Lys Thr Ala Ser
    210                 215                 220
Ile Ser Ile Ala Asp Pro Phe Phe Arg Ser Ala Gln Arg Trp Ile Ala
225                 230                 235                 240
Ala Leu Ala Gly Gly Ser Gly Ser Arg Lys Gly Lys Arg Gly Ser
                245                 250                 255
Lys Tyr Gly Pro Pro Cys Pro Pro Cys Pro Ala Pro Glu Phe Leu Gly
            260                 265                 270
Gly Pro Ser Val Phe Leu Phe Pro Pro Lys Pro Lys Asp Gln Leu Met
            275                 280                 285
Ile Ser Arg Thr Pro Glu Val Thr Cys Val Val Val Asp Val Ser Gln
            290                 295                 300
Glu Asp Pro Glu Val Gln Phe Asn Trp Tyr Val Asp Gly Val Glu Val
305                 310                 315                 320
His Asn Ala Lys Thr Lys Pro Arg Glu Glu Gln Phe Asn Ser Thr Tyr
                325                 330                 335
Arg Val Val Ser Val Leu Thr Val Leu His Gln Asp Trp Leu Ser Gly
            340                 345                 350
Lys Glu Tyr Lys Cys Lys Val Ser Lys Gly Leu Pro Ser Ser Ile
                355                 360                 365
Glu Lys Thr Ile Ser Asn Ala Thr Gly Gln Pro Arg Glu Pro Gln Val
            370                 375                 380
Tyr Thr Leu Pro Pro Ser Gln Glu Glu Met Thr Lys Asn Gln Val Ser
385                 390                 395                 400
Leu Thr Cys Leu Val Lys Gly Phe Tyr Pro Ser Asp Ile Ala Val Glu
                405                 410                 415
Trp Glu Ser Asn Gly Gln Pro Glu Asn Asn Tyr Lys Thr Thr Pro Pro
            420                 425                 430
Val Leu Asp Ser Asp Gly Ser Phe Phe Leu Tyr Ser Arg Leu Thr Val
            435                 440                 445
Asp Lys Ser Arg Trp Gln Glu Gly Asn Val Phe Ser Cys Ser Val Leu
450                 455                 460
His Glu Ala Leu His Asn His Tyr Thr Gln Lys Ser Leu Ser Leu Ser
465                 470                 475                 480
Leu Gly Lys Asp Glu Gly Gly Glu Asp Gly Ser Asp Ile Gln Met Thr
                485                 490                 495
Gln Thr Thr Ser Ser Leu Ser Ala Ser Leu Gly Asp Arg Val Thr Ile
            500                 505                 510
Ser Cys Arg Ala Ser Gln Asp Ile Ser Lys Tyr Leu Asn Trp Tyr Gln
            515                 520                 525
Gln Lys Pro Asp Gly Thr Val Lys Leu Leu Ile Tyr His Thr Ser Arg
            530                 535                 540
Leu His Ser Gly Val Pro Ser Arg Phe Ser Gly Ser Gly Ser Gly Thr
545                 550                 555                 560
Asp Tyr Ser Leu Thr Ile Ser Asn Leu Glu Gln Glu Asp Ile Ala Thr
                565                 570                 575
Tyr Phe Cys Gln Gln Gly Asn Thr Leu Pro Tyr Thr Phe Gly Gly Gly
            580                 585                 590
Thr Lys Leu Glu Ile Thr Gly Gly Gly Ser Gly Gly Gly Ser Gly Gly
```

```
                595                 600                 605
Gly Ser Glu Val Lys Leu Gln Glu Ser Gly Pro Gly Leu Val Ala Pro
610                 615                 620

Ser Gln Ser Leu Ser Val Thr Cys Thr Val Ser Gly Val Ser Leu Pro
625                 630                 635                 640

Asp Tyr Gly Val Ser Trp Ile Arg Gln Pro Pro Arg Lys Gly Leu Glu
                645                 650                 655

Trp Leu Gly Val Ile Trp Gly Ser Glu Thr Thr Tyr Tyr Asn Ser Ala
                660                 665                 670

Leu Lys Ser Arg Leu Thr Ile Ile Lys Asp Asn Ser Lys Ser Gln Val
                675                 680                 685

Phe Leu Lys Met Asn Ser Leu Gln Thr Asp Asp Thr Ala Ile Tyr Tyr
690                 695                 700

Cys Ala Lys His Tyr Tyr Tyr Gly Gly Ser Tyr Ala Met Asp Tyr Trp
705                 710                 715                 720

Gly Gln Gly Thr Ser Val Thr Val Ser Ser
                725                 730

<210> SEQ ID NO 83
<211> LENGTH: 726
<212> TYPE: PRT
<213> ORGANISM: Homo sapiens

<400> SEQUENCE: 83

Met Glu Phe Gly Leu Ser Trp Val Phe Leu Val Ala Ile Ile Lys Gly
1               5                   10                  15

Val Gln Cys Gln Phe Ser Val Leu Gly Pro Ser Gly Pro Ile Leu Ala
                20                  25                  30

Met Val Gly Glu Asp Ala Asp Leu Pro Cys His Leu Phe Pro Thr Met
            35                  40                  45

Ser Ala Glu Thr Met Glu Leu Lys Trp Val Ser Ser Ser Leu Arg Gln
50                  55                  60

Val Val Asn Val Tyr Ala Asp Gly Lys Glu Val Glu Asp Arg Gln Ser
65                  70                  75                  80

Ala Pro Tyr Arg Gly Arg Thr Ser Ile Leu Arg Asp Gly Ile Thr Ala
                85                  90                  95

Gly Lys Ala Ala Leu Arg Ile His Asn Val Thr Ala Ser Asp Ser Gly
            100                 105                 110

Lys Tyr Leu Cys Tyr Phe Gln Asp Gly Asp Phe Tyr Glu Lys Ala Leu
        115                 120                 125

Val Glu Leu Lys Val Ala Ala Leu Gly Ser Asn Leu His Val Glu Val
130                 135                 140

Lys Gly Tyr Glu Asp Gly Gly Ile His Leu Glu Cys Arg Ser Thr Gly
145                 150                 155                 160

Trp Tyr Pro Gln Pro Gln Ile Gln Trp Ser Asn Ala Lys Gly Glu Asn
                165                 170                 175

Ile Pro Ala Val Glu Ala Pro Val Val Ala Asp Gly Val Gly Leu Tyr
            180                 185                 190

Glu Val Ala Ala Ser Val Ile Met Arg Gly Gly Ser Gly Glu Gly Val
        195                 200                 205

Ser Cys Ile Ile Arg Asn Ser Leu Leu Gly Leu Glu Lys Thr Ala Ser
210                 215                 220

Ile Ser Ile Ala Asp Pro Phe Phe Arg Ser Ala Gln Pro Trp Gly Ser
225                 230                 235                 240
```

```
Gly Ser Asp Glu Gly Glu Asp Gly Ser Lys Tyr Gly Pro Pro Cys
                245                 250                 255

Pro Pro Cys Pro Ala Pro Glu Phe Leu Gly Gly Pro Ser Val Phe Leu
        260                 265                 270

Phe Pro Pro Lys Pro Lys Asp Gln Leu Met Ile Ser Arg Thr Pro Glu
        275                 280                 285

Val Thr Cys Val Val Val Asp Val Ser Gln Glu Asp Pro Glu Val Gln
        290                 295                 300

Phe Asn Trp Tyr Val Asp Gly Val Glu Val His Asn Ala Lys Thr Lys
305                 310                 315                 320

Pro Arg Glu Glu Gln Phe Asn Ser Thr Tyr Arg Val Val Ser Val Leu
            325                 330                 335

Thr Val Leu His Gln Asp Trp Leu Ser Gly Lys Glu Tyr Lys Cys Lys
            340                 345                 350

Val Ser Ser Lys Gly Leu Pro Ser Ser Ile Glu Lys Thr Ile Ser Asn
            355                 360                 365

Ala Thr Gly Gln Pro Arg Glu Pro Gln Val Tyr Thr Leu Pro Pro Ser
        370                 375                 380

Gln Glu Glu Met Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
            405                 410                 415

Pro Glu Asn Asn Tyr Lys Thr Thr Pro Pro Val Leu Asp Ser Asp Gly
            420                 425                 430

Ser Phe Phe Leu Tyr Ser Arg Leu Thr Val Asp Lys Ser Arg Trp Gln
        435                 440                 445

Glu Gly Asn Val Phe Ser Cys Ser Val Leu His Glu Ala Leu His Asn
450                 455                 460

His Tyr Thr Gln Lys Ser Leu Ser Leu Ser Leu Gly Lys Arg Lys Gly
465                 470                 475                 480

Gly Lys Arg Gly Ser Gly Ser Asp Ile Gln Met Thr Gln Thr Thr Ser
            485                 490                 495

Ser Leu Ser Ala Ser Leu Gly Asp Arg Val Thr Ile Ser Cys Arg Ala
        500                 505                 510

Ser Gln Asp Ile Ser Lys Tyr Leu Asn Trp Tyr Gln Gln Lys Pro Asp
        515                 520                 525

Gly Thr Val Lys Leu Leu Ile Tyr His Thr Ser Arg Leu His Ser Gly
        530                 535                 540

Val Pro Ser Arg Phe Ser Gly Ser Gly Ser Gly Thr Asp Tyr Ser Leu
545                 550                 555                 560

Thr Ile Ser Asn Leu Glu Gln Glu Asp Ile Ala Thr Tyr Phe Cys Gln
            565                 570                 575

Gln Gly Asn Thr Leu Pro Tyr Thr Phe Gly Gly Gly Thr Lys Leu Glu
            580                 585                 590

Ile Thr Gly Gly Gly Ser Gly Gly Gly Ser Gly Gly Gly Ser Glu Val
        595                 600                 605

Lys Leu Gln Glu Ser Gly Pro Gly Leu Val Ala Pro Ser Gln Ser Leu
        610                 615                 620

Ser Val Thr Cys Thr Val Ser Gly Val Ser Leu Pro Asp Tyr Gly Val
625                 630                 635                 640

Ser Trp Ile Arg Gln Pro Pro Arg Lys Gly Leu Glu Trp Leu Gly Val
            645                 650                 655

Ile Trp Gly Ser Glu Thr Thr Tyr Tyr Asn Ser Ala Leu Lys Ser Arg
```

```
                    660                 665                 670
Leu Thr Ile Ile Lys Asp Asn Ser Lys Ser Gln Val Phe Leu Lys Met
            675                 680                 685

Asn Ser Leu Gln Thr Asp Asp Thr Ala Ile Tyr Tyr Cys Ala Lys His
        690                 695                 700

Tyr Tyr Tyr Gly Gly Ser Tyr Ala Met Asp Tyr Trp Gly Gln Gly Thr
705                 710                 715                 720

Ser Val Thr Val Ser Ser
                725

<210> SEQ ID NO 84
<211> LENGTH: 724
<212> TYPE: PRT
<213> ORGANISM: Homo sapiens

<400> SEQUENCE: 84

Met Glu Phe Gly Leu Ser Trp Val Phe Leu Val Ala Ile Ile Lys Gly
1               5                   10                  15

Val Gln Cys Gln Trp Gln Val Thr Gly Pro Gly Lys Phe Val Gln Ala
            20                  25                  30

Leu Val Gly Glu Asp Ala Val Phe Ser Cys Ser Leu Phe Pro Glu Thr
        35                  40                  45

Ser Ala Glu Ala Met Glu Val Arg Phe Phe Arg Asn Gln Phe His Ala
    50                  55                  60

Val Val His Leu Tyr Arg Asp Gly Glu Asp Trp Glu Ser Lys Gln Met
65                  70                  75                  80

Pro Gln Tyr Arg Gly Arg Thr Glu Phe Val Lys Asp Ser Ile Ala Gly
                85                  90                  95

Gly Arg Val Ser Leu Arg Leu Lys Asn Ile Thr Pro Ser Asp Ile Gly
            100                 105                 110

Leu Tyr Gly Cys Trp Phe Ser Ser Gln Ile Tyr Asp Glu Glu Ala Thr
        115                 120                 125

Trp Glu Leu Arg Val Ala Ala Leu Gly Ser Leu Pro Leu Ile Ser Ile
    130                 135                 140

Val Gly Tyr Val Asp Gly Gly Ile Gln Leu Leu Cys Leu Ser Ser Gly
145                 150                 155                 160

Trp Phe Pro Gln Pro Thr Ala Lys Trp Lys Gly Pro Gln Gly Gln Asp
                165                 170                 175

Leu Ser Ser Asp Ser Arg Ala Asn Ala Asp Gly Tyr Ser Leu Tyr Asp
            180                 185                 190

Val Glu Ile Ser Ile Ile Val Gln Glu Asn Ala Gly Ser Ile Leu Cys
        195                 200                 205

Ser Ile His Leu Ala Glu Gln Ser His Glu Val Glu Ser Lys Val Leu
    210                 215                 220

Ile Gly Glu Thr Phe Phe Gln Pro Ser Pro Trp Arg Leu Ala Ser Gly
225                 230                 235                 240

Ser Gly Ser Arg Lys Gly Gly Lys Arg Gly Ser Lys Tyr Gly Pro Pro
                245                 250                 255

Cys Pro Pro Cys Pro Ala Pro Glu Phe Leu Gly Gly Pro Ser Val Phe
            260                 265                 270

Leu Phe Pro Pro Lys Pro Lys Asp Gln Leu Met Ile Ser Arg Thr Pro
        275                 280                 285

Glu Val Thr Cys Val Val Val Asp Val Ser Gln Glu Asp Pro Glu Val
    290                 295                 300
```

```
Gln Phe Asn Trp Tyr Val Asp Gly Val Glu Val His Asn Ala Lys Thr
305                 310                 315                 320
Lys Pro Arg Glu Glu Gln Phe Asn Ser Thr Tyr Arg Val Val Ser Val
            325                 330                 335
Leu Thr Val Leu His Gln Asp Trp Leu Ser Gly Lys Glu Tyr Lys Cys
        340                 345                 350
Lys Val Ser Ser Lys Gly Leu Pro Ser Ser Ile Glu Lys Thr Ile Ser
    355                 360                 365
Asn Ala Thr Gly Gln Pro Arg Glu Pro Gln Val Tyr Thr Leu Pro Pro
370                 375                 380
Ser Gln Glu Glu Met Thr Lys Asn Gln Val Ser Leu Thr Cys Leu Val
385                 390                 395                 400
Lys Gly Phe Tyr Pro Ser Asp Ile Ala Val Glu Trp Glu Ser Asn Gly
            405                 410                 415
Gln Pro Glu Asn Asn Tyr Lys Thr Thr Pro Pro Val Leu Asp Ser Asp
        420                 425                 430
Gly Ser Phe Phe Leu Tyr Ser Arg Leu Thr Val Asp Lys Ser Arg Trp
    435                 440                 445
Gln Glu Gly Asn Val Phe Ser Cys Ser Val Leu His Glu Ala Leu His
450                 455                 460
Asn His Tyr Thr Gln Lys Ser Leu Ser Leu Ser Leu Gly Lys Asp Glu
465                 470                 475                 480
Gly Gly Glu Asp Gly Ser Asp Val Val Met Thr Gln Thr Pro Leu Ser
            485                 490                 495
Leu Pro Val Ser Leu Gly Asp Gln Ala Ser Ile Ser Cys Arg Ser Ser
        500                 505                 510
Gln Ser Leu Val His Arg Asn Gly Asn Thr Tyr Leu His Trp Tyr Leu
    515                 520                 525
Gln Lys Pro Gly Gln Ser Pro Lys Leu Leu Ile His Lys Val Ser Asn
530                 535                 540
Arg Phe Ser Gly Val Pro Asp Arg Phe Ser Gly Ser Gly Ser Gly Thr
545                 550                 555                 560
Asp Phe Thr Leu Lys Ile Ser Arg Val Glu Ala Glu Asp Leu Gly Val
            565                 570                 575
Tyr Phe Cys Ser Gln Ser Thr His Val Pro Pro Leu Thr Phe Gly Ala
        580                 585                 590
Gly Thr Lys Leu Glu Leu Lys Gly Gly Gly Gly Ser Gly Gly Ser Gly
    595                 600                 605
Gly Gly Ser Glu Val Gln Leu Leu Gln Ser Gly Pro Glu Leu Glu Lys
610                 615                 620
Pro Gly Ala Ser Val Met Ile Ser Cys Lys Ala Ser Gly Ser Ser Phe
625                 630                 635                 640
Thr Gly Tyr Asn Met Asn Trp Val Arg Gln Asn Ile Gly Lys Ser Leu
            645                 650                 655
Glu Trp Ile Gly Ala Ile Asp Pro Tyr Tyr Gly Gly Thr Ser Tyr Asn
        660                 665                 670
Gln Lys Phe Lys Gly Arg Ala Thr Leu Thr Val Asp Lys Ser Ser Ser
    675                 680                 685
Thr Ala Tyr Met His Leu Lys Ser Leu Thr Ser Glu Asp Ser Ala Val
690                 695                 700
Tyr Tyr Cys Val Ser Gly Met Lys Tyr Trp Gly Gln Gly Thr Ser Val
705                 710                 715                 720
Thr Val Ser Ser
```

-continued

```
<210> SEQ ID NO 85
<211> LENGTH: 727
<212> TYPE: PRT
<213> ORGANISM: Homo sapiens

<400> SEQUENCE: 85

Met Glu Phe Gly Leu Ser Trp Val Phe Leu Val Ala Ile Ile Lys Gly
1               5                   10                  15

Val Gln Cys Gln Trp Gln Val Phe Gly Pro Asp Lys Pro Val Gln Ala
            20                  25                  30

Leu Val Gly Glu Asp Ala Ala Phe Ser Cys Phe Leu Ser Pro Lys Thr
        35                  40                  45

Asn Ala Glu Ala Met Glu Val Arg Phe Phe Arg Gly Gln Phe Ser Ser
    50                  55                  60

Val Val His Leu Tyr Arg Asp Gly Lys Asp Gln Pro Phe Met Gln Met
65                  70                  75                  80

Pro Gln Tyr Gln Gly Arg Thr Lys Leu Val Lys Asp Ser Ile Ala Glu
                85                  90                  95

Gly Arg Ile Ser Leu Arg Leu Glu Asn Ile Thr Val Leu Asp Ala Gly
            100                 105                 110

Leu Tyr Gly Cys Arg Ile Ser Ser Gln Ser Tyr Tyr Gln Lys Ala Ile
        115                 120                 125

Trp Glu Leu Gln Val Ser Ala Leu Gly Ser Val Pro Leu Ile Ser Ile
    130                 135                 140

Thr Gly Tyr Val Asp Arg Asp Ile Gln Leu Leu Cys Gln Ser Ser Gly
145                 150                 155                 160

Trp Phe Pro Arg Pro Thr Ala Lys Trp Lys Gly Pro Gln Gly Gln Asp
                165                 170                 175

Leu Ser Thr Asp Ser Arg Thr Asn Arg Asp Met His Gly Leu Phe Asp
            180                 185                 190

Val Glu Ile Ser Leu Thr Val Gln Glu Asn Ala Gly Ser Ile Ser Cys
        195                 200                 205

Ser Met Arg His Ala His Leu Ser Arg Glu Val Glu Ser Arg Val Gln
    210                 215                 220

Ile Gly Asp Thr Phe Phe Glu Pro Ile Ser Trp His Leu Ala Thr Lys
225                 230                 235                 240

Gly Ser Gly Ser Asp Glu Gly Glu Asp Gly Ser Lys Tyr Gly Pro
                245                 250                 255

Pro Cys Pro Pro Cys Pro Ala Pro Glu Phe Leu Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Ser Gly Lys Glu Tyr Lys
            340                 345                 350

Cys Lys Val Ser Ser Lys Gly Leu Pro Ser Ser Ile Glu Lys Thr Ile
        355                 360                 365

Ser Asn Ala Thr Gly Gln Pro Arg Glu Pro Gln Val Tyr Thr Leu Pro
```

```
                370                 375                 380
Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
            435                 440                 445

Trp Gln Glu Gly Asn Val Phe Ser Cys Ser Val Leu His Glu Ala Leu
        450                 455                 460

His Asn His Tyr Thr Gln Lys Ser Leu Ser Leu Ser Leu Gly Lys Arg
465                 470                 475                 480

Lys Gly Gly Lys Arg Gly Ser Gly Ser Asp Val Val Met Thr Gln Thr
                485                 490                 495

Pro Leu Ser Leu Pro Val Ser Leu Gly Asp Gln Ala Ser Ile Ser Cys
            500                 505                 510

Arg Ser Ser Gln Ser Leu Val His Arg Asn Gly Asn Thr Tyr Leu His
        515                 520                 525

Trp Tyr Leu Gln Lys Pro Gly Gln Ser Pro Lys Leu Leu Ile His Lys
    530                 535                 540

Val Ser Asn Arg Phe Ser Gly Val Pro Asp Arg Phe Ser Gly Ser Gly
545                 550                 555                 560

Ser Gly Thr Asp Phe Thr Leu Lys Ile Ser Arg Val Glu Ala Glu Asp
                565                 570                 575

Leu Gly Val Tyr Phe Cys Ser Gln Ser Thr His Val Pro Pro Leu Thr
            580                 585                 590

Phe Gly Ala Gly Thr Lys Leu Glu Leu Lys Gly Gly Ser Gly Gly Gly
        595                 600                 605

Gly Ser Gly Gly Gly Ser Glu Val Gln Leu Leu Gln Ser Gly Pro Glu
    610                 615                 620

Leu Glu Lys Pro Gly Ala Ser Val Met Ile Ser Cys Lys Ala Ser Gly
625                 630                 635                 640

Ser Ser Phe Thr Gly Tyr Asn Met Asn Trp Val Arg Gln Asn Ile Gly
                645                 650                 655

Lys Ser Leu Glu Trp Ile Gly Ala Ile Asp Pro Tyr Tyr Gly Gly Thr
            660                 665                 670

Ser Tyr Asn Gln Lys Phe Lys Gly Arg Ala Thr Leu Thr Val Asp Lys
        675                 680                 685

Ser Ser Ser Thr Ala Tyr Met His Leu Lys Ser Leu Thr Ser Glu Asp
    690                 695                 700

Ser Ala Val Tyr Tyr Cys Val Ser Gly Met Lys Tyr Trp Gly Gln Gly
705                 710                 715                 720

Thr Ser Val Thr Val Ser Ser
                725

<210> SEQ ID NO 86
<211> LENGTH: 729
<212> TYPE: PRT
<213> ORGANISM: Homo sapiens

<400> SEQUENCE: 86

Met Glu Phe Gly Leu Ser Trp Val Phe Leu Val Ala Ile Ile Lys Gly
1               5                   10                  15
```

```
Val Gln Cys Gln Phe Ser Val Leu Gly Pro Ser Gly Pro Ile Leu Ala
                20                  25                  30

Met Val Gly Glu Asp Ala Asp Leu Pro Cys His Leu Phe Pro Thr Met
            35                  40                  45

Ser Ala Glu Thr Met Glu Leu Lys Trp Val Ser Ser Ser Leu Arg Gln
        50                  55                  60

Val Val Asn Val Tyr Ala Asp Gly Lys Glu Val Glu Asp Arg Gln Ser
 65                  70                  75                  80

Ala Pro Tyr Arg Gly Arg Thr Ser Ile Leu Arg Asp Gly Ile Thr Ala
                85                  90                  95

Gly Lys Ala Ala Leu Arg Ile His Asn Val Thr Ala Ser Asp Ser Gly
            100                 105                 110

Lys Tyr Leu Cys Tyr Phe Gln Asp Gly Asp Phe Tyr Glu Lys Ala Leu
        115                 120                 125

Val Glu Leu Lys Val Ala Ala Leu Gly Ser Asp Leu His Val Asp Val
        130                 135                 140

Lys Gly Tyr Lys Asp Gly Gly Ile His Leu Glu Cys Arg Ser Thr Gly
145                 150                 155                 160

Trp Tyr Pro Gln Pro Gln Ile Gln Trp Ser Asn Asn Lys Gly Glu Asn
                165                 170                 175

Ile Pro Thr Val Glu Ala Pro Val Val Ala Asp Gly Val Gly Leu Tyr
            180                 185                 190

Ala Val Ala Ala Ser Val Ile Met Arg Gly Ser Ser Gly Glu Gly Val
        195                 200                 205

Ser Cys Thr Ile Arg Ser Ser Leu Leu Gly Leu Glu Lys Thr Ala Ser
210                 215                 220

Ile Ser Ile Ala Asp Pro Phe Phe Arg Ser Ala Gln Arg Trp Ile Ala
225                 230                 235                 240

Ala Leu Ala Gly Gly Ser Gly Ser Arg Lys Gly Gly Lys Arg Gly Ser
                245                 250                 255

Lys Tyr Gly Pro Pro Cys Pro Pro Cys Pro Ala Pro Glu Phe Leu Gly
            260                 265                 270

Gly Pro Ser Val Phe Leu Phe Pro Pro Lys Pro Lys Asp Gln Leu Met
        275                 280                 285

Ile Ser Arg Thr Pro Glu Val Thr Cys Val Val Val Asp Val Ser Gln
290                 295                 300

Glu Asp Pro Glu Val Gln Phe Asn Trp Tyr Val Asp Gly Val Glu Val
305                 310                 315                 320

His Asn Ala Lys Thr Lys Pro Arg Glu Glu Gln Phe Asn Ser Thr Tyr
                325                 330                 335

Arg Val Val Ser Val Leu Thr Val Leu His Gln Asp Trp Leu Ser Gly
            340                 345                 350

Lys Glu Tyr Lys Cys Lys Val Ser Ser Lys Gly Leu Pro Ser Ser Ile
        355                 360                 365

Glu Lys Thr Ile Ser Asn Ala Thr Gly Gln Pro Arg Glu Pro Gln Val
        370                 375                 380

Tyr Thr Leu Pro Pro Ser Gln Glu Glu Met Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Arg Leu Thr Val
```

```
                435                 440                 445
Asp Lys Ser Arg Trp Gln Glu Gly Asn Val Phe Ser Cys Ser Val Leu
    450                 455                 460
His Glu Ala Leu His Asn His Tyr Thr Gln Lys Ser Leu Ser Leu Ser
465                 470                 475                 480
Leu Gly Lys Asp Glu Gly Glu Asp Gly Ser Asp Val Val Met Thr
                485                 490                 495
Gln Thr Pro Leu Ser Leu Pro Val Ser Leu Gly Asp Gln Ala Ser Ile
                500                 505                 510
Ser Cys Arg Ser Ser Gln Ser Leu Val His Arg Asn Gly Asn Thr Tyr
            515                 520                 525
Leu His Trp Tyr Leu Gln Lys Pro Gly Gln Ser Pro Lys Leu Leu Ile
        530                 535                 540
His Lys Val Ser Asn Arg Phe Ser Gly Val Pro Asp Arg Phe Ser Gly
545                 550                 555                 560
Ser Gly Ser Gly Thr Asp Phe Thr Leu Lys Ile Ser Arg Val Glu Ala
                565                 570                 575
Glu Asp Leu Gly Val Tyr Phe Cys Ser Gln Ser Thr His Val Pro Pro
            580                 585                 590
Leu Thr Phe Gly Ala Gly Thr Lys Leu Glu Leu Lys Gly Gly Gly Ser
        595                 600                 605
Gly Gly Gly Ser Gly Gly Gly Ser Glu Val Gln Leu Leu Gln Ser Gly
610                 615                 620
Pro Glu Leu Glu Lys Pro Gly Ala Ser Val Met Ile Ser Cys Lys Ala
625                 630                 635                 640
Ser Gly Ser Ser Phe Thr Gly Tyr Asn Met Asn Trp Val Arg Gln Asn
                645                 650                 655
Ile Gly Lys Ser Leu Glu Trp Ile Gly Ala Ile Asp Pro Tyr Tyr Gly
            660                 665                 670
Gly Thr Ser Tyr Asn Gln Lys Phe Lys Gly Arg Ala Thr Leu Thr Val
        675                 680                 685
Asp Lys Ser Ser Ser Thr Ala Tyr Met His Leu Lys Ser Leu Thr Ser
    690                 695                 700
Glu Asp Ser Ala Val Tyr Tyr Cys Val Ser Gly Met Lys Tyr Trp Gly
705                 710                 715                 720
Gln Gly Thr Ser Val Thr Val Ser Ser
                725

<210> SEQ ID NO 87
<211> LENGTH: 725
<212> TYPE: PRT
<213> ORGANISM: Homo sapiens

<400> SEQUENCE: 87

Met Glu Phe Gly Leu Ser Trp Val Phe Leu Val Ala Ile Ile Lys Gly
1               5                   10                  15
Val Gln Cys Gln Phe Ser Val Leu Gly Pro Ser Gly Pro Ile Leu Ala
                20                  25                  30
Met Val Gly Glu Asp Ala Asp Leu Pro Cys His Leu Phe Pro Thr Met
            35                  40                  45
Ser Ala Glu Thr Met Glu Leu Lys Trp Val Ser Ser Ser Leu Arg Gln
        50                  55                  60
Val Val Asn Val Tyr Ala Asp Gly Lys Glu Val Glu Asp Arg Gln Ser
65                  70                  75                  80
```

```
Ala Pro Tyr Arg Gly Arg Thr Ser Ile Leu Arg Asp Gly Ile Thr Ala
                 85                  90                  95
Gly Lys Ala Ala Leu Arg Ile His Asn Val Thr Ala Ser Asp Ser Gly
            100                 105                 110
Lys Tyr Leu Cys Tyr Phe Gln Asp Gly Asp Phe Tyr Glu Lys Ala Leu
            115                 120                 125
Val Glu Leu Lys Val Ala Ala Leu Gly Ser Asn Leu His Val Glu Val
            130                 135                 140
Lys Gly Tyr Glu Asp Gly Gly Ile His Leu Glu Cys Arg Ser Thr Gly
145                 150                 155                 160
Trp Tyr Pro Gln Pro Gln Ile Gln Trp Ser Asn Ala Lys Gly Glu Asn
                165                 170                 175
Ile Pro Ala Val Glu Ala Pro Val Ala Asp Gly Val Gly Leu Tyr
                180                 185                 190
Glu Val Ala Ala Ser Val Ile Met Arg Gly Gly Ser Gly Glu Gly Val
                195                 200                 205
Ser Cys Ile Ile Arg Asn Ser Leu Leu Gly Leu Glu Lys Thr Ala Ser
    210                 215                 220
Ile Ser Ile Ala Asp Pro Phe Phe Arg Ser Ala Gln Pro Trp Gly Ser
225                 230                 235                 240
Gly Ser Asp Glu Gly Glu Asp Gly Ser Lys Tyr Gly Pro Pro Cys
                245                 250                 255
Pro Pro Cys Pro Ala Pro Glu Phe Leu Gly Gly Pro Ser Val Phe Leu
                260                 265                 270
Phe Pro Pro Lys Pro Lys Asp Gln Leu Met Ile Ser Arg Thr Pro Glu
                275                 280                 285
Val Thr Cys Val Val Val Asp Val Ser Gln Glu Asp Pro Glu Val Gln
                290                 295                 300
Phe Asn Trp Tyr Val Asp Gly Val Glu Val His Asn Ala Lys Thr Lys
305                 310                 315                 320
Pro Arg Glu Glu Gln Phe Asn Ser Thr Tyr Arg Val Val Ser Val Leu
                325                 330                 335
Thr Val Leu His Gln Asp Trp Leu Ser Gly Lys Glu Tyr Lys Cys Lys
                340                 345                 350
Val Ser Ser Lys Gly Leu Pro Ser Ser Ile Glu Lys Thr Ile Ser Asn
                355                 360                 365
Ala Thr Gly Gln Pro Arg Glu Pro Gln Val Tyr Thr Leu Pro Pro Ser
            370                 375                 380
Gln Glu Glu Met Thr Lys Asn Gln Val Ser Leu Thr Cys Leu Val Lys
385                 390                 395                 400
Gly Phe Tyr Pro Ser Asp Ile Ala Val Glu Trp Glu Ser Asn Gly Gln
                405                 410                 415
Pro Glu Asn Asn Tyr Lys Thr Thr Pro Pro Val Leu Asp Ser Asp Gly
                420                 425                 430
Ser Phe Phe Leu Tyr Ser Arg Leu Thr Val Asp Lys Ser Arg Trp Gln
            435                 440                 445
Glu Gly Asn Val Phe Ser Cys Ser Val Leu His Glu Ala Leu His Asn
    450                 455                 460
His Tyr Thr Gln Lys Ser Leu Ser Leu Ser Leu Gly Lys Arg Lys Gly
465                 470                 475                 480
Gly Lys Arg Gly Ser Gly Ser Asp Val Val Met Thr Gln Thr Pro Leu
                485                 490                 495
Ser Leu Pro Val Ser Leu Gly Asp Gln Ala Ser Ile Ser Cys Arg Ser
```

```
                500             505             510
    Ser Gln Ser Leu Val His Arg Asn Gly Asn Thr Tyr Leu His Trp Tyr
                    515             520             525
    Leu Gln Lys Pro Gly Gln Ser Pro Lys Leu Leu Ile His Lys Val Ser
                    530             535             540
    Asn Arg Phe Ser Gly Val Pro Asp Arg Phe Ser Gly Ser Gly Ser Gly
    545             550             555             560
    Thr Asp Phe Thr Leu Lys Ile Ser Arg Val Glu Ala Glu Asp Leu Gly
                        565             570             575
    Val Tyr Phe Cys Ser Gln Ser Thr His Val Pro Pro Leu Thr Phe Gly
                    580             585             590
    Ala Gly Thr Lys Leu Glu Leu Lys Gly Gly Gly Ser Gly Gly Gly Ser
                    595             600             605
    Gly Gly Gly Ser Glu Val Gln Leu Leu Gln Ser Gly Pro Glu Leu Glu
    610             615             620
    Lys Pro Gly Ala Ser Val Met Ile Ser Cys Lys Ala Ser Gly Ser Ser
    625             630             635             640
    Phe Thr Gly Tyr Asn Met Asn Trp Val Arg Gln Asn Ile Gly Lys Ser
                    645             650             655
    Leu Glu Trp Ile Gly Ala Ile Asp Pro Tyr Tyr Gly Gly Thr Ser Tyr
                    660             665             670
    Asn Gln Lys Phe Lys Gly Arg Ala Thr Leu Thr Val Asp Lys Ser Ser
                    675             680             685
    Ser Thr Ala Tyr Met His Leu Lys Ser Leu Thr Ser Glu Asp Ser Ala
                    690             695             700
    Val Tyr Tyr Cys Val Ser Gly Met Lys Tyr Trp Gly Gln Gly Thr Ser
    705             710             715             720
    Val Thr Val Ser Ser
                    725

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000
```

<210> SEQ ID NO 93

<400> SEQUENCE: 93

000

<210> SEQ ID NO 94
<211> LENGTH: 591
<212> TYPE: PRT
<213> ORGANISM: Homo sapiens

<400> SEQUENCE: 94

Met Glu Phe Gly Leu Ser Trp Val Phe Leu Val Ala Ile Ile Lys Gly
1               5                   10                  15

Val Gln Cys Gln Trp Gln Val Thr Gly Pro Gly Lys Phe Val Gln Ala
            20                  25                  30

Leu Val Gly Glu Asp Ala Val Phe Ser Cys Ser Leu Phe Pro Glu Thr
        35                  40                  45

Ser Ala Glu Ala Met Glu Val Arg Phe Phe Arg Asn Gln Phe His Ala
    50                  55                  60

Val Val His Leu Tyr Arg Asp Gly Glu Asp Trp Glu Ser Lys Gln Met
65                  70                  75                  80

Pro Gln Tyr Arg Gly Arg Thr Glu Phe Val Lys Asp Ser Ile Ala Gly
                85                  90                  95

Gly Arg Val Ser Leu Arg Leu Lys Asn Ile Thr Pro Ser Asp Ile Gly
            100                 105                 110

Leu Tyr Gly Cys Trp Phe Ser Ser Gln Ile Tyr Asp Glu Glu Ala Thr
        115                 120                 125

Trp Glu Leu Arg Val Ala Ala Leu Gly Ser Leu Pro Leu Ile Ser Ile
    130                 135                 140

Val Gly Tyr Val Asp Gly Gly Ile Gln Leu Leu Cys Leu Ser Ser Gly
145                 150                 155                 160

Trp Phe Pro Gln Pro Thr Ala Lys Trp Lys Gly Pro Gln Gly Gln Asp
                165                 170                 175

Leu Ser Ser Asp Ser Arg Ala Asn Ala Asp Gly Tyr Ser Leu Tyr Asp
            180                 185                 190

Val Glu Ile Ser Ile Ile Val Gln Glu Asn Ala Gly Ser Ile Leu Cys
        195                 200                 205

Ser Ile His Leu Ala Glu Gln Ser His Glu Val Glu Ser Lys Val Leu
    210                 215                 220

Ile Gly Glu Thr Phe Phe Gln Pro Ser Pro Trp Arg Leu Ala Ser Gly
225                 230                 235                 240

Ser Gly Ser Arg Lys Gly Gly Lys Arg Gly Ser Lys Tyr Gly Pro Pro
                245                 250                 255

Cys Pro Pro Cys Pro Ala Pro Glu Phe Leu Gly Gly Pro Ser Val Phe
            260                 265                 270

Leu Phe Pro Pro Lys Pro Lys Asp Gln Leu Met Ile Ser Arg Thr Pro
        275                 280                 285

Glu Val Thr Cys Val Val Val Asp Val Ser Gln Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Tyr Arg Val Val Ser Val
                325                 330                 335

Leu Thr Val Leu His Gln Asp Trp Leu Ser Gly Lys Glu Tyr Lys Cys

```
            340                 345                 350
Lys Val Ser Ser Lys Gly Leu Pro Ser Ser Ile Glu Lys Thr Ile Ser
        355                 360                 365

Asn Ala Thr Gly Gln Pro Arg Glu Pro Gln Val Tyr Thr Leu Pro Pro
    370                 375                 380

Ser Gln Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Arg Leu Thr Val Asp Lys Ser Arg Trp
        435                 440                 445

Gln Glu Gly Asn Val Phe Ser Cys Ser Val Leu His Glu Ala Leu His
    450                 455                 460

Asn His Tyr Thr Gln Lys Ser Leu Ser Leu Ser Leu Gly Lys Asp Glu
465                 470                 475                 480

Gly Gly Glu Asp Gly Ser Gly Ser Met Met Thr Gly Thr Ile Glu Thr
                485                 490                 495

Thr Gly Asn Ile Ser Ala Glu Lys Gly Ser Ile Ile Leu Gln Cys
            500                 505                 510

His Leu Ser Ser Thr Thr Ala Gln Val Thr Gln Val Asn Trp Glu Gln
        515                 520                 525

Gln Asp Gln Leu Leu Ala Ile Cys Asn Ala Asp Leu Gly Trp His Ile
    530                 535                 540

Ser Pro Ser Phe Lys Asp Arg Val Ala Pro Gly Pro Gly Leu Gly Leu
545                 550                 555                 560

Thr Leu Gln Ser Leu Thr Val Asn Asp Thr Gly Glu Tyr Phe Cys Ile
                565                 570                 575

Tyr His Thr Tyr Pro Asp Gly Thr Tyr Thr Gly Arg Ile Phe Leu
            580                 585                 590

<210> SEQ ID NO 95
<211> LENGTH: 592
<212> TYPE: PRT
<213> ORGANISM: Homo sapiens

<400> SEQUENCE: 95

Met Glu Phe Gly Leu Ser Trp Val Phe Leu Val Ala Ile Ile Lys Gly
1               5                   10                  15

Val Gln Cys Gln Trp Gln Val Phe Gly Pro Asp Lys Pro Val Gln Ala
            20                  25                  30

Leu Val Gly Glu Asp Ala Ala Phe Ser Cys Phe Leu Ser Pro Lys Thr
        35                  40                  45

Asn Ala Glu Ala Met Glu Val Arg Phe Phe Arg Gly Gln Phe Ser Ser
    50                  55                  60

Val Val His Leu Tyr Arg Asp Gly Lys Asp Gln Pro Phe Met Gln Met
65                  70                  75                  80

Pro Gln Tyr Gln Gly Arg Thr Lys Leu Val Lys Asp Ser Ile Ala Glu
                85                  90                  95

Gly Arg Ile Ser Leu Arg Leu Glu Asn Ile Thr Val Leu Asp Ala Gly
            100                 105                 110

Leu Tyr Gly Cys Arg Ile Ser Ser Gln Ser Tyr Gln Lys Ala Ile
        115                 120                 125
```

```
Trp Glu Leu Gln Val Ser Ala Leu Gly Ser Val Pro Leu Ile Ser Ile
    130                 135                 140

Thr Gly Tyr Val Asp Arg Asp Ile Gln Leu Leu Cys Gln Ser Ser Gly
145                 150                 155                 160

Trp Phe Pro Arg Pro Thr Ala Lys Trp Lys Gly Pro Gln Gly Gln Asp
                165                 170                 175

Leu Ser Thr Asp Ser Arg Thr Asn Arg Asp Met His Gly Leu Phe Asp
            180                 185                 190

Val Glu Ile Ser Leu Thr Val Gln Glu Asn Ala Gly Ser Ile Ser Cys
        195                 200                 205

Ser Met Arg His Ala His Leu Ser Arg Glu Val Glu Ser Arg Val Gln
    210                 215                 220

Ile Gly Asp Thr Phe Phe Glu Pro Ile Ser Trp His Leu Ala Thr Lys
225                 230                 235                 240

Gly Ser Gly Ser Asp Glu Gly Gly Asp Gly Ser Lys Tyr Gly Pro
                245                 250                 255

Pro Cys Pro Pro Cys Pro Ala Pro Glu Phe Leu Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Ser Gly Lys Glu Tyr Lys
            340                 345                 350

Cys Lys Val Ser Ser Lys Gly Leu Pro Ser Ser Ile Glu Lys Thr Ile
        355                 360                 365

Ser Asn Ala Thr Gly Gln Pro Arg Glu Pro Gln Val Tyr Thr Leu Pro
    370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
        435                 440                 445

Trp Gln Glu Gly Asn Val Phe Ser Cys Ser Val Leu His Glu Ala Leu
    450                 455                 460

His Asn His Tyr Thr Gln Lys Ser Leu Ser Leu Ser Leu Gly Lys Arg
465                 470                 475                 480

Lys Gly Gly Lys Arg Gly Ser Gly Ser Met Met Thr Gly Thr Ile Glu
                485                 490                 495

Thr Thr Gly Asn Ile Ser Ala Glu Lys Gly Gly Ser Ile Ile Leu Gln
            500                 505                 510

Cys His Leu Ser Ser Thr Thr Ala Gln Val Thr Gln Val Asn Trp Glu
        515                 520                 525

Gln Gln Asp Gln Leu Leu Ala Ile Cys Asn Ala Asp Leu Gly Trp His
    530                 535                 540

Ile Ser Pro Ser Phe Lys Asp Arg Val Ala Pro Gly Pro Gly Leu Gly
```

```
                545                 550                 555                 560
Leu Thr Leu Gln Ser Leu Thr Val Asn Asp Thr Gly Glu Tyr Phe Cys
                565                 570                 575
Ile Tyr His Thr Tyr Pro Asp Gly Thr Tyr Thr Gly Arg Ile Phe Leu
                580                 585                 590

<210> SEQ ID NO 96
<211> LENGTH: 619
<212> TYPE: PRT
<213> ORGANISM: Homo sapiens

<400> SEQUENCE: 96

Met Glu Phe Gly Leu Ser Trp Val Phe Leu Val Ala Ile Ile Lys Gly
1               5                   10                  15
Val Gln Cys Gln Trp Gln Val Thr Gly Pro Gly Lys Phe Val Gln Ala
                20                  25                  30
Leu Val Gly Glu Asp Ala Val Phe Ser Cys Ser Leu Phe Pro Glu Thr
            35                  40                  45
Ser Ala Glu Ala Met Glu Val Arg Phe Phe Arg Asn Gln Phe His Ala
        50                  55                  60
Val Val His Leu Tyr Arg Asp Gly Glu Asp Trp Glu Ser Lys Gln Met
65                  70                  75                  80
Pro Gln Tyr Arg Gly Arg Thr Glu Phe Val Lys Asp Ser Ile Ala Gly
                85                  90                  95
Gly Arg Val Ser Leu Arg Leu Lys Asn Ile Thr Pro Ser Asp Ile Gly
                100                 105                 110
Leu Tyr Gly Cys Trp Phe Ser Ser Gln Ile Tyr Asp Glu Glu Ala Thr
            115                 120                 125
Trp Glu Leu Arg Val Ala Ala Leu Gly Ser Leu Pro Leu Ile Ser Ile
        130                 135                 140
Val Gly Tyr Val Asp Gly Gly Ile Gln Leu Leu Cys Leu Ser Ser Gly
145                 150                 155                 160
Trp Phe Pro Gln Pro Thr Ala Lys Trp Lys Gly Pro Gln Gly Gln Asp
                165                 170                 175
Leu Ser Ser Asp Ser Arg Ala Asn Ala Asp Gly Tyr Ser Leu Tyr Asp
                180                 185                 190
Val Glu Ile Ser Ile Ile Val Gln Glu Asn Ala Gly Ser Ile Leu Cys
            195                 200                 205
Ser Ile His Leu Ala Glu Gln Ser His Glu Val Glu Ser Lys Val Leu
        210                 215                 220
Ile Gly Glu Thr Phe Phe Gln Pro Ser Pro Trp Arg Leu Ala Ser Gly
225                 230                 235                 240
Ser Gly Ser Arg Lys Gly Gly Lys Arg Gly Ser Lys Tyr Gly Pro Pro
                245                 250                 255
Cys Pro Pro Cys Pro Ala Pro Glu Phe Leu Gly Gly Pro Ser Val Phe
                260                 265                 270
Leu Phe Pro Pro Lys Pro Lys Asp Gln Leu Met Ile Ser Arg Thr Pro
            275                 280                 285
Glu Val Thr Cys Val Val Val Asp Val Ser Gln Glu Asp Pro Glu Val
        290                 295                 300
Gln Phe Asn Trp Tyr Val Asp Gly Val Glu Val His Asn Ala Lys Thr
305                 310                 315                 320
Lys Pro Arg Glu Glu Gln Phe Asn Ser Thr Tyr Arg Val Val Ser Val
                325                 330                 335
```

```
Leu Thr Val Leu His Gln Asp Trp Leu Ser Gly Lys Glu Tyr Lys Cys
                340                 345                 350

Lys Val Ser Ser Lys Gly Leu Pro Ser Ser Ile Glu Lys Thr Ile Ser
            355                 360                 365

Asn Ala Thr Gly Gln Pro Arg Glu Pro Gln Val Tyr Thr Leu Pro Pro
        370                 375                 380

Ser Gln Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Arg Leu Thr Val Asp Lys Ser Arg Trp
        435                 440                 445

Gln Glu Gly Asn Val Phe Ser Cys Ser Val Leu His Glu Ala Leu His
    450                 455                 460

Asn His Tyr Thr Gln Lys Ser Leu Ser Leu Ser Leu Gly Lys Asp Glu
465                 470                 475                 480

Gly Gly Glu Asp Gly Ser Gly Ser Gly Ala Pro Ala Gln Leu Pro Cys
                485                 490                 495

Ser Pro Thr Ile Pro Leu Gln Asp Leu Ser Leu Leu Arg Arg Ala Gly
            500                 505                 510

Val Thr Trp Gln His Gln Pro Asp Ser Gly Pro Pro Ala Ala Ala Pro
        515                 520                 525

Gly His Pro Leu Ala Pro Gly Pro His Pro Ala Pro Ser Ser Trp
    530                 535                 540

Gly Pro Arg Pro Arg Arg Tyr Thr Val Leu Ser Val Gly Pro Gly Gly
545                 550                 555                 560

Leu Arg Ser Gly Arg Leu Pro Leu Gln Pro Arg Val Gln Leu Asp Glu
                565                 570                 575

Arg Gly Arg Gln Arg Gly Asp Phe Ser Leu Trp Leu Arg Pro Ala Arg
            580                 585                 590

Arg Ala Asp Ala Gly Glu Tyr Arg Ala Ala Val His Leu Arg Asp Arg
        595                 600                 605

Ala Leu Ser Cys Arg Leu Arg Leu Arg Leu Gly
    610                 615

<210> SEQ ID NO 97
<211> LENGTH: 620
<212> TYPE: PRT
<213> ORGANISM: Homo sapiens

<400> SEQUENCE: 97

Met Glu Phe Gly Leu Ser Trp Val Phe Leu Val Ala Ile Ile Lys Gly
1               5                   10                  15

Val Gln Cys Gln Trp Gln Val Phe Gly Pro Asp Lys Pro Val Gln Ala
            20                  25                  30

Leu Val Gly Glu Asp Ala Ala Phe Ser Cys Phe Leu Ser Pro Lys Thr
        35                  40                  45

Asn Ala Glu Ala Met Glu Val Arg Phe Phe Arg Gly Gln Phe Ser Ser
    50                  55                  60

Val Val His Leu Tyr Arg Asp Gly Lys Asp Gln Pro Phe Met Gln Met
65                  70                  75                  80

Pro Gln Tyr Gln Gly Arg Thr Lys Leu Val Lys Asp Ser Ile Ala Glu
                85                  90                  95
```

```
Gly Arg Ile Ser Leu Arg Leu Glu Asn Ile Thr Val Leu Asp Ala Gly
            100                 105                 110

Leu Tyr Gly Cys Arg Ile Ser Gln Ser Tyr Tyr Gln Lys Ala Ile
        115                 120                 125

Trp Glu Leu Gln Val Ser Ala Leu Gly Ser Val Pro Leu Ile Ser Ile
130                 135                 140

Thr Gly Tyr Val Asp Arg Asp Ile Gln Leu Leu Cys Gln Ser Ser Gly
145                 150                 155                 160

Trp Phe Pro Arg Pro Thr Ala Lys Trp Lys Gly Pro Gln Gly Gln Asp
                165                 170                 175

Leu Ser Thr Asp Ser Arg Thr Asn Arg Asp Met His Gly Leu Phe Asp
            180                 185                 190

Val Glu Ile Ser Leu Thr Val Gln Glu Asn Ala Gly Ser Ile Ser Cys
        195                 200                 205

Ser Met Arg His Ala His Leu Ser Arg Glu Val Glu Ser Arg Val Gln
    210                 215                 220

Ile Gly Asp Thr Phe Phe Glu Pro Ile Ser Trp His Leu Ala Thr Lys
225                 230                 235                 240

Gly Ser Gly Ser Asp Glu Gly Gly Glu Asp Gly Ser Lys Tyr Gly Pro
                245                 250                 255

Pro Cys Pro Cys Pro Ala Pro Glu Phe Leu Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
            290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Ser Gly Lys Glu Tyr Lys
            340                 345                 350

Cys Lys Val Ser Ser Lys Gly Leu Pro Ser Ser Ile Glu Lys Thr Ile
        355                 360                 365

Ser Asn Ala Thr Gly Gln Pro Arg Glu Pro Gln Val Tyr Thr Leu Pro
370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
        435                 440                 445

Trp Gln Glu Gly Asn Val Phe Ser Cys Ser Val Leu His Glu Ala Leu
    450                 455                 460

His Asn His Tyr Thr Gln Lys Ser Leu Ser Leu Ser Leu Gly Lys Arg
465                 470                 475                 480

Lys Gly Gly Lys Arg Gly Ser Gly Ser Gly Ala Pro Ala Gln Leu Pro
                485                 490                 495

Cys Ser Pro Thr Ile Pro Leu Gln Asp Leu Ser Leu Leu Arg Arg Ala
            500                 505                 510
```

```
Gly Val Thr Trp Gln His Gln Pro Asp Ser Gly Pro Ala Ala Ala
            515                 520                 525

Pro Gly His Pro Leu Ala Pro Gly Pro His Pro Ala Ala Pro Ser Ser
    530                 535                 540

Trp Gly Pro Arg Pro Arg Arg Tyr Thr Val Leu Ser Val Gly Pro Gly
545                 550                 555                 560

Gly Leu Arg Ser Gly Arg Leu Pro Leu Gln Pro Arg Val Gln Leu Asp
                565                 570                 575

Glu Arg Gly Arg Gln Arg Gly Asp Phe Ser Leu Trp Leu Arg Pro Ala
            580                 585                 590

Arg Arg Ala Asp Ala Gly Glu Tyr Arg Ala Ala Val His Leu Arg Asp
        595                 600                 605

Arg Ala Leu Ser Cys Arg Leu Arg Leu Arg Leu Gly
    610                 615                 620

<210> SEQ ID NO 98
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 98 ccgccacc                                                              8

<210> SEQ ID NO 99
<211> LENGTH: 216
<212> TYPE: PRT
<213> ORGANISM: Artificial Sequence
<220> FEATURE:
<223> OTHER INFORMATION: Synthetic Sequence

<400> SEQUENCE: 99

Ala Pro Phe Asp Val Ile Gly Pro Pro Glu Pro Ile Leu Ala Val Val
1               5                   10                  15

Gly Glu Asp Ala Glu Leu Pro Cys Arg Leu Ser Pro Asn Ala Ser Ala
            20                  25                  30

Glu His Leu Glu Leu Arg Trp Phe Arg Lys Lys Val Ser Pro Ala Val
        35                  40                  45

Leu Val His Arg Asp Gly Arg Glu Gln Glu Ala Glu Gln Met Pro Glu
    50                  55                  60

Tyr Arg Gly Arg Ala Thr Leu Val Gln Asp Gly Ile Ala Lys Gly Arg
65                  70                  75                  80

Val Ala Leu Arg Ile Arg Gly Val Arg Val Ser Asp Asp Gly Glu Tyr
                85                  90                  95

Thr Cys Phe Phe Arg Glu Asp Gly Ser Tyr Glu Glu Ala Leu Val His
            100                 105                 110

Leu Lys Val Ala Ala Leu Gly Ser Asp Pro His Ile Ser Met Gln Val
        115                 120                 125

Gln Glu Asn Gly Glu Ile Cys Leu Glu Cys Thr Ser Val Gly Trp Tyr
    130                 135                 140

Pro Glu Pro Gln Val Gln Trp Arg Thr Ser Lys Gly Glu Lys Phe Pro
145                 150                 155                 160

Ser Thr Ser Glu Ser Arg Asn Pro Asp Glu Glu Gly Leu Phe Thr Val
                165                 170                 175

Ala Ala Ser Val Ile Ile Arg Asp Thr Ser Ala Lys Asn Val Ser Cys
            180                 185                 190
```

```
Tyr Ile Gln Asn Leu Leu Leu Gly Gln Glu Lys Lys Val Glu Ile Ser
            195                 200                 205

Ile Pro Ala Ser Ser Leu Pro Arg
    210                 215

<210> SEQ ID NO 100
<211> LENGTH: 215
<212> TYPE: PRT
<213> ORGANISM: Artificial Sequence
<220> FEATURE:
<223> OTHER INFORMATION: Synthetic Sequence

<400> SEQUENCE: 100

Ala Pro Phe Asp Val Ile Gly Pro Pro Glu Pro Ile Leu Ala Val Val
1               5                   10                  15

Gly Glu Asp Ala Glu Leu Pro Cys Arg Leu Ser Pro Asn Ala Ser Ala
            20                  25                  30

Glu His Leu Glu Leu Arg Trp Phe Arg Lys Lys Val Ser Pro Ala Val
        35                  40                  45

Leu Val His Arg Asp Gly Arg Glu Gln Glu Ala Glu Gln Met Pro Glu
    50                  55                  60

Tyr Arg Gly Arg Ala Thr Leu Val Gln Asp Gly Ile Ala Lys Gly Arg
65                  70                  75                  80

Val Ala Leu Arg Ile Arg Gly Val Arg Val Ser Asp Asp Gly Glu Tyr
                85                  90                  95

Thr Cys Phe Phe Arg Glu Asp Gly Ser Tyr Glu Glu Ala Leu Val His
            100                 105                 110

Leu Lys Val Ala Ala Leu Gly Ser Asp Pro His Ile Ser Met Gln Val
        115                 120                 125

Gln Glu Asn Gly Glu Ile Cys Leu Glu Cys Thr Ser Val Gly Trp Tyr
    130                 135                 140

Pro Glu Pro Gln Val Gln Trp Arg Thr Ser Lys Gly Glu Lys Phe Pro
145                 150                 155                 160

Ser Thr Ser Glu Ser Arg Asn Pro Asp Glu Glu Gly Leu Phe Thr Val
                165                 170                 175

Ala Ala Ser Val Ile Ile Arg Asp Thr Ser Ala Lys Asn Val Ser Cys
            180                 185                 190

Tyr Ile Gln Asn Leu Leu Leu Gly Gln Glu Lys Lys Val Glu Ile Ser
        195                 200                 205

Ile Pro Ala Ser Ser Leu Pro
    210                 215

<210> SEQ ID NO 101
<211> LENGTH: 432
<212> TYPE: PRT
<213> ORGANISM: Artificial Sequence
<220> FEATURE:
<223> OTHER INFORMATION: Synthetic Sequence

<400> SEQUENCE: 101

Lys Gln Ser Glu Asp Phe Arg Val Ile Gly Pro Ala His Pro Ile Leu
1               5                   10                  15

Ala Gly Val Gly Glu Asp Ala Leu Leu Thr Cys Gln Leu Leu Pro Lys
            20                  25                  30

Arg Thr Thr Met His Val Glu Val Arg Trp Tyr Arg Ser Glu Pro Ser
        35                  40                  45

Thr Pro Val Phe Val His Arg Asp Gly Val Glu Val Thr Glu Met Gln
    50                  55                  60
```

Met Glu Glu Tyr Arg Gly Trp Val Glu Trp Ile Glu Asn Gly Ile Ala
65                  70                  75                  80

Lys Gly Asn Val Ala Leu Lys Ile His Asn Ile Gln Pro Ser Asp Asn
                85                  90                  95

Gly Gln Tyr Trp Cys His Phe Gln Asp Gly Asn Tyr Cys Gly Glu Thr
            100                 105                 110

Ser Leu Leu Leu Lys Val Ala Gly Leu Gly Ser Ala Pro Ser Ile His
            115                 120                 125

Met Glu Gly Pro Gly Glu Ser Gly Val Gln Leu Val Cys Thr Ala Arg
130                 135                 140

Gly Trp Phe Pro Glu Pro Gln Val Tyr Trp Asp Ile Arg Gly Glu
145                 150                 155                 160

Lys Leu Leu Ala Val Ser Glu His Arg Ile Gln Asp Lys Asp Gly Leu
                165                 170                 175

Phe Tyr Ala Glu Ala Thr Leu Val Val Arg Asn Ala Ser Ala Glu Ser
            180                 185                 190

Val Ser Cys Leu Val His Asn Pro Val Leu Thr Glu Glu Lys Gly Ser
            195                 200                 205

Val Ile Ser Leu Pro Glu Lys Leu Gln Thr Glu Leu Ala Ser Leu Lys
210                 215                 220

Val Asn Gly Pro Ser Gln Pro Ile Leu Val Arg Val Gly Glu Asp Ile
225                 230                 235                 240

Gln Leu Thr Cys Tyr Leu Ser Pro Lys Ala Asn Ala Gln Ser Met Glu
                245                 250                 255

Val Arg Trp Asp Arg Ser His Arg Tyr Pro Ala Val His Val Tyr Met
            260                 265                 270

Asp Gly Asp His Val Ala Gly Glu Gln Met Ala Glu Tyr Arg Gly Arg
            275                 280                 285

Thr Val Leu Val Ser Asp Ala Ile Asp Glu Gly Arg Leu Thr Leu Gln
290                 295                 300

Ile Leu Ser Ala Arg Pro Ser Asp Asp Gly Gln Tyr Arg Cys Leu Phe
305                 310                 315                 320

Glu Lys Asp Asp Val Tyr Gln Glu Ala Ser Leu Asp Leu Lys Val Val
                325                 330                 335

Ser Leu Gly Ser Ser Pro Leu Ile Thr Val Glu Gly Gln Glu Asp Gly
            340                 345                 350

Glu Met Gln Pro Met Cys Ser Ser Asp Gly Trp Phe Pro Gln Pro His
            355                 360                 365

Val Pro Trp Arg Asp Met Glu Gly Lys Thr Ile Pro Ser Ser Ser Gln
370                 375                 380

Ala Leu Thr Gln Gly Ser His Gly Leu Phe His Val Gln Thr Leu Leu
385                 390                 395                 400

Arg Val Thr Asn Ile Ser Ala Val Asp Val Thr Cys Ser Ile Ser Ile
                405                 410                 415

Pro Phe Leu Gly Glu Glu Lys Ile Ala Thr Phe Ser Leu Ser Gly Trp
            420                 425                 430

<210> SEQ ID NO 102
<211> LENGTH: 220
<212> TYPE: PRT
<213> ORGANISM: Artificial Sequence
<220> FEATURE:
<223> OTHER INFORMATION: Synthetic Sequence

<400> SEQUENCE: 102

```
Gln Phe Ile Val Val Gly Pro Thr Asp Pro Ile Leu Ala Thr Val Gly
1               5                   10                  15

Glu Asn Thr Thr Leu Arg Cys His Leu Ser Pro Glu Lys Asn Ala Glu
            20                  25                  30

Asp Met Glu Val Arg Trp Phe Arg Ser Gln Phe Ser Pro Ala Val Phe
        35                  40                  45

Val Tyr Lys Gly Gly Arg Glu Arg Thr Glu Glu Gln Met Glu Glu Tyr
    50                  55                  60

Arg Gly Arg Thr Thr Phe Val Ser Lys Asp Ile Ser Arg Gly Ser Val
65                  70                  75                  80

Ala Leu Val Ile His Asn Ile Thr Ala Gln Glu Asn Gly Thr Tyr Arg
            85                  90                  95

Cys Tyr Phe Gln Glu Gly Arg Ser Tyr Asp Glu Ala Ile Leu His Leu
        100                 105                 110

Val Val Ala Gly Leu Gly Ser Lys Pro Leu Ile Ser Met Arg Gly His
        115                 120                 125

Glu Asp Gly Gly Ile Arg Leu Glu Cys Ile Ser Arg Gly Trp Tyr Pro
130                 135                 140

Lys Pro Leu Thr Val Trp Arg Asp Pro Tyr Gly Gly Val Ala Pro Ala
145                 150                 155                 160

Leu Lys Glu Val Ser Met Pro Asp Ala Asp Gly Leu Phe Met Val Thr
                165                 170                 175

Thr Ala Val Ile Ile Arg Asp Lys Ser Val Arg Asn Met Ser Cys Ser
            180                 185                 190

Ile Asn Asn Thr Leu Leu Gly Gln Lys Lys Glu Ser Val Ile Phe Ile
            195                 200                 205

Pro Glu Ser Phe Met Pro Ser Val Ser Pro Cys Ala
210                 215                 220

<210> SEQ ID NO 103
<211> LENGTH: 233
<212> TYPE: PRT
<213> ORGANISM: Artificial Sequence
<220> FEATURE:
<223> OTHER INFORMATION: Synthetic Sequence

<400> SEQUENCE: 103

Gln Phe Thr Val Val Gly Pro Ala Asn Pro Ile Leu Ala Met Val Gly
1               5                   10                  15

Glu Asn Thr Thr Leu Arg Cys His Leu Ser Pro Glu Lys Asn Ala Glu
            20                  25                  30

Asp Met Glu Val Arg Trp Phe Arg Ser Gln Phe Ser Pro Ala Val Phe
        35                  40                  45

Val Tyr Lys Gly Gly Arg Glu Arg Thr Glu Glu Gln Met Glu Glu Tyr
    50                  55                  60

Arg Gly Arg Ile Thr Phe Val Ser Lys Asp Ile Asn Arg Gly Ser Val
65                  70                  75                  80

Ala Leu Val Ile His Asn Val Thr Ala Gln Glu Asn Gly Ile Tyr Arg
            85                  90                  95

Cys Tyr Phe Gln Glu Gly Arg Ser Tyr Asp Glu Ala Ile Leu Arg Leu
        100                 105                 110

Val Val Ala Gly Leu Gly Ser Lys Pro Leu Ile Glu Ile Lys Ala Gln
        115                 120                 125

Glu Asp Gly Ser Ile Trp Leu Glu Cys Ile Ser Gly Gly Trp Tyr Pro
130                 135                 140
```

```
Glu Pro Leu Thr Val Trp Arg Asp Pro Tyr Gly Glu Val Pro Ala
145                 150                 155                 160

Leu Lys Glu Val Ser Ile Ala Asp Ala Asp Gly Leu Phe Met Val Thr
                165                 170                 175

Thr Ala Val Ile Ile Arg Asp Lys Tyr Val Arg Asn Val Ser Cys Ser
            180                 185                 190

Val Asn Asn Thr Leu Leu Gly Gln Glu Lys Glu Thr Val Ile Phe Ile
        195                 200                 205

Pro Glu Ser Phe Met Pro Ser Ala Ser Pro Trp Met Val Ala Leu Ala
    210                 215                 220

Val Ile Leu Thr Ala Ser Pro Trp Met
225                 230
```

<210> SEQ ID NO 104
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 104

```
Gln Val Thr Val Val Gly Pro Thr Asp Pro Ile Leu Ala Met Val Gly
1               5                   10                  15

Glu Asn Thr Thr Leu Arg Cys Cys Leu Ser Pro Glu Glu Asn Ala Glu
            20                  25                  30

Asp Met Glu Val Arg Trp Phe Gln Ser Gln Phe Ser Pro Ala Val Phe
        35                  40                  45

Val Tyr Lys Gly Gly Arg Glu Arg Thr Glu Glu Gln Lys Glu Glu Tyr
    50                  55                  60

Arg Gly Arg Thr Thr Phe Val Ser Lys Asp Ser Arg Gly Ser Val Ala
65                  70                  75                  80

Leu Ile Ile His Asn Val Thr Ala Glu Asp Asn Gly Ile Tyr Gln Cys
                85                  90                  95

Tyr Phe Gln Glu Gly Arg Ser Cys Asn Glu Ala Ile Leu His Leu Val
            100                 105                 110

Val Ala Gly Leu Asp Ser Glu Pro Val Ile Glu Met Arg Asp His Glu
        115                 120                 125

Asp Gly Gly Ile Gln Leu Glu Cys Ile Ser Gly Gly Trp Tyr Pro Lys
    130                 135                 140

Pro Leu Thr Val Trp Arg Asp Pro Tyr Gly Glu Val Val Pro Ala Leu
145                 150                 155                 160

Lys Glu Val Ser Thr Pro Asp Ala Asp Ser Leu Phe Met Val Thr Thr
                165                 170                 175

Ala Val Ile Ile Arg Asp Lys Ser Val Arg Asn Val Ser Cys Ser Ile
            180                 185                 190

Asn Asp Thr Leu Leu Gly Gln Lys Lys Glu Ser Val Ile Phe Ile Pro
        195                 200                 205

Glu Ser Phe Met Pro Ser Arg Ser Pro Cys Val
    210                 215
```

<210> SEQ ID NO 105
<211> LENGTH: 220
<212> TYPE: PRT
<213> ORGANISM: Artificial Sequence
<220> FEATURE:
<223> OTHER INFORMATION: Synthetic Sequence

```
-continued

<400> SEQUENCE: 105

Gln Trp Gln Val Thr Gly Pro Gly Lys Phe Val Gln Ala Leu Val Gly
1               5                   10                  15

Glu Asp Ala Val Phe Ser Cys Ser Leu Phe Pro Glu Thr Ser Ala Glu
            20                  25                  30

Ala Met Glu Val Arg Phe Phe Arg Asn Gln Phe His Ala Val Val His
        35                  40                  45

Leu Tyr Arg Asp Gly Glu Asp Trp Glu Ser Lys Gln Met Pro Gln Tyr
    50                  55                  60

Arg Gly Arg Thr Glu Phe Val Lys Asp Ser Ile Ala Gly Gly Arg Val
65                  70                  75                  80

Ser Leu Arg Leu Lys Asn Ile Thr Pro Ser Asp Ile Gly Leu Tyr Gly
                85                  90                  95

Cys Trp Phe Ser Ser Gln Ile Tyr Asp Glu Glu Ala Thr Trp Glu Leu
            100                 105                 110

Arg Val Ala Ala Leu Gly Ser Leu Pro Leu Ile Ser Ile Val Gly Tyr
        115                 120                 125

Val Asp Gly Gly Ile Gln Leu Leu Cys Leu Ser Ser Gly Trp Phe Pro
    130                 135                 140

Gln Pro Thr Ala Lys Trp Lys Gly Pro Gln Gly Gln Asp Leu Ser Ser
145                 150                 155                 160

Asp Ser Arg Ala Asn Ala Asp Gly Tyr Ser Leu Tyr Asp Val Glu Ile
                165                 170                 175

Ser Ile Ile Val Gln Glu Asn Ala Gly Ser Ile Leu Cys Ser Ile His
            180                 185                 190

Leu Ala Glu Gln Ser His Glu Val Glu Ser Lys Val Leu Ile Gly Glu
        195                 200                 205

Thr Phe Phe Gln Pro Ser Pro Trp Arg Leu Ala Ser
    210                 215                 220

<210> SEQ ID NO 106
<211> LENGTH: 225
<212> TYPE: PRT
<213> ORGANISM: Artificial Sequence
<220> FEATURE:
<223> OTHER INFORMATION: Synthetic Sequence

<400> SEQUENCE: 106

Gln Phe Ser Val Leu Gly Pro Ser Gly Pro Ile Leu Ala Met Val Gly
1               5                   10                  15

Glu Asp Ala Asp Leu Pro Cys His Leu Phe Pro Thr Met Ser Ala Glu
            20                  25                  30

Thr Met Glu Leu Lys Trp Val Ser Ser Ser Leu Arg Gln Val Val Asn
        35                  40                  45

Val Tyr Ala Asp Gly Lys Glu Val Glu Asp Arg Gln Ser Ala Pro Tyr
    50                  55                  60

Arg Gly Arg Thr Ser Ile Leu Arg Asp Gly Ile Thr Ala Gly Lys Ala
65                  70                  75                  80

Ala Leu Arg Ile His Asn Val Thr Ala Ser Asp Ser Gly Lys Tyr Leu
                85                  90                  95

Cys Tyr Phe Gln Asp Gly Asp Phe Tyr Glu Lys Ala Leu Val Glu Leu
            100                 105                 110

Lys Val Ala Ala Leu Gly Ser Asp Leu His Val Asp Val Lys Gly Tyr
        115                 120                 125

Lys Asp Gly Gly Ile His Leu Glu Cys Arg Ser Thr Gly Trp Tyr Pro
```

```
                130                 135                 140
Gln Pro Gln Ile Gln Trp Ser Asn Asn Lys Gly Glu Asn Ile Pro Thr
145                 150                 155                 160

Val Glu Ala Pro Val Val Ala Asp Gly Val Gly Leu Tyr Ala Val Ala
                165                 170                 175

Ala Ser Val Ile Met Arg Gly Ser Ser Gly Glu Gly Val Ser Cys Thr
                180                 185                 190

Ile Arg Ser Ser Leu Leu Gly Leu Glu Lys Thr Ala Ser Ile Ser Ile
                195                 200                 205

Ala Asp Pro Phe Phe Arg Ser Ala Gln Arg Trp Ile Ala Ala Leu Ala
                210                 215                 220

Gly
225

<210> SEQ ID NO 107
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 107

Gln Phe Ser Val Leu Gly Pro Ser Gly Pro Ile Leu Ala Met Val Gly
1               5                   10                  15

Glu Asp Ala Asp Leu Pro Cys His Leu Phe Pro Thr Met Ser Ala Glu
                20                  25                  30

Thr Met Glu Leu Lys Trp Val Ser Ser Ser Leu Arg Gln Val Val Asn
                35                  40                  45

Val Tyr Ala Asp Gly Lys Glu Val Glu Asp Arg Gln Ser Ala Pro Tyr
            50                  55                  60

Arg Gly Arg Thr Ser Ile Leu Arg Asp Gly Ile Thr Ala Gly Lys Ala
65                  70                  75                  80

Ala Leu Arg Ile His Asn Val Thr Ala Ser Asp Ser Gly Lys Tyr Leu
                85                  90                  95

Cys Tyr Phe Gln Asp Gly Asp Phe Tyr Glu Lys Ala Leu Val Glu Leu
                100                 105                 110

Lys Val Ala Ala Leu Gly Ser Asn Leu His Val Glu Val Lys Gly Tyr
                115                 120                 125

Glu Asp Gly Gly Ile His Leu Glu Cys Arg Ser Thr Gly Trp Tyr Pro
                130                 135                 140

Gln Pro Gln Ile Gln Trp Ser Asn Ala Lys Gly Glu Asn Ile Pro Ala
145                 150                 155                 160

Val Glu Ala Pro Val Val Ala Asp Gly Val Gly Leu Tyr Glu Val Ala
                165                 170                 175

Ala Ser Val Ile Met Arg Gly Gly Ser Gly Glu Gly Val Ser Cys Ile
                180                 185                 190

Ile Arg Asn Ser Leu Leu Gly Leu Glu Lys Thr Ala Ser Ile Ser Ile
                195                 200                 205

Ala Asp Pro Phe Phe Arg Ser Ala Gln Pro Trp
                210                 215

<210> SEQ ID NO 108
<211> LENGTH: 219
<212> TYPE: PRT
<213> ORGANISM: Artificial Sequence
<220> FEATURE:
<223> OTHER INFORMATION: Synthetic Sequence
```

<400> SEQUENCE: 108

```
Gln Phe Ser Val Leu Gly Pro Ser Gly Pro Ile Leu Ala Met Val Gly
1               5                   10                  15
Glu Asp Ala Asp Leu Pro Cys His Leu Phe Pro Thr Met Ser Ala Glu
            20                  25                  30
Thr Met Glu Leu Arg Trp Val Ser Ser Leu Arg Gln Val Val Asn
        35                  40                  45
Val Tyr Ala Asp Gly Lys Glu Val Glu Asp Arg Gln Ser Ala Pro Tyr
    50                  55                  60
Arg Gly Arg Thr Ser Ile Leu Arg Asp Gly Ile Thr Ala Gly Lys Ala
65                  70                  75                  80
Ala Leu Arg Ile His Asn Val Thr Ala Ser Asp Ser Gly Lys Tyr Leu
                85                  90                  95
Cys Tyr Phe Gln Asp Gly Asp Phe Tyr Glu Lys Ala Leu Val Glu Leu
            100                 105                 110
Lys Val Ala Ala Leu Gly Ser Asp Leu His Ile Glu Val Lys Gly Tyr
            115                 120                 125
Glu Asp Gly Gly Ile His Leu Glu Cys Arg Ser Thr Gly Trp Tyr Pro
        130                 135                 140
Gln Pro Gln Ile Lys Trp Ser Asp Thr Lys Gly Glu Asn Ile Pro Ala
145                 150                 155                 160
Val Glu Ala Pro Val Val Ala Asp Gly Val Gly Leu Tyr Ala Val Ala
                165                 170                 175
Ala Ser Val Ile Met Arg Gly Ser Ser Gly Gly Gly Val Ser Cys Ile
            180                 185                 190
Ile Arg Asn Ser Leu Leu Gly Leu Glu Lys Thr Ala Ser Ile Ser Ile
            195                 200                 205
Ala Asp Pro Phe Phe Arg Ser Ala Gln Pro Trp
        210                 215
```

<210> SEQ ID NO 109
<211> LENGTH: 221
<212> TYPE: PRT
<213> ORGANISM: Artificial Sequence
<220> FEATURE:
<223> OTHER INFORMATION: Synthetic Sequence

<400> SEQUENCE: 109

```
Gln Trp Gln Val Phe Gly Pro Asp Lys Pro Val Gln Ala Leu Val Gly
1               5                   10                  15
Glu Asp Ala Ala Phe Ser Cys Phe Leu Ser Pro Lys Thr Asn Ala Glu
            20                  25                  30
Ala Met Glu Val Arg Phe Phe Arg Gly Gln Phe Ser Ser Val Val His
        35                  40                  45
Leu Tyr Arg Asp Gly Lys Asp Gln Pro Phe Met Gln Met Pro Gln Tyr
    50                  55                  60
Gln Gly Arg Thr Lys Leu Val Lys Asp Ser Ile Ala Glu Gly Arg Ile
65                  70                  75                  80
Ser Leu Arg Leu Glu Asn Ile Thr Val Leu Asp Ala Gly Leu Tyr Gly
                85                  90                  95
Cys Arg Ile Ser Ser Gln Ser Tyr Tyr Gln Lys Ala Ile Trp Glu Leu
            100                 105                 110
Gln Val Ser Ala Leu Gly Ser Val Pro Leu Ile Ser Ile Thr Gly Tyr
            115                 120                 125
```

Val Asp Arg Asp Ile Gln Leu Leu Cys Gln Ser Ser Gly Trp Phe Pro
130                 135                 140

Arg Pro Thr Ala Lys Trp Lys Gly Pro Gln Gly Gln Asp Leu Ser Thr
145                 150                 155                 160

Asp Ser Arg Thr Asn Arg Asp Met His Gly Leu Phe Asp Val Glu Ile
                165                 170                 175

Ser Leu Thr Val Gln Glu Asn Ala Gly Ser Ile Ser Cys Ser Met Arg
                180                 185                 190

His Ala His Leu Ser Arg Glu Val Glu Ser Arg Val Gln Ile Gly Asp
            195                 200                 205

Thr Phe Phe Glu Pro Ile Ser Trp His Leu Ala Thr Lys
210                 215                 220

<210> SEQ ID NO 110
<211> LENGTH: 222
<212> TYPE: PRT
<213> ORGANISM: Artificial Sequence
<220> FEATURE:
<223> OTHER INFORMATION: Synthetic Sequence

<400> SEQUENCE: 110

Ser Ser Glu Val Lys Val Leu Gly Pro Glu Tyr Pro Ile Leu Ala Leu
1               5                   10                  15

Val Gly Glu Glu Val Glu Phe Pro Cys His Leu Trp Pro Gln Leu Asp
                20                  25                  30

Ala Gln Gln Met Glu Ile Arg Trp Phe Arg Ser Gln Thr Phe Asn Val
            35                  40                  45

Val His Leu Tyr Gln Glu Gln Gln Glu Leu Pro Gly Arg Gln Met Pro
        50                  55                  60

Ala Phe Arg Asn Arg Thr Lys Leu Val Lys Asp Asp Ile Ala Tyr Gly
65                  70                  75                  80

Ser Val Val Leu Gln Leu His Ser Ile Ile Pro Ser Asp Lys Gly Thr
                85                  90                  95

Tyr Gly Cys Arg Phe His Ser Asp Asn Phe Ser Gly Glu Ala Leu Trp
            100                 105                 110

Glu Leu Glu Val Ala Gly Leu Gly Ser Asp Pro His Leu Ser Leu Glu
        115                 120                 125

Gly Phe Lys Glu Gly Gly Ile Gln Leu Arg Leu Arg Ser Ser Gly Trp
130                 135                 140

Tyr Pro Lys Pro Lys Val Gln Trp Arg Asp His Gln Gly Gln Cys Leu
145                 150                 155                 160

Pro Pro Glu Phe Glu Ala Ile Val Trp Asp Ala Gln Asp Leu Phe Ser
                165                 170                 175

Leu Glu Thr Ser Val Val Val Arg Ala Gly Ala Leu Ser Asn Val Ser
            180                 185                 190

Val Ser Ile Gln Asn Leu Leu Leu Ser Gln Lys Lys Glu Leu Val Val
        195                 200                 205

Gln Ile Ala Asp Val Phe Val Pro Gly Ala Ser Ala Trp Lys
210                 215                 220

<210> SEQ ID NO 111
<211> LENGTH: 228
<212> TYPE: PRT
<213> ORGANISM: Artificial Sequence
<220> FEATURE:
<223> OTHER INFORMATION: Synthetic Sequence

<400> SEQUENCE: 111

```
Ser Ile Trp Lys Ala Asp Phe Asp Val Thr Gly Pro His Ala Pro Ile
1               5                   10                  15

Leu Ala Met Ala Gly Gly His Val Glu Leu Gln Cys Gln Leu Phe Pro
            20                  25                  30

Asn Ile Ser Ala Glu Asp Met Glu Leu Arg Trp Tyr Arg Cys Gln Pro
        35                  40                  45

Ser Leu Ala Val His Met His Glu Arg Gly Met Asp Met Asp Gly Glu
    50                  55                  60

Gln Lys Trp Gln Tyr Arg Gly Arg Thr Thr Phe Met Ser Asp His Val
65                  70                  75                  80

Ala Arg Gly Lys Ala Met Val Arg Ser His Arg Val Thr Thr Phe Asp
                85                  90                  95

Asn Arg Thr Tyr Cys Cys Arg Phe Lys Asp Gly Val Lys Phe Gly Glu
            100                 105                 110

Ala Thr Val Gln Val Gln Val Ala Gly Leu Gly Arg Glu Pro Arg Ile
        115                 120                 125

Gln Val Thr Asp Gln Gln Asp Gly Val Arg Ala Glu Cys Thr Ser Ala
    130                 135                 140

Gly Cys Phe Pro Lys Ser Trp Val Glu Arg Arg Asp Phe Arg Gly Gln
145                 150                 155                 160

Ala Arg Pro Ala Val Thr Asn Leu Ser Ala Ser Ala Thr Thr Arg Leu
                165                 170                 175

Trp Ala Val Ala Ser Ser Leu Thr Leu Trp Asp Arg Ala Val Glu Gly
            180                 185                 190

Leu Ser Cys Ser Ile Ser Ser Pro Leu Leu Pro Glu Arg Arg Lys Val
        195                 200                 205

Ala Glu Ser His Leu Pro Ala Thr Phe Ser Arg Ser Ser Gln Phe Thr
    210                 215                 220

Ala Trp Lys Ala
225
```

HETERODIMERIC PROTEINS FOR MODULATING GAMMA DELTA T CELLS

PRIORITY

This Application is a continuation of U.S. application Ser. No. 16/741,146, filed Jan. 13, 2020. U.S. application Ser. No. 16/741,146 is a continuation of International Application No. PCT/US20/12589, filed Jan. 7, 2020, which claims the benefit of, and priority to, US Application Nos. 62/941,176, filed Nov. 27, 2019, 62/876,346, filed Jul. 19, 2019, and 62/789,344, filed Jan. 7, 2019, each of which is hereby incorporated by reference in its entirety.

TECHNICAL FIELD

The present technology relates to heterodimeric proteins that find use in the treatment of diseases, such as immunotherapies for cancer and autoimmunity.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: SHK-029C1 116981-5029 ST25 ; date created: May 15, 2020; file size: 376,057 bytes).

BACKGROUND

The modulation of protein-protein interactions is a useful mechanism for therapeutic intervention in various diseases and pathologies. Soluble binding proteins which interact with ligands can potentially sequester the ligand away from the receptor, thereby reducing the activation of that particular receptor pathway. Alternatively, sequestration of the ligand may delay its elimination or degradation, thereby increasing its duration of effect and biological activity. Additionally, soluble ligands may be utilized to either activate or inhibit specific receptors.

Gamma delta T cells amount to up to 5% of all T cells in a human, but they play an important role against cancer. Recent research has indicated that the amount of gamma delta T cells that infiltrate a tumor is an excellent predictor of a favorable outcome for the patient. Further, unlike the alpha beta T cells commonly used in CAR-T therapy, gamma delta T cells play a role in the innate immune response. The prognostic significance of gamma delta T cells in cancer has prompted an effort to manipulate gamma delta T cells as a therapeutic strategy for cancer. Current approaches are limited to ex vivo strategies, where a patients gamma delta T cells are either harvested and modified to express a chimeric antigen receptor, and/or expanded to greater numbers in cell culture, followed by infusion of the modified gamma delta T cells back into the cancer patient (Front Immunol. 2018 Jun. 26; 9:1409). Strategies to manipulate gamma delta T cells directly in cancer patients have been hampered by an inability to conclusively identify the molecular entities directly recognized by the gamma delta T cell receptor (Nat Immunol. 2019 February; 20(2): 121-128). In fact, the most widely accepted activators of gamma delta T cells include largely intracellular molecules such as heat shock proteins, intermediates of the non-mevalonate pathway of isopentyl pyrophosphate (IPP) biosynthesis (including HMB-PP), intracellular bacteria (eg. mycobacteria and *listeria*), viruses (eg. cytomegalovirus), and other lipid antigens.

Accordingly, there remains a need for novel compositions and methods gamma-delta T cell engagement that do not require use of the above molecules.

SUMMARY

Accordingly, in one aspect, the present technology provides a heterodimeric protein comprising (a) a first domain comprising one or more butyrophilin family proteins, or a fragment thereof; (b) a second domain comprising a targeting domain, the targeting domain being selected from an (i) antibody, antibody-like molecule, or antigen binding fragment thereof, and (ii) a extracellular domain; and (c) a linker that adjoins the first and second domain and which facilitates heterodimerization. In some embodiments, the heterodimeric protein comprises two of the same butyrophilin family proteins or two different butyrophilin family proteins. In some embodiments, the heterodimeric protein comprises two individual polypeptide chains which self-associate. In some embodiments, the butyrophilin family proteins comprise a V-type domain and/or a B30.2 domain. In some embodiments, the first domain is a butyrophilin-like (BTNL) family protein, such as BTNL1, BTN1A1, BTNL2, BTN2A1, BTN2A2, BTN2A3, BTNL3, BTN3A1, BTN3A2, BTN3A3, BTNL6, BTNL8, BTNL9, BTNL10, and SKINT.

In some embodiments, the targeting domain is an antibody, an antibody-like molecule, or antigen binding fragment thereof. The antigen-like molecule may be selected from a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; an Affimer, a Microbody; an aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; a DuoBody, a Fv, a Fab, a Fab', and a F(ab')$_2$.

In some embodiments, the targeting domain is an extracellular domain. In some embodiments, the targeting domain is capable of binding an antigen on the surface of a cancer cell. Exemplary the targeting domain specifically binds one of CD19, PSMA, GD2, PSCA, BCMA, CD123, B7-H3, CD20, CD30, CD33, CD38, CEA, CLEC12A, DLL3, EGFRvIII, EpCAM, CD307, FLT3, GPC3, gpA33, HER2, MUC16, P-cadherin, SSTR2, and mesothelin.

In some embodiments, the first polypeptide chain and the second polypeptide chain heterodimers through electrostatic interactions between positively charged amino acid residues and negatively charged amino acid residues on the first and second charge polarized core domains. In some embodiments, the positively charged amino acid residues may include one or more of amino acids selected from His, Lys, and Arg. In some embodiments, the negatively charged amino acid residues may include one or more amino acids selected from Asp and Glu.

Accordingly, in some embodiments, each of the first and/or second charge polarized core domains comprises proteins having positively or negatively charged amino acid residues at the amino and carboxy terminus of the core domain. In an illustrative embodiment, the first charge polarized core domain may comprise a protein having positively charged amino acids at the amino terminus which are adjoined by a linker (e.g., a stabilizing domain) to a protein having negatively charged amino acid residues at the carboxy terminus. In such an embodiment, the second charge polarized core domain may comprise a protein having negatively charged amino acids at the amino terminus which are adjoined by a linker (e.g., a stabilizing domain) to a protein having positively charged amino acid residues at the carboxy terminus. In another illustrative embodiment, the first charge polarized core domain may comprise a protein having negatively charged amino acids at the amino terminus which are adjoined by a linker (e.g., a stabilizing domain) to a protein having positively charged amino acid residues at the carboxy terminus. In such an embodiment, the second charge polarized core domain may comprise proteins having positively charged amino acids at the amino terminus which are adjoined by a linker (e.g., a stabilizing domain) to a protein having negatively charged amino acid residues at the carboxy terminus.

In various embodiments, each of the first and/or second charge polarized core domains further comprise a linker (e.g., a stabilizing domain) which adjoins the proteins having positively or negatively charged amino acids. In some embodiments, the linker (e.g., a stabilizing domain) is optionally selected from a flexible amino acid sequence, IgG hinge region, or antibody sequence. In an embodiment, the linker (e.g., a stabilizing domain) comprises the hinge-CH2-CH3 Fc domain derived from IgG1, optionally human IgG1. In another embodiment, the linker (e.g., a stabilizing domain) comprises the hinge-CH2-CH3 Fc domain derived from IgG4, optionally human IgG4.

In some embodiments, the heterodimeric protein is capable of engaging gamma-delta T cells.

In embodiments, in a heterochimeric protein, the first domain is selected from Table 1, e.g. one or more ECDs from Table 1, e.g. 2 ECDs of Table 1.

In embodiments, the first domain comprises a portion of an extracellular domain of a Type 1 transmembrane protein, wherein the portion of the extracellular domain is capable of binding the Type 1 transmembrane protein's receptor/ligand. In embodiments, the Type 1 transmembrane protein is selected from lymphocyte-activation gene 3 (LAG-3), programmed cell death protein 1 (PD-1), and T cell immunoreceptor with Ig and ITIM domains (TIGIT).

In embodiments, the protein modulates the function of gamma delta T cells.

In embodiments, the protein on the amino- or carboxy-terminus is natively heterodimeric, and wherein the protein on the opposite terminus is not natively heterodimeric.

In embodiments the heterodimeric protein is a complex of two polypeptide chains.

In embodiments the heterodimeric protein comprises an alpha chain and a beta chain wherein the alpha chain and the beta chain each independently comprise (a) a first domain comprising a butyrophilin family protein, or fragment thereof; (b) a second domain comprising a targeting domain, the targeting domain being selected from an (i) antibody, antibody-like molecule, or antigen binding fragment thereof, and (ii) a extracellular domain; and (c) a linker that adjoins the first and second domain.

In embodiments the alpha chain and the beta chain self-associate to form the heterodimer.

In various aspects, the heterodimeric protein of the present technology is used for contemporaneous activation and targeting of gamma delta T cells to tumor cells, modulating a patient's immune response, and/or stimulating proliferation of gamma delta T cells in vivo. Accordingly, in various aspects, the heterodimeric protein of the present technology is used in a method for treating cancer, infectious, or autoimmune diseases comprising administering an effective amount of a pharmaceutical composition comprising the heterodimeric protein to a patient in need thereof.

In various aspects, the heterodimeric protein of the present technology is used for stimulating proliferation of gamma delta T cells by administering an effective amount of a pharmaceutical composition of the present technology to a subject in need thereof thereby causing an in vivo proliferation of gamma delta T cells and/or contacting an effective amount of a pharmaceutical composition of the present technology with a cell derived from a subject in need thereof thereby causing an ex vivo proliferation of gamma delta T cells.

In various aspects, the heterodimeric protein of the present technology is used for stimulating proliferation of gamma delta T cells in the absence of heat shock proteins, intermediates of the non-mevalonate pathway of isopentyl pyrophosphate (IPP) biosynthesis (including HMB-PP), intracellular bacteria (eg. mycobacteria and *listeria*), viruses (eg. cytomegalovirus), and other lipid antigens.

Also in various aspects, the present heterodimeric protein is used in a method for treating autoimmune diseases comprising administering an effective amount of a pharmaceutical composition comprising the heterodimeric protein to a patient in need thereof. In further aspects, the present heterodimeric protein is used in a method for treating infections, including without limitation, viral infections or other intracellular pathogens. In still further aspects, the present heterodimeric protein is used in a method for treating cancers.

Also provided in various aspects are pharmaceutical compositions comprising the heterodimeric protein of any of the embodiments disclosed herein, expression vectors comprising a nucleic acids encoding the heterodimeric protein of any of the embodiments disclosed herein, or host cells comprising expression vectors comprising a nucleic acids encoding the heterodimeric protein of any of the embodiments disclosed herein. Any aspect or embodiment disclosed herein can be combined with any other aspect or embodiment as disclosed herein.

BRIEF DESCRIPTION OF THE FIGURES

FIG. 9A shows a bar graph of the proportion of gamma delta T cells staining positive for CD107a by flow cytometry following the indicated co-culture. CD107a is a marker of cell degranulation, which occurs when T cells release cytolytic granules containing perforin and granzymes. These data indicate that the GADLEN construct stimulated a dose-dependent CD107a expression in isolated gamma delta T cells. gd=gamma delta T cells. FIG. 9B shows a bar graph illustrating dose-dependent upregulation of CD69 (a cell surface marker of activated T cells). Notably, only minor increases in CD107a or CD69 expression were noted when gamma delta T cells were co-cultured with WEHI-3 tumor cells in the absence of the GADLEN construct.

FIG. 10A shows a bar graph illustrating the proportion of gamma delta T cells staining positive for CD107a by flow cytometry following co-culture. gd=gamma delta T cells. CD107a is a marker of cell degranulation, which occurs when T cells release cytolytic granules containing perforin and granzymes. These data indicate that the GADLEN construct stimulated dose-dependent CD107a expression in isolated gamma delta T cells (FIG. 10A). FIG. 10B shows a bar graph illustrating the dose-dependent upregulation of CD69 (a cell surface marker of activated T cells). Notably, only minor increases in CD107a or CD69 expression are noted when gamma delta T cells were co-cultured with A20 tumor cells in the absence of the GADLEN construct.

11B). Each group contained ≥5 mice, and representative flow cytometry plots using one mouse from each group are shown. FIG. 11A shows the frequency of CD20+ cells in the peripheral blood. These data indicated that 24 hours after treatment, the frequency of CD20+ cells had not significantly changed for the vehicle, anti-PD1 or anti-CD19 antibody treated groups, however, the frequency of CD20+ B cells in the BTNL1/6-CD19scFv GADLEN protein treated group had reduced by >10 fold. FIG. 11B shows the frequency of gamma delta T cells in the peripheral blood of mice out of total CD3+ T cells. These data indicated that whereas <1% of circulating CD3+ T cells expressed the gamma delta TCR in vehicle, anti-PD1 or anti-CD19 antibody treated mice, the proportion of gamma delta T cells has increased >10 fold within 24 hours of treatment with the BTNL1/6-CD19scFv GADLEN protein.

FIG. 12B shows the frequency of CD20+ B cells 24 hours after the indicated treatment in Balb.c mice with established A20 tumors. Similarly, FIG. 12C indicates the frequency of CD19+ B cells (all data shown as mean±SEM, and FIG. 12D shows the frequency of CD20+B cells 24 hours after the indicated treatment in Balb.c mice with established WEHI-3 tumors. The data illustrate that while the anti-CD19 treatment antibody competed with the CD19 detection antibody, the antibody treatment had not truly depleted B cells in the peripheral blood because the frequenc of CD20+ B cells (where there is no competition between the CD19 treatment antibody and the CD20 detection antibody) had not significantly changed. In contrast, all mice treated with the BTNL1/6-CD19scFv GADLEN protein showed near complete depletion of peripheral blood B cells within 24 hours of treatment.

FIG. 13B shows the frequency of gamma delta T cells in mice bearing established WEHI-3 tumors 24 hours after the indicated treatment (all data shown as mean±SEM with ≥5 mice/group). These data illustrated that the BTNL1/6-CD19scFv GADLEN protein had stimulated rapid proliferation of mouse gamma delta T cells within 24 hours of treatment.

FIG. 18B indicates the proportion of human gamma delta T cells expressing the activation marker, CD69, from the same co-cultures as panel A. The data indicate that the BTNL3/8-CD19scFv and BTN3A1/3A2-CD19scFv GADLEN constructs both cause CD107a degranulation and CD69 expression in human gamma delta T cells, similar to what was observed in mouse gamma delta T cells using the species-specific construct. The increased activity of the BTN3A1/3A2 construct in this assay is likely a result of the higher proportion of Vγ9+gamma delta T cells in peripheral blood, which are the gamma delta T cell population that selectively respond to a BTN3A1/3A2 heterodimer. Gamma delta T cells isolated from human intestinal epithelium would be comparatively enriched for Vγ4+gamma delta T cells, and therefore be selectively responsive to a BTNL3/8 GADLEN construct.

FIGS. 32A-32C show the in vivo anti-tumor activity of BTNL1/6-Fc-CD19scFv GADLEN in aWEHI3 tumor model. FIG. 32A shows a line graph of the average tumor growth of a WEHI-3 (leukemia) tumors. WEHI-3 cells were inoculated subcutaneously on the rear flank. When the average starting tumor volume (STV) reached 90.92 mm$^3$ (day 0), treatments were begun. The treatment groups were anti-PD1 (clone RMP1-14), anti-CD19 (clone 1D3), and BTNL1/6-Fc-CD19scFv were each given in 3 doses IP; 100 µg per dose on days 0, 3, and 6. Vehicle alone was used as a negative control. Tumor growth was assessed over a 17-day time course. FIG. 32B shows a bar graph of tumor size on day 8. FIG. 32C shows a bar graph of tumor size on day 10. Error is SEM and statistical significance was determined using one-way ANOVA.

DETAILED DESCRIPTION

Figure 1:
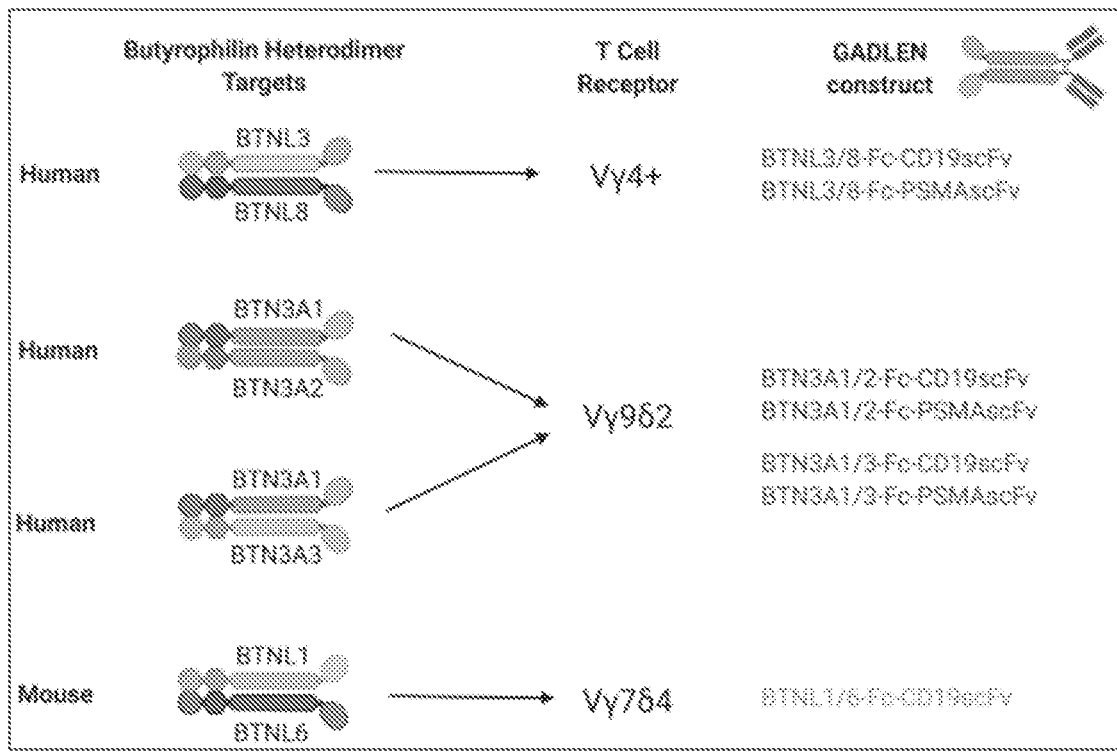
FIG. 1 shows the illustrations for various non-limiting protein engineering embodiments of the present technology. Top panel shows an illustrative heterodimeric protein of the present technology comprising i) a human butyrophilin 3/8 heterodimer adjoined to either a human CD19-specific or PSMA-specific scFv, ii) a human butyrophilin 3A1/3A2 heterodimer adjoined to either a human CD19-specific or PSMA-specific scFv, iii) a human butyrophilin 3A1/3A3 heterodimer adjoined to either a human CD19-specific or PSMA-specific scFv, or iv) a mouse butyrophilin 1/6 heterodimer adjoined to a mouse CD19-specific scFv. As shown in the middle panel, the butyrophilin family members contemplated in a heterodimeric construct include but are not limited to: BTN1A1, BTN2A1, BTN2A2, BTN2A3, BTN3A3, BTNL2, BTNL9, BTNL10, SKINT, etc. Other antigen-targets for a butyrophilin heterodimeric construct include but are not limited to: GD2, PSCA, BCMA, CD123, B7-H3, CD20, CD30, CD33, CD38, CEA, CLEC12A, DLL3, EGFRvIII, EpCAM, CD307, FLT3, GPC3, gpA33, HER2, MUC16, P-cadherin, SSTR2, mesothelin, etc (middle panel). Without wishing to be bound by theory, the proposed mechanism of action for a butyrophilin heterodimer construct targeting either CD19 or PSMA as illustrated in the bottom panel. In this example, engagement of gamma delta T cells to CD19 or PSMA positive tumor cells is enhanced due to the butyrophilin heterodimer simultaneously engaging a tumor antigen and the gamma delta T cell receptor. The contemplated GAmma DELta T cell ENgager constructs are referred to herein as 'GADLEN' fusion proteins.
Figure 1:
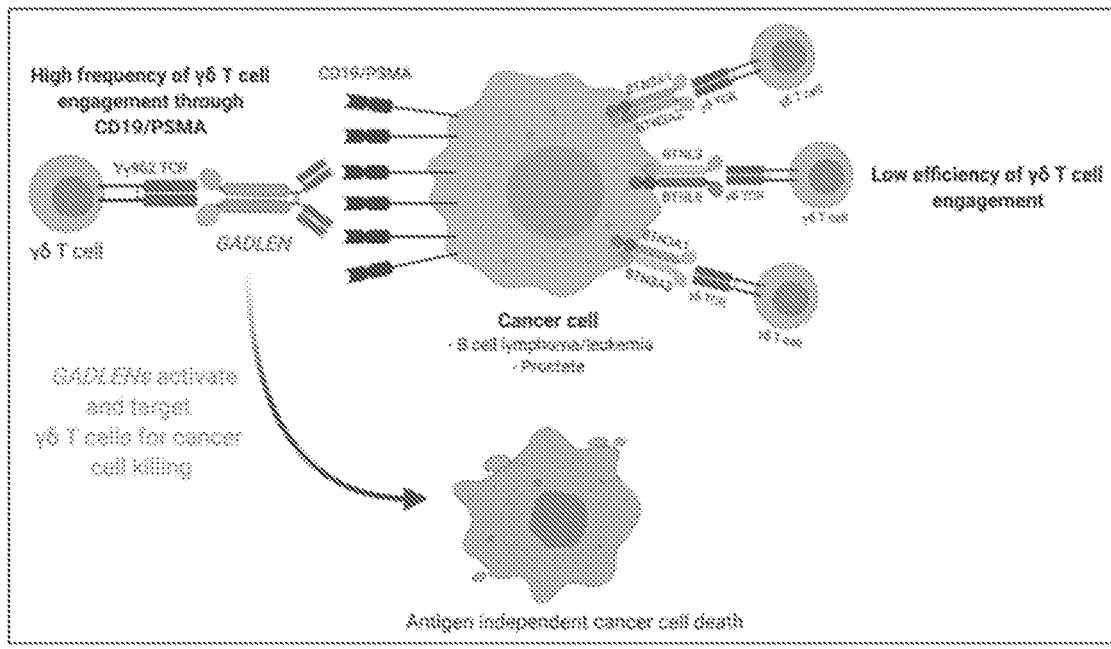

The present technology is directed to novel chimeric proteins that have the ability to, inter alia, target gamma delta T cells and cause their activation, while also forming a synapse with, e.g., tumor cells. Thus, the present multifunctional chimeric proteins provide for unique means to modulate a subject's immune system for therapy.

The Heterodimeric Proteins of the Present Technology

In one aspect, the present technology relates to heterodimeric proteins comprising: (a) a first domain comprising one or more butyrophilin family proteins, or a fragment thereof; (b) a second domain comprising a targeting domain, the targeting domain being selected from an (i) antibody, antibody-like molecule, or antigen binding fragment thereof, and (ii) a extracellular domain; and (c) a linker that adjoins the first and second domain. In some embodiments, the heterodimeric protein of the invention comprises two polypeptide chains, wherein the first polypeptide chain and the second polypeptide chain comprise (a) a first domain comprising one or more butyrophilin family proteins, or a fragment thereof; (b) a second domain comprising a targeting domain, the targeting domain being selected from an (i) antibody, antibody-like molecule, or antigen binding fragment thereof, and (ii) a extracellular domain; and (c) a linker that adjoins the first and second domain. In some embodiments, the heterodimeric protein comprises two individual polypeptide chains which self-associate. In some embodiments, the first domain comprising one or more butyrophilin family proteins, or a fragment thereof of the first and the second polypeptide chain are the same. In some embodiments, the second domain comprising a targeting domain of the first and the second polypeptide chain are the same. In some embodiments, the linker that adjoins the first and second domain are the same.

The Butyrophilin Family Proteins, or Fragments Thereof

The heterodimeric proteins of any of the embodiments disclosed herein comprise a first domain comprising one or more butyrophilin family proteins, or a fragment thereof. In some embodiments, the butyrophilin family proteins are selected from BTNL1, BTN1A1, BTNL2, BTN2A1, BTN2A2, BTN2A3, BTNL3, BTN3A1, BTN3A2, BTN3A3, BTNL6, BTNL8, BTNL9, BTNL10, and SKINT. In some embodiments, the first domain comprises: (a) any one of BTNL1, BTN1A1, BTNL2, BTN2A1, BTN2A2, BTN2A3, BTNL3, BTN3A1, BTN3A2, BTN3A3, BTNL6, BTNL8, BTNL9, BTNL10, and SKINT; and (b) any one of BTNL1, BTN1A1, BTNL2, BTN2A1, BTN2A2, BTN2A3, BTNL3, BTN3A1, BTN3A2, BTN3A3, BTNL6, BTNL8, BTNL9, BTNL10, and SKINT. In some embodiments, the first domain comprises: (a) any one of human BTNL1, human BTN1A1, human BTNL2, human BTN2A1, human BTN2A2, human BTN2A3, human BTNL3, human BTN3A1, human BTN3A2, human BTN3A3, human BTNL6, human BTNL8, human BTNL9, human BTNL10, and human SKINT, and (b) any one of human BTNL1, human BTN1A1, human BTNL2, human BTN2A1, human BTN2A2, human BTN2A3, human BTNL3, human BTN3A1, human BTN3A2, human BTN3A3, human BTNL6, human BTNL8, human BTNL9, human BTNL10, and human SKINT.

In some embodiments, the first domain comprises a fragment of butyrophilin family proteins, wherein the fragment is capable of binding a gamma delta T cell receptor and is optionally an extracellular domain, optionally comprising one or more of an immunoglobulin V (IgV)- and IgC-like domain. In some embodiments, the first domain comprises a fragment of butyrophilin family proteins, wherein the fragment is capable of binding a gamma delta T cell receptor selected from a Vγ4, Vγ9δ2, or Vγ7δ4 TCR.

In some embodiments, the first domain comprises two of the same butyrophilin family proteins. In some embodiments, wherein the first domain comprises two different butyrophilin family proteins. In some embodiments, the butyrophilin family proteins comprise a V-type domain. Suitable butyrophilin family proteins or fragments thereof are derived from the native butyrophilin family proteins that comprise a B30.2 domain in the cytosolic tail of the full length protein.

An illustrative amino acid sequence of mouse BTNL1 suitable in the present technology is:

```
                                          (SEQ ID NO: 47)
EVSWFSVKGPAEPITVLLGTEATLPCQLSPEQSAARMHIRWYRAQPTPAV

LVFHNGQEQGEVQMPEYRGRTQMVRQAIDMGSVALQIQQVQASDDGLYHC

QFTDGFTSQEVSMELRVIGLGSAPLVHMTGPENDGIRVLCSSSGWFPKPK

VQWRDTSGNMLLSSSELQTQDREGLFQVEVSLLVTDRAIGNVICSIQNPM

YDQEKSKAILLPEPFFPKTCPWK
```

An illustrative amino acid sequence of mouse BTNL6 suitable in the present technology (:

```
                                          (SEQ ID NO: 48)
EQLPEYSQRTSLVKEQFHQGTAAVRILNVQAPDSGIYICHFKQGVFYEEA

ILELKVAAMGSVPEVYIKGPEDGGVCVVCITSGWYPEPQVHWKDSRGEKL

TASLEIHSEDAQGLFRTETSLVVRDSSVRNVTCSTFNPILGQEKAMAMFL

PEPFFPKVSPWKP
```

An illustrative amino acid sequence of human BTNL3 suitable in the present technology is the following:

```
                                          (SEQ ID NO: 49)
QWQVTGPGKFVQALVGEDAVFSCSLFPETSAEAMEVRFFRNQFHAVVHLY

RDGEDWESKQMPQYRGRTEFVKDSIAGGRVSLRLKNITPSDIGLYGCWFS
```

-continued
```
SQIYDEEATWELRVAALGSLPLISIVGYVDGGIQLLCLSSGWFPQPTAKW

KGPQGQDLSSDSRANADGYSLYDVEISIIVQENAGSILCSIHLAEQSHEV

ESKVLIGETFFQPSPWRLAS
```

An illustrative amino acid sequence of human BTN3A1 suitable in the present technology:

```
                                          (SEQ ID NO: 50)
QFSVLGPSGPILAMVGEDADLPCHLFPTMSAETMELKWVSSSLRQVVNVY

ADGKEVEDRQSAPYRGRTSILRDGITAGKAALRIHNVTASDSGKYLCYFQ

DGDFYEKALVELKVAALGSDLHVDVKGYKDGGIHLECRSTGWYPQPQIQW

SNNKGENIPTVEAPVVADGVGLYAVAASVIMRGSSGEGVSCTIRSSLLGL

EKTASISIADPFFRSAQRWIAALAG
```

An illustrative amino acid sequence of human BTN3A2 suitable in the present technology

```
                                          (SEQ ID NO: 51)
QFSVLGPSGPILAMVGEDADLPCHLFPTMSAETMELKWVSSSLRQVVNVY

ADGKEVEDRQSAPYRGRTSILRDGITAGKAALRIHNVTASDSGKYLCYFQ

DGDFYEKALVELKVAALGSNLHVEVKGYEDGGIHLECRSTGWYPQPQIQW

SNAKGENIPAVEAPVVADGVGLYEVAASVIMRGGSGEGVSCIIRNSLLGL

EKTASISIADPFFRSAQPW
```

An illustrative amino acid sequence of human BTNL8 suitable in the present technology is as follows:

```
                                          (SEQ ID NO: 52)
QWQVFGPDKPVQALVGEDAAFSCFLSPKTNAEAMEVRFFRGQFSSVVHLY

RDGKDQPFMQMPQYQGRTKLVKDSIAEGRISLRLENITVLDAGLYGCRIS

SQSYYQKAIWELQVSALGSVPLISITGYVDRDIQLLCQSSGWFPRPTAKW

KGPQGQDLSTDSRTNRDMHGLFDVEISLTVQENAGSISCSMRHAHLSREV

ESRVQIGDTFFEPISWHLATK
```

The Second Domain Comprising a Targeting Domain

The heterodimeris proteins of any of the embodiments disclosed herein comprise a second domain comprising a targeting domain. In some embodiments, the targeting domain is an antibody-like molecule, or antigen binding fragment thereof. In some embodiments, the antibody-like molecule is selected from a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; an Affimer, a Microbody; an aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; a DuoBody, a Fv, a Fab, a Fab', and a F(ab')$_2$. In some embodiments, the antibody-like molecule is an scFv. In some embodiments, the targeting domain is an extracellular domain. In some embodiments, the targeting domain is capable of binding an antigen on the surface of a cancer cell. In some embodiments, the targeting domain specifically binds one of CD19, PSMA, GD2, PSCA, BCMA, CD123, B7-H3, CD20, CD30, CD33, CD38, CEA, CLEC12A, DLL3, EGFRvIII, EpCAM, CD307, FLT3, GPC3, gpA33, HER2, MUC16, P-cadherin, SSTR2, and mesothelin. In some embodiments, the targeting domain comprises a portion of the extracellular domain of LAG-3, PD-1, TIGIT, CD19, or PSMA. In some embodiments, the targeting domain specifically binds CD19. In some embodiments, the targeting domain specifically binds PSMA.

Illustrative sequences of second domain comprising a targeting domain are provided below:

An illustrative targeting domain is scFVh19, which is the heavy chain variable domain of an scFV specific to human CD19, and has the following sequence:

(SEQ ID NO: 53)
DIQLTQSPASLAVSLGQRATISCKASQSVDYDGDSYLNWYQQIPGQPPKL

LIYDASNLVSGIPPRFSGSGSGTDFTLNIHPVEKVDAATYHCQQSTEDPW

TFGGGTKLEIK

An illustrative targeting domain is scFVlh19, which is light chain variable domain of an scFV specific to human CD19, and has the following sequence:

(SEQ ID NO: 54)
EVQLVESGGGLVQPGGSLTLSCAASRFMISEYHMHWVRQAPGKGLEWVST

INPAGTTDYAESVKGRFTISRDNAKNTLYLQMNSLKPEDTAVYYCDSYGY

RGQGTQVTV

An illustrative targeting domain is scFVlPSMA, which is light chain variable domain of an scFV specific to human PSMA, and has the following sequence:

(SEQ ID NO: 55)
RKGGKRGSGSGQTVVTQEPSLTVSPGGTVTLTCASSTGAVTSGNYPNWVQ

QKPGQAPRGLIGGTKFLVPGTPARFSGSLLGGKAALTLSGVQPEDEAEYY

CTLWYSNRWVFGGGTKLTVL

An illustrative targeting domain is scFvCD19, which an scFV specific to human CD19, and has the following sequence:

(SEQ ID NO: 56)
QVQLQQSGAELVRPGSSVKISCKASGYAFSSYWMNWVKQRPGQGLEWIGQ

IWPGDGDTNYNGKFKGKATLTADESSSTAYMQLSSLASEDSAVYFCARRE

TTTVGRYYYAMDYWGQGTTVTVSSGGGGSGGGGSGGGGSDIQLTQSPASL

AVSLGQRATISCKASQSVDYDGDSYLNWYQQIPGQPPKLLIYDASNLVSG

IPPRFSGSGSGTDFTLNIHPVEKVDAATYHCQQSTEDPWTFGGGTKLEIK

An illustrative targeting domain is scFvCD19VHVL, which an scFV specific to mouse CD19, and has the following sequence:

(SEQ ID NO: 57)
EVQLQQSGAELVRPGTSVKLSCKVSGDTITFYYMHFVKQRPGQGLEWIGR

IDPEDESTKYSEKFKNKATLTADTSSNTAYLKLSSLTSEDTATYFCIYGG

YYFDYWGQGVMVTVSSGGGGSGGGGSGGGGSDIQMTQSPASLSTSLGETV

TIQCQASEDIYSGLAWYQQKPGKSPQLLIYGASDLQDGVPSRFSGSGSGT

QYSLKITSMQTEDEGVYFCQQGLTYPRTFGGGTKLELK

An illustrative targeting domain is scFvCD19VLVH, which an scFV specific to mouse CD19, and has the following sequence:

(SEQ ID NO: 58)
DIQMTQSPASLSTSLGETVTIQCQASEDIYSGLAWYQQKPGKSPQLLIYG

ASDLQDGVPSRFSGSGSGTQYSLKITSMQTEDEGVYFCQQGLTYPRTFGG

GTKLELKGGGGSGGGGSGGGGSEVQLQQSGAELVRPGTSVKLSCKVSGDT

ITFYYMHFVKQRPGQGLEWIGRIDPEDESTKYSEKFKNKATLTADTSSNT

AYLKLSSLTSEDTATYFCIYGGYYFDYWGQGVMVTVSS

An illustrative targeting domain is 19scFv3, which an scFV specific to human CD19, and has the following sequence:

(SEQ ID NO: 59)
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEITGGGSGGGSGGGSEVKLQESGPGLVAPSQSLSVTCTVSGVSLPD

YGVSWIRQPPRKGLEWLGVIWGSETTYYNSALKSRLTIIKDNSKSQVFLK

MNSLQTDDTAIYYCAKHYYYGGSYAMDYWGQGTSVTVSS

An illustrative targeting domain is GD2scFv3, which an scFV specific to human GD2, and has the following sequence (SEQ ID NO: 60)
GTDFTLKISRVEAEDLGVYFCSQSTHVPPLTFGAGTKLELKGGGSGGGSG

GGSEVQLLQSGPELEKPGASVMISCKASGSSFTGYNMNWVRQNIGKSLEW

IGAIDPYYGGTSYNQKFKGRATLTVDKSSSTAYMHLKSLTSEDSAVYYCV

SGMKYWGQGTSVTVSS

The Linker Domain that Adjoins the First and the Second Domain

In some embodiments, the linker that adjoins the first and second domain comprises a charge polartized core domain. In various embodiments, each of the first and second charge polarized core domains comprises proteins having positively or negatively charged amino acid residues at the amino and carboxy terminus of the core domain. In an illustrative embodiment, the first charge polarized core domain may comprise a protein having positively charged amino acids at the amino terminus which are adjoined by a linker (e.g., a stabilizing domain) to a protein having negatively charged amino acid residues at the carboxy terminus. The second charge polarized core domain may comprise a protein having negatively charged amino acids at the amino terminus which are adjoined by a linker (e.g., a stabilizing domain) to a protein having positively charged amino acid residues at the carboxy terminus.

In another illustrative embodiment, the first charge polarized core domain may comprise a protein having negatively charged amino acids at the amino terminus which are adjoined by a linker (e.g., a stabilizing domain) to a protein having positively charged amino acid residues at the carboxy terminus. The second charge polarized core domain may comprise proteins having positively charged amino acids at the amino terminus which are adjoined by a linker (e.g., a stabilizing domain) to a protein having negatively charged amino acid residues at the carboxy terminus.

In various embodiments, formation of heterodimeric proteins is driven by electrostatic interactions between the positively charged and negatively charged amino acid residues located at the amino and carboxy termini of the first and second charge polarized core domains. Further, formation of homodimeric proteins is prevented by the repulsion between the positively charged amino acid residues or negatively charged amino acid residues located at the amino and carboxy termini of the first and second charge polarized core domains.

In various embodiments, the protein comprising positively and/or negatively charged amino acid residues at the amino or carboxy terminus of the charge polarized core domains is about 2 to about 50 amino acids long. For example, the protein comprising positively and/or negatively charged amino acid residues at either terminus of the charge polarized core domain may be about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long.

In various embodiments, the protein comprising positively charged amino acid residues may include one or more of amino acids selected from His, Lys, and Arg. In various embodiments, the protein comprising negatively charged amino acid residues may include one or more amino acids selected from Asp and Glu.

In various embodiments, each of the first and/or second charge polarized core domains may comprise a protein comprising an amino acid sequence as provided in the Table below or an amino acid sequence having at least 90%, or 93%, or 95%, or 97%, or 98%, or 99% identity thereto.

| SEQ ID NO. | Sequence |
|---|---|
| 1 | $Y_nX_nY_nX_nY_n$ (where X is a positively charged amino acid such as arginine, histidine or lysine and Y is a spacer amino acid such as serine or glycine) |
| 2 | $Y_nZ_nY_nZ_nY_n$ (where Z is a negatively charged amino acid such as aspartic acid or glutamic acid and Y is a spacer amino acid such as serine or glycine) |
| 3 | $YY_nXX_nYY_nXX_nYY_n$ (where X is a positively charged amino acid such as arginine, histidine or lysine and Y is a spacer amino acid such as serine or glycine) |
| 4 | $YY_nZZ_nYY_nZZ_nYY_n$ (where Z is a negatively charged amino acid such as aspartic acid or glutamic acid and Y is a spacer amino acid such as serine or glycine) |
| 5 | $Y_nX_nCY_nX_nY_n$ (where X is a positively charged amino acid such as arginine, histidine or lysine and Y is a spacer amino acid such as serine or glycine) |
| 6 | $Y_nZ_nCY_nZ_nY_n$ (where Z is a negatively charged amino acid such as aspartic acid or glutamic acid and Y is a spacer amino acid such as serine or glycine) |
| 7 | GSGSRKGGKRGS |
| 8 | GSGSRKCGKRGS |
| 9 | GSGSDEGGEDGS |
| 10 | GSGSDECGEDGS |

For example, in an embodiment, each of the first and second charge polarized core domains may comprise a peptide comprising the sequence $YY_nXX_nYY_nXX_nYY_n$ (where X is a positively charged amino acid such as arginine, histidine or lysine and Y is a spacer amino acid such as serine or glycine; SEQ ID NO: 3). Illustrative peptide sequences include, but are not limited to, RKGGKR (SEQ ID NO: 11) or GSGSRKGGKRGS (SEQ ID NO: 12).

In another illustrative embodiment, each of the first and second charge polarized core domains may comprise a peptide comprising the sequence $YY_nZZ_nYY_nZZ_nYY_n$ (where Z is a negatively charged amino acid such as aspartic acid or glutamic acid and Y is a spacer amino acid such as serine or glycine). Illustrative peptide sequences include, but are not limited to, DEGGED (SEQ ID NO: 13) or GSGS-DEGGEDGS (SEQ ID NO: 14).

In one aspect, the present technology provides a heterodimeric protein comprising (a) a first domain comprising one or more butyrophilin family proteins, or a fragment thereof; (b) a second domain comprising a targeting domain, the targeting domain being selected from an (i) antibody, antibody-like molecule, or antigen binding fragment thereof, and (ii) a extracellular domain; and (c) a linker that adjoins the first and second domain. In some embodiments, the heterodimeric protein comprises two individual polypeptide chains which self-associate. In some embodiments, the linker facilitates heterodimerization. In some embodiments, the heterodimeric protein comprises two of the same butyrophilin family proteins or two different butyrophilin family proteins. In some embodiments, the butyrophilin family proteins comprise a V-type domain and/or a B30.2 domain. In some embodiments, the first domain is a butyrophilin-like (BTNL) family protein, such as BTNL1, BTN1A1, BTNL2, BTN2A1, BTN2A2, BTN2A3, BTNL3, BTN3A1, BTN3A2, BTN3A3, BTNL6, BTNL8, BTNL9, BTNL10, and SKINT.

Illustrative sequences of linkers that adjoins the first and second domain, also referred to herein as a core domain are provided below:

In some embodiments, the core domain has the following sequence:

(SEQ ID NO: 15)
SKYGPPCPPCPAPEFLGGPSVFLFPPKPKDQLMISRTPEVTCVVVDVSQE

DPEVQFNWYVDGVEVHNAKTKPREEQFNSTYRVVSVLTVLHQDWLSGKEY

KCKVSSKGLPSSIEKTISNATGQPREPQVYTLPPSQEEMTKNQVSLTCLV

KGFYPSDIAVEWESNGQPENNYKTTPPVLDSDGSFFLYSRLTVDKSRWQE

GNVFSCSVLHEALHNHYTQKSLSLSLGKIEGRMD.

In some embodiments, the core domain has the following sequence:

(SEQ ID NO: 61)
CPPCPAPEFLGGPSVFLFPPKPKDQLMISRTPEVTCVVVDVSQEDPEVQF

NWYVDGVEVHNAKTKPREEQFNSTYRVVSVLTVLHQDWLSGKEYKCKVSS

KGLPSSIEKTISNATGQPREPQVYTLPPSQEEMTKNQVSLTCLVKGFYPS

DIAVEWESNGQPENNYKTTPPVLDSDGSFFLYSRLTVDKSRWQEGNVFSC

SVLHEALHNHYTQKSLSLSLGK.

In some embodiments, the core domain is a KIHT22Y protein having the following sequence:

(SEQ ID NO: 62)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

YCLVKGFYPSDIAVEWESNGQPENNYKTTPPVLDSDGSFFLYSKLTVDKS

RWQQGNVFSCSVMHEALHNHYTQKSLSLSPGK.

In some embodiments, the core domain is a KIHY86T protein having the following sequence:

(SEQ ID NO: 63)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLTSKLTVDKS

RWQQGNVFSCSVMHEALHNHYTQKSLSLSPGK.

In some embodiments, the core domain is a KIHY86T protein having the following sequence:

(SEQ ID NO: 64)
VEHDCGKTKPCICTVPEVSSVFIFPPKPKDVLTITLTPKVTCVVVGLSKDGPEVQFSWFV

DGVEVHTAQTQPREEQFNSTFRSVSELPIMHQDWLNGKEFKCRVNSAAFPAPIEKTIS

KTKGRPKAPQVYTIFPPKEQMAKDKVSLTCMITDFFPEDITVEWQWNGQPAENYKN

TQPIMDTDGSYFVYSKLNVQKSNWEAGNTFTCSVLHEGLHNHHTEKSLSHSPGK

The sequence of an illustrative charge polarized core domain (positive-negative) is provided below:

(SEQ ID NO: 16)
GSGSRKGGKRGSKYGPP

CPPCPAPEFLGGPSVFLFPPKPKDQLMIS

RTPEVTCVVVDVSQEDPEVQFNWYVDGVEVHNAKTKPREEQFNS

TYRVVSVLTVLHQDWLSGKEYKCKVSSKGLPSSIEKTISNATGQPR

EPQVYTLPPSQEEMTKNQVSLTCLVKGFYPSDIAVE

WESNGQPENNYKTTPPVLDSDGSFFLYSRLTVDKSR

WQEGNVFSCSVLHEALHNHYTQKSLSLSLGKDEGGEDSGS.

The sequence of an illustrative charge polarized core domain (negative-positive) is provided below:

(SEQ ID NO: 17)
GSGSDEGGEDGSKYGPPCPPCPAPEFLGGPSVFLFPPKPKD

QLMISRTPEVTCVVVDVSQEDPEVQFNWYVDGVEVHNAKTKPREEQFN

STYRVVSVLTVLHQDWLSGKEYKCKVSSKGLPSSIEKTISNATGQPRE

PQVYTLPPSQEEMTKNQVSLTCLVKGFYPSDIAVEWESNGQPENN

YKTTPPVLDSDGSFFLYSRLTVDKSRWQEGNVFSCSVLHEALHNHY

TQKSLSLSLGKRKGGKRGSGS.

The sequence of an illustrative charge polarized core domain (negative-positive) is provided below:

(SEQ ID NO: 65)
CPPCPAPEFLGGPSVFLFPPKPKDQLMISRTPEVTCVVVDVSQE

DPEVQFNWYVDGVEVHNAKTKPREEQFNSTYRVVSVTVLHQDWLSGK

EYKCKVSSKGIPSSIEKTISNATGQPREPQVYTLPPSQEEMTKNQVSL

TCLVKGFYPSDIAVEWESNGQPENNYKTTPPVLDSDGSFFLYSRL

TVDKSRWQEGNVFSCSVLHEALHNHYTQKSLSLSLGK.

In various embodiments, the protein comprising the charged amino acid residues may further comprise one or more cysteine residues to facilitate disulfide bonding between the electrostatically charged core domains as an additional method to stabilize the heterodimer.

In various embodiments, each of the first and second charge polarized core domains comprises a linker sequence which may optionally function as a stabilizing domain. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et. al., (2000), Protein Eng. 13(5):309-312, the entire contents of which are hereby incorporated by reference.

In some embodiments, the linker (e.g., a stabilizing domain) is a synthetic linker such as PEG.

In other embodiments, the linker (e.g., a stabilizing domain) is a polypeptide. In some embodiments, the linker (e.g., a stabilizing domain) is less than about 500 amino acids long, about 450 amino acids long, about 400 amino acids long, about 350 amino acids long, about 300 amino acids long, about 250 amino acids long, about 200 amino acids long, about 150 amino acids long, or about 100 amino acids long. For example, the linker (e.g., a stabilizing domain) may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long.

In various embodiments, the linker (e.g., a stabilizing domain) is substantially comprised of glycine and serine residues (e.g., about 30%, or about 40%, or about 50%, or about 60%, or about 70%, or about 80%, or about 90%, or about 95%, or about 97% glycines and serines).

In various embodiments, the linker (e.g., a stabilizing domain) is a hinge region of an antibody (e.g., of IgG, IgA, IgD, and IgE, inclusive of subclasses (e.g., IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2. In other embodiments, the linker may be derived from human IgG4 and contain one or more mutations to enhance dimerization (including S228P) or FcRn binding.

According to crystallographic studies, the immunoglobulin hinge region can be further subdivided functionally into three regions: the upper hinge region, the core region, and the lower hinge region. See Shin et al., 1992 Immunological Reviews 130:87. The upper hinge region includes amino acids from the carboxyl end of $C_{H1}$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the CH2 domain and includes residues in CH2. Id. The core hinge region of wild-type human IgG1 contains the sequence Cys-Pro-Pro-Cys which, when dimerized by disulfide bond formation, results in a cyclic octapeptide believed to act as a pivot, thus conferring flexibility. In various embodiments, the present linker (e.g., a stabilizing domain) comprises, one, or two, or three of the upper hinge region, the core region, and the lower hinge region of any antibody (e.g., of IgG, IgA, IgD, and IgE, inclusive of subclasses (e.g., IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In various embodiments, the linker (e.g., a stabilizing domain) of the present technology comprises one or more glycosylation sites.

In various embodiments, the linker (e.g., a stabilizing domain) comprises an Fc domain of an antibody (e.g., of IgG, IgA, IgD, and IgE, inclusive of subclasses (e.g., IgG1, IgG2, IgG3, and IgG4, and IgA1 and IgA2)). In various embodiments, the linker (e.g., a stabilizing domain) comprises a hinge-CH2-CH3 Fc domain derived from a human IgG4 antibody. In various embodiments, the linker (e.g., a stabilizing domain) comprises a hinge-CH2-CH3 Fc domain derived from a human IgG1 antibody. In some embodiments, the Fc domain exhibits increased affinity for and enhanced binding to the neonatal Fc receptor (FcRn). In some embodiments, the Fc domain includes one or more mutations that increases the affinity and enhances binding to FcRn. Without wishing to be bound by theory, it is believed that increased affinity and enhanced binding to FcRn increases the in vivo half-life of the present heterodimeric proteins.

In some embodiments, the Fc domain contains one or more amino acid substitutions at amino acid residue 250, 252, 254, 256, 308, 309, 311, 428, 433 or 434 (in accordance with Kabat numbering), or equivalents thereof. In an embodiment, the amino acid substitution at amino acid residue 250 is a substitution with glutamine. In an embodiment, the amino acid substitution at amino acid residue 252 is a substitution with tyrosine, phenylalanine, tryptophan or threonine. In an embodiment, the amino acid substitution at amino acid residue 254 is a substitution with threonine. In an embodiment, the amino acid substitution at amino acid residue 256 is a substitution with serine, arginine, glutamine, glutamic acid, aspartic acid, or threonine. In an embodiment, the amino acid substitution at amino acid residue 308 is a substitution with threonine. In an embodiment, the amino acid substitution at amino acid residue 309 is a substitution with proline. In an embodiment, the amino acid substitution at amino acid residue 311 is a substitution with serine. In an embodiment, the amino acid substitution at amino acid residue 385 is a substitution with arginine, aspartic acid, serine, threonine, histidine, lysine, alanine or glycine. In an embodiment, the amino acid substitution at amino acid residue 386 is a substitution with threonine, proline, aspartic acid, serine, lysine, arginine, isoleucine, or methionine. In an embodiment, the amino acid substitution at amino acid residue 387 is a substitution with arginine, proline, histidine, serine, threonine, or alanine. In an embodiment, the amino acid substitution at amino acid residue 389 is a substitution with proline, serine or asparagine. In an embodiment, the amino acid substitution at amino acid residue 428 is a substitution with leucine. In an embodiment, the amino acid substitution at amino acid residue 433 is a substitution with arginine, serine, isoleucine, proline, or glutamine. In an embodiment, the amino acid substitution at amino acid residue 434 is a substitution with histidine, phenylalanine, or tyrosine.

In some embodiments, the Fc domain (e.g., comprising an IgG constant region) comprises one or more mutations such as substitutions at amino acid residue 252, 254, 256, 433, 434, or 436 (in accordance with Kabat numbering). In an embodiment, the IgG constant region includes a triple M252Y/S254T/T256E mutation or YTE mutation. In another embodiment, the IgG constant region includes a triple H433K/N434F/Y436H mutation or KFH mutation. In a further embodiment, the IgG constant region includes an YTE and KFH mutation in combination.

In some embodiments, the modified humanized antibodies of the invention comprise an IgG constant region that contains one or more mutations at amino acid residues 250, 253, 307, 310, 380, 428, 433, 434, and 435. Illustrative mutations include T250Q, M428L, T307A, E380A, I253A, H310A, M428L, H433K, N434A, N434F, N434S, and H435A. In an embodiment, the IgG constant region comprises a M428L/N434S mutation or LS mutation. In another embodiment, the IgG constant region comprises a T250Q/M428L mutation or QL mutation. In another embodiment, the IgG constant region comprises an N434A mutation. In another embodiment, the IgG constant region comprises a T307A/E380A/N434A mutation or AAA mutation. In another embodiment, the IgG constant region comprises an I253A/H310A/H435A mutation or IHH mutation. In another embodiment, the IgG constant region comprises a H433K/N434F mutation. In another embodiment, the IgG constant region comprises a M252Y/S254T/T256E and a H433K/N434F mutation in combination.

In various embodiments, mutations are introduced to increase stability and/or half-life of the Fc domain. An illustrative Fc stabilizing mutant is S228P. Additional illustrative Fc half-life extending mutants are T250Q, M428L, V308T, L309P, and Q311S and the present linkers (e.g., stabilizing domains) may comprise 1, or 2, or 3, or 4, or 5 of these mutants.

Additional illustrative mutations in the IgG constant region are described, for example, in Robbie, et al., Antimicrobial Agents and Chemotherapy (2013), 57(12):6147-6153, Dall'Acqua et al., JBC (2006), 281 (33): 23514-24, Dall'Acqua et al., Journal of Immunology (2002), 169:5171-80, Ko et al., Nature (2014) 514:642-645, Grevys et al., Journal of Immunology. (2015), 194(11):5497-508, and U.S. Pat. No. 7,083,784, the entire contents of which are hereby incorporated by reference.

In various embodiments, the linker may be flexible, including without limitation highly flexible. In various embodiments, the linker may be rigid, including without limitation a rigid alpha helix.

In various embodiments, the linker may be functional. For example, without limitation, the linker may function to improve the folding and/or stability, improve the expression, improve the pharmacokinetics, and/or improve the bioactivity of the present heterodimeric protein. In another example, the linker may function to target the heterodimeric protein to a particular cell type or location.

The Heterodimeric Proteins

In one aspect, the present technology provides a heterodimeric protein comprising: (a) a first domain comprising one or more butyrophilin family proteins, or a fragment thereof; (b) a second domain comprising a targeting domain, the targeting domain being selected from an (i) antibody, antibody-like molecule, or antigen binding fragment thereof, and (ii) a extracellular domain; and (c) a linker that adjoins the first and second domain.

In embodiments the heterodimeric protein is a complex of two polypeptide chains.

In embodiments the heterodimeric protein comprises an alpha chain and a beta chain wherein the alpha chain and the beta chain each independently comprise (a) a first domain comprising a butyrophilin family protein, or fragment thereof; (b) a second domain comprising a targeting domain, the targeting domain being selected from an (i) antibody, antibody-like molecule, or antigen binding fragment thereof, and (ii) a extracellular domain; and (c) a linker that adjoins the first and second domain.

In embodiments the alpha chain and the beta chain self-associate to form the heterodimer.

In some embodiments, the first domain comprises two of the same butyrophilin family proteins. In some embodiments, wherein the first domain comprises two different butyrophilin family proteins. In some embodiments, the butyrophilin family proteins comprise a V-type domain. In some embodiments, the butyrophilin family proteins or fragments thereof are derived from the native butyrophilin family proteins that comprise a B30.2 domain in the cytosolic tail.

In some embodiments, the butyrophilin family proteins are selected from BTNL1, BTN1A1, BTNL2, BTN2A1, BTN2A2, BTN2A3, BTNL3, BTN3A1, BTN3A2, BTN3A3, BTNL6, BTNL8, BTNL9, BTNL10, and SKINT. In some embodiments, the first domain comprises: (a) any one of BTNL1, BTN1A1, BTNL2, BTN2A1, BTN2A2, BTN2A3, BTNL3, BTN3A1, BTN3A2, BTN3A3, BTNL6, BTNL8, BTNL9, BTNL10, and SKINT; and (b) any one of BTNL1, BTN1A1, BTNL2, BTN2A1, BTN2A2, BTN2A3, BTNL3, BTN3A1, BTN3A2, BTN3A3, BTNL6, BTNL8, BTNL9, BTNL10, and SKINT. In some embodiments, the first domain comprises: (a) any one of human BTNL1, human BTN1A1, human BTNL2, human BTN2A1, human BTN2A2, human BTN2A3, human BTNL3, human BTN3A1, human BTN3A2, human BTN3A3, human BTNL6, human BTNL8, human BTNL9, human BTNL10, and human SKINT, and (b) any one of human BTNL1, human BTN1A1, human BTNL2, human BTN2A1, human BTN2A2, human BTN2A3, human BTNL3, human BTN3A1, human BTN3A2, human BTN3A3, human BTNL6, human BTNL8, human BTNL9, human BTNL10, and human SKINT.

In some embodiments, the first domain comprises a fragment of butyrophilin family proteins, wherein the fragment is capable of binding a gamma delta T cell receptor and is optionally an extracellular domain, optionally comprising one or more of an immunoglobulin V (IgV)- and IgC-like domain. In some embodiments, the first domain comprises a fragment of butyrophilin family proteins, wherein the fragment is capable of binding a gamma delta T cell receptor selected from a Vγ4, Vγ9δ2, or Vγ7δ4 TCR.

In some embodiments, the first domain comprises a polypeptide having an amino acid sequence of: (a) any one of SEQ ID NOs: 49-52; and (b) any one of SEQ ID NOs: 49-52. In some embodiments, the first domain comprises: (a) BTNL3 and BTNL8; (b) BTN3A1 and BTN3A2; (c) BTN3A1 and BTN3A3; or (d) BTNL1 and BTNL6. In some embodiments, the first domain comprises: (a) human BTNL3 and human BTNL8; (b) human BTN3A1 and human BTN3A2; or (c) human BTN3A1 and human BTN3A3. In some embodiments, the first domain comprises a polypeptide having (a) an amino acid sequence having at least 90%, or 95%, or 97%, or 98%, or 99% identity with SEQ ID NO: 49, and an amino acid sequence having at least 90%, or 95%, or 97%, or 98%, or 99% identity with SEQ ID NO: 52; or (b) an amino acid sequence having at least 90%, or 95%, or 97%, or 98%, or 99% identity with SEQ ID NO: 50, and an amino acid sequence having at least 90%, or 95%, or 97%, or 98%, or 99% identity with SEQ ID NO: 51. In some embodiments, the first domain comprises a polypeptide having an amino acid sequence of (a) SEQ ID NO: 49 and SEQ ID NO: 52; or (b) SEQ ID NO: 50 and SEQ ID NO: 51.

Additionally, or alternatively, in any of the embodiments disclosed herein, in the targeting domain is an antibody, or antigen binding fragment thereof. In some embodiments, the targeting domain is an antibody-like molecule, or antigen binding fragment thereof. In some embodiments, the antibody-like molecule is selected from a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; an Affimer, a Microbody; an aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; a DuoBody, a Fv, a Fab, a Fab', and a F(ab')$_2$. In some embodiments, the antibody-like molecule is an scFv. In some embodiments, the targeting domain is an extracellular domain. In some embodiments, the targeting domain is capable of binding an antigen on the surface of a cancer cell. In some embodiments, the targeting domain specifically binds one of CD19, PSMA, GD2, PSCA, BCMA, CD123, B7-H3, CD20, CD30, CD33, CD38, CEA, CLEC12A, DLL3, EGFRvIII, EpCAM, CD307, FLT3, GPC3, gpA33, HER2, MUC16, P-cadherin, SSTR2, and mesothelin. In some embodiments, the targeting domain comprises a portion of the extracellular domain of LAG-3, PD-1, TIGIT, CD19, or PSMA. In some embodiments, the targeting domain specifically binds CD19. In some embodiments, the targeting domain specifically binds PSMA. Additionally or alternatively, in some embodiments, the targeting domain is a polypeptide having an amino acid sequence with at least 90%, or 95%, or 97%, or 98%, or 99% identity with a polypeptide selected from SEQ ID NOs: 53-60. In some embodiments, the targeting domain is a polypeptide having an amino acid sequence of selected from SEQ ID NOs: 53-60.

Additionally or alternatively, in some embodiments, the linker comprises (a) a first charge polarized core domain adjoined to a butyrophilin family protein, optionally at the carboxy terminus, and (b) a second charge polarized core domain adjoined to a butyrophilin family protein, optionally at the carboxy terminus. In some embodiments, the linker forms a heterodimer through electrostatic interactions between positively charged amino acid residues and negatively charged amino acid residues on the first and second charge polarized core domains. In some embodiments, the first and/or second charge polarized core domain comprises a polypeptide linker, optionally selected from a flexible amino acid sequence, IgG hinge region, or antibody sequence. In some embodiments, the linker is a synthetic linker, optionally PEG. In some embodiments, the linker comprises the hinge-CH2-CH3 Fc domain derived from IgG1, optionally human IgG1. In some embodiments, the linker comprises the hinge-CH2-CH3 Fc domain derived from IgG4, optionally human IgG4. In some embodiments, the first and/or second charge polarized core domain further comprise peptides having positively and/or negatively charged amino acid residues at the amino and/or carboxy terminus of the charge polarized core domain. In some embodiments, the positively charged amino acid residues include one or more of amino acids selected from His, Lys, and Arg. In some embodiments, the positively charged amino acid residues are present in a peptide comprising positively charged amino acid residues in the first and/or the second charge polarized core domains.

In some embodiments, the peptide comprising positively charged amino acid residues comprises a sequence selected from $Y_nX_nY_nX_nY_n$ (where X is a positively charged amino acid such as arginine, histidine or lysine and Y is a spacer amino acid such as serine or glycine) (SEQ ID NO: 1), $YY_nXX_nYY_nXX_nYY_n$ (where X is a positively charged amino acid such as arginine, histidine or lysine and Y is a spacer amino acid such as serine or glycine) (SEQ ID NO: 3), and $Y_nX_nCY_nX_nY_n$ (where X is a positively charged amino acid such as arginine, histidine or lysine and Y is a spacer amino acid such as serine or glycine) (SEQ ID NO: 5). In some embodiments, the peptide comprising positively charged amino acid residues comprises the sequence RKGGKR (SEQ ID NO: 11) or GSGSRKGGKRGS (SEQ ID NO: 12). In some embodiments, the negatively charged amino acid residues may include one or more amino acids selected from Asp and Glu. In some embodiments, the negatively charged amino acid residues are present in a peptide comprising negatively charged amino acid residues in the first and/or the second charge polarized core domains. In some embodiments, the peptide comprising negatively charged amino acid residues comprises a sequence selected from $Y_nZ_nY_nZ_nY_n$ (where Z is a negatively charged amino acid such as aspartic acid or glutamic acid and Y is a spacer amino acid such as serine or glycine) (SEQ ID NO: 2), $YY_nZZ_nYY_nZZ_nYY_n$ (where Z is a negatively charged amino acid such as aspartic acid or glutamic acid and Y is a spacer amino acid such as serine or glycine) (SEQ ID NO: 4), and $Y_nZ_nCY_nZ_nY_n$ (where Z is a negatively charged amino acid such as aspartic acid or glutamic acid and Y is a spacer amino acid such as serine or glycine) (SEQ ID NO: 6). In some embodiments, the peptide comprising negatively charged amino acid residues comprises the sequence DEGGED (SEQ ID NO: 13) or GSGSDEGGEDGS (SEQ ID NO: 14).

Additionally or alternatively, in some embodiments, the first domain and/or the heterodimeric protein modulates or is capable of modulating a γδ (gamma delta) T cell. In some embodiments, the gamma delta T cell is selected from a cell expressing Vγ4, Vγ9δ2, or Vγ7δ4. In some embodiments, the first domain comprises BTNL3 and BTNL8 and it modulates a Vγ4-expressing T cell. In some embodiments, the first domain comprises BTNL3A1 and BTNL3A2 and it modulates a Vγ9δ2-expressing T cell. In some embodiments, the first domain comprises BTNL3A1 and BTNLA3 and it modulates a Vγ9δ2-expressing T cell. In some embodiments, the first domain comprises BTNL1 and BTNL6 and it modulates a Vγ7δ4-expressing T cell. In some embodiments, the modulation of a gamma delta T cell is activation of a gamma delta T cell.

Additionally or alternatively, in some embodiments, the heterodimeric protein is capable of forming a synapse between a gamma delta T cell and a tumor cell. In some embodiments, the heterodimeric protein is capable of contemporaneous activation and targeting of gamma delta T cells to tumor cells.

In some embodiments, the heterodimeric protein comprises an amino acid sequence having at least 90%, or at least 91%, or at least 92%, or at least 93%, or at least 94%, or at least 95%, or at least 96%, or at least 97%, or at least 98%, or at least 98%, or at least 99% sequence identity to one or more of SEQ ID NOs: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32. SEQ ID NO: 33, SEQ ID NO: 35, SEQ ID NO: 36, SEQ ID NO: 37, SEQ ID NO: 38, SEQ ID NO: 39, SEQ ID NO: 40, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 94, SEQ ID NO: 95, SEQ ID NO: 96, SEQ ID NO: 97, each optionally with a leader sequence omitted.

In embodiments, the present heterodimeric proteins comprise a portion of a butyrophilin-like (BTNL) proteins. In an illustrative embodiment, the first domain is a butyrophilin-like (BTNL) family protein. Examples of BTNL family proteins include BTNL1, BTNL3, BTNL6, BTNL8, BTN3A1, BTN3A2, and BTN3A3. In embodiments, the heterotrimeric protein modulates the function of gamma delta T cells. In embodiments, in addition to the BTNL family protein, the heterodimeric proteins further comprise a portion of the extracellular domain of LAG-3, PD-1, or TIGIT and which is capable of binding its receptor/ligand on the surface of a cancer cell. In embodiments, in addition to the BTNL family protein, the heterodimeric proteins further comprise an antibody or fragment thereof (e.g., comprising a portion of the antigen-binding domain of an antibody and/or a CDR3 that binds a tumor epitope) and which is capable of binding an antigen on the surface of a cancer cell.

In embodiments, the present heterodimeric proteins comprise a portion of a butyrophilin-like (BTNL) proteins. In an illustrative embodiment, the first domain is a butyrophilin-like (BTNL) family protein. Examples of BTNL family proteins include BTNL1, BTNL3, BTNL6, BTNL8, BTN3A1, BTN3A2, and BTN3A3. In embodiments, the heterotrimeric protein modulates the function of gamma delta T cells. In embodiments, in addition to the BTNL family protein, the heterodimeric proteins further comprise a portion of the extracellular domain of LAG-3, PD-1, TIGIT, CD19, PSMA, or antibody-derived binding domain (e g. CDR3, Fab, scFv domain, etc.) targeting a tumor antigen (such as CD19 or PSMA) and which is capable of binding its receptor/ligand on the surface of a cancer cell. In embodiments, in addition to the BTNL family protein, the heterodimeric proteins further comprise an antibody or fragment thereof (e.g., comprising a portion of the antigen-binding domain of an antibody) and which is capable of binding an antigen on the surface of a cancer cell.

In embodiments, the second domain is a LAG-3 protein.
In embodiments, the second domain is a PD-1 protein.
In embodiments, the second domain is a TIGIT protein.
In embodiments, the second domain is a CD19 protein binding domain, such as an scFv, CDR3, or Fab. In embodiments, the second domain is a CD19 protein and the heterodimeric protein further comprise an antibody or fragment thereof (e.g., comprising a portion of the antigen-binding domain of an antibody) and which is capable of binding an antigen on the surface of a cancer cell.

In embodiments, the second domain is a PSMA protein binding domain, such as an scFv, CDR3, or Fab. In embodiments, the second domain is a PSMA protein and the heterodimeric protein further comprise an antibody or fragment thereof (e.g., comprising a portion of the antigen-binding domain of an antibody) and which is capable of binding an antigen on the surface of a cancer cell.

In an illustrative embodiment, the second domain is a receptor for EGP such as EGFR (ErbB1), ErbB2, ErbB3 and ErbB4.

In an illustrative embodiment, the second domain is a receptor for insulin or an insulin analog such as the insulin receptor and/or IGF1 or IGF2 receptor.

In an illustrative embodiment, the second domain is a receptor for EPO such as the EPO receptor (EPOR) receptor and/or the ephrin receptor (EphR)

In various embodiments, the heterodimeric protein may comprise a domain of a soluble (e.g., non-membrane associated) protein. In various embodiments, the heterodimeric protein may comprise a fragment of the soluble protein which is involved in signaling (e.g., a portion of the soluble protein which interacts with a receptor).

In various embodiments, the heterodimeric protein may comprise the extracellular domain of a transmembrane protein. In various embodiments, one of the extracellular domains transduces an immune inhibitory signal and one of the extracellular domains transduces an immune stimulatory signal.

In some embodiments, an extracellular domain refers to a portion of a transmembrane protein which is capable of interacting with the extracellular environment. In various embodiments, an extracellular domain refers to a portion of a transmembrane protein which is sufficient to bind to a ligand or receptor and effective transmit a signal to a cell. In various embodiments, an extracellular domain is the entire amino acid sequence of a transmembrane protein which is external of a cell or the cell membrane. In various embodiments, an extracellular domain is the that portion of an amino acid sequence of a transmembrane protein which is external of a cell or the cell membrane and is needed for signal transduction and/or ligand binding as may be assayed using methods know in the art (e.g., in vitro ligand binding and/or cellular activation assays).

In various embodiments, the heterodimeric protein may comprise an antibody binding domain (e.g. CDR3, Fab, scFv domain, etc.). In various embodiments, one of the antibody binding domains transduces an immune inhibitory signal and one of the antibody binding domains transduces an immune stimulatory signal.

In some embodiments, an immune inhibitory signal refers to a signal that diminishes or eliminates an immune response. For example, in the context of oncology, such signals may diminish or eliminate antitumor immunity. Under normal physiological conditions, inhibitory signals are useful in the maintenance of self-tolerance (e.g., prevention of autoimmunity) and also to protect tissues from damage when the immune system is responding to pathogenic infection. For instance, without limitation, immune inhibitory signal may be identified by detecting an increase in cellular proliferation, cytokine production, cell killing activity or phagocytic activity when such an inhibitory signal is blocked.

In some embodiments, an immune stimulatory signal refers to a signal that enhances an immune response. For example, in the context of oncology, such signals may enhance antitumor immunity. For instance, without limitation, immune stimulatory signal may be identified by directly stimulating proliferation, cytokine production, killing activity or phagocytic activity of leukocytes. Specific examples include direct stimulation of cytokine receptors such as IL-2R, IL-7R, IL-15R, IL-17R or IL-21R using fusion proteins encoding the ligands for such receptors (IL-2, IL-7, IL-15, IL-17 or IL-21, respectively). Stimulation from any one of these receptors may directly stimulate the proliferation and cytokine production of individual T cell subsets.

In some embodiments, the extracellular domain or antibody binding domain (e.g. CDR3, Fab, scFv domain, etc.) may be used to produce a soluble protein to competitively inhibit signaling by that receptor's ligand. For instance, without limitation, competitive inhibition of PD-L1 or PD-L2 could be achieved using PD-1, or competitive inhibition of PVR could be achieved using TIGIT. In some embodiments, the extracellular domain or antibody binding domain (e.g. CDR3, Fab, scFv domain, etc.) may be used to provide artificial signaling.

In some embodiments, the present heterodimeric proteins deliver or mask an immune inhibitory signal. In some embodiments, the present heterodimeric proteins deliver or mask an immune stimulatory signal.

In various embodiments, the present heterodimeric proteins comprise two independent binding domains, each from one subunit of a heterodimeric human protein. Illustrative proteins that may be formed as part of the heterodimeric protein of the invention are provided in Table 1. In various embodiments, the present heterodimeric proteins have one of the illustrative proteins provided in Table 1. In various embodiments, the present heterodimeric proteins have two of the illustrative proteins provided in Table 1.

TABLE 1

Illustrative butyrophilin-like (BTNL) family protein which may be incorporated into the present compositions and methods include the following proteins (as used herein, "Entry" refers to the protein entry in the Uniprotdatabase and "Entry name" refers to the protein entry in the Uniprot database):

| Entry/ Name | Protein names Gene names | ECD Sequence | SEQ ID NO |
|---|---|---|---|
| Q13410 BT1A1_HUMAN | Butyrophilin subfamily 1 member A1 Butyrophilin subfamily 1 member A1; BTN1A1 BTN | APFDVIGPPEPILAVVGEDAELPCRLSPNASAEHL ELRWFRKKVSPAVLVHRDGREQEAEQMPEYRGR ATLVQDGIAKGRVALRIRGVRVSDDGEYTCFFRE DGSYEEALVHLKVAALGSDPHISMQVQENGEICL ECTSVGWYPEPQVQWRTSKGEKFPSTSESRNPDE EGLFTVAASVIIRDTSAKNVSCYIQNLLLGQEKKV EISIPASSLPR | 99 |
| Q13410 BT1A1_HUMAN | Butyrophilin subfamily 1 member A1 BTN1A1 BTN | APFDVIGPPEPILAVVGEDAELPCRLSPNASAEHL ELRWFRKKVSPAVLVHRDGREQEAEQMPEYRGR ATLVQDGIAKGRVALRIRGVRVSDDGEYTCFFRE DGSYEEALVHLKVAALGSDPHISMQVQENGEICL ECTSVGWYPEPQVQWRTSKGEKFPSTSESRNPDE EGLFTVAASVIIRDTSAKNVSCYIQNLLLGQEKKV EISIPASSLP | 100 |
| Q4VA N1Q4 VAN1_HUMAN | BTN1A1 protein BTN1A1 | | |
| Q4VAN2 Q4VAN2_HUMAN | Butyrophilin, subfamily 1, member A. BTN1A1 | | |
| Q9UIR0 BTNL2_HUMAN | Butyrophilin- like protein 2 BTNL2 | KQSEDFRVIGPAHPILAGVGEDALLTCQLLPKRTT MHVEVRWYRSEPSTPVFVHRDGVEVTEMQMEE YRGWVEWIENGIAKGNVALKIHNIQPSDNGQYW CHFQDGNYCGETSLLLKVAGLGSAPSIHMEGPGE SGVQLVCTARGWFPEPQVYWEDIRGEKLLAVSE HRIQDKDGLFYAEATLVVRNASAESVSCLVHNPV LTEEKGSVISLPEKLQTELASLKVNGPSQPILVRV GEDIQLTCYLSPKANAQSMEVRWDRSHRYPAVH VYMDGDHVAGEQMAEYRGRTVLVSDAIDEGRLT LQILSARPSDDGQYRCLFEKDDVYQEASLDLKV VSLGSSPLITVEGQEDGEMQPMCSSDGWFPQPHV PWRDMEGKTIPSSSQALTQGSHGLFHVQTLLRVT NISAVDVTCSISIPFLGEEKIATFSLSGW | 101 |
| F8WBA1 F8WBA1_HUMAN | Butyrophilin- like protein 2 BTNL2 | | |
| F6UPS5 F6UPS5_HUMAN | Butyrophilin- like protein 2 BTNL2 | | |
| F8WDK6 F8WDK6_HUMAN | Butyrophilin- like protein 2 BTNL2 | | |

TABLE 1-continued

Illustrative butyrophilin-like (BTNL) family protein which may be incorporated into the present compositions and methods include the following proteins (as used herein, "Entry" refers to the protein entry in the Uniprotdatabase and "Entry name" refers to the protein entry in the Uniprot database):

| Entry/ Name | Protein names Gene names | ECD Sequence | SEQ ID NO |
|---|---|---|---|
| A0A0G2JJ84 A0A0G2JJ84_HUMAN | Butyrophilin-like protein 2 BTNL2 | | |
| X5D146 X5D146_HUMAN | BTNL2 BTNL2 | | |
| A0A0G2JPB7 A0A0G2JPB7_HUMAN | BTNL2 | | |
| A0PJV4 A0PJV4_HUMAN | BTNL2 protein BTNL2 | | |
| I7HPB5 I7HPB5_HUMAN | Butyrophilin-like 2 (MHC class II a . . . BTNL2 RP5-107715.2-002 | | |
| A0A1U9X7B7 A0A1U9X7B7_HUMAN | BTNL2 | | |
| X5CF33 X5CF33_HUMAN | BTNL2 BTNL2 hCG_43715 | | |
| A0A1U9X7C0 A0A1U9X7C0_HUMAN | BTNL2 | | |
| A0A1U9X7C3 A0A1U9X7C3_HUMAN | Truncated BTNL2 | | |
| A0A1U9X7C4 A0A1U9X7C4_HUMAN | Truncated BTNL2 | | |
| Q7KYR7 BT2A1_HUMAN | Butyrophilin subfamily 2 member A1 BTN2A1 BT2.1, BTF1 | QFIVVGPTDPILATVGENTTLRCHLSPEKNAEDM EVRWFRSQFSPAVFVYKGGRERTEEQMEEYRGRT TFVSKDISRGSVALVIHNITAQENGTYRCYFQEGR SYDEAILHLVVAGLGSKPLISMRGHEDGGIRLECI SRGWYPKPLTVWRDPYGGVAPALKEVSMPDAD GLFMVTTAVIIRDKSVRNMSCSINNTLLGQKKES VIFIPESFMPSVSPCA | 102 |
| H7BYC3 H7BYC3_HUMAN | Butyrophilin subfamily 2 member A1 BTN2A1 | | |
| H7C542 H7C542_HUMAN | Butyrophilin subfamily 2 member A1 BTN2A1 | | |
| C9JNC3 C9JNC3_HUMAN | Butyrophilin subfamily 2 member A1 BTN2A1 | | |

TABLE 1-continued

Illustrative butyrophilin-like (BTNL) family protein which may be incorporated into the present compositions and methods include the following proteins (as used herein, "Entry" refers to the protein entry in the Uniprotdatabase and "Entry name" refers to the protein entry in the Uniprot database):

| Entry/ Name | Protein names Gene names | ECD Sequence | SEQ ID NO |
|---|---|---|---|
| Q8WVV5 BT2A2_HUMAN | Butyrophilin subfamily 2 member A2 BTN2A2 BT2.2, BTF2 | QFTVVGPANPILAMVGENTTLRCHLSPEKNAED MEVRWFRSQFSPAVFVYKGGRERTEEQMEEYRG RITFVSKDINRGSVALVIHNVTAQENGIYRCYFQE GRSYDEAILRLVVAGLGSKPLIEIKAQEDGSIWLE CISGGWYPEPLTVWRDPYGEVVPALKEVSIADAD GLFMVTTAVIIRDKYVRNVSCSVNNTLLGQEKET VIFIPESFMPSASPWMVALAVILTASPWM | 103 |
| A0A02 4R038 A0A02 4R038_HUMAN | Butyrophilin, subfamily 2, member A . . . BTN2A2 hCG_1980289 | | |
| C9J8J5 C9J8J5_HUMAN | Butyrophilin subfamily 2 member A2 BTN2A2 | | |
| C9IZY2 C9IZY2_HUMAN | Butyrophilin subfamily 2 member A2 BTN2A2 | | |
| B4E3J1 B4E3J1_HUMAN | cDNA FLJ52852, highly similar to Ho . . . | | |
| C9IY66 C9IY66_HUMAN | Butyrophilin subfamily 2 member A2 BTN2A2 | | |
| C9J8R3 C9J8R3_HUMAN | Butyrophilin subfamily 2 member A2 BTN2A2 | | |
| C9JAJ6 C9JAJ6_HUMAN | Butyrophilin subfamily 2 member A2 BTN2A2 | | |
| C9JWH2 C9JWH2_HUMAN | Butyrophilin subfamily 2 member A2 BTN2A2 | | |
| H7C4E8 H7C4E8_HUMAN | Butyrophilin subfamily 2 member A2 BTN2A2 | | |
| F8WC65 F8WC65_HUMAN | Butyrophilin subfamily 2 member A2 BTN2A2 | | |
| Q96KV6 BT2A3_HUMAN | Putative butyrophilin subfamily 2 m . . . BTN2A3P BT N2A3 | QVTVVGPTDPILAMVGENTTLRCCLSPEENAED MEVRWFQSQFSPAVFVYKGGRERTEEQKEEYRG RTTFVSKDSRGSVALIIHNVTAEDNGIYQCYFQEG RSCNEAILHLVVAGLDSEPVIEMRDHEDGGIQLEC ISGGWYPKPLTVWRDPYGEVVPALKEVSTPDAD SLFMVTTAVIIRDKSVRNVSCSINDTLLGQKKESV IFIPESFMPSRSPCV | 104 |

TABLE 1-continued

Illustrative butyrophilin-like (BTNL) family protein which may be incorporated into the present compositions and methods include the following proteins (as used herein, "Entry" refers to the protein entry in the Uniprotdatabase and "Entry name" refers to the protein entry in the Uniprot database):

| Entry/ Name | Protein names Gene names | ECD Sequence | SEQ ID NO |
| --- | --- | --- | --- |
| Q6UXE8 BTNL3_HUMAN | Butyrophilin-like protein 3 BTNL3 BTNLR, COLF4100, UNQ744/PRO1472 | QWQVTGPGKFVQALVGEDAVFSCSLFPETSAEA MEVRFFRNQFHAVVHLYRDGEDWESKQMPQYR GRTEFVKDSIAGGRVSLRLKNITPSDIGLYGCWFS SQIYDEEATWELRVAALGSLPLISIVGYVDGGIQL LCLSSGWFPQPTAKWKGPQGQDLSSDSRANADG YSLYDVEISIIVQENAGSILCSIHLAEQSHEVESKV LIGETFFQPSPWRLAS | 105 |
| L8EAU7 L8EAU7_HUMAN | Alternative protein BTNL3 BTNL3 | | |
| O00481 BT3A1_HUMAN | Butyrophilin subfamily 3 member A1 BTN3A1 BTF5 | QFSVLGPSGPILAMVGEDADLPCHLFPTMSAETM ELKWVSSSLRQVVNVYADGKEVEDRQSAPYRGR TSILRDGITAGKAALRIHNVTASDSGKYLCYFQD GDFYEKALVELKVAALGSDLHVDVKGYKDGGIH LECRSTGWYPQPQIQWSNNKGENIPTVEAPVVAD GVGLYAVAASVIMRGSSGEGVSCTIRSSLLGLEKT ASISIADPFFRSAQRWIAALAG | 106 |
| E7EPR2 E7EPR2_HUMAN | Butyrophilin subfamily 3 member A1 BTN3A1 | | |
| E9PFB8 E9PFB8_HUMAN | Butyrophilin subfamily 3 member A1 BTN3A1 | | |
| A6PVC0 A6PVC0_HUMAN | Butyrophilin subfamily 3 member A1 BTN3A1 | | |
| P78410 BT3A2_HUMAN | Butyrophilin subfamily 3 member A2 BTN3A2 BT3.2, BTF3, BTF4 | QFSVLGPSGPILAMVGEDADLPCHLFPTMSAETM ELKWVSSSLRQVVNVYADGKEVEDRQSAPYRGR TSILRDGITAGKAALRIHNVTASDSGKYLCYFQD GDFYEKALVELKVAALGSNLHVEVKGYEDGGIH LECRSTGWYPQPQIQWSNAKGENIPAVEAPVVAD GVGLYEVAASVIMRGGSGEGVSCIIRNSLLGLEKT ASISIADPFFRSAQPW | 107 |
| A0A02 4QZZ1 A0A02 4QZZ1_HUMAN | Butyrophilin, subfamily 3, member A . . . BTN3A2 hCG_17993 | | |
| S4R3N0 S4R3N0_HUMAN | Butyrophilin subfamily 3 member A2 BTN3A2 | | |
| E9PJE9 E9PJE9_HUMAN | Butyrophilin subfamily 3 member A2 BTN3A2 | | |
| E9PIU5 E9PIU5_HUMAN | Butyrophilin subfamily 3 member A2 BTN3A2 | | |

TABLE 1-continued

Illustrative butyrophilin-like (BTNL) family protein which may be incorporated into the present compositions and methods include the following proteins (as used herein, "Entry" refers to the protein entry in the Uniprotdatabase and "Entry name" refers to the protein entry in the Uniprot database):

| Entry/ Name | Protein names Gene names | ECD Sequence | SEQ ID NO |
|---|---|---|---|
| E9PRR1 E9PRR1_HUMAN | Butyrophilin subfamily 3 member A2 BTN3A2 | | |
| E9PRX1 E9PRX1_HUMAN | Butyrophilin subfamily 3 member A2 BTN3A2 | | |
| O00478 BT3A3_HUMAN | Butyrophilin subfamily 3 member A3 BTN3A3 BTF3 | QFSVLGPSGPILAMVGEDADLPCHLFPTMSAETM ELRWVSSSLRQVVNVYADGKEVEDRQSAPYRGR TSILRDGITAGKAALRIHNVTASDSGKYLCYFQD GDFYEKALVELKVAALGSDLHIEVKGYEDGGIHL ECRSTGWYPQPQIKWSDTKGENIPAVEAPVVADG VGLYAVAASVIMRGSSGGGVSCIIRNSLLGLEKTA SISIADPFFRSAQPW | 108 |
| A0A02 4R042 A0A02 4R042_HUMAN | Butyrophilin, subfamily 3, member A... BTN3A3 hCG_17992 | | |
| A0A08 9GIA6 A0A08 9GIA6_HUMAN | Butyrophilin subfamily 3 member A3 . . . BTN3A3 | | |
| C9JUV8 C9JUV8_HUMAN | Butyrophilin subfamily 3 member A3 BTN3A3 | | |
| C9JQT8 C9JQT8_HUMAN | Butyrophilin subfamily 3 member A3 BTN3A3 | | |
| C9JVU4 C9JVU4_HUMAN | Butyrophilin subfamily 3 member A3 BTN3A3 | | |
| C9J3Q8 C9J3Q8_HUMAN | Butyrophilin subfamily 3 member A3 BTN3A3 | | |
| C9JZT5 C9JZT5_HUMAN | Butyrophilin subfamily 3 member A3 BTN3A3 | | |
| C9J877 C9J877_HUMAN | Butyrophilin subfamily 3 member A3 BTN3A3 | | |
| C9JNZ3 C9JNZ3_HUMAN | Butyrophilin subfamily 3 member A3 BTN3A3 | | |
| Q6UX41 BTNL8_HUMAN | Butyrophilin- like protein 8 BTNL8 UNQ702/ PRO1347 | QWQVFGPDKPVQALVGEDAAFSCFLSPKTNAEA MEVRFFRGQFSSVVHLYRDGKDQPFMQMPQYQ GRTKLVKDSIAEGRISLRLENITVLDAGLYGCRISS QSYYQKAIWELQVSALGSVPLISITGYVDRDIQLL | 109 |

TABLE 1-continued

Illustrative butyrophilin-like (BTNL) family protein
which may be incorporated into the present
compositions and methods include the following proteins
(as used herein, "Entry" refers to the protein entry in the
Uniprotdatabase and "Entry name" refers to the protein entry
in the Uniprot database):

| Entry/<br>Name | Protein<br>names<br>Gene names | ECD Sequence | SEQ<br>ID<br>NO |
|---|---|---|---|
| D6RIR7<br>D6RIR7_HUMAN | Butyrophilin-<br>like protein 8<br>BTNL8 | CQSSGWFPRPTAKWKGPQGQDLSTDSRTNRDMH<br>GLFDVEISLTVQENAGSISCSMRHAHLSREVESRV<br>QIGDTFFEPISWHLATK | |
| D6R9I8<br>D6R9I8_HUMAN | Butyrophilin-<br>like protein 8<br>BTNL8 | | |
| Q6UXG8<br>BTNL9_HUMAN | Butyrophilin-<br>like protein 9<br>BTNL9 UNQ1900/<br>PRO4346 | SSEVKVLGPEYPILALVGEEVEFPCHLWPQLDAQ<br>QMEIRWFRSQTFNVVHLYQEQQELPGRQMPAFR<br>NRTKLVKDDIAYGSVVLQLHSIIPSDKGTYGCRFH<br>SDNFSGEALWELEVAGLGSDPHLSLEGFKEGGIQ<br>LRLRSSGWYPKPKVQWRDHQGQCLPPEFEAIVW<br>DAQDLFSLETSVVVRAGALSNVSVSIQNLLLSQK<br>KELVVQIADVFVPGASAWK | 110 |
| A0A1<br>S5UZ21<br>A0A1<br>S5UZ21_HUMAN | Butyrophilin-<br>like protein 9<br>BTNL9 | | |
| B7Z4Y8<br>B7Z4Y8_HUMAN | Butyrophilin-<br>like protein 9<br>BTNL9 | | |
| Q8N324<br>Q8N324_HUMAN | BTNL9<br>protein<br>BTNL9 | | |
| A8MVZ5<br>BTNLA_HUMAN | Butyrophilin-<br>like protein 10<br>BTNL10 | SIWKADFDVTGPHAPILAMAGGHVELQCQLFPNI<br>SAEDMELRWYRCQPSLAVHMHERGMDMDGEQ<br>KWQYRGRTTFMSDHVARGKAMVRSHRVTTFDN<br>RTYCCRFKDGVKFGEATVQVQVAGLGREPRIQV<br>TDQQDGVRAECTSAGCFPKSWVERRDFRGQARP<br>AVTNLSASATTRLWAVASSLTLWDRAVEGLSCSIS<br>SPLLPERRKVAESHLPATFSRSSQFTAWKA | 111 |

In various embodiments, the present heterodimeric proteins may be engineered to target one or more molecules that reside on human leukocytes including, without limitation, the extracellular domains (where applicable) of SLAMF4, IL-2Rα, IL-2 R β, ALCAM, B7-1, IL-4 R, B7-H3, BLAME/SLAMFS, CEACAM1, IL-6 R, IL-7 Rα, IL-10R α, IL-10 Rβ, IL-12 Rβ 1, IL-12 R β 2, CD2, IL-13 R α 1, IL-13, CD3, CD4, ILT2/CDS5j, ILT3/CDS5k, ILT4/CDS5d, ILT5/CDS5a, lutegrin α 4/CD49d, CDS, Integrin α E/CD103, CD6, Integrin α M/CD 11 b, CDS, Integrin α X/CD11c, Integrin β 2/CD1S, KIR/CD15S, KIR2DL1, CD2S, KIR2DL3, KIR2DL4/CD15Sd, CD31/PECAM-1, KIR2DS4, LAG-3, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 R γ, Osteopontin, CRACC/SLAMF7, PD-1, CRTAM, PSGL-1, CTLA-4, CX3CR1, CX3CL1, L-Selectin, SIRP β 1, SLAM, TCCR/WSX-1, DNAM-1, Thymopoietin, EMMPRIN/CD147, TIM-1, EphB6, TIM-2, TIM-3, TIM-4, Fcγ RIII/CD16, TIM-6, Granulysin, ICAM-1/CD54, ICAM-2/CD102, IFN-γR1, IFN-γ R2, TSLP, IL-1 R1 and TSLP R.

In some embodiments, the present heterodimeric proteins may be engineered to target one or more molecules involved in immune inhibition, including for example: CTLA-4, PD-L1, PD-L2, PD-1, BTLA, HVEM, TIM3, GALS, LAG3, VISTA/VSIG8, KIR, 2B4, TIGIT, CD160 (also referred to as BY55), CHK 1 and CHK2 kinases, A2aR, CEACAM (e.g., CEACAM-1, CEACAM-3 and/or CEACAM-5), and various B-7 family ligands (including, but are not limited to, B7-1, B7-2, B7-DC, B7-H1, B7-H2, B7-H3, B7-H4, B7-H5, B7-H6 and B7-H7).

In some embodiments, the present heterodimeric proteins comprise an extracellular domain of an immune inhibitory agent. In some embodiments, the present heterodimeric proteins comprise an antibody binding domain (e g. CDR3, Fab, scFv domain, etc.) directed against an immune inhibitory agent.

In some embodiments, the present heterodimeric proteins comprise an extracellular domain of a soluble or membrane protein which has immune inhibitory properties. In some embodiments, the present heterodimeric proteins comprise an antibody binding domain (e.g. CDR3, Fab, scFv domain, etc.) which has immune inhibitory properties In some embodiments, the present heterodimeric proteins simulate binding of an inhibitory signal ligand to its cognate receptor but inhibit the inhibitory signal transmission to an immune cell (e.g., a T cell, macrophage or other leukocyte).

In various embodiments, the heterodimeric protein comprises an immune inhibitory receptor extracellular domain or antibody binding domain (e.g. CDR3, Fab, scFv domain, etc.) and an immune stimulatory ligand extracellular domain or antibody binding domain (e.g. CDR3, Fab, scFv domain, etc.) which can, without limitation, deliver an immune stimulation to a T cell while masking a tumor cell's immune inhibitory signals. In various embodiments, the heterodimeric protein delivers a signal that has the net result of T cell activation.

In some embodiments, the present heterodimeric proteins comprise an extracellular domain of a soluble or membrane protein which has immune stimulatory properties. In some embodiments, the present heterodimeric proteins comprise an antibody binding domain (e g. CDR3, Fab, scFv domain, etc.) which has immune stimulatory properties.

In various embodiments, the present heterodimeric protein may comprise variants of any of the known cytokines, growth factors, and/or hormones. In various embodiments, the present heterodimeric proteins may comprise variants of any of the known receptors for cytokines, growth factors, and/or hormones. In various embodiments, the present heterodimeric proteins may comprises variants of any of the known extracellular domains, for instance, a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the known amino acid or nucleic acid sequences.

In various embodiments, the present heterodimeric protein may comprise an amino acid sequence having one or more amino acid mutations relative to any of the known protein sequences. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g., selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Mutations may also be made to the nucleotide sequences of the heterodimeric proteins by reference to the genetic code, including taking into account codon degeneracy.

In various embodiments, the present chimeric protein is or comprises an amino acid sequence having at least 90%, or at least 91%, or at least 92%, or at least 93%, or at least 94%, or at least 95%, or at least 96%, or at least 97%, or at least 98%, or at least 98%, or at least 99% (e.g. about 90%, or about 91%, or about 92%, or about 93%, or about 94%, or about 95%, or about 96%, or about 97%, or about 98%, or about 98%, or about 99%) sequence identity to one or more of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32. SEQ ID NO: 33, SEQ ID NO: 35, SEQ ID NO: 36, SEQ ID NO: 37, SEQ ID NO: 38, SEQ ID NO: 39, SEQ ID NO: 40, SEQ ID NO: 40, SEQ ID NO: 41, SEQ ID NO: 42, SEQ ID NO: 43, SEQ ID NO: 44, SEQ ID NO: 45, SEQ ID NO: 46, each optionally with the leader sequence (as indicated with double underlining elsewhere herein, or, in embodiments: MEFGLSWVFLVAIIKGVQC (SEQ ID NO: 47)) omitted.

In any of these sequence, the core domain having the following amino acid sequence is or comprises an amino acid sequence having at least 90%, or at least 91%, or at least 92%, or at least 93%, or at least 94%, or at least 95%, or at least 96%, or at least 97%, or at least 98%, or at least 98%, or at least 99% (e.g. about 90%, or about 91%, or about 92%, or about 93%, or about 94%, or about 95%, or about 96%, or about 97%, or about 98%, or about 98%, or about 99%) sequence identity to SEQ ID NO: 34.

In various embodiments, the present heterodimeric proteins are capable of, and can be used in methods comprising, promoting immune activation (e.g., against tumors). In various embodiments, the present heterodimeric proteins are capable of, and can be used in methods comprising, suppressing immune inhibition (e.g., that allows tumors to survive). In various embodiments, the present heterodimeric protein provides improved immune activation and/or improved suppression of immune inhibition.

In various embodiments, the present heterodimeric proteins are capable of, or can be used in methods comprising, modulating the amplitude of an immune response, e.g., modulating the level of effector output. In some embodiments, e.g., when used for the treatment of cancer, the present heterodimeric protein alters the extent of immune stimulation as compared to immune inhibition to increase the amplitude of a T cell response, including, without limitation, stimulating increased levels of cytokine production, proliferation or target killing potential.

In embodiments, a subject is further administered autologous or allogeneic gamma delta T cells that were expanded ex vivo.

In embodiments, a subject is further administered autologous or allogeneic T cells that express a Chimeric Antigen Receptor (i.e., CAR-T cells). CAR-T cells are described in, as examples, Eshhar, et al., *PNAS USA.* 90(2):720-724, 1993; Geiger, et al., *J Immunol.* 162(10):5931-5939, 1999; Brentjens, et al., *Nat Med.* 9(3):279-286, 2003; Cooper, et al., *Blood* 101(4):1637-1644, 2003; Imai, et al., *Leukemia.* 18:676-684, 2004, Pang, et al., *Mol Cancer.* 2018; 17:91, and Schmidts, et al., *Front. Immunol* 2018; 9:2593; the entire contents of which are hereby incorporated by reference.

In embodiments, the heterodimeric proteins act synergistically when used in combination with Chimeric Antigen Receptor (CAR) T-cell therapy. In an illustrative embodiment, the heterodimeric proteins act synergistically when used in combination with CAR T-cell therapy in treating a tumor or cancer. In an embodiment, the heterodimeric proteins act synergistically when used in combination with CAR T-cell therapy in treating blood-based tumors. In an embodiment, the heterodimeric proteins act synergistically when used in combination with CAR T-cell therapy in treating solid tumors. For example, use of heterodimeric proteins and CAR T-cells may act synergistically to reduce or eliminate the tumor or cancer, or slow the growth and/or progression and/or metastasis of the tumor or cancer. In various embodiments, the heterodimeric proteins of the invention induce CAR T-cell division. In various embodiments, the heterodimeric proteins of the invention induce CAR T-cell proliferation. In various embodiments, the heterodimeric proteins of the invention prevents anergy of the CAR T cells.

In various embodiments, the CAR T-cell therapy comprises CAR T cells that target antigens (e.g., tumor antigens) such as, but not limited to, carbonic anhydrase IX (CAIX), 5T4, CD19, CD20, CD22, CD30, CD33, CD38, CD47, CS1, CD138, Lewis-Y, L1-CAM, MET, MUC1, MUC16, ROR-1, IL13R$\alpha$2, gp100, prostate stem cell antigen (PSCA), prostate-specific membrane antigen (PSMA), B-cell maturation antigen (BCMA), human papillomavirus type 16 E6 (HPV-16 E6), CD171, folate receptor alpha (FR-$\alpha$), GD2, GPC3, human epidermal growth factor receptor 2 (HER2), $\kappa$ light chain, mesothelin, EGFR, EGFRvIII, ErbB, fibroblast activation protein (FAP), carcinoembryonic antigen (CEA), PMSA, Receptor Tyrosine Kinase Like Orphan Receptor 1 (ROR1), TAG72, and vascular endothelial growth factor receptor 2 (VEGF-R2), as well as other tumor antigens well known in the art. Additional illustrative tumor antigens include, but are not limited to MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, T-cell receptor/CD3-zeta chain, MAGE-family of tumor antigens (e.g., MAGE-AL MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, $\alpha$-fetoprotein, E-cadherin, $\alpha$-catenin, $\beta$-catenin and $\gamma$-catenin, p120ctn, gp100 Pmel117, PRAME, NY-ESO-1, cdc27, adenomatous polyposis *coli* protein (APC), fodrin, Connexin 37, Ig-idiotype, p15, gp75, GM2 and GD2 gangliosides, viral products such as human papilloma virus proteins, Smad family of tumor antigens, lmp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD37, CD56, CD70, CD74, CD138, AGS16, MUC1, GPNMB, Ep-CAM, PD-L1, and PD-L2.

Exemplary CAR T-cell therapy include, but are not limited to, JCAR014 (Juno Therapeutics), JCAR015 (Juno Therapeutics), JCAR017 (Juno Therapeutics), JCAR018 (Juno Therapeutics), JCAR020 (Juno Therapeutics), JCAR023 (Juno Therapeutics), JCAR024 (Juno Therapeutics), CTL019 (Novartis), KTE-C19 (Kite Pharma), BPX-401 (Bellicum Pharmaceuticals), BPX-501 (Bellicum Pharmaceuticals), BPX-601 (Bellicum Pharmaceuticals), bb2121 (Bluebird Bio), CD-19 Sleeping Beauty cells (Ziopharm Oncology), UCART19 (Cellectis), UCART123 (Cellectis), UCART38 (Cellectis), UCARTCS1 (Cellectis), OXB-302 (Oxford BioMedica, MB-101 (Mustang Bio) and CAR T-cells developed by Innovative Cellular Therapeutics.

In embodiments, the CAR-T cells are autologous or allogeneic gamma delta T cells.

In various embodiments the present heterodimeric proteins, in some embodiments are capable of, or find use in methods involving, masking an inhibitory ligand on the surface of a tumor cell and replacing that immune inhibitory ligand with an immune stimulatory ligand.

Accordingly, the present heterodimeric proteins, in some embodiments are capable of, or find use in methods involving, reducing or eliminating an inhibitory immune signal and/or increasing or activating an immune stimulatory signal. For example, a tumor cell bearing an inhibitory signal (and thus evading an immune response) may be substituted for a positive signal binding on a T cell that can then attack a tumor cell. Accordingly, in some embodiments, an inhibitory immune signal is masked by the present heterodimeric proteins and a stimulatory immune signal is activated. Such beneficial properties are enhanced by the single construct approach of the present heterodimeric proteins. For instance, the signal replacement can be effected nearly simultaneously and the signal replacement is tailored to be local at a site of clinical importance (e.g., the tumor microenvironment).

In various embodiments, the present heterodimeric proteins are capable of, or find use in methods comprising, stimulating or enhancing the binding of immune stimulatory receptor/ligand pairs.

In other embodiments, the present heterodimeric proteins are capable of, or find use in methods involving, enhancing, restoring, promoting and/or stimulating immune modulation. In some embodiments, the present heterodimeric proteins described herein, restore, promote and/or stimulate the activity or activation of one or more immune cells against tumor cells including, but not limited to: T cells, cytotoxic T lymphocytes, T helper cells, natural killer (NK) cells, natural killer T (NKT) cells, anti-tumor macrophages (e.g., M1 macrophages), B cells, and dendritic cells. In some embodiments, the present heterodimeric proteins enhance, restore, promote and/or stimulate the activity and/or activation of T cells, including, by way of a non-limiting example, activating and/or stimulating one or more T-cell intrinsic signals, including a pro-survival signal; an autocrine or paracrine growth signal; a p38 MAPK-, ERK-, STAT-, JAK-, AKT- or PI3K-mediated signal; an anti-apoptotic signal; and/or a signal promoting and/or necessary for one or more of: proinflammatory cytokine production or T cell migration or T cell tumor infiltration.

In some embodiments, the present heterodimeric proteins are capable of, or find use in methods involving, causing an increase of one or more of T cells (including without limitation cytotoxic T lymphocytes, T helper cells, natural killer T (NKT) cells), B cells, natural killer (NK) cells, natural killer T (NKT) cells, dendritic cells, monocytes, and macrophages (e.g., one or more of M1 and M2) into a tumor or the tumor microenvironment. In some embodiments, the present heterodimeric proteins are capable of, or find use in methods involving, inhibiting and/or causing a decrease in recruitment of immunosuppressive cells (e.g., myeloid-derived suppressor cells (MDSCs), regulatory T cells (Tregs), tumor associated neutrophils (TANs), M2 macrophages, and tumor associated macrophages (TAMs)) to the tumor and/or tumor microenvironment (TME). In some embodiments, the present therapies may alter the ratio of M1 versus M2 macrophages in the tumor site and/or TME to favor M1 macrophages.

In embodiments, the heterotrimeric protein modulates the function of gamma delta T cells.

In various embodiments, the present heterodimeric proteins are capable of, and can be used in methods comprising, inhibiting and/or reducing T cell inactivation and/or immune tolerance to a tumor, comprising administering an effective amount of a heterodimeric protein described herein to a subject. In some embodiments, the present heterodimeric proteins are able to increase the serum levels of various cytokines including, but not limited to, one or more of IFNγ, IL-2, IL-4, IL-5, IL-6, IL-9, IL-10, IL-13, IL-17A, IL-17F, and IL-22. In some embodiments, the present heterodimeric proteins are capable of enhancing IL-2, IL-4, IL-5, IL-10, IL-13, IL-17A, IL-22, or IFNγ in the serum of a treated subject.

In various embodiments, the present heterodimeric proteins inhibit, block and/or reduce cell death of an anti-tumor CD8+ and/or CD4+ T cell; or stimulate, induce, and/or increase cell death of a pro-tumor T cell. T cell exhaustion is a state of T cell dysfunction characterized by progressive loss of proliferative and effector functions, culminating in clonal deletion. Accordingly, a pro-tumor T cell refers to a state of T cell dysfunction that arises during many chronic infections and cancer. This dysfunction is defined by poor proliferative and/or effector functions, sustained expression of inhibitory receptors and a transcriptional state distinct from that of functional effector or memory T cells. Exhaustion prevents optimal control of infection and tumors. In addition, an anti-tumor CD8+ and/or CD4+ T cell refers to T cells that can mount an immune response to a tumor. Illustrative pro-tumor T cells include, but are not limited to, Tregs, CD4+ and/or CD8+ T cells expressing one or more checkpoint inhibitory receptors, Th2 cells and Th17 cells. Checkpoint inhibitory receptors refers to receptors (e.g., CTLA-4, B7-H3, B7-H4, TIM-3) expressed on immune cells that prevent or inhibit uncontrolled immune responses.

In various embodiments, the present heterodimeric proteins are capable of, and can be used in methods comprising, increasing a ratio of effector T cells to regulatory T cells. Illustrative effector T cells include ICOS$^+$ effector T cells; cytotoxic T cells (e.g., αβ TCR, CD3$^+$, CD8$^+$, CD45RO$^+$); CD4$^+$ effector T cells (e.g., αβ TCR, CD3$^+$, CD4$^+$, CCR7$^+$, CD62Lhi, IL$^-$ 7R/CD127$^+$); CD8$^+$ effector T cells (e.g., αβ TCR, CD3$^+$, CD8$^+$, CCR7$^+$, CD62Lhi, IL$^-$ 7R/CD127$^+$); effector memory T cells (e.g., CD62Llow, CD44$^+$, TCR, CD3$^+$, IL$^-$7 R/CD127$^+$, IL-15R$^+$, CCR7low); central memory T cells (e.g., CCR7$^+$, CD62L+, CD27$^+$; or CCR7hi, CD44$^+$, CD62Lhi, TCR, CD3$^+$, IL-7R/CD127$^+$, IL-15R); CD62L$^+$ effector T cells; CD8$^+$ effector memory T cells (TEM) including early effector memory T cells (CD27$^+$ CD62L$^-$) and late effector memory T cells (CD27$^-$CD62L$^-$) (TemE and TemL, respectively); CD127($^+$)CD25(low/−) effector T cells; CD127($^-$)CD25($^-$) effector T cells; CD8$^+$ stem cell memory effector cells (TSCM) (e.g., CD44(low) CD62L(high)CD122(high)sca($^+$); TH1 effector T-cells (e.g., CXCR3$^+$, CXCR6$^+$ and CCR5$^+$; or αβ TCR, CD3$^+$, CD4$^+$, IL-12R$^+$, IFNγR$^+$, CXCR3$^+$), TH2 effector T cells (e.g., CCR3$^+$, CCR4$^+$ and CCR8$^+$; or αβ TCR, CD3$^+$, CD4$^+$, IL-4R$^+$, IL-33R$^+$, CCR4$^+$, IL-17RB$^+$, CRTH2$^+$); TH9 effector T cells (e.g., αβ TCR, CD3$^+$, CD4$^+$); TH17 effector T cells (e.g., αβ TCR, CD3$^+$, CD4$^+$, IL-23R$^+$, CCR6$^+$, IL-1R$^+$); CD4$^+$CD45RO$^+$CCR7$^+$ effector T cells, CD4$^+$ CD45RO$^+$CR7($^-$) effector T cells; and effector T cells secreting IL-2, IL-4 and/or IFN-γ. Illustrative regulatory T cells include ICOS$^+$ regulatory T cells, CD4$^+$CD25$^+$ FOXP3$^+$ regulatory T cells, CD4$^+$CD25$^+$ regulatory T cells, CD4$^+$CD25$^-$ regulatory T cells, CD4$^+$CD25high regulatory T cells, TIM-3$^+$M-1$^+$ regulatory T cells, lymphocyte activation gene-3 (LAG-3)$^+$ regulatory T cells, CTLA-4/CD152$^+$ regulatory T cells, neuropilin-1 (Nrp-1)$^+$ regulatory T cells, CCR4$^+$CCR8$^+$ regulatory T cells, CD62L (L-selectin)$^+$ regulatory T cells, CD45RBlow regulatory T cells, CD127low regulatory T cells, LRRC32/GARP$^+$ regulatory T cells, CD39$^+$ regulatory T cells, GITR$^+$ regulatory T cells, LAP$^+$ regulatory T cells, 1B11$^+$ regulatory T cells, BTLA$^+$ regulatory T cells, type 1 regulatory T cells (Tr1 cells), T helper type 3 (Th3) cells, regulatory cell of natural killer T cell phenotype (NKTregs), CD8$^+$ regulatory T cells, CD8$^+$ CD28$^-$ regulatory T cells and/or regulatory T-cells secreting IL-10, IL-35, TGF-β, TNF-α, Galectin-1, IFN-γ and/or MCP1.

In various embodiments, the present heterodimeric proteins are capable of, and can be used in methods comprising, transiently stimulating effector T cells for no longer than about 12 hours, about 24 hours, about 48 hours, about 72 hours or about 96 hours or about 1 week or about 2 weeks. In various embodiments, the present heterodimeric proteins are capable of, and can be used in methods comprising, transiently depleting or inhibiting regulatory T cells for no longer than about 12 hours, about 24 hours, about 48 hours, about 72 hours or about 96 hours or about 1 week or about 2 weeks. In various embodiments, the transient stimulation of effector T cells and/or transient depletion or inhibition of regulatory T cells occurs substantially in a patient's bloodstream or in a particular tissue/location including lymphoid tissues such as for example, the bone marrow, lymph-node, spleen, thymus, mucosa-associated lymphoid tissue (MALT), non-lymphoid tissues, or in the tumor microenvironment.

In various embodiments, the present heterodimeric proteins provide advantages including, without limitation, ease of use and ease of production. This is because two distinct immunotherapy agents are combined into a single product which allows for a single manufacturing process instead of two independent manufacturing processes. In addition, administration of a single agent instead of two separate agents allows for easier administration and greater patient compliance. Further, in contrast to, for example, monoclonal antibodies, which are large multimeric proteins containing numerous disulfide bonds and post-translational modifications such as glycosylation, the present heterodimeric proteins are easier and more cost effective to manufacture.

In various embodiments, the present heterodimeric proteins provide synergistic therapeutic effects as it allows for improved site-specific interplay of two immunotherapy agents. In some embodiments, the present heterodimeric proteins provide the potential for reducing off-site and/or systemic toxicity.

Diseases; Methods of Treatment, and Patient Selections

In one aspect, the present technology provides a method of treating cancer, comprising administering to a subject in need thereof an effective amount of a pharmaceutical composition of any of the embodiments disclosed herein to a subject in need thereof. In some embodiments, the cancer is a lymphoma. In some embodiments, the cancer is a leukemia. In some embodiments, the cancer is a Hodgkin's and non-Hodgkin's lymphoma, B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; or chronic myeloblastic leukemia. In some embodiments, the cancer is basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome. In some embodiments, the cancer is prostate cancer. In some embodiments, the cancer is an epithelial-derived carcinoma. In some embodiments, the cancer is known to express the antigenic target of the second domain of the heterodimeric protein. In some embodiments, the cancer is known to contain mutations which limit recognition by alpha beta T cells, including but not limited to mutations in MHC I, beta 2 microglobulin, TAP, etc.

In some embodiments, the subject is further administered autologous or allogeneic gamma delta T cells that were expanded ex vivo. In some embodiments, the autologous or allogeneic gamma delta T cells express a Chimeric Antigen Receptor. In some embodiments, the subject is further administered autologous or allogeneic T cells that express a Chimeric Antigen Receptor.

In one aspect, the present technology provides a method of treating an autoimmune disease or disorder, comprising administering an effective amount of a pharmaceutical composition of any of the embodiments disclosed herein to a subject in need thereof, wherein the autoimmune disease or disorder is optionally selected from rheumatoid arthritis, systemic lupus erythematosus, diabetes mellitus, ankylosing spondylitis, Sjögren's syndrome, inflammatory bowel diseases (e.g., colitis ulcerosa, Crohn's disease), multiple sclerosis, sarcoidosis, psoriasis, Grave's disease, Hashimoto's thyroiditis, psoriasis, hypersensitivity reactions (e.g., allergies, hay fever, asthma, and acute edema cause type I hypersensitivity reactions), and vasculitis.

In various embodiments, the present technology pertains to the use of the heterodimeric proteins for the treatment of one or more autoimmune diseases or disorders. In various embodiments, the treatment of an autoimmune disease or disorder may involve modulating the immune system with the present heterodimeric proteins to favor immune inhibition over immune stimulation. Illustrative autoimmune diseases or disorders treatable with the present heterodimeric proteins include those in which the body's own antigens become targets for an immune response, such as, for example, rheumatoid arthritis, systemic lupus erythematosus, diabetes mellitus, ankylosing spondylitis, Sjögren's syndrome, inflammatory bowel diseases (e.g., colitis ulcerosa, Crohn's disease), multiple sclerosis, sarcoidosis, psoriasis, Grave's disease, Hashimoto's thyroiditis, psoriasis, hypersensitivity reactions (e.g., allergies, hay fever, asthma, and acute edema cause type I hypersensitivity reactions), and vasculitis.

Illustrative autoimmune diseases or conditions that may be treated or prevented using the heterodimeric protein of the invention include, but are not limited to, multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection), pernicious anemia, rheumatoid arthritis, systemic lupus erythematosus, dermatomyositis, Sjogren's syndrome, lupus erythematosus, multiple sclerosis, myasthenia gravis, Reiter's syndrome, Grave's disease, and other autoimmune diseases.

In various embodiments, the present technology pertains to cancers and/or tumors; for example, the treatment or prevention of cancers and/or tumors. As described elsewhere herein, the treatment of cancer may involve in various embodiments, modulating the immune system with the present heterodimeric proteins to favor immune stimulation over immune inhibition.

Cancers or tumors refer to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also, included are cells having abnormal proliferation that is not impeded by the immune system (e.g., virus infected cells). The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

The cancer may have an origin from any tissue. The cancer may originate from melanoma, colon, breast, or prostate, and thus may be made up of cells that were originally skin, colon, breast, or prostate, respectively. The cancer may also be a hematological malignancy, which may be leukemia or lymphoma. The cancer may invade a tissue such as liver, lung, bladder, or intestinal.

Representative cancers and/or tumors of the present technology include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer;

retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In embodiments, the cancer is an epithelial-derived carcinoma.

In some embodiments, the heterodimeric protein is used to treat a subject that has a treatment-refractory cancer. In some embodiments, the heterodimeric protein is used to treat a subject that is refractory to one or more immune-modulating agents. For example, in some embodiments, the heterodimeric protein is used to treat a subject that presents no response to treatment, or even progress, after 12 weeks or so of treatment. For instance, in some embodiments, the subject is refractory to a PD-1 and/or PD-L1 and/or PD-L2 agent, including, for example, nivolumab (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), Ibrutinib (PHARMACYCLICS/ABBVIE), atezolizumab (TECENTRIQ, GENENTECH), and/or MPDL328OA (ROCHE)-refractory patients. For instance, in some embodiments, the subject is refractory to an anti-CTLA-4 agent, e.g., ipilimumab (YERVOY)-refractory patients (e.g., melanoma patients). Accordingly, in various embodiments the present technology provides methods of cancer treatment that rescue patients that are non-responsive to various therapies, including monotherapy of one or more immune-modulating agents.

In various embodiments, the present technology provides heterodimeric proteins which target a cell or tissue within the tumor microenvironment. In some embodiments, the cell or tissue within the tumor microenvironment expresses one or more targets or binding partners of the heterodimeric protein. The tumor microenvironment refers to the cellular milieu, including cells, secreted proteins, physiological small molecules, and blood vessels in which the tumor exists. In some embodiments, the cells or tissue within the tumor microenvironment are one or more of: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T cells; macrophages; neutrophils; and other immune cells located proximal to a tumor. In various embodiments, the present heterodimeric protein targets a cancer cell. In some embodiments, the cancer cell expresses one or more of targets or binding partners of the heterodimeric protein.

In various embodiments, the heterodimeric protein of the invention may target a cell (e.g., cancer cell or immune cell) that expresses any of the receptors as described herein. For example, the heterodimeric protein of the invention may target a cell that expresses any of the receptors for a cytokine, growth factor, and/or hormone as described herein.

In some embodiments, the present methods provide treatment with the heterodimeric protein in a patient who is refractory to an additional agent, such "additional agents"

being described elsewhere herein, inclusive, without limitation, of the various chemotherapeutic agents described herein.

In some aspects, the present chimeric agents are used to eliminate intracellular pathogens. In some aspects, the present chimeric agents are used to treat one or more infections. In some embodiments, the present heterodimeric proteins are used in methods of treating viral infections (including, for example, HIV and HCV), parasitic infections (including, for example, malaria), and bacterial infections. In various embodiments, the infections induce immunosuppression. For example, HIV infections often result in immunosuppression in the infected subjects.

Accordingly, as described elsewhere herein, the treatment of such infections may involve, in various embodiments, modulating the immune system with the present heterodimeric proteins to favor immune stimulation over immune inhibition. Alternatively, the present technology provides methods for treating infections that induce immunoactivation. For example, intestinal helminth infections have been associated with chronic immune activation. In these embodiments, the treatment of such infections may involve modulating the immune system with the present heterodimeric proteins to favor immune inhibition over immune stimulation.

In various embodiments, the present technology provides methods of treating viral infections including, without limitation, acute or chronic viral infections, for example, of the respiratory tract, of papilloma virus infections, of herpes simplex virus (HSV) infection, of human immunodeficiency virus (HIV) infection, and of viral infection of internal organs such as infection with hepatitis viruses. In some embodiments, the viral infection is caused by a virus of family Flaviviridae. In some embodiments, the virus of family Flaviviridae is selected from Yellow Fever Virus, West Nile virus, Dengue virus, Japanese Encephalitis Virus, St. Louis Encephalitis Virus, and Hepatitis C Virus. In other embodiments, the viral infection is caused by a virus of family Picornaviridae, e.g., poliovirus, rhinovirus, coxsackievirus. In other embodiments, the viral infection is caused by a member of Orthomyxoviridae, e.g., an influenza virus. In other embodiments, the viral infection is caused by a member of Retroviridae, e.g., a lentivirus. In other embodiments, the viral infection is caused by a member of Paramyxoviridae, e.g., respiratory syncytial virus, a human parainfluenza virus, rubulavirus (e.g., mumps virus), measles virus, and human metapneumovirus. In other embodiments, the viral infection is caused by a member of Bunyaviridae, e.g., hantavirus. In other embodiments, the viral infection is caused by a member of Reoviridae, e.g., a rotavirus.

In various embodiments, the present technology provides methods of treating parasitic infections such as protozoan or helminths infections. In some embodiments, the parasitic infection is by a protozoan parasite. In some embodiments, the oritiziab parasite is selected from intestinal protozoa, tissue protozoa, or blood protozoa. Illustrative protozoan parasites include, but are not limited to, Entamoeba hystolytica, Giardia lamblia, Cryptosporidium muris, Trypanosomatida gambiense, Trypanosomatida rhodesiense, Trypanosomatida crusi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Trichomonas vaginalis, and Histomonas meleagridis. In some embodiments, the parasitic infection is by a helminthic parasite such as nematodes (e.g., Adenophorea). In some embodiments, the parasite is selected from Secementea (e.g., Trichuris trichiura, Ascaris lumbricoides, Enterobius vermicularis, Ancylostoma duodenale, Necator americanus, Strongyloides stercoralis, Wuchereria bancrofti, Dracunculus medinensis). In some embodiments, the parasite is selected from trematodes (e.g., blood flukes, liver flukes, intestinal flukes, and lung flukes). In some embodiments, the parasite is selected from: Schistosoma mansoni, Schistosoma haematobium, Schistosoma japonicum, Fasciola hepatica, Fasciola giganfica, Heterophyes heterophyes, Paragonimus westermani. In some embodiments, the parasite is selected from cestodes (e.g., Taenia solium, Taenia saginata, Hymenolepis nana, Echinococcus granulosus).

In various embodiments, the present technology provides methods of treating bacterial infections. In various embodiments, the bacterial infection is by gram-positive bacteria, gram-negative bacteria, aerobic and/or anaerobic bacteria. In various embodiments, the bacteria are selected from, but not limited to, Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella and other organisms. In some embodiments, the bacteria is selected from, but not limited to, Pseudomonas aeruginosa, Pseudomonas fluorescens, Pseudomonas acidovorans, Pseudomonas alcaligenes, Pseudomonas pufida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceficus, Acinetobacter haemolyficus, Yersinia enterocolitica, Yersinia pestis, Yersinia pseudotuberculosis, Yersinia intermedia, Bordetella pertussis, Bordetella parapertussis, Bordetella bronchisepfica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis, or Staphylococcus saccharolyticus.

In still another other aspect, the present technology is directed toward methods of treating and preventing T cell-mediated diseases and disorders, such as, but not limited to diseases or disorders described elsewhere herein and inflammatory disease or disorder, graft-versus-host disease (GVHD), transplant rejection, and T cell proliferative disorder.

In some aspects, the present chimeric agents are used in methods of activating a T cell, e.g., via the extracellular domain having an immune stimulatory signal or antibody binding domain (e.g. CDR3, Fab, scFv domain, etc.) having an immune stimulatory signal.

In some aspects, the present chimeric agents are used in methods of preventing the cellular transmission of an immunosuppressive signal.

Combination Therapies and Conjugation

In some embodiments, the invention provides for heterodimeric proteins and methods that further comprise administering an additional agent to a subject. In some embodiments, the invention pertains to co-administration and/or co-formulation. Any of the compositions described herein may be co-formulated and/or co-administered.

In some embodiments, any heterodimeric protein described herein acts synergistically when co-administered with another agent and is administered at doses that are lower than the doses commonly employed when such agents are used as monotherapy. In various embodiments, any agent referenced herein may be used in combination with any of the heterodimeric proteins described herein.

In various embodiments, any of the heterodimeric proteins disclosed herein may be co-administered with another heterodimeric protein disclosed herein. Without wishing to be bound by theory, it is believed that a combined regimen involving the administration of one or more heterodimeric proteins which induce an innate immune response and one or more heterodimeric proteins which induce an adaptive immune response may provide synergistic effects (e.g., synergistic anti-tumor effects).

In various embodiments, any heterodimeric protein which induces an innate immune response may be utilized in the present technology. In various embodiments, any heterodimeric protein which induces an adaptive immune response may be utilized in the present technology.

In some embodiments, inclusive of, without limitation, cancer applications, the present technology pertains to chemotherapeutic agents as additional agents. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, Ill.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In various embodiments, inclusive of, without limitation, cancer applications, the present additional agent is one or more immune-modulating agents selected from an agent that blocks, reduces and/or inhibits PD-1 and PD-L1 or PD-L2 and/or the binding of PD-1 with PD-L1 or PD-L2 (by way of non-limiting example, one or more of nivolumab (ONO-4538/BMS-936558, MDX1106, OPDIVO, BRISTOL MYERS SQUIBB), pembrolizumab (KEYTRUDA, Merck), MK-3475 (MERCK), BMS 936559 (BRISTOL MYERS SQUIBB), atezolizumab (TECENTRIQ, GENENTECH), MPDL328OA (ROCHE)), an agent that increases and/or stimulates CD137 (4-1BB) and/or the binding of CD137 (4-1BB) with one or more of 4-1BB ligand (by way of non-limiting example, urelumab (BMS-663513 and anti-4-1BB antibody), and an agent that blocks, reduces and/or inhibits the activity of CTLA-4 and/or the binding of CTLA-4 with one or more of AP2M1, CD80, CD86, SHP-2, and PPP2R5A and/or the binding of OX40 with OX40L (by way of non-limiting example GBR 830 (GLENMARK), MEDI6469 (MEDIMMUNE).

In some embodiments, inclusive of, without limitation, infectious disease applications, the present technology pertains to anti-infectives as additional agents. In some embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In some embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In some embodiments, inclusive, without limitation, of autoimmune applications, the additional agent is an immunosuppressive agent. In some embodiments, the immunosuppressive agent is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present technology include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, fluclo- ronide, flunisolide, fluoromethalone, fluperolone, fluprednisolone, hydrocortisone, meprednisone, parametha- sone, prednisolone, prednisone, beclomethasone dipropionate. (NSAIDS) that may be used in the present technology, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In some embodiments, the immunosupressive agent may be cytostatics such as alkylating agents, antimetabolites (e.g., azathioprine, methotrexate), cytotoxic antibiotics, antibodies (e.g., basiliximab, daclizumab, and muromonab), anti-immunophilins (e.g., cyclosporine, tacrolimus, sirolimus), inteferons, opioids, TNF binding proteins, mycophenolates, and small biological agents (e.g., fingolimod, myriocin).

In some embodiments, the heterodimeric proteins (and/or additional agents) described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of turicamycin, etc. Additionally, the derivative can contain one or more non-classical amino acids. In still other embodiments, the heterodimeric proteins (and/or additional agents) described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The heterodimeric proteins (and/or additional agents) described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Formulations

In one aspect, the present technology provides a pharmaceutical composition, comprising the heterodimeric protein of any of the embodiments disclosed herein.

The heterodimeric proteins (and/or additional agents) described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

In some embodiments, the compositions described herein are in the form of a pharmaceutically acceptable salt.

Further, any heterodimeric protein (and/or additional agents) described herein can be administered to a subject as a component of a composition that comprises a pharmaceutically acceptable carrier or vehicle. Such compositions can optionally comprise a suitable amount of a pharmaceutically acceptable excipient so as to provide the form for proper administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

In some embodiments, the compositions described herein are resuspended in a saline buffer (including, without limitation TBS, PBS, and the like).

In various embodiments, the heterodimeric proteins may by conjugated and/or fused with another agent to extend half-life or otherwise improve pharmacodynamic and pharmacokinetic properties. In some embodiments, the heterodimeric proteins may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In various embodiments, each of the individual heterodimeric proteins is fused to one or more of the agents described in BioDrugs (2015) 29:215-239, the entire contents of which are hereby incorporated by reference.

Administration, Dosing, and Treatment Regimens

The present technology includes the described heterodimeric protein (and/or additional agents) in various formulations. Any heterodimeric protein (and/or additional agents) described herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. DNA or RNA constructs encoding the protein sequences may also be used. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the formulations comprising the heterodimeric protein (and/or additional agents) can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

The formulations comprising the heterodimeric protein (and/or additional agents) of the present technology may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art)

In one embodiment, any heterodimeric protein (and/or additional agents) described herein is formulated in accordance with routine procedures as a composition adapted for a mode of administration described herein.

Routes of administration include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In some embodiments, the administering is effected orally or by parenteral injection. In most instances, administration results in the release of any agent described herein into the bloodstream.

Any heterodimeric protein (and/or additional agents) described herein can be administered orally. Such heterodimeric proteins (and/or additional agents) can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

In specific embodiments, it may be desirable to administer locally to the area in need of treatment. In one embodiment, for instance in the treatment of cancer, the heterodimeric protein (and/or additional agents) are administered in the tumor microenvironment (e.g., cells, molecules, extracellular matrix and/or blood vessels that surround and/or feed a tumor cell, inclusive of, for example, tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T cells; macrophages; neutrophils; and other immune cells located proximal to a tumor) or lymph node and/or targeted to the tumor microenvironment or lymph node. In various embodiments, for instance in the treatment of cancer, the heterodimeric protein (and/or additional agents) are administered intratumorally.

In the various embodiments, the present heterodimeric protein allows for a dual effect that provides less side effects than are seen in conventional immunotherapy (e.g., treatments with one or more of OPDIVO, KEYTRUDA, YERVOY, and TECENTRIQ). For example, the present heterodimeric proteins reduce or prevent commonly observed immune-related adverse events that affect various tissues and organs including the skin, the gastrointestinal tract, the kidneys, peripheral and central nervous system, liver, lymph nodes, eyes, pancreas, and the endocrine system; such as hypophysitis, colitis, hepatitis, pneumonitis, rash, and rheumatic disease. Further, the present local administration, e.g., intratumorally, obviate adverse event seen with standard systemic administration, e.g., IV infusions, as are used with conventional immunotherapy (e.g., treatments with one or more of OPDIVO, KEYTRUDA, YERVOY, and TECENTRIQ).

Dosage forms suitable for parenteral administration (e.g., intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g., lyophilized composition), which can be dissolved or suspended in sterile injectable medium immediately before use. They may contain, for example, suspending or dispersing agents known in the art.

The dosage of any heterodimeric protein (and/or additional agents) described herein as well as the dosing schedule can depend on various parameters, including, but not limited to, the disease being treated, the subject's general health, and the administering physician's discretion. Any heterodimeric protein described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional agent, to a subject in need thereof. In various embodiments any heterodimeric protein and additional agent described herein are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days apart, 4 days apart, 5 days apart, 6 days apart, 1 week apart, 2 weeks apart, 3 weeks apart, or 4 weeks apart.

In various embodiments, the present technology relates to the co-administration of a heterodimeric protein which induces an innate immune response and another heterodimeric protein which induces an adaptive immune response. In such embodiments, the heterodimeric protein which induces an innate immune response may be administered before, concurrently with, or subsequent to administration of the heterodimeric protein which induces an adaptive immune response. For example, the heterodimeric proteins may be administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days apart, 4 days apart, 5 days apart, 6 days apart, 1 week apart, 2 weeks apart, 3 weeks apart, or 4 weeks apart. In an illustrative embodiment, the heterodimeric protein which induces an innate immune response and the heterodimeric protein which induces an adaptive response are administered 1 week apart, or administered on alternate weeks (i.e., administration of the heterodimeric protein inducing an innate immune response is followed 1 week later with administration of the heterodimeric protein which induces an adaptive immune response and so forth).

The dosage of any heterodimeric protein (and/or additional agents) described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

For administration of any heterodimeric protein (and/or additional agents) described herein by parenteral injection, the dosage may be about 0.1 mg to about 250 mg per day, about 1 mg to about 20 mg per day, or about 3 mg to about 5 mg per day. Generally, when orally or parenterally administered, the dosage of any agent described herein may be about 0.1 mg to about 1500 mg per day, or about 0.5 mg to about 10 mg per day, or about 0.5 mg to about 5 mg per day, or about 200 to about 1,200 mg per day (e.g., about 200 mg, about 300 mg, about 400 mg, about 500 mg, about 600 mg, about 700 mg, about 800 mg, about 900 mg, about 1,000 mg, about 1,100 mg, about 1,200 mg per day).

In some embodiments, administration of the heterodimeric protein (and/or additional agents) described herein is by parenteral injection at a dosage of about 0.1 mg to about 1500 mg per treatment, or about 0.5 mg to about 10 mg per treatment, or about 0.5 mg to about 5 mg per treatment, or about 200 to about 1,200 mg per treatment (e.g., about 200 mg, about 300 mg, about 400 mg, about 500 mg, about 600 mg, about 700 mg, about 800 mg, about 900 mg, about 1,000 mg, about 1,100 mg, about 1,200 mg per treatment).

In some embodiments, a suitable dosage of the heterodimeric protein (and/or additional agents) is in a range of about 0.01 mg/kg to about 100 mg/kg of body weight, or about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, inclusive of all values and ranges therebetween.

In another embodiment, delivery can be in a vesicle, in particular a liposome (see Langer, 1990, *Science* 249:1527-1533; Treat et al., in *Liposomes in the Therapy of Infectious Disease and Cancer*, Lopez-Berestein and Fidler (eds.), Liss, New York, pp. 353-365 (1989).

Any heterodimeric protein (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); *Ranger and Peppas*, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105).

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Administration of any heterodimeric protein (and/or additional agents) described herein can, independently, be one to four times daily or one to four times per month or one to six times per year or once every two, three, four or five years. Administration can be for the duration of one day or one month, two months, three months, six months, one year, two years, three years, and may even be for the life of the subject.

The dosage regimen utilizing any heterodimeric protein (and/or additional agents) described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. Any heterodimeric protein (and/or additional agents) described herein can be administered in a single daily dose, or the total daily dosage can be administered in divided doses of two, three or four times daily. Furthermore, any heterodimeric protein (and/or additional agents) described herein can be administered continuously rather than intermittently throughout the dosage regimen.

Cells and Nucleic Acids

In one aspect, the present technology provides an expression vector, comprising a nucleic acid encoding the first and/or second polypeptide chains of the heterodimeric protein of any of any of the embodiments disclosed herein. In some embodiments, the expression vector is a mammalian expression vector. In some embodiments, the expression vector comprises DNA or RNA. In some embodiments, In one aspect, the present technology provides a host cell comprising the expression vector of any one of the embodiments disclosed herein.

In various embodiments, the present technology provides an expression vector, comprising a nucleic acid encoding the heterodimeric protein (e.g., a heterodimeric protein comprising a first and second polypeptide chains) described herein. In various embodiments, the expression vector comprises DNA or RNA. In various embodiments, the expression vector is a mammalian expression vector.

Both prokaryotic and eukaryotic vectors can be used for expression of the heterodimeric protein. Prokaryotic vectors include constructs based on *E. coli* sequences (see, e.g., Makrides, *Microbiol Rev* 1996, 60:512-538). Non-limiting examples of regulatory regions that can be used for expression in *E. coli* include lac, trp, lpp, phoA, recA, tac, T3, T7 and $\lambda P_L$. Non-limiting examples of prokaryotic expression vectors may include the λgt vector series such as λgt11 (Huynh et al., in "DNA Cloning Techniques, Vol. I: A Practical Approach," 1984, (D. Glover, ed.), pp. 49-78, IRL Press, Oxford), and the pET vector series (Studier et al., *Methods Enzymol* 1990, 185:60-89). Prokaryotic host-vector systems cannot perform much of the post-translational processing of mammalian cells, however. Thus, eukaryotic host-vector systems may be particularly useful. A variety of regulatory regions can be used for expression of the heterodimeric proteins in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the β-interferon gene, and the hsp70 gene (see, Williams et al., *Cancer Res* 1989, 49:2735-42; and Taylor et al., *Mol Cell Biol* 1990, 10:165-75). Heat shock promoters or stress promoters also may be advantageous for driving expression of the fusion proteins in recombinant host cells.

In some embodiments, expression vectors of the invention comprise a nucleic acid encoding at least the first and/or second polypeptide chains of the heterodimeric proteins (and/or additional agents), or a complement thereof, operably linked to an expression control region, or complement thereof, that is functional in a mammalian cell. The expression control region is capable of driving expression of the operably linked blocking and/or stimulating agent encoding nucleic acid such that the blocking and/or stimulating agent is produced in a human cell transformed with the expression vector.

Expression control regions are regulatory polynucleotides (sometimes referred to herein as elements), such as promoters and enhancers, that influence expression of an operably linked nucleic acid. An expression control region of an expression vector of the invention is capable of expressing operably linked encoding nucleic acid in a human cell. In an embodiment, the cell is a tumor cell. In another embodiment, the cell is a non-tumor cell. In an embodiment, the expression control region confers regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

In an embodiment, the present technology contemplates the use of inducible promoters capable of effecting high level of expression transiently in response to a cue. For example, when in the proximity of a tumor cell, a cell transformed with an expression vector for the heterodimeric protein (and/or additional agents) comprising such an expression control sequence is induced to transiently produce a high level of the agent by exposing the transformed cell to an appropriate cue. Illustrative inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

Expression control regions and locus control regions include full-length promoter sequences, such as native promoter and enhancer elements, as well as subsequences or polynucleotide variants which retain all or part of full-length or non-variant function. As used herein, the term "functional" and grammatical variants thereof, when used in reference to a nucleic acid sequence, subsequence or fragment, means that the sequence has one or more functions of native nucleic acid sequence (e.g., non-variant or unmodified sequence).

As used herein, "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

Expression systems functional in human cells are well known in the art, and include viral systems. Generally, a promoter functional in a human cell is any DNA sequence capable of binding mammalian RNA polymerase and initiating the downstream (3D transcription of a coding sequence into mRNA. A promoter will have a transcription initiating region, which is usually placed proximal to the 5' end of the coding sequence, and typically a TATA box located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40. Introns may also be included in expression constructs.

There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also suitable for in vivo transduction. In some situations, it is desirable to provide a targeting agent, such as an antibody or ligand specific for a tumor cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), FIp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003). In addition, direct and targeted genetic integration strategies may be used to insert nucleic acid sequences encoding the chimeric fusion proteins including CRISPR/CAS9, zinc finger, TALEN, and meganuclease gene-editing technologies.

In one aspect, the invention provides expression vectors for the expression of the heterodimeric proteins (and/or additional agents) that are viral vectors. Many viral vectors useful for gene therapy are known (see, e.g., Lundstrom, Trends Biotechnol., 21: 1 17, 122, 2003. Illustrative viral vectors include those selected from Antiviruses (LV), retroviruses (RV), adenoviruses (AV), adeno-associated viruses (AAV), and a viruses, though other viral vectors may also be used. For in vivo uses, viral vectors that do not integrate into the host genome are suitable for use, such as a viruses and adenoviruses. Illustrative types of a viruses include Sindbis virus, Venezuelan equine encephalitis (VEE) virus, and Semliki Forest virus (SFV). For in vitro uses, viral vectors that integrate into the host genome are suitable, such as retroviruses, AAV, and Antiviruses. In one embodiment, the invention provides methods of transducing a human cell in vivo, comprising contacting a solid tumor in vivo with a viral vector of the invention.

In various embodiments, the present technology provides a host cell, comprising the expression vector comprising the heterodimeric protein described herein.

Expression vectors can be introduced into host cells for producing the present heterodimeric proteins. Cells may be cultured in vitro or genetically engineered, for example Useful mammalian host cells include, without limitation, cells derived from humans, monkeys, and rodents (see, for example, Kriegler in "Gene Transfer and Expression: A Laboratory Manual," 1990, New York, Freeman & Co.). These include monkey kidney cell lines transformed by SV40 (e.g., COS-7, ATCC CRL 1651); human embryonic kidney lines (e.g., 293, 293-EBNA, or 293 cells subcloned for growth in suspension culture, Graham et al., *J Gen Virol* 1977, 36:59); baby hamster kidney cells (e.g., BHK, ATCC CCL 10); Chinese hamster ovary-cells-DHFR (e.g., CHO, Urlaub and Chasin, *Proc Natl Acad Sci USA* 1980, 77:4216); DG44 CHO cells, CHO-K1 cells, mouse sertoli cells (Mather, *Biol Reprod* 1980, 23:243-251); mouse fibroblast cells (e.g., NIH-3T3), monkey kidney cells (e.g., CV1 ATCC CCL 70); African green monkey kidney cells. (e.g., VERO-76, ATCC CRL-1587); human cervical carcinoma cells (e.g., HELA, ATCC CCL 2); canine kidney cells (e.g., MDCK, ATCC CCL 34); buffalo rat liver cells (e.g., BRL 3A, ATCC CRL 1442); human lung cells (e.g., W138, ATCC CCL 75); human liver cells (e.g., Hep G2, HB 8065); and mouse mammary tumor cells (e.g., MMT 060562, ATCC CCL51). Illustrative cancer cell types for expressing the fusion proteins described herein include mouse fibroblast cell line, NIH3T3, mouse Lewis lung carcinoma cell line, LLC, mouse mastocytoma cell line, P815, mouse lymphoma cell line, EL4 and its ovalbumin transfectant, E. G7, mouse melanoma cell line, B16F10, mouse fibrosarcoma cell line, MC57, and human small cell lung carcinoma cell lines, SCLC #2 and SCLC #7.

Host cells can be obtained from normal or affected subjects, including healthy humans, cancer patients, and patients with an infectious disease, private laboratory deposits, public culture collections such as the American Type Culture Collection, or from commercial suppliers.

Cells that can be used for production of the present heterodimeric proteins in vitro, ex vivo, and/or in vivo include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells (e.g., as obtained from bone marrow), umbilical cord blood, peripheral blood, fetal liver, etc. The choice of cell type depends on the type of tumor or infectious disease being treated or prevented, and can be determined by one of skill in the art.

Production and purification of Fc-containing macromolecules (such as Fc fusion proteins) has become a standardized process, with minor modifications between products. For example, many Fc containing macromolecules are produced by human embryonic kidney (HEK) cells (or variants thereof) or Chinese Hamster Ovary (CHO) cells (or variants thereof) or in some cases by bacterial or synthetic methods. Following production, the Fc containing macromolecules that are secreted by HEK or CHO cells are purified through binding to Protein A columns and subsequently 'polished' using various methods. Generally speaking, purified Fc containing macromolecules are stored in liquid form for some period of time, frozen for extended periods of time or in some cases lyophilized. In various embodiments, production of the heterodimeric proteins contemplated herein may have unique characteristics as compared to traditional Fc containing macromolecules. In certain examples, the heterodimeric proteins may be purified using specific chromatography resins, or using chromatography methods that do not depend upon Protein A capture. In other embodiments, the heterodimeric proteins may be purified in an oligomeric state, or in multiple oligomeric states, and enriched for a specific oligomeric state using specific methods. Without being bound by theory, these methods could include treatment with specific buffers including specified salt concentrations, pH and additive compositions. In other examples, such methods could include treatments that favor one oligomeric state over another. The heterodimeric proteins obtained herein may be additionally 'polished' using methods that are specified in the art. In some embodiments, the heterodimeric proteins are highly stable and able to tolerate a wide range of pH exposure (between pH 3-12), are able to tolerate a large number of freeze/thaw stresses (greater than 3 freeze/thaw cycles) and are able to tolerate extended incubation at high temperatures (longer than 2 weeks at 40 degrees C.). In other embodiments, the heterodimeric proteins are shown to remain intact, without evidence of degradation, deamidation, etc. under such stress conditions.

Subjects and/or Animals

In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g., GFP). In some embodiments, the subject and/or animal is a transgenic animal comprising a fluorescent cell.

In some embodiments, the subject and/or animal is a human. In some embodiments, the human is a pediatric human. In other embodiments, the human is an adult human. In other embodiments, the human is a geriatric human. In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the invention pertains to veterinary use. In a specific embodiment, the non-human animal is a household pet. In another specific embodiment, the non-human animal is a livestock animal Kits The invention provides kits that can simplify the administration of any agent described herein. An illustrative kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

Definitions

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About is understood to be within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

A stated range is understood to be any value between and at the limits of the stated range. As examples, a range between 1 and 5 includes 1, 2, 3, 4, and 5; a range between 1 and 10 includes 1, 2, 3, 4, 5, 6, 7, 8, 9, and 10; and a range between 1 and 100 includes 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100.

Unless defined otherwise, all technical and scientific terms used herein have the same meaning as commonly understood by one of ordinary skill in the art to which the invention pertains. Although other probes, compositions, methods, and kits similar, or equivalent, to those described herein can be used in the practice of the present technology, the preferred materials and methods are described herein. It is to be understood that the terminology used herein is for the purpose of describing particular embodiments only, and is not intended to be limiting.

Any aspect or embodiment described herein can be combined with any other aspect or embodiment as disclosed herein.

The invention will be further described in the following examples, which do not limit the scope of the invention described in the claims.

EXAMPLES

The present invention is further illustrated by the following example, which should not be construed as limiting in any way.

Example 1: Construction and Characterization of Heterodimers Comprising Butyrophilin-Like (BTNL) Family Proteins of the Present Technology Various non-limiting protein engineering embodiments of the present technology are shown in FIG. 1. As shown in FIG. 1 (top panel), the heterodimeric proteins of the present technology comprise a butyrophilin family member, a core domain, and an antigen-target. Accordingly, the exemplary heterodimeric proteins of the present technology include:
  i) a human butyrophilin 3/8 heterodimer adjoined to either a human CD19-specific or PSMA-specific scFv;
  ii) a human butyrophilin 3A1/3A2 heterodimer adjoined to either a human CD19-specific or PSMA-specific scFv;
  iii) a human butyrophilin 3A1/3A3 heterodimer adjoined to either a human CD19-specific or PSMA-specific scFv; and
  iv) a mouse butyrophilin 1/6 heterodimer adjoined to a mouse CD19-specific scFv.

The butyrophilin family members contemplated in a heterodimeric construct include but are not limited to: BTN1A1, BTN2A1, BTN2A2, BTN2A3, BTN3A3, BTNL2, BTNL9, BTNL10, SKINT, etc (FIG. 1 (middle panel)). Other antigen-targets for a butyrophilin heterodimeric construct include but are not limited to: GD2, PSCA, BCMA, CD123, B7-H3, CD20, CD30, CD33, CD38, CEA, CLEC12A, DLL3, EGFRvIII, EpCAM, CD307, FLT3, GPC3, gpA33, HER2, MUC16, P-cadherin, SSTR2, mesothelin, etc (FIG. 1 (middle panel)).

Without being bound by theory, the proposed mechanism of action for a butyrophilin heterodimer construct targeting either CD19 or PSMA as illustrated in the bottom panel. In this example, engagement of gamma delta T cells to CD19 or PSMA positive tumor cells is enhanced due to the butyrophilin heterodimer simultaneously engaging a tumor antigen and the gamma delta T cell receptor. The contemplated GAmma DELta T cell ENgager constructs are referred to herein as GADLEN' fusion proteins.

The sequences of exemplary embodiments of GADLEN fusion proteins are provided in the Table below (double underlined sequences are the leader sequence, single underlined is the linker):

| SEQ ID NO Species Description | Sequence |
| --- | --- |
| 66 | <u><u>MKKTLLLAVVFLVLATIKESVQC</u></u><u>Q</u>WQVTGPGKFVQALVGEDAVFSCSLFPETSAE |
| Human | AMEVRFFRNQFHAVVHLYRDGEDWESKQMPQYRGRTEFVKDSIAGGRV |
| BTNL3 | SLRLKNITPSDIGLYGCWFSSQIYDEEATWELRVAALGSLPLISIVGYVDG |
| Alpha- | GIQLLCLSSGWFPQPTAKWKGPQGQDLSSDSRANADGYSLYDVEISIIVQE |
| scFVh19 | NAGSILCSIHLAEQSHEVESKVLIGETFFQPSPWRLASGSGSRKGGKRGSK |

| SEQ ID NO Species Description | Sequence |
|---|---|
| | YGPPCPPCPAPEFLGGPSVFLFPPKPKDTLMISRTPEVTCVVVDVSQEDPE |
| | VQFNWYVDGVEVHNAKTKPREEQFNSTYRVVSVLTVLHQDWLNGKEYK |
| | CKVSNKGLPSSIEKTISKAKGQPREPQVYTLPPSQEEMTKNQVSLTCLVKG |
| | FYPSDIAVEWESNGQPENNYKTTPPVLDSDGSFFLYSKLTVDKSRWQEGN |
| | VFSCSVLHEALHNHYTQKSLSLSLGKDEGGEDGSGSDIQLTQSPASLAVSL |
| | GQRATISCKASQSVDYDGDSYLNWYQQIPGQPPKLLIYDASNLVSGIPPRF |
| | SGSGSGTDFTLNIHPVEKVDAATYHCQQSTEDPWTFGGGTKLEIK* |
| 67<br>Human<br>BTNL8-Beta-<br>scFVlh19 | MEFGLSWVFLVAILKGVQCQWQVFGPDKPVQALVGEDAAFSCFLSPKTNA<br>EAMEVRFFRGQFSSVVHLYRDGKDQPFMQMPYQGRTKLVKDSIAEGRI<br>SLRLENITVLDAGLYGCRISSQSYYQKAIWELQVSALGSVPLISITGYVDR<br>DIQLLCQSSGWFPRPTAKWKGPQGQDLSTDSRTNRDMHGLFDVEISLTVQ<br>ENAGSISCSMRHAHLSREVESRVQIGDTFFEPISWHLATKGSGSDEGGEDG<br>SKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKE<br>YKCKVSNKGLPSSIEKTISKAKGQPREPQVYTLPPSQEEMTKNQVSLTCLV<br>KGFYPSDIAVEWESNGQPENNYKTTPPVLQSDGSFFLYSRLTVDKSRWQE<br>GNVFSCSVLHEALHNHYTQKSLSLSLGKRKGGKRGSGSIQLTQSPAIMSA<br>SPGEKVTMTCRASSSVSYMNWYQQKSGTSPKRWIYDTSKVASGVPYRFS<br>GSGSGTSYSLTISSMEAEDAATYYCQQWSSNPLTFGAGTKLELK* |
| 68<br>Human<br>BTNL3-<br>Alpha-<br>scFVhPSMA | MEFGLSWVFLVAILKGVQCQWQVTGPGKFVQALVGEDAVFSCSLFPETSAE<br>AMEVRFFRNQFHAVVHLYRDGEDWESKQMPYRGRTEFVKDSIAGGRV<br>SLRLKNITPSDIGLYGCWFSSQIYDEEATWELRVAALGSLPLISIVGYVDG<br>GIQLLCLSSGWFPQPTAKWKGPQGQDLSSDSRANADGYSLYDVEISIIVQE<br>NAGSILCSIHLAEQSHEVESKVLIGETFFQPSPWRLASGSGSRKGGKRGSK<br>YGPPCPPCPAPEFLGGPSVFLFPPKPKDTLMISRTPEVTCVVVDVSQEDPE<br>VQFNWYVDGVEVHNAKTKPREEQFNSTYRVVSVLTVLHQDWLNGKEYK<br>CKVSNKGLPSSIEKTISKAKGQPREPQVYTLPPSQEEMTKNQVSLTCLVKG<br>FYPSDIAVEWESNGQPENNYKTTPPVLDSDGSFFLYSPLTVDKSRWQEGN<br>VFSCSVLHEALHNHYTQKSLSLSLGKDEGGEDGSGSEVQLVESGGGLV<br>QPGGSLTLSCAASRFMISEYHMHWVRQAPGKGLEWVSTINPAGTTDYAE<br>SVKGRFTISRDNAKNTLYLQMNSLKPEDTAVYYCDSYGYRGQGTQVTV* |
| 69<br>Human<br>BTNL8-Beta-<br>scFV1PSMA | MEFGLSWVFLVAILKGVQCQWQVFGPDKPVQALVGEDAAFSCFLSPKTNA<br>EAMEVRFFRGQFSSVVHLYRDGKDQPFMQMPYQGRTKLVKDSIAEGRI<br>SLRLENITVLDAGLYGCRISSQSYYQKAIWELQVSALGSVPLISITGYVDR<br>DIQLLCQSSGWFPRPTAKWKGPQGQDLSTDSRTNRDMHGLFDVEISLTVQ<br>ENAGSISCSMRHAHLSREVESRVQIGDTFFEPISWHLATKGSGSDEGGEDG<br>SKYGPPCPPCPAPEFLGGPSVFLFPPKPKDTLMISRTPEVTCVVVDVSQED<br>PEVQFNWYVDGVEVHNAKTKPREEQFNSTYRVVSVLTVLHQDWLNGKE<br>YKCKVSNKGLPSSIEKTISKAKGQPREPQVYTLPPSQEEMTKNQVSLTCLV |

| SEQ ID NO Species Description | Sequence |
|---|---|
| | KAFYPSDIAVEWESNGQPENNYKTTPPVLDSDGSFFLYSKLTVDKSRWQ |
| | GNVFSCSVMHEALHNHYTQKSLSLSLGKRKGGKRGSGSGQTVVTQEPSLT |
| | VSPGGTVTLTCASSTGAVTSGNYPNWVQQKPGQAPRGLIGGTKFLVPGTP |
| | ARFSGSLLGGKAALTLSGVQPEDEAEYYCTLWYSNRWVFGGGTKLTVL* |
| 70 Human BTN3A1- Alpha- scFvCD19 | MKMASSLSFLLLLFSLCLYPGCDSQFSVLGPSGPILAMVGEDADLPCHLFPTMSAETMELKWVSSSLRQVVNVYADGKEVEDRQSAPYRGRTSILRDGITAGKAALRIHNVTASDSGKYLCYFQDGDFYEKALVELKVAALGSDLHVDVKGYKDGGIHLECRSTGWYPQPQIQWSNNKGENIPTVEAPVVADGVGLYAVAASVIMRGSSGEGVSCTIRSSLLGLEKTASISIADPFFRSAQRWIAALAGGSGSRKGGKRGSKYGPPCPPCPAPEFLGGPSVFLFPPKPKDQLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSKLTVDKSRWQEGNVFSCSVMHEALHNHYTQKSLSLSLGKDEGGEDGSQVQLQQSGAELVRPGSSVKISCKASGYAFSSYWMNWVKQRPGQGLEWIGQIWPGDGDTNYNGKFKGKATLTADESSSTAYMQLSSLASEDSAVYFCARRETTTVGRYYYAMDYWGQGTTVTVSSGGGGSGGGGSGGGGSDIQLTQSPASLAVSLGQRATISCKASQSVDYDGDSYLNWYQQIPGQPPKLLIYDASNLVSGIPPRFSGSGSGTDFTLNIHPVEKVDAATYHCQQSTEDPWTFGGGTKLEIK |
| 71 Human BTN3A2- Beta- scFvCD19 | MKMASSLSFLLLLFSLCLYPGCDSQFSVLGPSGPILAMVGEDADLPCHLFPTMSAETMELKWVSSSLRQVVNVYADGKEVEDRQSAPYRGRTSILRDGITAGKAALRIHNVTASDSGKYLCYFQDGDFYEKALVELKVAALGSNLHVEVKGYEDGGIHLECRSTGWYPQPQIQWSNAKGENIPAVEAPVVADGVGLYEVAASVIMRGGSGEGVSCIIRNSLLGLEKTASISIADPFFRSAQPWGSGSDEGGEDGSKYGPPCPPCPAPEFLGGPSVFLFPPKPKDQLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKRKGGKRGSGSQVQLQQSGAELVRPGSSVKISCKASGYAFSSYWMNWVKQRPGQGLEWIGQIWPGDGDTNYNGKFKGKATLTADESSSTAYMQLSSLASEDSAVYFCARRETTTVGRYYYAMDYWGQGTTVTVSSGGGGSGGGGSGGGGSDIQLTQSPASLAVSLGQRATISCKASQSVDYDGDSYLNWYQQIPGQPPKLLIYDASNLVSGIPPRFSGSGSGTDFTLNIHPVEKVDAATYHCQQSTEDPWTFGGGTKLEIK |
| 72 Human BTNL3- Alpha- scFvCD19-2 | MKMASSLSFLLLLFSLCLYPGCDSQWQVTGPGKFVQALVGEDAVFSCSLFPETSAEAMEVRFFRNQFHAVVHLYRDGEDWESKQMPQYRGRTEFVKDSIAGGRVSLRLKNITPSDIGLYGCWFSSQIYDEEATWELRVAALGSLPLISIVGYVDGGIQLLCLSSGWFPQPTAKWKGPQGQDLSSDSRANADGYSLYDVEISIIVQENAGSILCSIHLAEQSHEVESKVLIGETFFQPSPWRLASGSGSRKGGKRGSK |

| SEQ ID NO Species Description | Sequence |
|---|---|
| | YGPP*CPPCPAPEFLGGPSVFLFPPKPKDTLMISRTPEVTCVVVDVSQEDPE* *VQFNWYVDGVEVHNAKTKPREEQFNSTYRVVSVLTVLHQDWLNGKEYK* *CKVSNKGLPSSIEKTISKAKGQPREPQVYTLPPSQEEMTKNQVSLTCLVKG* *FYPSDIAVEWESNGQPENNYKTTPPVLDSDGSFFLYSRLTVDKSRWQEGN* *VFSCSVMHEALHNHYTQKSLSLSLGK*DEGGEDGSQVQLQQSGAELVRPG SSVKISCKASGYAFSSYWMNWVKQRPGQGLEWIGQIWPGDGDTNYNGK FKGKATLTADESSSTAYMQLSSLASEDSAVYFCARRETTTVGRYYYAMD YWGQGTTVTVSSGGGGSGGGGSGGGGSDIQLTQSPASLAVSLGQRATISC KASQSVDYDGDSYLNWYQQIPGQPPKLLIYDASNLVSGIPPRFSGSGSGTD FTLNIHPVEKVDAATYHCQQSTEDPWTFGGGTKLEIK |
| 73 Human BTNL8-Beta-scFvCD19-2 | *MSFGLSVVFLVALIKGVQC*QWQVFGPDKPVQALVGEDAAFSCFLSPKTNA EAMEVRFFRGQFSSVVHLYRDGKDQPFMQMPQYQGRTKLVKDSIAEGRI SLRLENITVLDAGLYGCRISSQSYYQKAIWELQVSALGSVPLISITGYVDR DIQLLCQSSGWFPRPTAKWKGPQGQDLSTDSRTNRDMHGLFDVEISLTVQ ENAGSISCSMRHAHLSREVESRVQIGDTFFEPISWHLATKGSGSDEGGEDG SKYGPP*CPPCPAPEFLGGPSVFLFPPKPKDTLMISRTPEVTCVVVDVSQED* *PEVQFNWYVDGVEVHNAKTKPREEQFNSTYRVVSVLTVLHQDWLSGKE* *YKCKVSSKGLPSSIEKTISNATGQPREPQVYTLPPSQEEMTRNQVSLTCLV* *KGFYPSDIAVEWESNGQPENNYKTTPPVLQSDGSFFLYSRLTVDKSRWQG* *GNVFSCSVLHEALHNHYTQKSLSLSLGK*RKGGKRGSGSQVQLQQSGAEL VRPGSSVKISCKASGYAFSSYWMNWVKQRPGQGLEWIGQIWPGDGDTN YNGKFKGKATLTADESSSTAYMQLSSLASEDSAVYFCARRETTTVGRYY YAMDYWGQGTTVTVSSGGGGSGGGGSGGGGSDIQLTQSPASLAVSLGQ RATISCKASQSVDYDGDSYLNWYQQIPGQPPKLLIYDASNLVSGIPPRFSG SGSGTDFTLNIHPVEKVDAATYHCQQSTEDPWTFGGGTKLEIK |
| 74 Human BTNL3-KIHT22Y-scFvCD19-2 | *MHPGLSNVPLAVALWLYGVA*QWQVTGPGKFVQALVGEDAVFSCSLFPETSAE AMEVRFFRNQFHAVVHLYRDGEDWESKQMPQYRGRTEFVKDSIAGGRV SLRLKNITPSDIGLYGCWFSSQIYDEEATWELRVAALGSLPLISIVGYVDG GIQLLCLSSGWFPQPTAKWKGPQGQDLSSDSRANADGYSLYDVEISIIVQE NAGSILCSIHLAEQSHEVESKVLIGETFFQPSPWRLASEPKSCDKTHTCPPC PAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKA LPAPIEKTISKAKGQPREPQVYTLPPSRDELTKNQVSLYCLVKGFYPSDIA VEWESNGQPENNYKTTPPVLDSDGSFFLYSKLTVDKSRWQQGNVFSCSV MHEALHNHYTQKSLSLSPGKGGGSQVQLQQSGAELVRPGSSVKISCKAS GYAFSSYWMNWVKQRPGQGLEWIGQIWPGDGDTNYNGKFKGKATLTA DESSSTAYMQLSSLASEDSAVYFCARRETTTVGRYYYAMDYWGQGTTV TVSSGGGGSGGGGSGGGGSDIQLTQSPASLAVSLGQRATISCKASQSVDY |

| SEQ ID NO Species Description | Sequence |
|---|---|
| | DGDSYLNWYQQIPGQPPKLLIYDASNLVSGIPPRFSGSGSGTDFTLNIHPVE |
| | KVDAATYHCQQSTEDPWTFGGGTKLEIK |
| 75 Human BTNL8- KIHY86T- scFvCD19-2 | MEFGLSWVFLVAILKGVQCWQVFGPDKPVQALVGEDAAFSCFLSPKTNA EAMEVRFFRGQFSSVVHLYRDGKDQPFMQMPQYQGRTKLVKDSIAEGRI SLRLENITVLDAGLYGCRISSQSYYQKAIWELQVSALGSVPLISITGYVDR DIQLLCQSSGWFPRPTAKWKGPQGQDLSTDSRTNRDMHGLFDVEISLTVQ ENAGSISCSMRHAHLSREVESRVQIGDTFFEPISWHLATKEPKSCDKTHTC PPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSN KALPAPIEKTISKAKGQPREPQVYTLPPSRDELTKNQVSLTCLVKGFYPSDI AVEWESNGQPENNYKTTPPVLDSDGSFFLTSKLTVDKSRWQQGNVFSCS VMHEALHNHYTQKSLSLSPGKGGGSQVQLQQSGAELVRPGSSVKISCKA SGYAFSSYWMNWVKQRPGQGLEWIGQIWPGDGDTNYNGKFKGKATLT ADESSSTAYMQLSSLASEDSAVYFCARRETTTVGRYYYAMDYWGQGTT VTVSSGGGGSGGGGSGGGGSDIQLTQSPASLAVSLGQRATISCKASQSVD YDGDSYLNWYQQIPGQPPKLLIYDASNLVSGIPPRFSGSGSGTDFTLNIHP VEKVDAATYHCQQSTEDPWTFGGGTKLEIK |
| 76 Mouse BTNL1- Alpha- scFvCD19V HVL | MEFGLSWVFLVAILKGVQCEVSWFSVKGPAEPITVLLGTEATLPCQLSPEQS AARMHIRWYRAQPTPAVLVFHNGQEQGEVQMPEYRGRTQMVRQAIDM GSVALQIQQVQASDDGLYHCQFTDGFTSQEVSMELRVIGLGSAPLVHMT GPENDGIRVLCSSSGWFPKPKVQWRDTSGNMLLSSSELQTQDREGLFQVE VSLLVTDRAIGNVICSIQNPMYDQEKSKAILLPEPFFPKTCPWKGSGSDEG GEDGVPRDCGCKPCICTVPEVSSVFIFPPKPKDVLTITLTPKVTCVVVDISK DDPEVQFSWFVDDVEVHTAQTQPREEQFNSTFRSVSELPIMHQDWLNGK EFKCRVNSAAPPAPIEKTISKTKGRPKAPQVYTIPPPKEQMSKDKVSLTCM ITDFFPEDITVEWQWNGQPAENYKNTPIMDTDGSYFVYSKLNVQKSNW EAGNTFTCSVLHEGLHNHHTEKSLSHSPGIRKGGKRGSGSEVQLQQSGAE LVRPGTSVKLSCKVSGDTITFYYMHFVKQRPGQGLEWIGRIDPEDESTKY SEKFKNKATLTADTSSNTAYLKLSSLTSEDTATYFCIYGGYYFDYWGQGV MVTVSSGGGGSGGGGSGGGGSDIQMTQSPASLSTSLGETVTIQCQASEDI YSGLAWYQQKPGKSPQLLIYGASDLQDGVPSRFSGSGSGTQYSLKITSMQ TEDEGVYFCQQGLTYPRTFGGGTKLELK |
| 77 Mouse BTNL6-Beta- scFvCD19V HVL | MEFGLSWVFLVAILKGVQCEQLPEYSQRTSLVKEQFHQGTAAVRILNVQAP DSGIYICHFKQGVFYEEAILELKVAAMGSVPEVYIKGPEDGGVCVVCITSG WYPEPQVHWKDSRGEKLTASLEIHSEDAQGLFRTETSLVVRDSSVRNVTC STFNPILGQEKAMAMFLPEPFFPKVSPWKPGSGSDEGGEDGVPRDCGCKP CICTVPEVSSVFIFPPKPKDVLTITLTPKVTCVVVDISKDDPEVQFSWFVDD VEVHTAQTQPREEQFNSTFRSVSELPIMHQDWLNGKEFKCRVNSAAPPAP |

| SEQ ID NO Species Description | Sequence |
|---|---|
| | ISKTLSKPKGPPKAPQVYTIPPPKEQMAKDKVSLTCMITDFFPEDITVEWQ |
| | WNGQPAENYKNTQPIMDTDGSYFVYSKLNVQKSNWEAGNTFTCSVLHE |
| | GLHNHHTEKSLSHSPGK RKGGKRGSGSEVQLQQSGAELVRPGTSVKLSCK |
| | VSGDTITFYYMHFVKQRPGQGLEWIGRIDPEDESTKYSEKFKNKATLTAD |
| | TSSNTAYLKLSSLTSEDTATYFCIYGGYYFDYWGQGVMVTVSSGGGGSG |
| | GGGSGGGGSDIQMTQSPASLSTSLGETVTIQCQASEDIYSGLAWYQQKPG |
| | KSPQLLIYGASDLQDGVPSRFSGSGSGTQYSLKITSMQTEDEGVYFCQQG |
| | LTYPRTFGGGTKLELK |
| 78 Mouse BTNL1-Alpha-scFvCD19VL VH | *MEFGLSWVFLVAIIKGVQC*EVSWFSVKGPAEPITVLLGTEATLPCQLSPEQS AARMHIRWYRAQPTPAVLVFHNGQEQGEVQMPEYRGRTQMVRQAIDM GSVALQIQQVQASDDGLYHCQFTDGFTSQEVSMELRVIGLGSAPLVHMT GPENDGIRVLCSSSGWFPKPKVQWRDTSGNMLLSSSELQTQDREGLFQVE VSLLVTDRAIGNVICSIQNPMYDQEKSKAILLPEPFFPKTCPWKGSGSDEG GEDGVPRDCGKKPCICTVPEVSSVFIFPPKPKDVLTITLTPKVTCVVVDISK DDPEVQFSWFVDDVEVHTAQPRESQFNSTFRSVSELPIMHQDWLNGK EFKCRVNSAAFPAPIEKTISKTKGRPKAPQVYTIPPPKEQMAKDKVSLTCM ITDFFPEDITVEWQWNGQPAENYKNTQPIMDTDGSYFVYSKLNVQKSNW EAGNTFTCSVLHEGLHNHHTEKSLSHSPGK RKGGKRGSGSDIQMTQSPAS LSTSLGETVTIQCQASEDIYSGLAWYQQKPGKSPQLLIYGASDLQDGVPSR FSGSGSGTQYSLKITSMQTEDEGVYFCQQGLTYPRTFGGGTKLELKGGGG SGGGGSGGGGSEVQLQQSGAELVRPGTSVKLSCKVSGDTITFYYMHFVK QRPGQGLEWIGRIDPEDESTKYSEKFKNKATLTADTSSNTAYLKLSSLTSE DTATYFCIYGGYYFDYWGQGVMVTVSS |
| 79 Mouse BTNL6-Beta-scFvCD19VL VH | *MEFGLSWVFLVAIIKGVQC*EQLPEYSQRTSLVKEQFHQGTAAVRILNVQAP DSGIYICHFKQGVFYEEAILELKVAAMGSVPEVYIKGPEDGGVCVVCITSG WYPEPQVHWKDSRGEKLTASLEIHSEDAQGLFRTETSLVVRDSSVRNVTC STFNPILGQEKAMAMFLPEPFFPKVSPWKPGSGSDEEGEDGV YSVHTAQKPPSEQFNSTFRSVSELPIMHQDWLNGKEFKCRVNSAAPPAS IEKTISKTKGRPKASQVYTIPPPEQMREDKVSLTCMITDFFPEDMIYEWQ WNGQPAENYKNTQPIMDTDGSYFVYSKLNVQKSNWEAGNTFTCSVLHE GLHNHHTEKSLSHSPGK RKGGKRGSGSDIQMTQSPASLSTSLGETVTIQCQ CICTVPEVSSVFIFPPKPKDVLTITLTPKVTCVVVDISKDDPEVQFSWFVDD ASEDIYSGLAWYQQKPGKSPQLLIYGASDLQDGVPSRFSGSGSGTQYSLKI TSMQTEDEGVYFCQQGLTYPRTFGGGTKLELKGGGGSGGGGSGGGGSEV QLQQSGAELVRPGTSVKLSCKVSGDTITFYYMHFVKQRPGQGLEWIGRID PEDESTKYSEKFKNKATLTADTSSNTAYLKLSSLTSEDTATYFCIYGGYYF DYWGQGVMVTVSS |
| 80 Human | *MEFGLSWVFLVAIIKGVQC*QWQVTGPGKFVQALVGEDAVFSCSLFPETSAE AMEVRFFRNQFHAVVHLYRDGEDWESKQMPQYRGRTEFVKDSIAGGRV |

| SEQ ID NO Species Description | Sequence |
|---|---|
| BTNL3-A-19scFv3 | SLRLKNITPSDIGLYGCWFSSQIYDEEATWELRVAALGSLPLISIVGYVDG GIQLLCLSSGWFPQPTAKWKGPQGQDLSSDSRANADGYSLYDVEISIIVQE NAGSILCSIHLAEQSHEVESKVLIGETFFQPSPWRLASGSGSRKGGKRGSK YGPPCPPCPAPEFLGGPSVFLFPPKPKDQLMISRTPEVTCVVVDVSQE DPEVQFNWYVDGVEVHNAKTKPREEQFNSTYRVVSVLTVLHQDWLS GKEYKCKVSSKGLPSSIEKTISNATGQPREPQVYTLPPSQEEMTKNQV SLTCLVKGFYPSDIAVEWESNGQPENNYKTTPPVLDSDGSFFLYSRLT VDKSRWQEGNVFSCSVLHEALHNHYTQKSLSLSLGKDEGGEDGSDIQ MTQTTSSLSASLGDRVTISCRASQDISKYLNWYQQKPDGTVKLLIYHTSR LHSGVPSRFSGSGSGTDYSLTISNLEQEDIATYFCQQGNTLPYTFGGGTKL EITGGGSGGGSGGGSEVKLQESGPGLVAPSQSLSVTCTVSGVSLPDYGVS WIRQPPRKGLEWLGVIWGSETTYYNSALKSRLTIIKDNSKSQVFLKMNSL QTDDTAIYYCAKHYYYGGSYAMDYWGQGTSVTVSS* |
| 81 Human BTNL8-A-19scFv3 | *MEFGLSWVFLVAIIKGVQC*QWQVFGPDKPVQALVGEDAAFSCFLSPKTNA EAMEVRFFRGQFSSVVHLYRDGKDQPFMQMPQYQGRTKLVKDSIAEGRI SLRLENITVLDAGLYGCRISSQSYYQKAIWELQVSALGSVPLISITGYVDR DIQLLCQSSGWFPRPTAKWKGPQGQDLSTDSRTNRDMHGLFDVEISLTVQ ENAGSISCSMRHAHLSREVESRVQIGDTFFEPISWHLATKGSGSDEGGEDG SKYGPPCPPCPAPEFLGGPSVFLFPPKPKDQLMISRTPEVTCVVVDVSQED PEVQFNWYVDGVEVHNAKTKPREEQFNSTYRVVSVLTVLHQDWLSGKE YKCKVSSKGLPSSIEKTISNATGQPREPQVYTLPPSQEEMTKNQVSLTCLV KGFYPSDIAVEWESNGQPENNYKTTPPVLDSDGSFFLYSRLTVDKSRWQE GNVFSCSVLHEALHNHYTQKSLSLSLGKRKGGKRGSGSDIQMTQTTSSLS ASLGDRVTISCRASQDISKYLNWYQQKPDGTVKLLIYHTSRLHSGVPSRFS GSGSGTDYSLTISNLEQEDIATYFCQQGNTLPYTFGGGTKLEITGGGSGGG SGGGSEVKLQESGPGLVAPSQSLSVTCTVSGVSLPDYGVSWIRQPPRKGL EWLGVIWGSETTYYNSALKSRLTIIKDNSKSQVFLKMNSLQTDDTAIYYC AKHYYYGGSYAMDYWGQGTSVTVSS* |
| 82 Human BTN3A1-A-19scFv3 | *MEFGLSWVFLVAIIKGVQC*QFSVLGPSGPILAMVGEDADLPCHLFPTMSAE TMELKWVSSSLRQVVNVYADGKEVEDRQSAPYRGRTSILRDGITAGKAA LRIHNVTASDSGKYLCYFQDGDFYEKALVELKVAALGSDLHVDVKGYK DGGIHLECRSTGWYPQPQIQWSNNKGENIPTVEAPVVADGVGLYAVAAS VIMRGSSGEGVSCTIRSSLLGLEKTASISIADPFFRSAQRWIAALAGGSGSR KGGKRGSKYGPPCPPCPAPEFLGGPSVFLFPPKPKDQLMISRTPEVTCVVV DVSQEDPEVQFNWYVDGVEVHNAKTKPREEQFNSTYRVVSVLTVLHQD WLSGKEYKCKVSSKGLPSSIEKTISNATGQPREPQVYTLPPSQEEMTKNQ VSLTCLVKGFYPSDIAVEWESNGQPENNYKTTPPVLDSDGSFFLYSRLTV DKSRWQEGNVFSCSVLHEALHNHYTQKSLSLSLGKDEGGEDGSDIQMTQ |

| SEQ ID NO Species Description | Sequence |
|---|---|
| | TTSSLSASLGDRVTISCRASQDISKYLNWYQQKPDGTVKLLIYHTSRLHSG |
| | VPSRFSGSGSGTDYSLTISNLEQEDIATYFCQQGNTLPYTFGGGTKLEITGG |
| | GSGGGSGGGSEVKLQESGPGLVAPSQSLSVTCTVSGVSLPDYGVSWIRQP |
| | PRKGLEWLGVIWGSETTYYNSALKSRLTIIKDNSKSQVFLKMNSLQTDDT |
| | AIYYCAKHYYYGGSYAMDYWGQGTSVTVSS |
| 83 Human BTN3A2-B- 19scFv3 | *MEFGLSWVFLVAIIKGVQC*QFSVLGPSGPILAMVGEDADLPCHLFPTMSAE TMELKWVSSSLRQVVNVYADGKEVEDRQSAPYRGRTSILRDGITAGKAA LRIHNVTASDSGKYLCYFQDGDFYEKALVELKVAALGSNLHVEVKGYED GGIHLECRSTGWYPQPQIQWSNAKGENIPAVEAPVVADGVGLYEVAASVI MRGGSGEGVSCIIRNSLLGLEKTASISIADPFFRSAQPWGSGSDEGGEDGS KYGPPCPPCPAPEFLGGPSVFLFPPKPKDQLMISRTPEVTCVVVDVSQEDP EVQFNWYVDGVEVHNAKTKPREEQFNSTYRVVSVLTVLHQDWLSGKEY KCKVSSKGLPSSIEKTISNATGQPREPQVYTLPPSQEEMTKNQVSLTCLVK GFYPSDIAVEWESNGQPENNYKTTPPVLDSDGSFFLYSRLTVDKSRWQEG NVFSCSVLHEALHNHYTQKSLSLSLGKRKGGKRGSGSDIQMTQTTSSLSA SLGDRVTISCRASQDISKYLNWYQQKPDGTVKLLIYHTSRLHSGVPSRFSG SGSGTDYSLTISNLEQEDIATYFCQQGNTLPYTFGGGTKLEITGGGSGGGS GGGSEVKLQESGPGLVAPSQSLSVTCTVSGVSLPDYGVSWIRQPPRKGLE WLGVIWGSETTYYNSALKSRLTIIKDNSKSQVFLKMNSLQTDDTAIYYCA KHYYYGGSYAMDYWGQGTSVTVSS |
| 84 Human BTNL3-A- GD2scFv3 | *MEFGLSWVFLVAIIKGVQC*QWQVTGPGKFVQALVGEDAVFSCSLFPETSAE AMEVRFFRNQFHAVVHLYRDGEDWESKQMPQYRGRTEFVKDSIAGGRV SLRLKNITPSDIGLYGCWFSSQIYDEEATWELRVAALGSLPLISIVGYVDG GIQLLCLSSGWFPQPTAKWKGPQGQDLSSDSRANADGYSLYDVEISIIVQE NAGSILCSIHLAEQSHEVESKVLIGETFFQPSPWRLASGSGSRKGGKRGSK YGPPCPPCPAPEFLGGPSVFLFPPKPKDQLMISRTPEVTCVVVDVSQEDPE VQFNWYVDGVEVHNAKTKPREEQFNSTYRVVSVLTVLHQDWLSGKEYK CKVSSKGLPSSIEKTISNATGQPREPQVYTLPPSQEEMTKNQVSLTCLVKG FYPSDIAVEWESNGQPENNYKTTPPVLDSDGSFFLYSRLTVDKSRWQEGN VFSCSVLHEALHNHYTQKSLSLSLGKDEGGEDGSDVVMTQTPLSLPVSLG DQASISCRSSQSLVHRNGNTYLHWYLQKPGQSPKLLIHKVSNRFSGVPDR FSGSGSGTDFTLKISRVEAEDLGVYFCSQSTHVPPLTFGAGTKLELKGGGS GGGSGGGSEVQLLQSGPELEKPGASVMISCKASGSSFTGYNMNWVRQNI GKSLEWIGAIDPYYGGTSYNQKFKGRATLTVDKSSSTAYMHLKSLTSEDS AVYYCVSGMKYWGQGTSVTVSS |
| 85 Human BTNL8-B- | *MEFGLSWVFLVAIIKGVQC*QWQVVFGPDKPVQALVGEDAAFSCFLSPKTNA EAMEVRFFRGQFSSVVHLYRDGKDQPFMQMPQYQGRTKLVKDSIAESRI SLRLENITVLDAGLYGCRISSQSYYQKAIWELQVSALGSVPLISITGYVDR |

-continued

| SEQ ID NO Species Description | Sequence |
|---|---|
| GD2scFv3 | DIQLLCQSSGWFPRPTAKWKGPQGQDLSTDSRTNRDMHGLFDVEISLTVQ |
| | ENAGSISCSMRHAHLSREVESRVQIGDTFFEPISWHLATKGSGSDEGGEDG |
| | SKYGPPCPPCPAPEFLGGPSVFLFPPKPKDQLMISRTPEVTCVVVDVSQED |
| | PEVQFNWYVDGVEVHNAKTKPREEQFNSTYRVVSVLTVLHQDWLSGKE |
| | YKCKVSSKGLPSSIEKTISNATGQPREPQVYTLPPSQEEMTKNQVSLTCLV |
| | KGFYPSDIAVEWESNGQPENNYKTTPPVLDSDGSFFLYSRLTVDKSRWQE |
| | GNVFSCSVLHEALHNHYTQKSLSLSLGKRKGGKRGSGSDVVMTQTPLSL |
| | PVSLGDQASISCRSSQSLVHRNGNTYLHWYLQKPGQSPKLLIHKVSNRFS |
| | GVPDRFSGSGSGTDFTLKISRVEAEDLGVYFCSQSTHVPPLTFGAGTKLEL |
| | KGGGSGGGSGGGSEVQLLQSGPELEKPGASVMISCKASGSSFTGYNMNW |
| | VRQNIGKSLEWIGAIDPYYGGTSYNQKFKGRATLTVDKSSSTAYMHLKSL |
| | TSEDSAVYYCVSGMKYWGQGTSVTVSS |
| 86 Human BTN3A1-A-GD2scFv3 | *MEFGLSWVFLVAIIKGVQC*QFSVLGPSGPILAMVGEDADLPCHLFPTMSAE |
| | TMELKWVSSSLRQVVNVYADGKEVEDRQSAPYRGRTSILRDGITAGKAA |
| | LRIHNVTASDSGKYLCYFQDGDFYEKALVELKVAALGSDLHVDVKGYK |
| | DGGIHLECRSTGWYPQPQIQWSNNKGENIPTVEAPVVADGVGLYAVAAS |
| | VIMRGSSGVSVSCTIRSSLLGLEKTASISIADPFFRSAQRWIAALAGGSGSR |
| | KGGKRGSKYGPPCPPCPAPEFLGGPSVFLFPPKPKDQLMISRTPEVTCVVV |
| | DVSQEDPEVQFNWYVDGVEVHNAKTKPREEQFNSTYRVVSVLTVLHQD |
| | WLSGKEYKCKVSSKGLPSSIEKTISNATGQPREPQVYTLPPSQEEMTKNQ |
| | VSLTCLVKGFYPSDIAVEWESNGQPENNYKTTPPVLDSDGSFFLYSRLTV |
| | DKSRWQEGNVFSCSVLHEALHNHYTQKSLSLSLGKDEGGEDGSDVVMT |
| | QTPLSLPVSLGDQASISCRSSQSLVHRNGNTYLHWYLQKPGQSPKLLIHK |
| | VSNRFSGVPDRFSGSGSGTDFTLKISRVEAEDLGVYFCSQSTHVPPLTFGA |
| | GTKLELKGGGSGGGSGGGSEVQLLQSGPELEKPGASVMISCKASGSSFTG |
| | YNMNWVRQNIGKSLEWIGAIDPYYGGTSYNQKFKGRATLTVDKSSSTAY |
| | MHLKSLTSEDSAVYYCVSGMKYWGQGTSVTVSS |
| 87 Human BTN3A2-B-GD2scFv3 | *MEFGLSWVFLVAIIKGVQC*QFSVLGPSGPILAMVGEDADLPCHLFPTMSAE |
| | TMELKWVSSSLRQVVNVYADGKEVEDRQSAPYRGRTSILRDGITAGKAA |
| | LRIHNVTASDSGKYLCYFQDGDFYEKALVELKVAALGSNLHVEVKGYED |
| | GGIHLECRSTGWYPQPQIQWSNAKGENIPAVEAPVVADGVGLYEVAASVI |
| | MRGGSGEGVSCIIRNSLLGLEKTASISIADPFFRSAQPWGSGSDEGGEDGS |
| | KYGPPCPPCPAPEFLGGPSVFLFPPKPKDQLMISRTPEVTCVVVDVSQEDP |
| | EVQFNWYVDGVEVHNAKTKPREEQFNSTYRVVSVLTVLHQDWLSGKEY |
| | KCKVSSKGLPSSIEKTISNATGQPREPQVYTLPPSQEEMTKNQVSLTCLVK |
| | GFYPSDIAVEWESNGQPENNYKTTPPVLDSDGSFFLYSRLTVDKSRWQEG |
| | NVFSCSVLHEALHNHYTQKSLSLSLGKRKGGKRGSGSDVVMTQTPLSLP |
| | VSLGDQASISCRSSQSLVHRNGNTYLHWYLQKPGQSPKLLIHKVSNRFSG |

| SEQ ID NO Species Description | Sequence |
|---|---|
| | VPDRFSGSGSGTDFTLKISRVEAEDLGVYFCSQSTHVPPLTFGAGTKLELK GGGSGGGSGGGSEVQLLQSGPELEKPGASVMISCKASGSSFTGYNMNWV RQNIGKSLEWIGAIDPYYGGTSYNQKFKGRATLTVDKSSTAYMHLKSLT SEDSAVYYCVSGMKYWGQGTSVTVSS |
| 88-93 | Intentionally omitted. |
| 94 Human BTNL3- Alpha- vTIGIT | MRFLSVVFLVAIIKPVQCQWQVTGPGKFVQALVGEDAVFSCSLFPETSAE AMEVRFFRNQFHAVVHLYRDGEDWESKQMPQYRGRTEFVKDSIAGGRV SLRLKNITPSDIGLYGCWFSSQIYDEEATWELRVAALGSLPLISIVGYVDG GIQLLCLSSGWFPQPTAKWKGPQGQDLSSDSRANADGYSLYDVEISIIVQE NAGSILCSIHLAEQSHEVESKVLIGETFFQPSPWRLASGSGSRKGGKRGSK YGPPCPPCPAPEFLGGPSVFLFPPKPKDQLMISRTPEVTCVVVDVSQEDPE VQFNWYVDGVEVHNAKTKPREEQFNSTYRVVSVLTVLHQDWLSGKEYK CKVSSKGLPSSIEKTISKATGQPREPQVYTLPPSQEEMTKNQVSLTCLVKG VESCSVLHEALHNHYTQKSLSLSLGKDEGGEDGSGSMMTGTIETTGNISA VESCSVLHEALHNHYTQKSLSLSLGKDEGGEDGSGSMMTGTIETTGNISA EKGGSIILQCHLSSTTAQVTQVNWEQQDQLLAICNADLGWHISPSFKDRV APGPGLGLTLQSLTVNDTGEYFCIYHTYPDGTYTGRIFL* |
| 95 Human BTNL8-Beta- vTIGIT | MRFLSVVFLVAIIKPVQCQWQVFGPDKPVQALVGEDAAFSCFLSPKTNA EAMEVRFFRGQFSSVVHLYRDGKDQPFMQMPYQGRTKLVKDSIAEGRI SLRLENITVLDAGLYGCRISSQSYYQKAIWELQVSALGSVPLISITGYVDR DIQLLCQSSGWFPRPTAKWKGPQGQDLSTDSRTNRDMHGLFDVEISLTVQ ENAGSISCSMRHAHLSREVESRVQIGDTFFEPISWHLATKGSGSDEGGEDG SKYGPPCPPCPAPEFLGGPSVFLFPPKPKDQLMISRTPEVTCVVVDVSQED PEVQFNWYVDGVEVHNAKTKPREEQFNSTYRVVSVLTVLHQDWLSGKE YKCKVSNKGLPSSIEKTISNATGQPREPQVYTLPPSQEEMTKNQVSLTCLV KGFYPSDIAVEWESNGQPENNYKTTPPVLDSDGSFFLYSRLTVDKSRWQE GNVFSCSVLHEALHSHYTQESLSLSLGKRKGGKRGSGSMMTGTIETTGNI SAEKGGSIILQCHLSSTTAQVTQVNWEQQDQLLAICNADLGWHISPSFKD RVAPGPGLGLTLQSLTVNDTGEYFCIYHTYPDGTYTGRIFL* |
| 96 Human BTNL3- Alpha- vLAG3 | MRFLSVVFLVAIIKPVQCQWQVTGPGKFVQALVGEDAVFSCSLFPETSAE AMEVRFFRNQFHAVVHLYRDGEDWESKQMPQYRGRTEFVKDSIAGGRV SLRLKNITPSDIGLYGCWFSSQIYDEEATWELRVAALGSLPLISIVGYVDG GIQLLCLSSGWFPQPTAKWKGPQGQDLSSDSRANADGYSLYDVEISIIVQE NAGSILCSIHLAEQSHEVESKVLIGETFFQPSPWRLASGSGSRKGGKRGSK YGPPCPPCPAPEFLGGPSVFLFPPKPKDQLMISRTPEVTCVVVDVSQEDPE VQFNWYVDGVEVHNAKTKPREEQFNSTYRVVSVLTVLHQDWLSGKEYK CKVSNKGLPSSIEKTISNATGQPREPQVYTLPPSQEEMTKNQVSLTCLVKG FYPSDIAVEWESNGQPENNYKTTPPVLGSDGSFFLYSKLTVDKSRWQEGN VFSCSVLHEALHSHYTQESLSLSLGKDEGGEDGSGSGAPAQLPCSPTIPLQ |

| SEQ ID NO Species Description | Sequence |
|---|---|
| | DLSLLRRAGVTWQHQPDSGPPAAAPGHPLAPGPHPAAPSSWGPRPRRYT |
| | VLSVGPGGLRSGRLPLQPRVQLDERGRQRGDFSLWLRPARRADAGEYRA |
| | AVHLRDRALSCRLRLRLG* |
| 97 Human BTNL8-Beta- vLAG3 | *MEFGLSWVFLVAIIKGVQC*QWQVFGPDKPVQALVGEDAAFSCFLSPKTNA EAMEVRFFRGQFSSVVHLYRDGKDQPFMQMPQYQGRTKLVKDSIAVGRI SLRLENITVLDAGLYGCRISSQSYYQKAIWELQVSALGSVPLISITGYVDR DIQLLCQSSGWFPRPTAKWKGPQGQDLSTDSRTNRDMHGLFDVEISLTVQ ENAGSISCSMRHAHLSREVESRVQIGDTFFEPISWHLATKGSGSDVSGEDG SKYGPP*CPPCPAPEFLGGPSVFLFPPKPKDQLMISRTPEVTCVVVDVSQED PEVQFNWYVDGVEVHNAKTKPREEQFNSTYRVVSVLTVLHQDWLNGKE YKCKVSNKGLPSSIEKTISKAKGQPREPQVYTLPPSQEEMTKNQVSLTCLV KGFYPSDIAVEWESNGQPENNYKTTPPVLDSDGSFFLYSRLTVDKSRWQE GNVFSCSVMHEALHNHYTQKSLSLSLGK*RKGGKRGSGSGAPAQLPCSPTI PLQDLSLLRRAGVTWQHQPDSGPPAAAPGHPLAPGPHPAAPSSWGPRPRR YTVLSVGPGGLRSGRLPLQPRVQLDERGRQRGDFSLWLRPARRADAGEY RAAVHLRDRALSCRLRLRLG* |

The italicized portion of the sequences in the above table is a leader sequence. In some embodiments, the leader sequence is absent. In some embodiments, optionally with the leader sequence (as indicated with doubleunderlining elsewhere herein, or, in embodiments: MEFGLSWVFLVAIIKGVQC (SEQ ID NO: 47)) is omitted. In some embodiments, the nucleotide sequence encoding a GADLEN fusion protein of the present technology further comprise a Kozak sequence. In some embodiments, the nucleotide sequence of Kozak sequence is CCGCCACC (SEQ ID NO: 98).

Example 2: Characterization of GADLEN Proteins of the Present Technology

Figure 2:
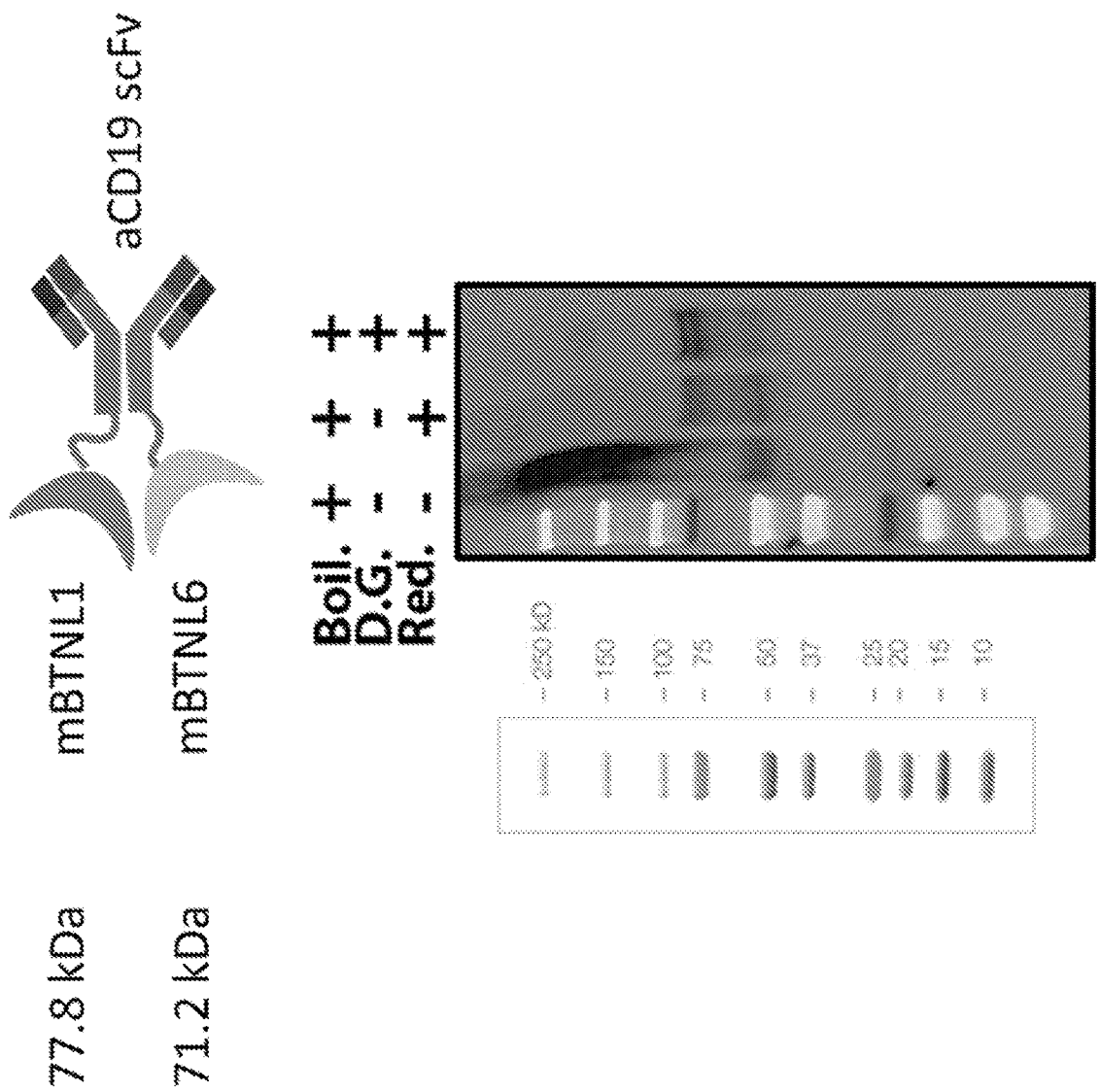
FIG. 2 shows the Western blot analysis of a purified mouse BTNL1/6-CD19 scFv GADLEN protein. The protein was generated by dual-transfection of CHO cells with both a BTNL1-CD19 scFv ('alpha', predicted MW=77.8 kDa) and a BTNL6-CD19 scFv ('beta', predicted MW=71.2 kDa) construct, in which the so-called alpha and beta constructs contained linker domains which facilitated heterodimerization of the desired BTNL1/6-CD19 scFv GADLEN protein. The purified protein was analyzed by Western blot using non-reduced (left lane), reduced (middle lane) and both reduced and deglycosylated (right lane) conditions, following detection with an anti-mouse Fc antibody. The results indicate the presence of a disulfide-linked protein that reduces to two individual proteins (following disruption of the interchain disulfide bonds with β-mercaptoethanol) with molecular weights consistent with the predicted molecular weights for the alpha and beta chains. Based on the similarity between the reduced and both reduced and deglycosylated lanes, the GADLEN construct appears to have few glycosylations.

The BTNL1/6-CD19 scFv GADLEN protein was generated by dual-transfection of CHO cells with both a BTNL1-CD19 scFv ('alpha', predicted MW=77.8 kDa) and a BTNL6-CD19 scFv ('beta', predicted MW=71.2 kDa) construct, in which the so-called alpha and beta constructs contained linker domains which facilitated heterodimerization of the desired BTNL1/6-CD19 scFv GADLEN protein. The purified protein was analyzed by Western blot using non-reducing, reducing, and both reducing and deglycosylating conditions, following detection with an anti-mouse Fc antibody. As shown in FIG. 2, the purified mouse BTNL1/6-CD19 scFv GADLEN protein appeared as a high molecular weight band in non-reducing conditions (left lane), which resolved in two bands in reducing conditions (middle lane) and in and both reducing and deglycosylating conditions (right lane). These results indicate the presence of a disulfide-linked protein that reduces to two individual proteins (following disruption of the interchain disulfide bonds with β-mercaptoethanol) with molecular weights consistent with the predicted molecular weights for the alpha and beta chains. Based on the similarity between the reducing, and both reducing and deglycosylating conditions lanes, the GADLEN construct appears to have few glycosylations.

Figure 3:
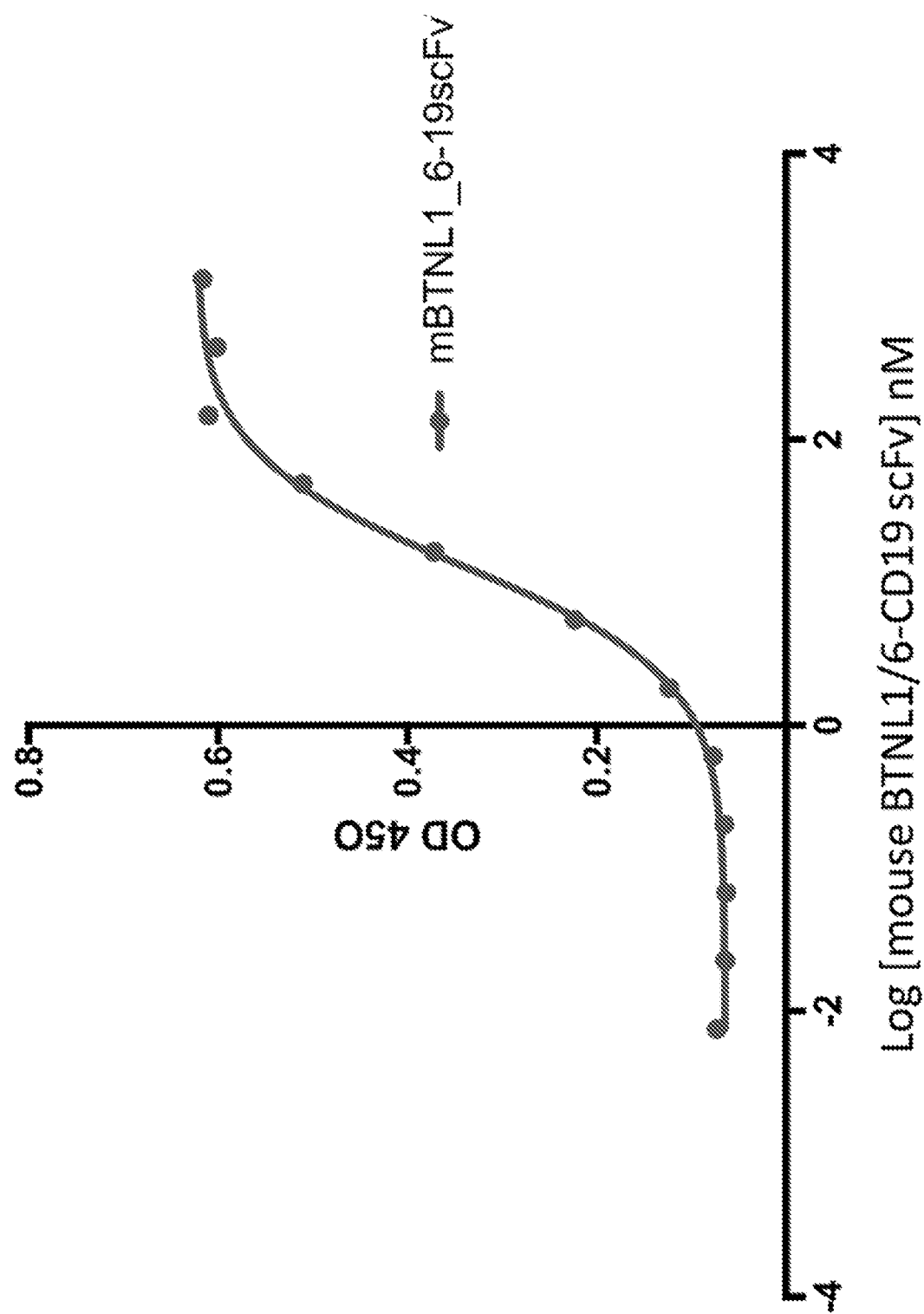
FIG. 3 depicts the quantitation of the purified mouse BTNL 1/6-CD19 scFv GADLEN using an Fc-specific ELISA method.

The purified mouse BTNL 1/6-CD19 scFv GADLEN was detected using an Fc-specific ELISA. As shown in FIG. 3, the purified mouse BTNL 1/6-CD19 scFv GADLEN could be quantitated using an Fc-specific ELISA method.

Figure 4:
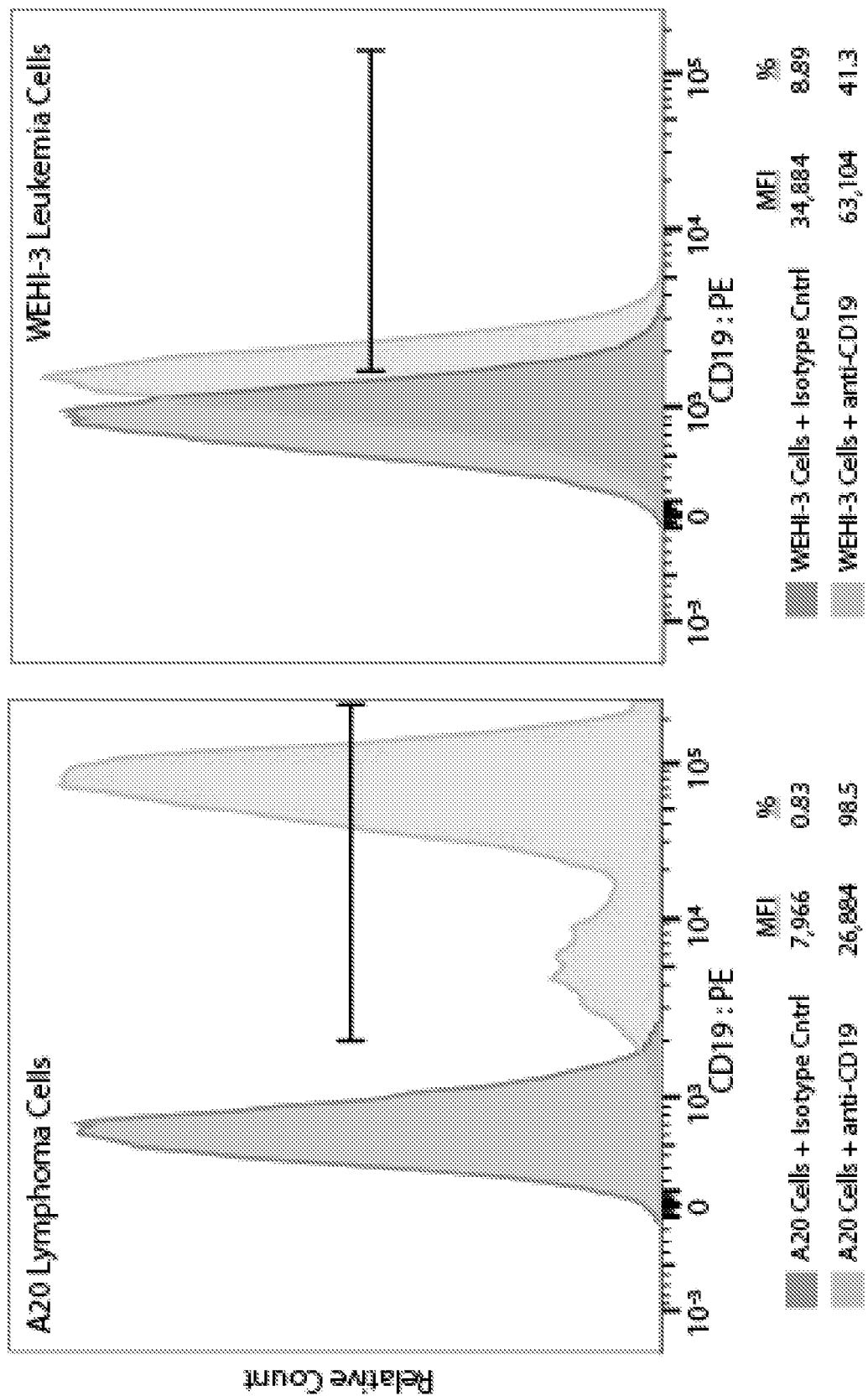
FIG. 4 illustrates exemplary flow cytometry profiles for two different mouse tumor cell lines (A20, mouse lymphoma) and WEHI-3 (mouse leukemia), which express CD19 at different densities (A20 at a higher density than WEHI-3).

To understand whether the GADLEN proteins of the present technology can bind to cancer cells, flow cytometry-based experiments were performed. As shown in FIG. 4, two different mouse tumor cell lines (A20, mouse lymphoma) and WEHI-3 (mouse leukemia), which express CD19 at different densities (A20 at a higher density than WEHI-3), bound the BTNL 1/6-CD19 scFv GADLEN protein. A20 cells, which express at a higher density of CD19 compared to WEHI-3 cells, bound also showed higher intensities of binding compared to WEHI-3 cells (FIG. 4).

Figure 5:
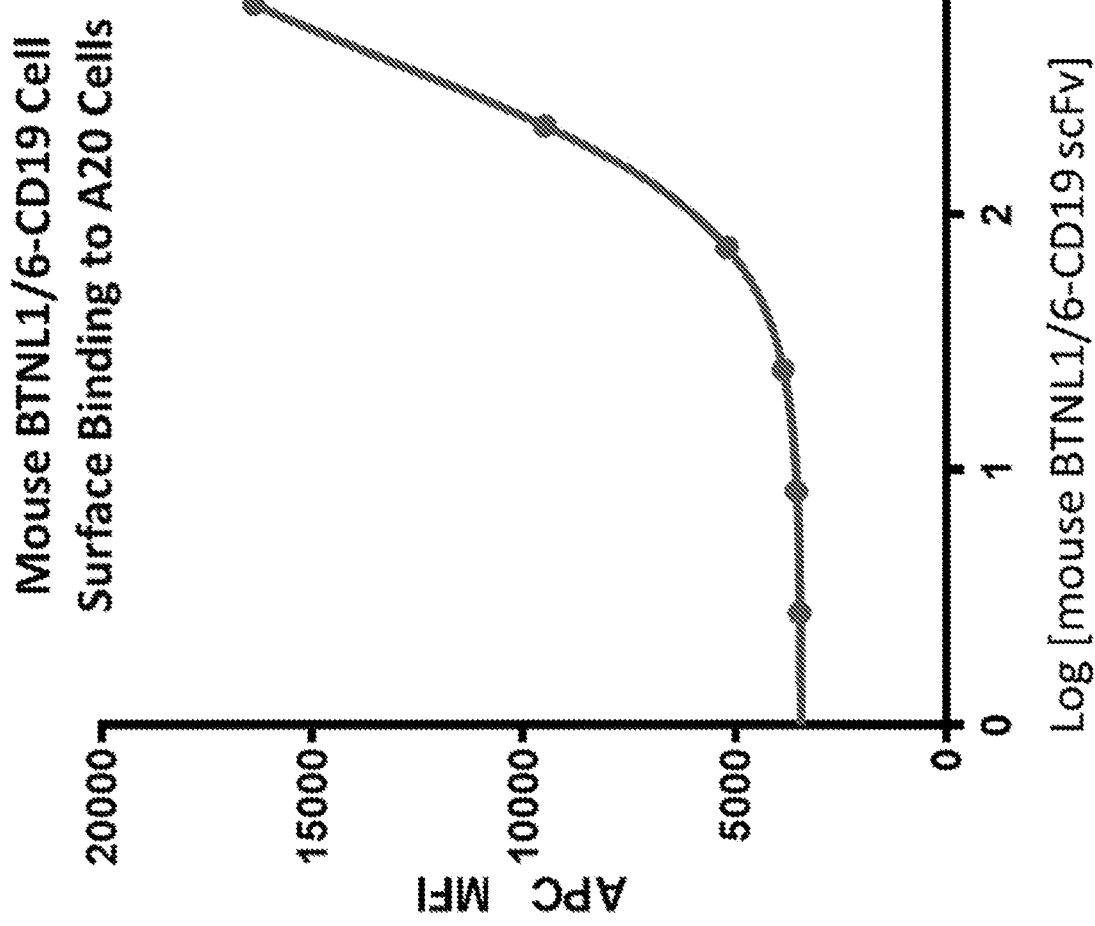
FIG. 5 provides an example of purified mouse BTNL 1/6-CD19 scFv GADLEN cell surface binding to A20 cells as detected by flow cytometry. In the assay, the purified mouse BTNL 1/6-CD19 scFv GADLEN construct was used to stain cells, and was then detected with an APC-conjugated anti-mouse Fc antibody.

In another assay, the purified mouse BTNL 1/6-CD19 scFv GADLEN construct was used to stain A20 cells, and followed by incubation with an APC-conjugated anti-mouse Fc antibody. Cells were detected by flow cytometry. As shown in FIG. 5, purified mouse BTNL 1/6-CD19 scFv GADLEN exhibited cell surface binding to A20 cells as detected by flow cytometry.

Figure 6:
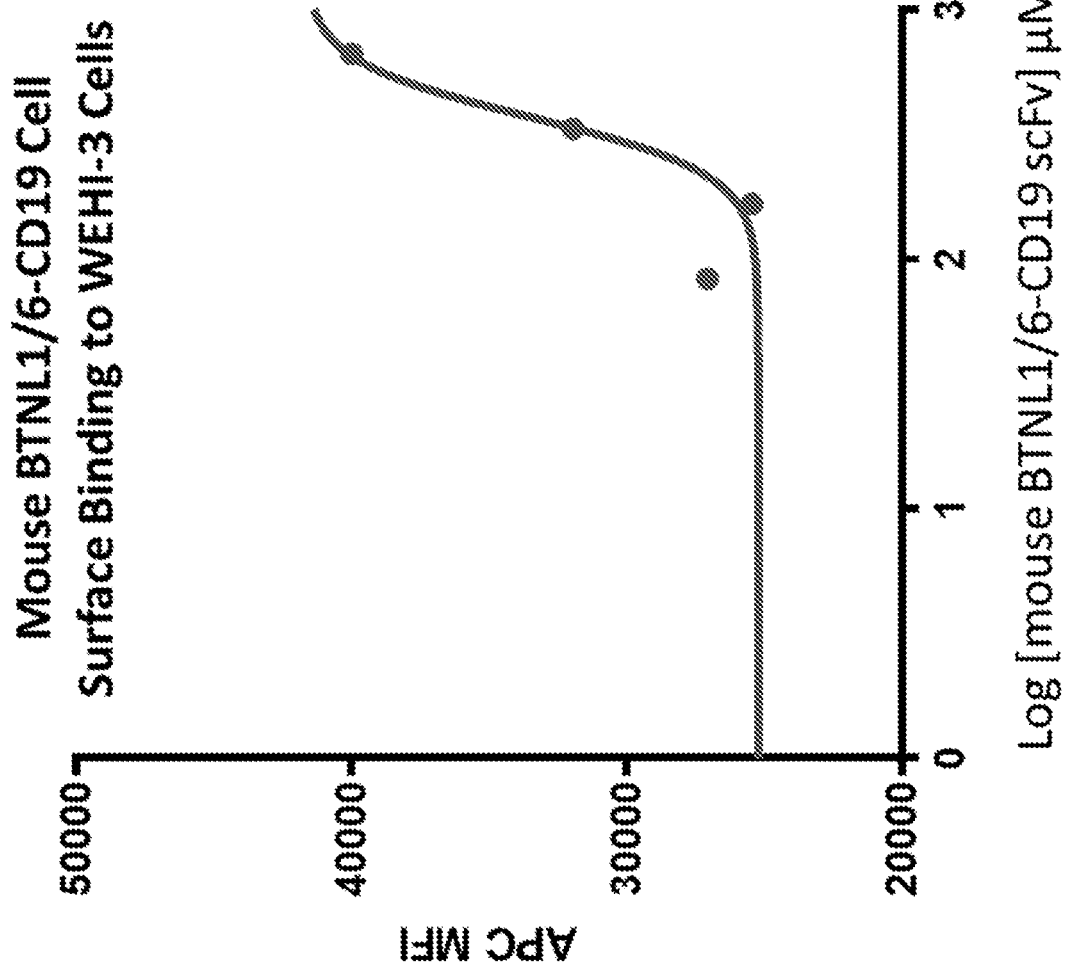
FIG. 6 provides an example of purified mouse BTNL 1/6-CD19 scFv GADLEN cell surface binding to WEHI-3 cells as detected by flow cytometry. In the assay, the purified mouse BTNL 1/6-CD19 scFv GADLEN construct was used to stain cells, and was then detected with an APC-conjugated anti-mouse Fc antibody.

Another assay for detecting the binding of CD19 scFv GADLEN construct WEHI-3 cells was performed. In the assay, the purified mouse BTNL 1/6-CD19 scFv GADLEN construct was used to stain WEHI-3 cells, and was then detected with an APC-conjugated anti-mouse Fc antibody. As shown in FIG. 6, the purified mouse BTNL 1/6-CD19 scFv GADLEN showed cell surface binding to WEHI-3 cells as detected by flow cytometry.

These results demonstrate that GADLEN proteins of the present technology immunospecifically bind to cell surface.

Accordingly, GADLEN proteins of the present technology are useful in the methods disclosed herein.

Example 3: In Vitro Activity of the GADLEN Proteins of the Present Technology

Figure 7:
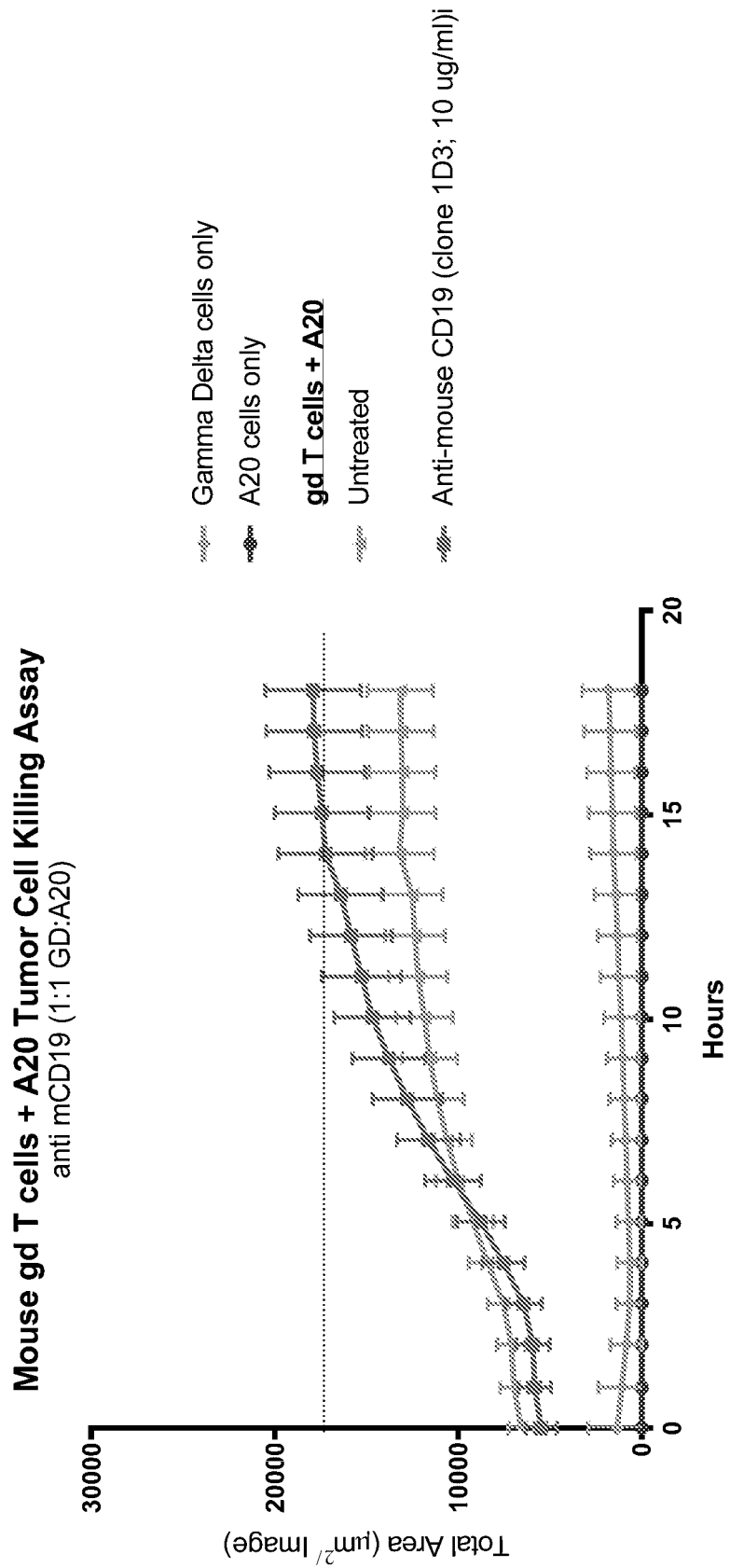
FIG. 7 provides representative results of a mouse gamma delta T cell/mouse tumor cell killing assay mediated by a CD19-specific antibody. In these studies, purified mouse gamma delta T cells (isolated from mouse intestinal epithelium) were co-cultured with mouse A20 lymphoma cells alone (triangles) or together with an anti-mouse CD19 specific antibody (squares, clone 1D3) at a gamma delta T cells:A20 tumor cell ratio of 1:1, for 18 hours with live imaging every hour in an Incucyte imager. A20 cells alone (circles) and gamma delta T cells alone (diamonds) were included as negative controls. The A20 tumor cells were labeled with green fluorescence, and the assay included a red-fluorescent dye specific for Annexin-5, as an indicator of cell death. The y-axis in the figure indicates the overlap between green and red fluorescence, which occurs when green-labeled A20 tumor cells undergo cell death and stain dual-positive for red-labeled Annexin-5.

The in vitro activity was characterized using a cell lysis. In these studies, purified mouse gamma delta T cells (isolated from mouse intestinal epithelium) were co-cultured with mouse A20 lymphoma cells alone or together with an anti-mouse CD19 specific antibody (clone 1D3) at a gamma delta T cells:A20 tumor cell ratio of 1:1, for 18 hours with live imaging every hour in an Incucyte imager. A20 cells alone and gamma delta T cells alone were included as negative controls. The A20 tumor cells were labeled with green fluorescence, and the assay included a red-fluorescent dye specific for Annexin-5, as an indicator of cell death. FIG. 7 provides representative results of a mouse gamma delta T cell/mouse tumor cell killing assay mediated by the CD19-specific antibody. The y-axis in the figure indicates the overlap between green and red fluorescence, which occurs when green-labeled A20 tumor cells undergo cell death and stain dual-positive for red-labeled Annexin-5. As shown in FIG. 7, the combination of A20 lymphoma cells, gamma delta T cells and anti-mouse CD19 specific antibody clone 1D3 (squares) showed higher level of cell lysis compared to untreated A20 cells and gamma delta T cells (triangles). A20 tumor cells alone (circles) or gamma delta T cells alone (diamonds), the negative controls, showed background lysis activity (FIG. 7).

Figure 8:
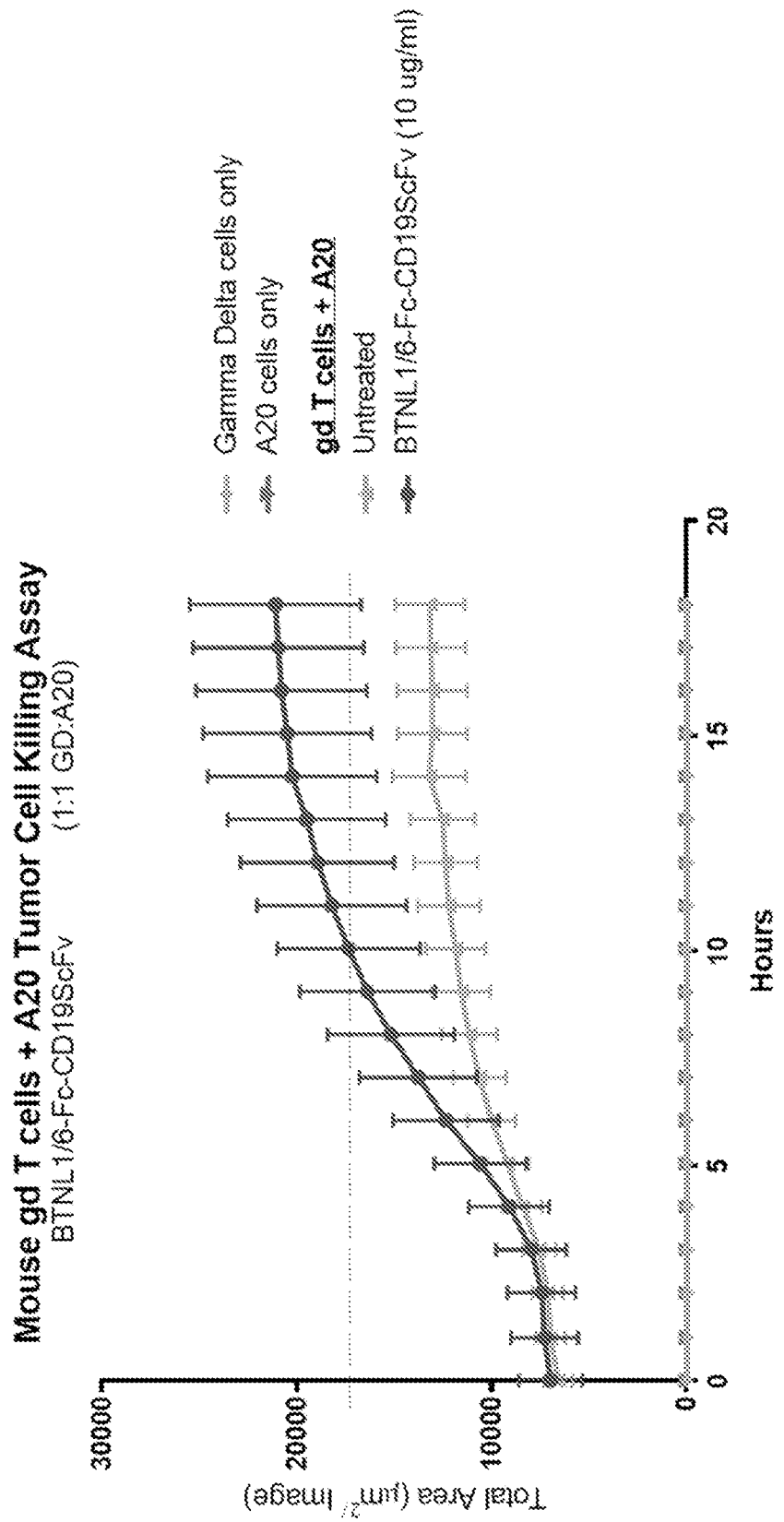
FIG. 8 provides the representative results from the same gamma delta based A20 killing assay shown in FIG. 7, mediated by the BTNL1/6-CD19scFv GADLEN construct of the present technology. Purified mouse gamma delta T cells (isolated from mouse intestinal epithelium) were co-cultured with mouse A20 lymphoma cells alone (triangles) or together with BTNL1/6-CD19scFv GADLEN construct (circles). A20 cells alone (inverted triangles) and gamma delta T cells alone (diamonds) were included as negative controls. The mean maximum A20 killing activity from FIG. 7 is indicated with the dashed line, and the killing activity in the presence of the GADLEN construct was observed to be superior to that observed with the CD19 specific antibody. In both FIGS. 7 and 8, the elevated reading at time 0 hours suggests that rapid A20 cell killing occurs, since there is a ~30 minute delay between the addition of the cells and reagents and the initial image captured by the Incucyte reader and indicated as 0 hours.

Then, the in vitro activity of the purified mouse BTNL 1/6-CD19 scFv GADLEN was characterized using a cell lysis assay. Purified mouse gamma delta T cells (isolated from mouse intestinal epithelium) were co-cultured with mouse A20 lymphoma cells alone or together with BTNL1/6-CD19scFv GADLEN. A20 cells alone and gamma delta T cells alone were included as negative controls. The A20 tumor cells were labeled with green fluorescence, and the assay included a red-fluorescent dye specific for Annexin-5, as an indicator of cell death. FIG. 8 provides the representative results. The y-axis in the figure indicates the overlap between green and red fluorescence, which occurs when green-labeled A20 tumor cells undergo cell death and stain dual-positive for red-labeled Annexin-5. As shown in FIG. 8, BTNL1/6-CD19scFv GADLEN cultured with purified mouse gamma delta T cells (isolated from mouse intestinal epithelium) and mouse A20 lymphoma cells (circles) provided higher levels of lysis than untreated purified mouse gamma delta T cells and A20 lymphoma cells (triangles). A20 cells alone (inverted triangles) and gamma delta T cells alone (diamonds) showed only background levels of lysis. In FIGS. 7 and 8, the mean maximum A20 killing activity from FIG. 7 is indicated with the dashed line, and the killing activity in the presence of the GADLEN construct was observed to be superior to that observed with the CD19 specific antibody. In both FIGS. 7 and 8, the elevated reading at time 0 hours suggests that rapid A20 cell killing occurs, since there is a ~30 minute delay between the addition of the cells and reagents and the initial image captured by the Incucyte reader and indicated as 0 hours.

These results demonstrate that GADLEN proteins of the present technology immunospecifically bind to and induce efficient cell lysis of target cells. Accordingly, GADLEN proteins of the present technology are useful in the methods disclosed herein.

Figure 9B:
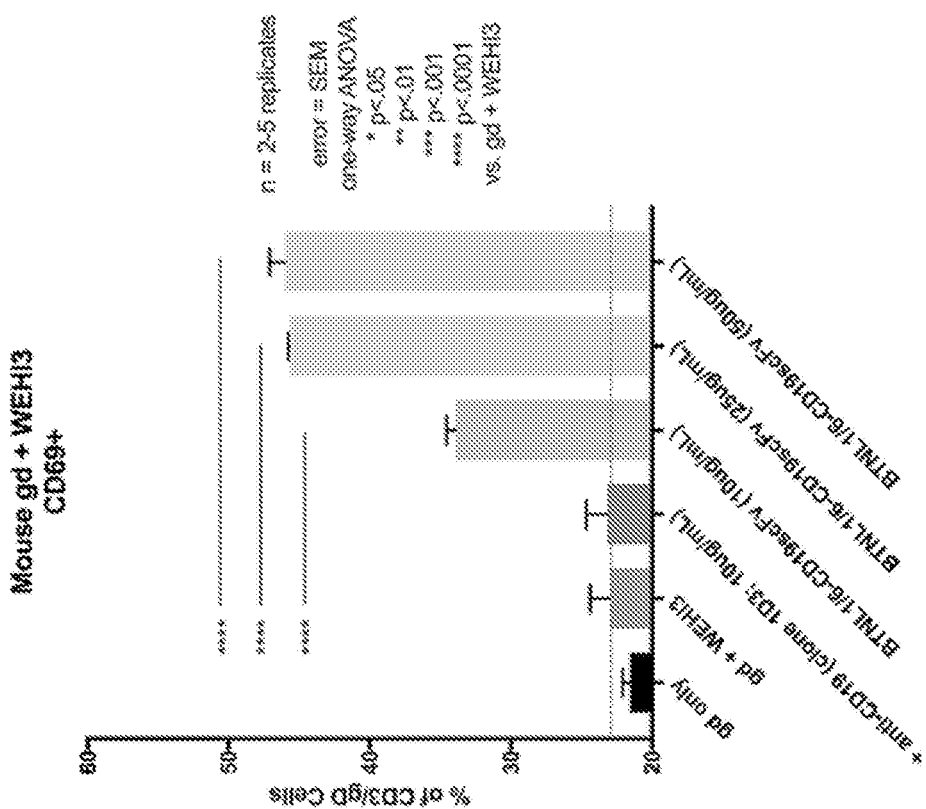
FIGS. 9A-9B provide an example of a different gamma delta T cells:tumor cell killing assay, in which mouse gamma delta T cells (isolated from intestinal epithelium) were co-cultured for 4-5 hours with WEHI-3 tumor cells alone, or in combination with an anti-CD19 antibody or an increasing concentration of the BTNL1/6-CD19scFv GADLEN construct.
Figure 9A:
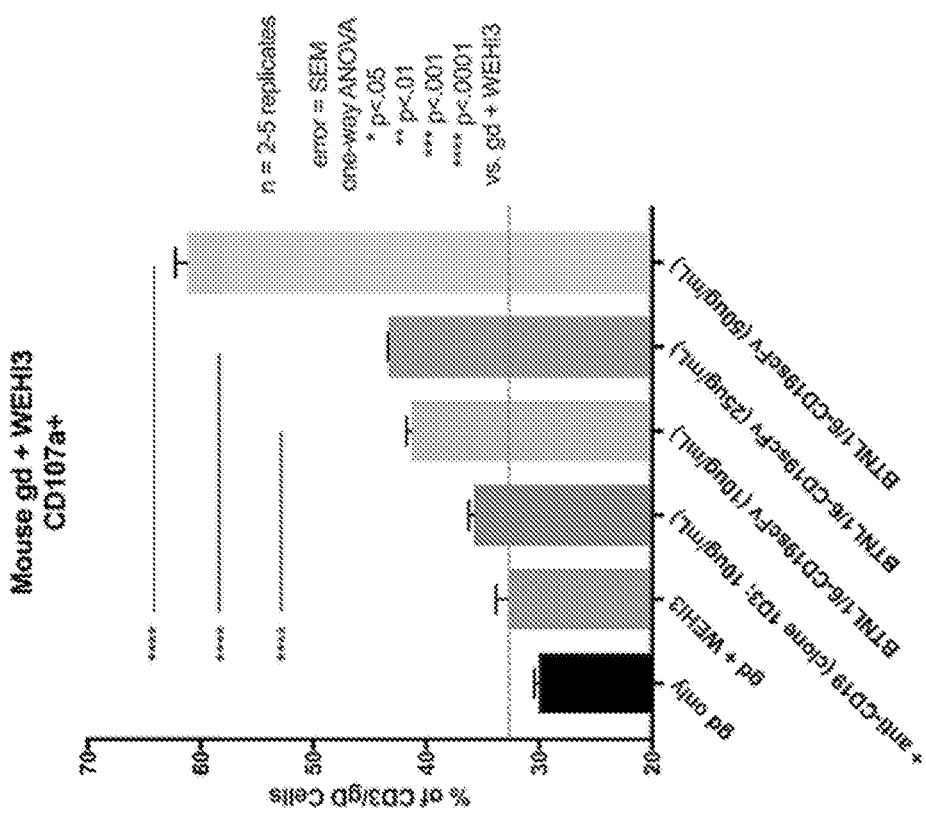

To understand the mechanism of observed lysis, a different gamma delta T cells:tumor cell killing assay was performed and CD107a was studied in WEHI3 cells. CD107a is a marker of cell degranulation, which occurs when T cells release cytolytic granules containing perforin and granzymes. Mouse gamma delta T cells (isolated from intestinal epithelium) were co-cultured for 4-5 hours with WEHI-3 tumor cells alone, or in combination with an anti-CD19 antibody or an increasing concentration of the BTNL1/6-CD19scFv GADLEN construct. Gamma delta T cells alone was used as a negative control, and WEHI3 cells+gamma delta T cells were used to control the gamma delta T cells activity without an antibody. The proportion of gamma delta T cells staining positive for CD107a by flow cytometry was measured by flow cytometry following the indicated co-culture, and plotted as a bar graph of the proportion of gamma delta T cells staining positive for CD107a. As shown in FIG. 9A, compared to Gamma delta T cells alone, or WEHI3 cells+gamma delta T cells, addition of the GADLEN construct led to a dose-dependent CD107a expression in isolated gamma delta T cells. Notably, only a minor increase in CD107a expression was noted when gamma delta T cells were co-cultured with WEHI-3 tumor cells in the absence of the GADLEN construct. To further validate activation of gamma delta T cells, CD69, a cell surface marker of activated T cells, was studied by flow cytometry and plotted as a bar graph of the proportion of gamma delta T cells staining positive for CD69. As shown in FIG. 9B, addition of the GADLEN construct to WEHI3 cells+gamma delta T cells caused a dose-dependent upregulation of CD69. Notably, only minor increase in CD69 expression was observed when gamma delta T cells were co-cultured with WEHI-3 tumor cells in the absence of the GADLEN construct.

Figure 10B:
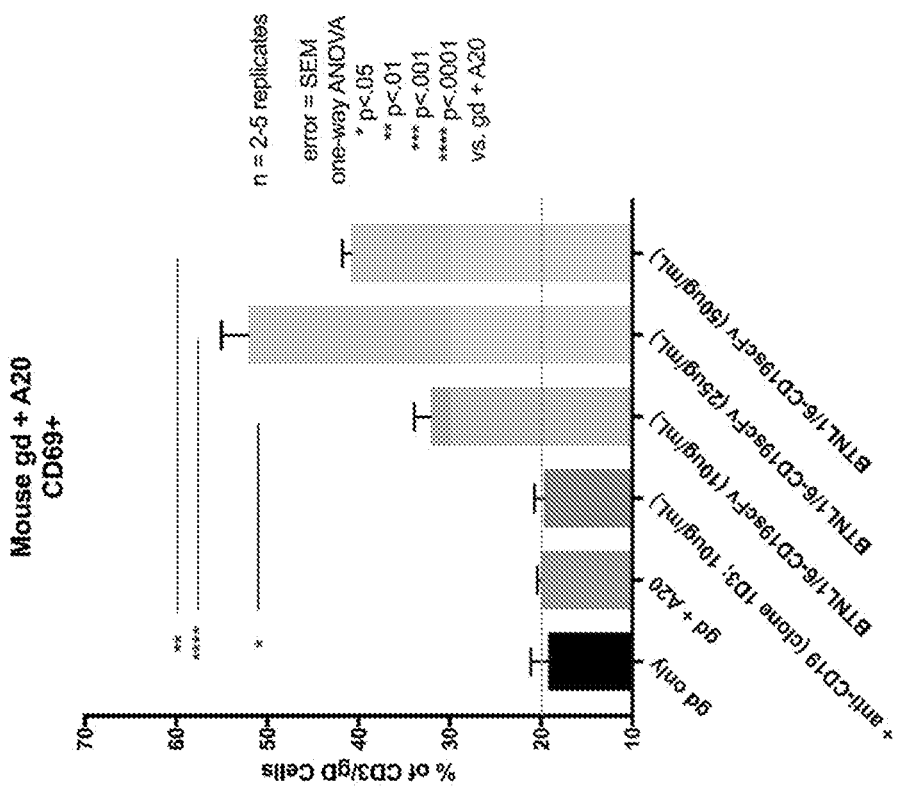
FIGS. 10A-10B provide another example of the CD107a degranulation assay, in which mouse gamma delta T cells (isolated from intestinal epithelium) were co-cultured for 4-5 hours with A20 tumor cells alone, or in combination with an anti-CD19 antibody or an increasing concentration of the BTNL1/6-CD19scFv GADLEN construct.
Figure 10A:
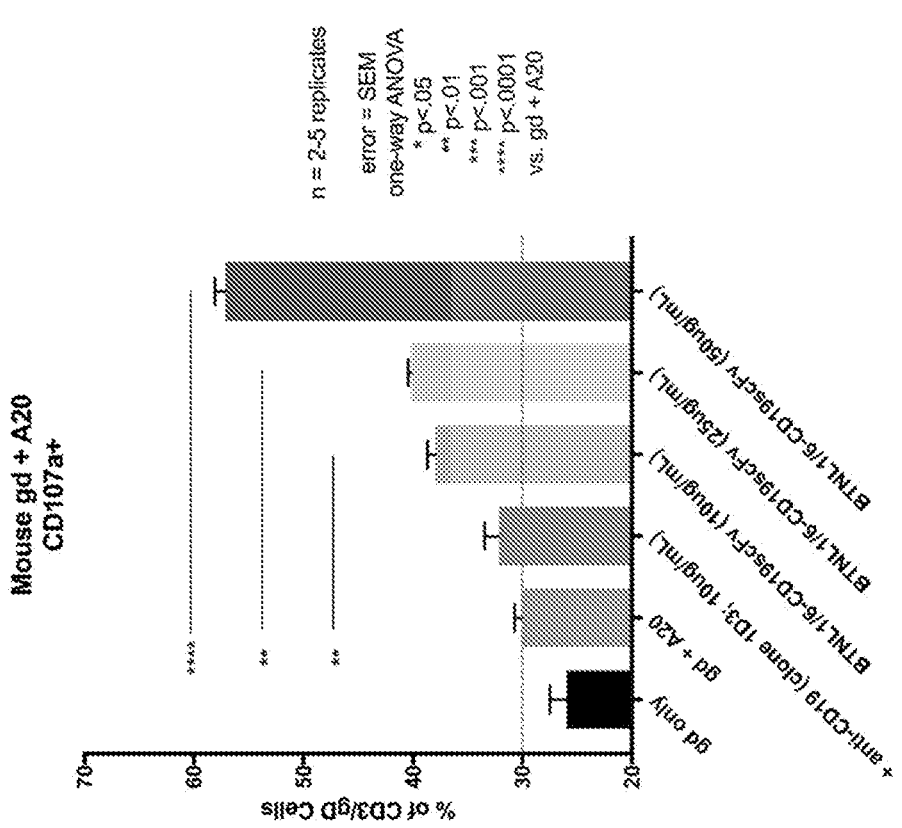

The assay for upregulation of CD107a and CD69 was repeated in A20 cells. Mouse gamma delta T cells (isolated from intestinal epithelium) were co-cultured for 4-5 hours with A20 tumor cells alone, or in combination with an anti-CD19 antibody or an increasing concentration of the BTNL1/6-CD19scFv GADLEN construct. Gamma delta T cells alone was used as a negative control, and A20 cells+gamma delta T cells were used to control the gamma delta T cells activity without an antibody. The proportion of gamma delta T cells staining positive for CD107a by flow cytometry was measured by flow cytometry following the indicated co-culture, and plotted as a bar graph of the proportion of gamma delta T cells staining positive for CD107a. As shown in FIG. 10A, compared to Gamma delta T cells alone, or A20 cells+gamma delta T cells, addition of the GADLEN construct led to a dose-dependent CD107a expression in isolated gamma delta T cells. Notably, only a minor increase in CD107a expression was noted when gamma delta T cells were co-cultured with A20 tumor cells in the absence of the GADLEN construct. To further validate activation of gamma delta T cells, CD69, a cell surface marker of activated T cells, was studied by flow cytometry and plotted as a bar graph of the proportion of gamma delta T cells staining positive for CD69. As shown in FIG. 10B, addition of the GADLEN construct to A20 cells+gamma delta T cells caused a dose-dependent upregulation of CD69. Notably, only minor increase in CD69 expression was observed when gamma delta T cells were co-cultured with A20 tumor cells in the absence of the GADLEN construct.

These results demonstrate that GADLEN proteins of the present technology induce contemporaneous activation and targeting of gamma delta T cells to tumor cells. Accordingly, GADLEN proteins of the present technology are useful in the methods of modulating a patient's immune response disclosed herein.

Example 4: In Vivo Activity of the GADLEN Proteins of the Present Technology

Figure 11B:
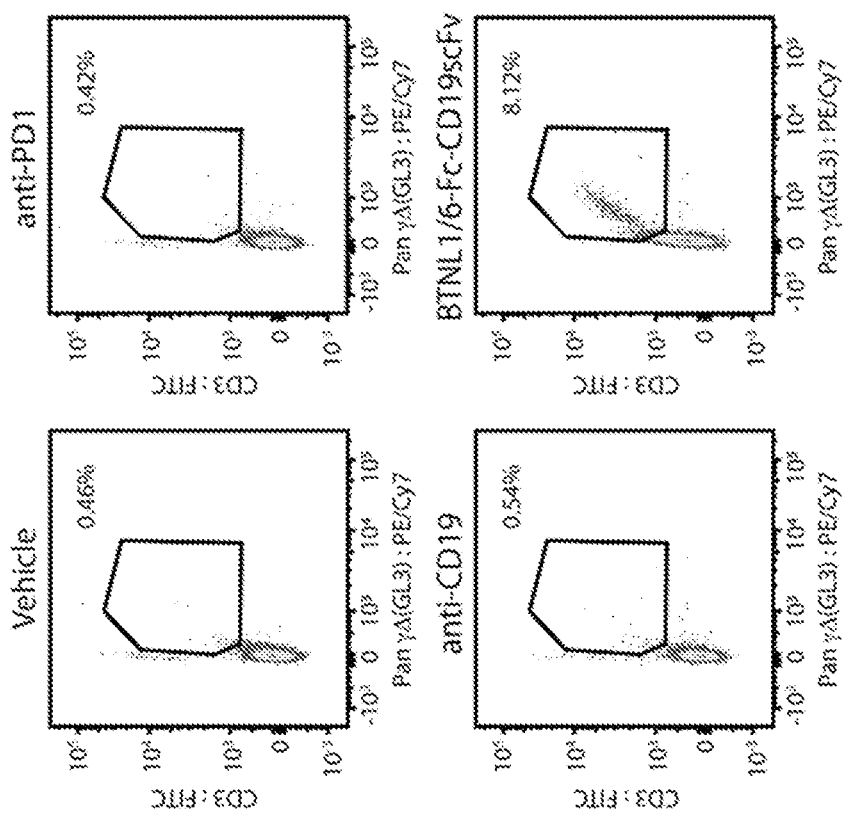
FIGS. 11A-11B provide a representative series of flow cytometry plots from an in vivo study in Balb.c mice treated with a vehicle control, anti-PD1 antibody, anti-CD19 antibody, or the BTNL1/6-CD19scFv GADLEN protein. Briefly, Balb.c mice were implanted in A20 tumor cells in the hind flank and those tumors grew to approximately 40 mm$^3$ before the first treatment with anti-PD1 antibody, anti-CD19 antibody, or the BTNL1/6-CD19scFv GADLEN protein (all dosed at 100 μg/mouse). 24 hours following the first treatment, peripheral blood was collected from each mouse and analyzed for the proportion of CD20+ B cells (FIG. 11A) and CD3+gamma delta TCR+ T cells (FIG.
Figure 11A:
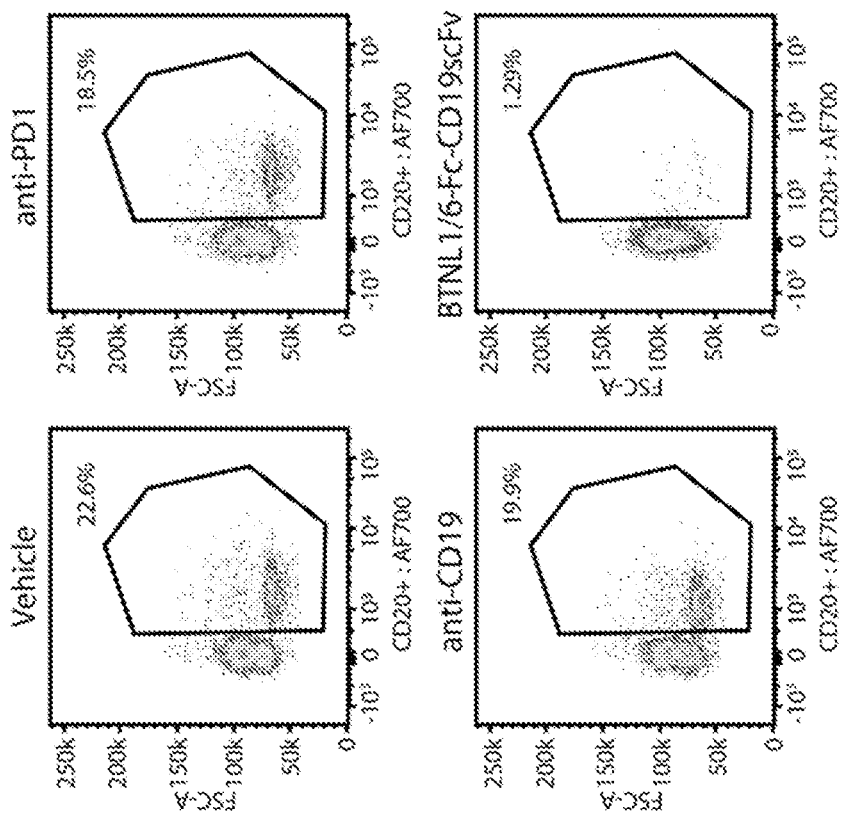

The effect of GADLEN proteins of the present technology on B cells and T cells was evaluated next. Towards this goal, Balb.c mice were implanted in A20 tumor cells in the hind flank. When those tumors grew to approximately 40 mm$^3$, the mice were randomly assigned to four groups containing ≥5 mice. The four groups were dosed with (i) vehicle only, (ii) anti-PD1 antibody, (iii) anti-CD19 antibody, or (iv) the BTNL1/6-CD19scFv GADLEN protein (all dosed at 100 µg/mouse). 24 hours following the first treatment, peripheral blood was collected from each mouse and analyzed for the proportion of CD20+ B cells and CD3+gamma delta TCR+ T cells by flow cytometry. As shown in FIG. 11A, the frequency of CD20+ B cells in the BTNL1/6-CD19scFv GADLEN protein treated group (1.29%) had reduced to by >10 fold compared to the vehicle only group (22.6%). In contrast, the frequency of CD20+ cells in the peripheral blood of anti-PD1 (18.5%) or anti-CD19 (19.9) antibody-treated groups had not significantly changed compared to the vehicle only group (22.6%). As shown in FIG. 11B, the frequency of gamma delta T cells in the peripheral blood of mice in the BTNL1/6-CD19scFv GADLEN protein treated group (8.12%) significantly increased compared to compared to the vehicle only group (0.46%). In contrast, the frequency of gamma delta T cells in the peripheral blood of mice in anti-PD1 (0.42%) or anti-CD19 (0.54) antibody-treated groups had not significantly changed compared to the vehicle only group (0.46%). These data indicated that whereas <1% of circulating CD3+ T cells expressed the gamma delta TCR in vehicle, anti-PD1 or anti-CD19 antibody treated mice, the proportion of gamma delta T cells has increased >10 fold within 24 hours of treatment with the BTNL1/6-CD19scFv GADLEN protein.

These results demonstrate that GADLEN proteins of the present technology stimulate the proliferation of gamma delta T cells in vivo. Accordingly, GADLEN proteins of the present technology are useful in the methods of treatment disclosed herein.

To extend these observation further, the effect of GADLEN proteins of the present technology on CD19+ and CD20+ B cells was evaluated. Balb.c mice were implanted in A20 tumor cells or WEHI-3 in the hind flank. When those tumors grew to approximately 40 mm$^3$, the mice were randomly assigned to four groups each containing ≥5 mice. The four groups were dosed with (i) vehicle only, (ii) anti-PD1 antibody, (iii) anti-CD19 antibody, or (iv) the BTNL1/6-CD19scFv GADLEN protein (all dosed at 100 µg/mouse). 24 hours following the first treatment, peripheral blood was collected from each mouse and analyzed for the proportion of CD19+ B cells and CD20+ B cells by flow cytometry. Shown in FIGS. 12A-12D are bar graphs showing CD19+(FIGS. 12A and 12C) or CD20+ B cells (FIGS. 12B and 12D) plotted as mean±SEM with >5 mice/group bearing A20 tumors (FIGS. 12A-12B) or WEHI-3 tumors (FIGS. 12C-12D).

Figure 12A:
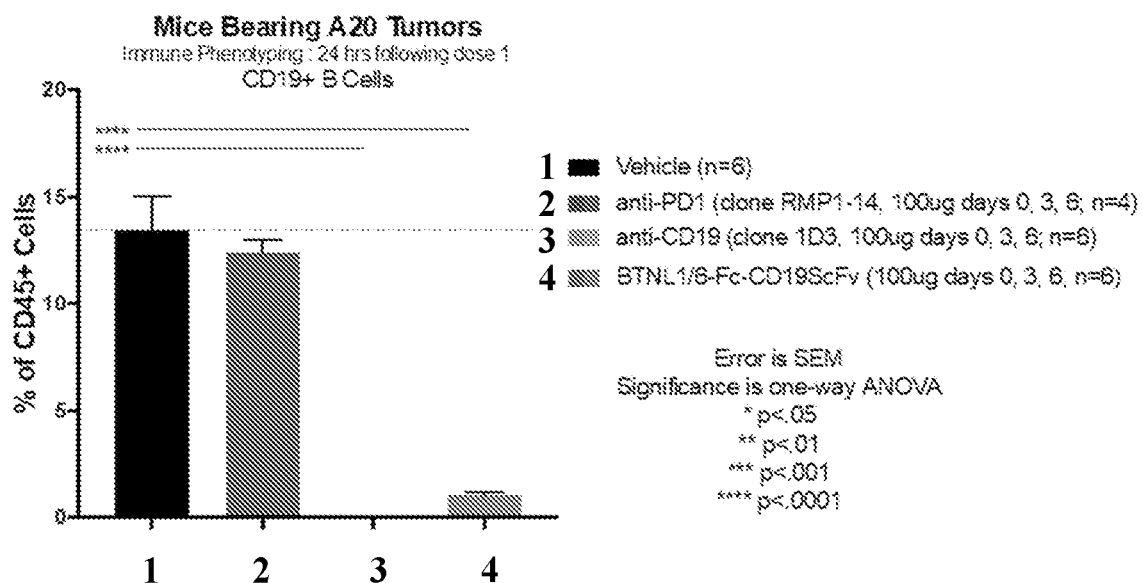
FIGS. 12A-12D provide an expanded a representative expanded series of flow cytometry plots from an in vivo study carried out as described in FIGS. 11A-11B. Specifically, FIG. 12A indicates the frequency of CD19+ B cells (all data shown as mean±SEM with >5 mice/group)
Figure 12B:
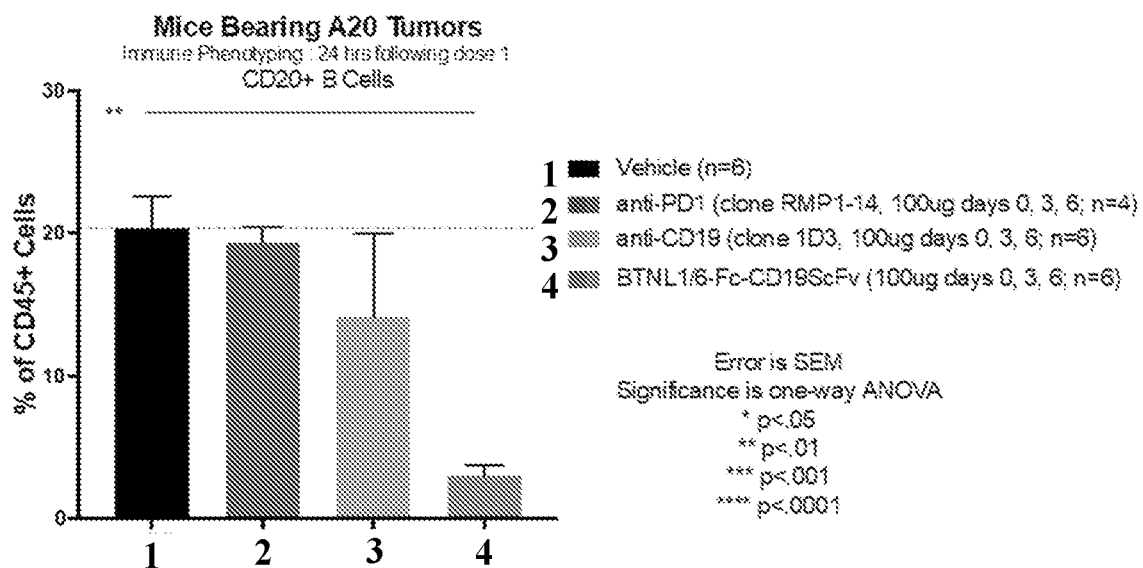
Figure 12C:
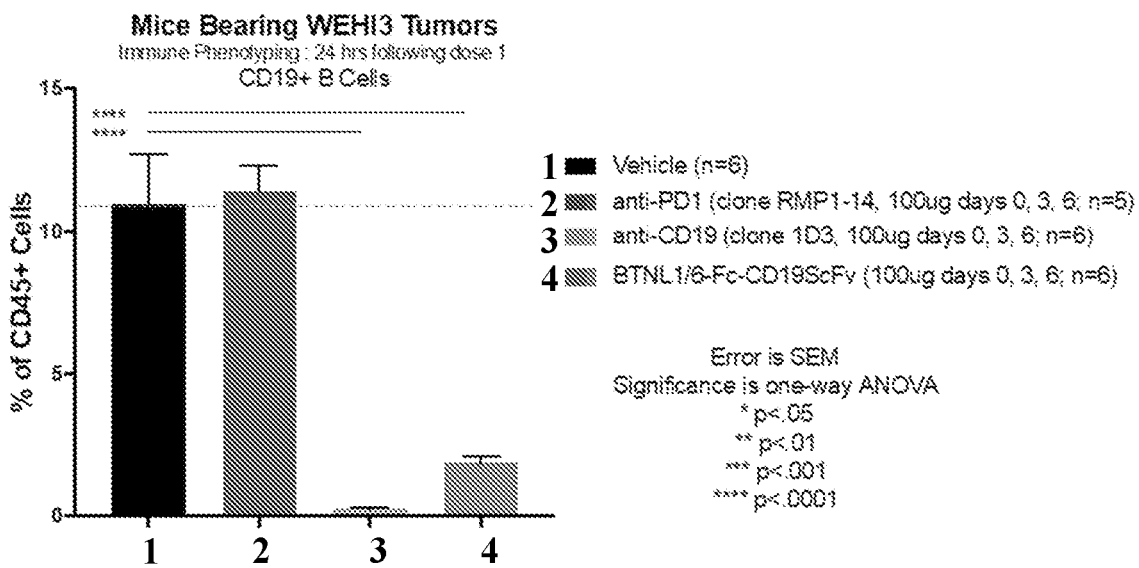
Figure 12D:
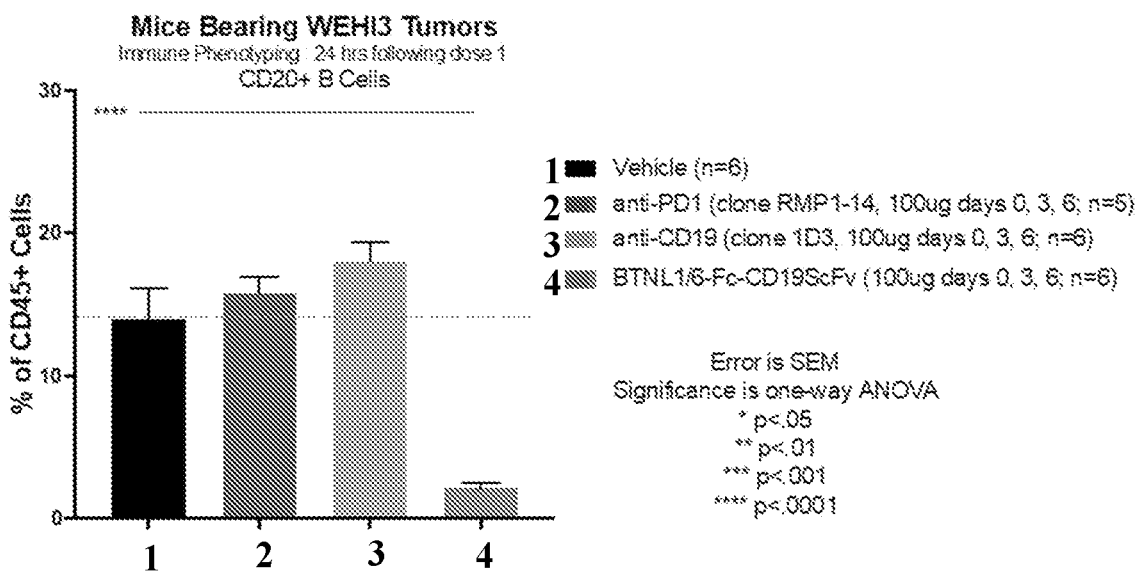

As shown in FIG. 12A, the treatment with either anti-CD19 antibody, or the BTNL1/6-CD19scFv GADLEN protein led to a significant reduction in detection of CD19+ B cells compared to vehicle only control-treated mice in mice bearing A20 tumors. Similarly, as shown in FIG. 12C, the treatment with either anti-CD19 antibody, or the BTNL1/6-CD19scFv GADLEN protein led to a significant reduction in detection of CD19+ B cells compared to vehicle only control-treated mice in mice bearing WEHI-3 tumors. To understand whether the anti-CD19 antibody had an effect on detection of CD19 antigen, CD20 expression was evaluated. As shown in FIG. 12B, the frequency of CD20+ B cells significantly reduced in the BTNL1/6-CD19scFv GADLEN protein-treated mice compared to vehicle only control-treated mice in mice bearing A20 tumors. In contrast, the frequency of CD20+ B cells in the anti-CD19-treated mice did not show significant reduction. Similarly, as shown in FIG. 12D, the frequency of CD20+ B cells significantly reduced in the BTNL1/6-CD19scFv GADLEN protein-treated mice compared to vehicle only control-treated mice in Balb.c mice with established WEHI-3 tumors. In contrast, the frequency of CD20+ B cells in the anti-CD19-treated mice did not show significant reduction.

These data illustrate that while the anti-CD19 treatment antibody competed with the CD19 detection antibody, the antibody treatment had not truly depleted B cells in the peripheral blood because the frequenc of CD20+ B cells (where there is no competition between the CD19 treatment antibody and the CD20 detection antibody) had not significantly changed. In contrast, all mice treated with the BTNL1/6-CD19scFv GADLEN protein showed near complete depletion of peripheral blood B cells within 24 hours of treatment.

The effect of BTNL1/6-CD19scFv GADLEN protein on gamma delta T cells was evaluated. Balb.c mice were implanted in A20 tumor cells or WEHI-3 in the hind flank. When those tumors grew to approximately 40 mm$^3$, the mice were randomly assigned to four groups each containing ≥5 mice. The four groups were dosed with (i) vehicle only, (ii) anti-PD1 antibody, (iii) anti-CD19 antibody, or (iv) the BTNL1/6-CD19scFv GADLEN protein (all dosed at 100 µg/mouse). 24 hours following the first treatment, peripheral blood was collected from each mouse and analyzed for the proportion of gamma delta cells by flow cytometry.

Figure 13A:
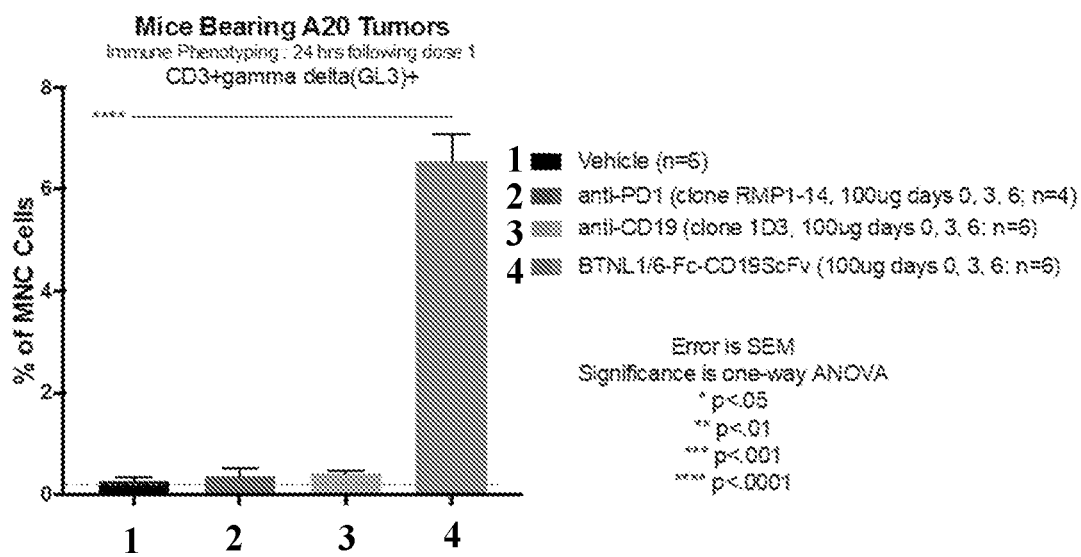
FIGS. 13A-13B provide an expanded a representative expanded series of flow cytometry plots from an in vivo study carried out as described in FIGS. 11A-11B. Specifically, FIG. 13A indicates the frequency of gamma delta T cells in mice bearing established A20 tumors.
Figure 13B:
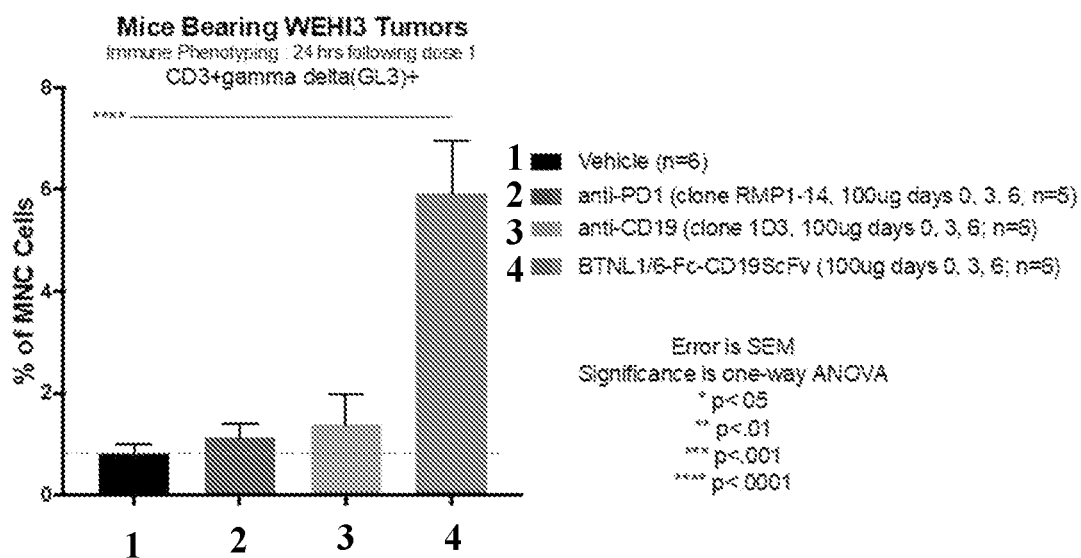

As shown in FIG. 13A, the frequency of gamma delta T cells in mice bearing established A20 tumors significantly increased in in the BTNL1/6-CD19scFv GADLEN protein-treated mice compared to vehicle only control-treated mice in mice bearing A20 tumors. In contrast, the treatment with anti-PD1 antibody or anti-CD19 antibody did not have a significant effect on the frequency of gamma delta T cells in mice bearing established A20 tumors compared to vehicle only control-treated mice. Likewise, as shown in FIG. 13B, the frequency of gamma delta T cells in mice bearing established WEHI-3 tumors significantly increased in in the BTNL1/6-CD19scFv GADLEN protein-treated mice compared to vehicle only control-treated mice in mice bearing A20 tumors. In contrast, the treatment with anti-PD1 antibody or anti-CD19 antibody did not have a significant effect on the frequency of gamma delta T cells in mice bearing established WEHI-3 tumors compared to vehicle only control-treated mice. These data illustrated that the BTNL1/6-CD19scFv GADLEN protein had stimulated rapid proliferation of mouse gamma delta T cells within 24 hours of treatment.

These results demonstrate that GADLEN proteins of the present technology induce a near complete depletion of peripheral blood B cells and stimulate rapid proliferation of gamma delta T cells within 24 hours of treatment and thereby modulate the immune response in a subject in need thereof. Accordingly, GADLEN proteins of the present technology are useful in the methods of treatment disclosed herein.

Figure 32B:
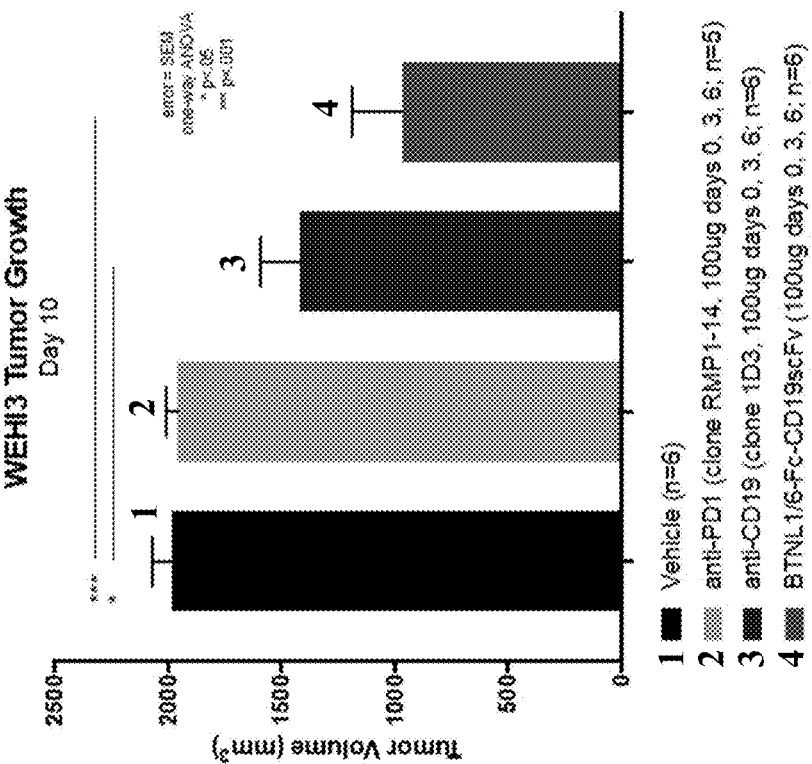
Figure 32C:
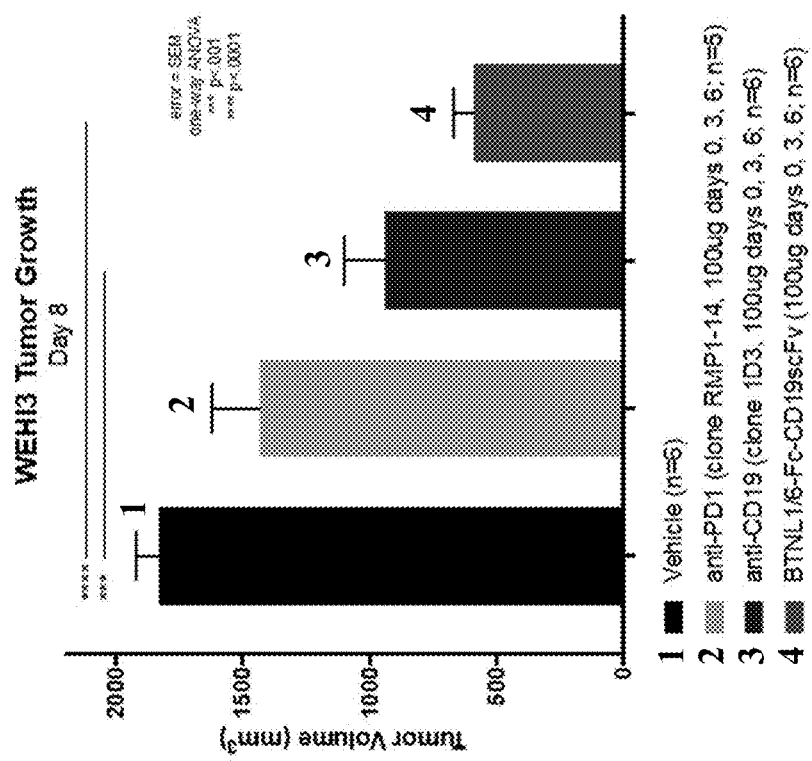

The anti-tumor activity of BTNL1/6-Fc-CD19scFv GADLEN protein was evaluated using the WEHI3 tumor model. WEHI-3 cells were inoculated subcutaneously on the rear flank. When the average starting tumor volume (STV)

reached 90.92 mm³ (day 0), treatments were begun. The treatment groups were anti-PD1 (clone RMP1-14), anti-CD19 (clone 1D3), and BTNL1/6-Fc-CD19scFv were each given in 3 doses IP; 100 μg per dose on days 0, 3, and 6. Vehicle alone was used as a negative control. Tumor growth was assessed over a 17-day time course. Tumor volumes were measured and plotted as a function of time. As shown in FIG. 32A, the average tumor growth of a WEHI-3 (leukemia) tumors educed in BTNL1/6-Fc-CD19scFv-treated mice compared to the vehicle alone-treated mice. Tumor growth was also accessed on day 8 and day 10. As shown in FIG. 32B, the BTNL1/6-Fc-CD19scFv GADLEN-treated mice showed significantly smaller tumors compared to the vehicle alone-treated mice on day 8. The activity of BTNL1/6-Fc-CD19scFv GADLEN was more significant than that of anti-CD19 (clone 1D3) on day 8 (FIG. 32B). Similarly, as shown in FIG. 32C, the BTNL1/6-Fc-CD19scFv GADLEN-treated mice showed significantly smaller tumors compared to the vehicle alone-treated mice on day 10. The activity of BTNL1/6-Fc-CD19scFv GADLEN was more significant than that of anti-CD19 (clone 1D3) on day 10 (FIG. 32C).

Figure 33:
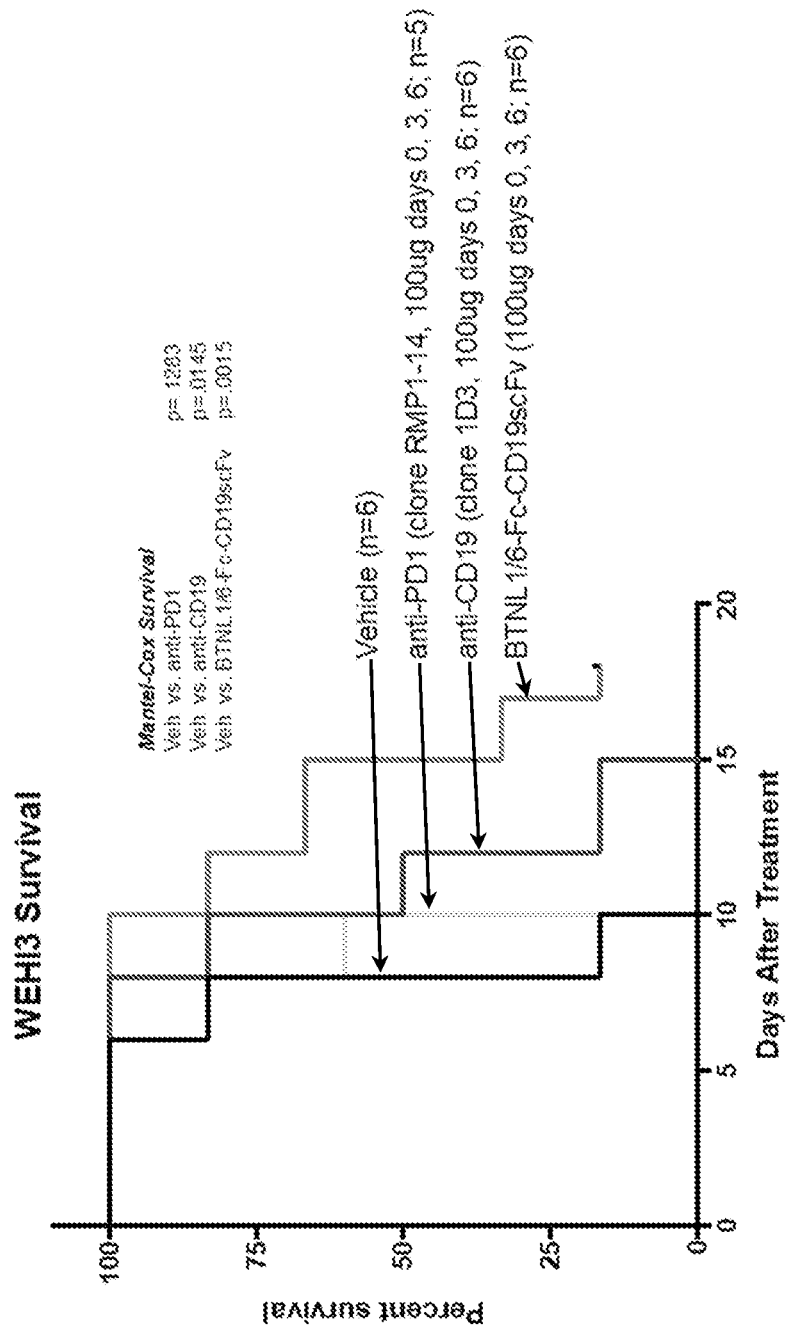
FIG. 33 shows the Kaplan-Meier curves of mice from FIGS. 32A-32C. Survival was assessed over an 18-day time course, following the first treatment on day 0. Significance between survival curves was determined using Mantel-Cox.

The effect of BTNL1/6-Fc-CD19scFv GADLEN treatment on survival was evaluated using Kaplan-Meier curve of mice from FIGS. 32A-32C. Significance between survival curves was determined using Mantel-Cox. As shown in FIG. 33, anti-PD1 (clone RMP1-14), anti-CD19 (clone 1D3), and BTNL1/6-Fc-CD19scFv, showed an improved Mantel-Cox survival p=0.1283, 0.0145, and 0.0015, respectively. Therefore, while anti-PD1 (clone RMP1-14), anti-CD19 (clone 1D3), and BTNL1/6-Fc-CD19scFv showed improved survival, the activity of BTNL1/6-Fc-CD19scFv GADLEN was more significant than that of anti-PD1 (clone RMP1-14) and anti-CD19 (clone 1D3) (FIG. 33).

These results demonstrate that GADLEN proteins of the present technology have a significant anti-tumor activity, which provides a significantly improved survival in subjects in need thereof. Accordingly, GADLEN proteins of the present technology are useful in the methods of treatment of cancer disclosed herein.

Figure 14:
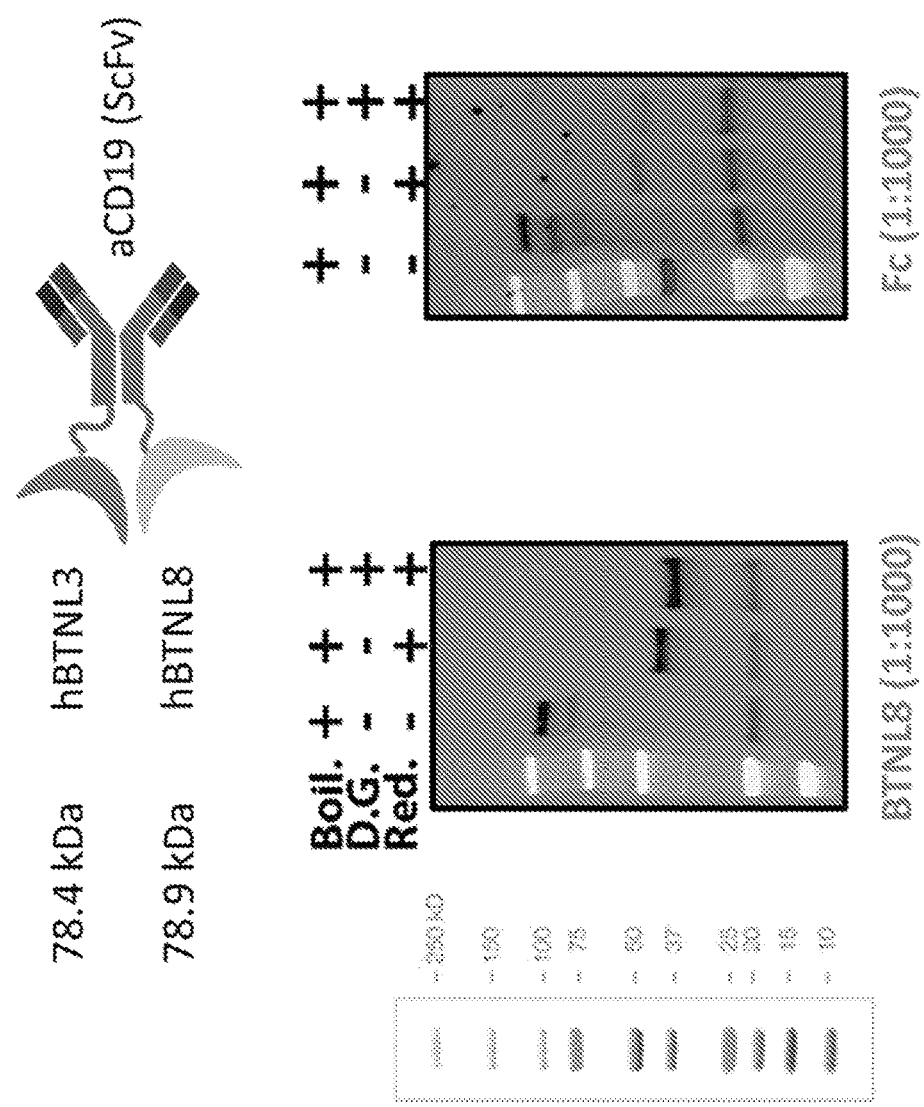
FIG. 14 provides Western blot analysis of a purified human BTNL3/8-CD19 scFv GADLEN protein. The protein was generated by dual-transfection of CHO cells with both a BTNL3-CD19 scFv ('alpha', predicted MW=78.4 kDa) and a BTNL8-CD19 scFv ('beta', predicted MW=78.9 kDa) construct, in which the so-called alpha and beta constructs contained linker domains which facilitated heterodimerization of the desired BTNL 3/8-CD19 scFv GADLEN protein. The purified protein was analyzed by Western blot using non-reducing (left lane), reducing (middle lane) and both reducing and deglycosylating (right lane) conditions, following detection with an anti-human BTNL8 antibody (left blot) or anti-human Fc antibody (right blot). The results indicated the presence of a disulfide-linked protein that reduces to a single band of roughly half the molecular weight of the non-reduced band (following disruption of the interchain disulfide bonds with β-mercaptoethanol). Because the molecular weights of the alpha and beta chains are so similar, a doublet band could not be detected under reducing conditions in this study. A minor reduction in molecular weight was observed in both reduced and deglycosylated protein (third lane) compared to reduced protein, indicating that the GADLEN construct is likely to be a glycosylated protein.

Example 5: Characterization of BTNL3/8-CD19 scFv GADLEN Protein and BTN3A1/3A2-CD19 scFv GADLEN Protein of the Present Technology The BTNL3/8-CD19 scFv GADLEN protein was generated by dual-transfection of CHO cells with both a BTNL3-CD19 scFv ('alpha', predicted MW=78.4 kDa) and a BTNL8-CD19 scFv ('beta', predicted MW=78.9 kDa) construct (see the cartoon on the top of FIG. 14), in which the so-called alpha and beta constructs contained linker domains which facilitated heterodimerization of the desired BTNL 3/8-CD19 scFv GADLEN protein. The BTNL3/8-CD19 scFv GADLEN protein was purified and analyzed by western blot using non-reducing, reducing, and both reducing and deglycosylating conditions, following detection with an anti-human BTNL8 antibody or anti-human Fc antibody.

Figure 15:
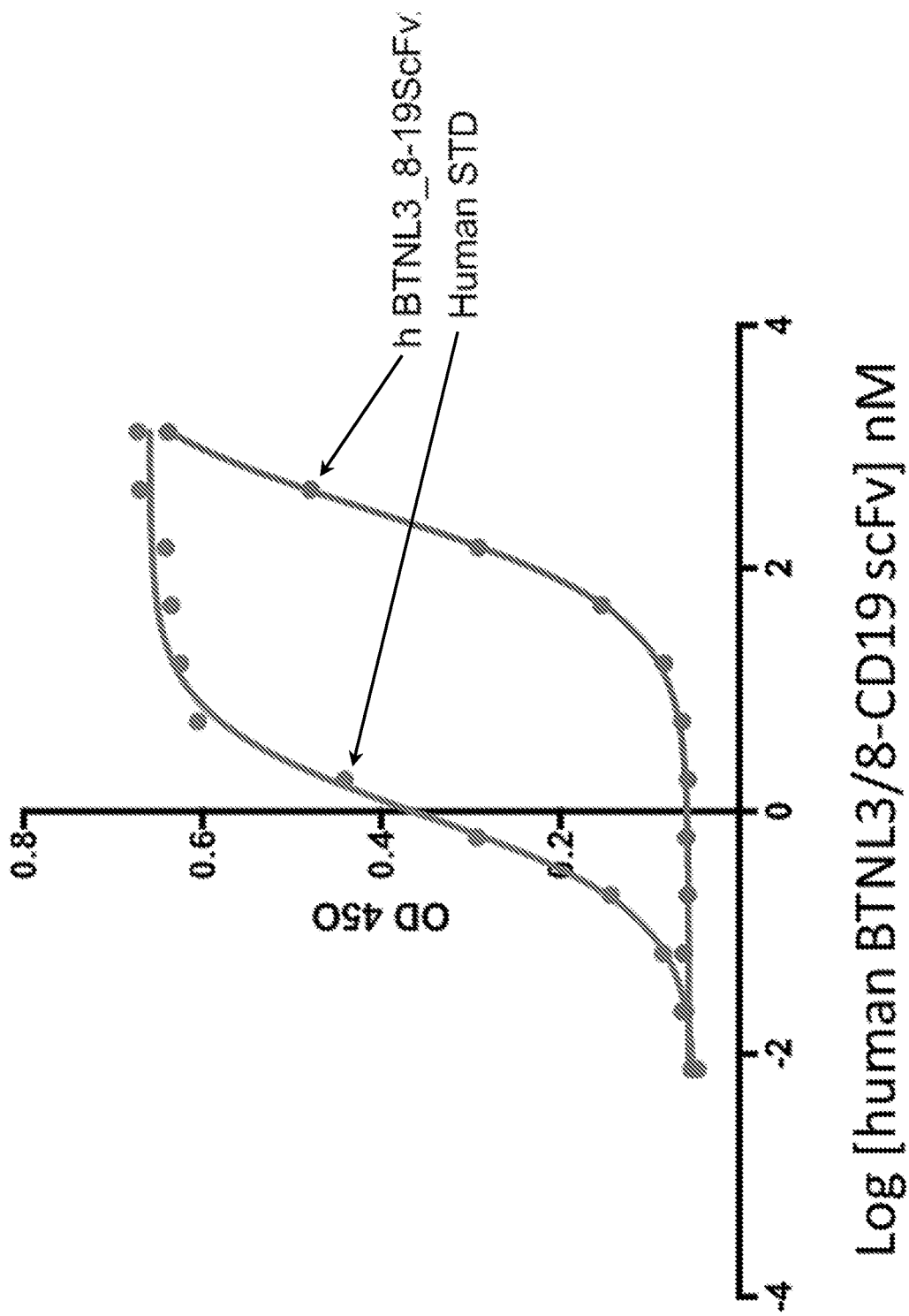
FIG. 15 depicts quantitation of the purified human BTNL 3/8-CD19 scFv GADLEN using an Fc-specific ELISA method.
Figure 16:
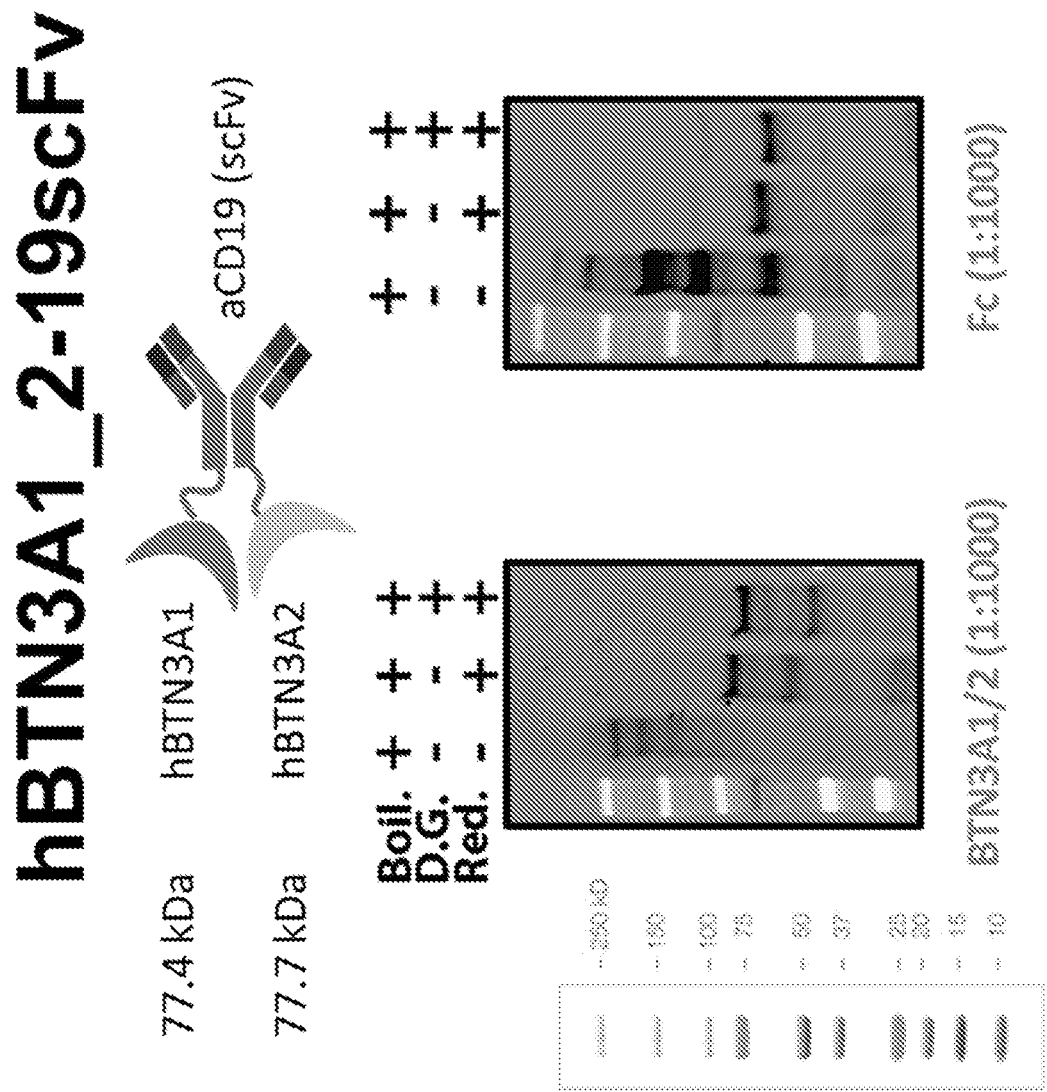
FIG. 16 provides Western blot analysis of a purified human BTN3A1/3A2-CD19 scFv GADLEN protein. The protein was generated by dual-transfection of CHO cells with both a BTN3A1-CD19 scFv ('alpha', predicted MW=77.4 kDa) and a BTN3A2-CD19 scFv ('beta', predicted MW=77.7 kDa) construct, in which the so-called alpha and beta constructs contained linker domains which facilitated heterodimerization of the desired BTN 3A1/3A2-CD19 scFv GADLEN protein. The purified protein was analyzed by Western blot using non-reducing (left lane), reducing (middle lane) and both reducing and deglycosylating (right lane) conditions, following detection with an anti-human BTN3A1/2 antibody (left blot) or anti-human Fc antibody (right blot). These results indicated the presence of a disulfide-linked protein that reduces to a single band of roughly half the molecular weight of the non-reducing band (following disruption of the interchain disulfide bonds with β-mercaptoethanol). Because the molecular weights of the alpha and beta chains are similar, a doublet band could not be detected under reducing conditions in this study. There was a minor reduction in molecular weight between the reducing and both reducing and deglycosylating conditions lanes, indicating that the GADLEN construct appears to be a glycosylated protein. A series of background bands were also present in the gel, which are likely due to either non-specific binding for each antibody and/or cleaved or incompletely translated proteins which are common in transient transfection productions with multiple plasmids.

As shown in FIG. 16, BTNL3/8-CD19 scFv GADLEN protein was recognized by both an anti-human BTNL8 antibody (left blot) or anti-human Fc antibody (right blot). The purified non-reduced human BTNL3/8-CD19 scFv GADLEN protein showed mobility consistent with a dimer of a BTNL3-CD19 scFv ('alpha', predicted MW=78.4 kDa) and a BTNL8-CD19 scFv ('beta', predicted MW=78.9 kDa) (left lanes in FIG. 14). Reducing (middle lanes in FIG. 14) and both reducing and deglycosylating (right lanes in FIG. 14) produced bands expected for BTNL3-CD19 scFv ('alpha', predicted MW=78.4 kDa) and BTNL8-CD19 scFv ('beta', predicted MW=78.9 kDa). These results indicated the presence of a disulfide-linked protein that reduces to a single band of roughly half the molecular weight of the non-reduced band (following disruption of the interchain disulfide bonds with β-mercaptoethanol). Because the molecular weights of the alpha and beta chains are so similar, a doublet band could not be detected under reducing conditions in this study. A small reduction in molecular weight was observed in both reduced and deglycosylated protein (third lanes) compared to reduced protein (second lanes), indicating that the GADLEN construct is likely to be a glycosylated protein. As shown in FIG. 15, depicts the purified human BTNL 3/8-CD19 scFv GADLEN protein could be quantitated using an Fc-specific ELISA method.

BTN3A1/3A2-CD19 scFv GADLEN protein was generated by dual-transfection of CHO cells with both a BTN3A1-CD19 scFv ('alpha', predicted MW=77.4 kDa) and a BTN3A2-CD19 scFv ('beta', predicted MW=77.7 kDa) construct ((see the cartoon on the top of FIG. 16), in which the so-called alpha and beta constructs contained linker domains which facilitated heterodimerization of the desired BTN 3A1/3A2-CD19 scFv GADLEN protein. The BTN3A1/3A2-CD19 scFv GADLEN protein was purified and analyzed by western blot using non-reducing, reducing, and both reducing and deglycosylating conditions, following detection with an anti-human BTN3A1/2 antibody or anti-human Fc antibody.

As shown in FIG. 16, BTN3A1/3A2-CD19 scFv GADLEN protein was recognized by both an anti-human BTN3A1/2 antibody (left blot in FIG. 16) or anti-human Fc antibody (right blot in FIG. 16). The non-reduced BTN3A1/3A2-CD19 scFv GADLEN protein (left lanes in FIG. 16) showed a mobility consistent with a dimer of the BTN3A1-CD19 scFv ('alpha', predicted MW=77.4 kDa) and the BTN3A2-CD19 scFv ('beta', predicted MW=77.7 kDa). In contrast, reduced (middle lanes in FIG. 16) as well as both reduced and deglycosylated (right lanes in FIG. 16) revealed the monomers: BTN3A1-CD19 scFv ('alpha', predicted MW=77.4 kDa) and the BTN3A2-CD19 scFv ('beta', predicted MW=77.7 kDa). These results indicated the presence of a disulfide-linked protein that reduces to a single band of roughly half the molecular weight of the non-reduced band (following disruption of the interchain disulfide bonds with β-mercaptoethanol). Because the molecular weights of the alpha and beta chains are similar, a doublet band could not be detected under reducing conditions in this study. There was a small reduction in molecular weight between the reduced and both reduced and deglycosylated lanes, indicating that the GADLEN construct appears to be a glycosylated protein. A series of background bands were also present in the gel, which are likely due to either non-specific binding for each antibody and/or cleaved or incompletely translated proteins which are common in transient transfection productions with multiple plasmids.

Figure 17:
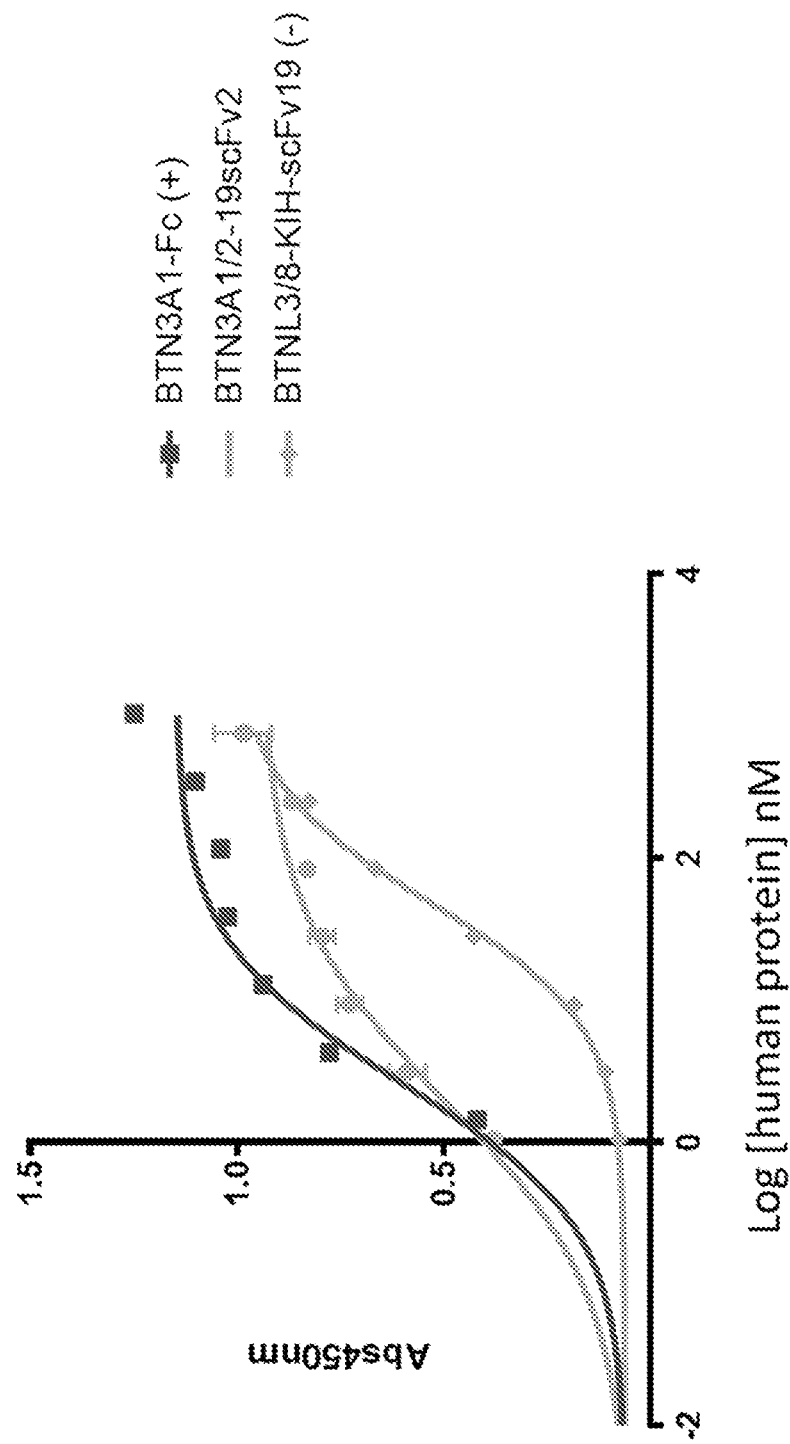
FIG. 17 depicts quantitation of the purified human BTNL 3A1/3A2-CD19 scFv GADLEN using an Fc-specific ELISA method. A positive control (recombinant BTN3A1-Fc; squares) was compared to the BTN3A1/3A2-CD19scFv construct (diamonds), as well as to a control BTNL3/8-KIH-CD19scFv protein that includes the 'knob-in-hole' mutations in the linker domain to facilitate heterodimerization (circles).

As shown in FIG. 17, the purified human BTN 3A1/3A2-CD19 scFv GADLEN could be quantitated using an Fc-specific ELISA method. A positive control (recombinant BTN3A1-Fc; squares in FIG. 17) was compared to the BTN3A1/3A2-CD19scFv construct (diamonds in FIG. 17), as well as to a control BTNL3/8-KIH-CD19scFv protein that includes the 'knob-in-hole' mutations in the linker domain to facilitate heterodimerization (circles in FIG. 17).

Example 6: In Vitro Activity of BTNL3/8-CD19 scFv GADLEN Protein and BTN3A1/3A2-CD19 scFv GADLEN Protein of the Present Technology The assay for upregulation of CD107a was performed using the BTNL3/8-CD19 scFv GADLEN protein and BTN3A1/3A2-CD19 scFv GADLEN protein in human Raji tumor cells (human Burkitt lymphoma cell line). Human gamma delta T cells isolated from human peripheral blood (total of >11 replicates from >3 human donors) were co-cultured for 4-5 hours with Raji tumor cells alone, or together with the anti-human CD20 antibody (Rituximab), BTNL3/8-CD19scFv, BTN3A1/3A2-CD19scFv, HMBPP (positive control) or BTN3A1/3A2-CD19scFv in addition to HMBPP. Gamma delta T cells alone was used as a negative control, and Raji cells+gamma delta T cells were used to control the gamma delta T cells activity without an antibody. The proportion of gamma delta T cells staining positive for CD107a by flow cytometry was measured by flow cytometry following the indicated co-culture, and plotted as a bar graph of the proportion of gamma delta T cells staining positive for CD107a.

Figure 18B:
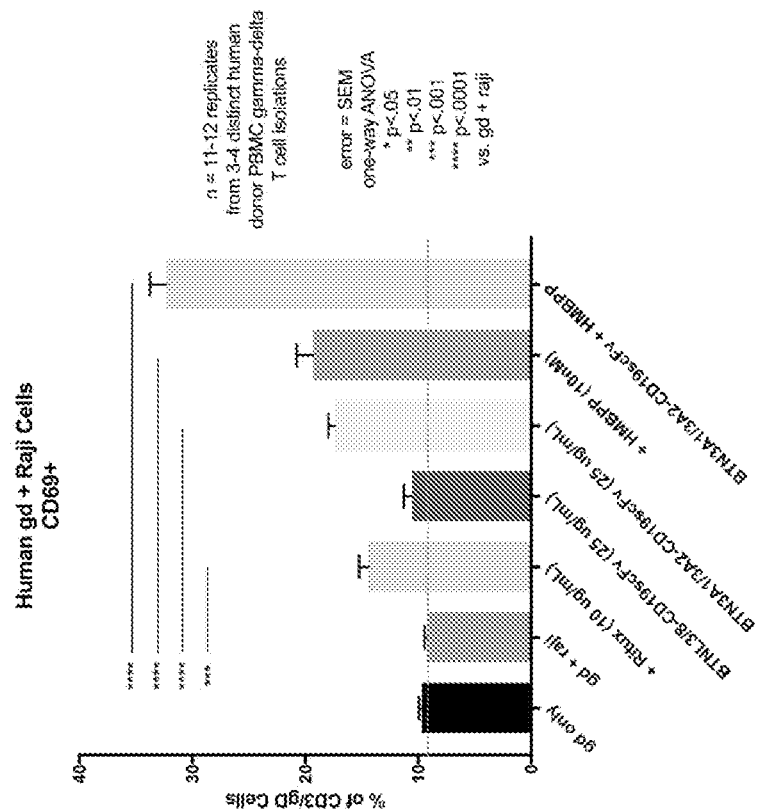
FIGS. 18A-18B provides an example of CD07a degranulation assay, carried out as described in FIGS. 10A-10B, that has been adapted for human gamma delta T cells/tumor cells and the human GADLEN proteins in this case. Specifically, FIG. 18A indicates the frequency of CD107a+ human gamma delta T cells in cell cultures containing human gamma delta T cells isolated from human peripheral blood (total of >11 replicates from >3 human donors) following a 4-5 hour co-culture with human Raji tumor cells (human Burkitt lymphoma cell line) either alone or together with the anti-human CD20 antibody (Rituximab), BTNL3/8-CD19scFv, BTN3A1/3A2-CD19scFv, HMBPP (positive control) or BTN3A1/3A2-CD19scFv in addition to HMBPP.
Figure 18A:
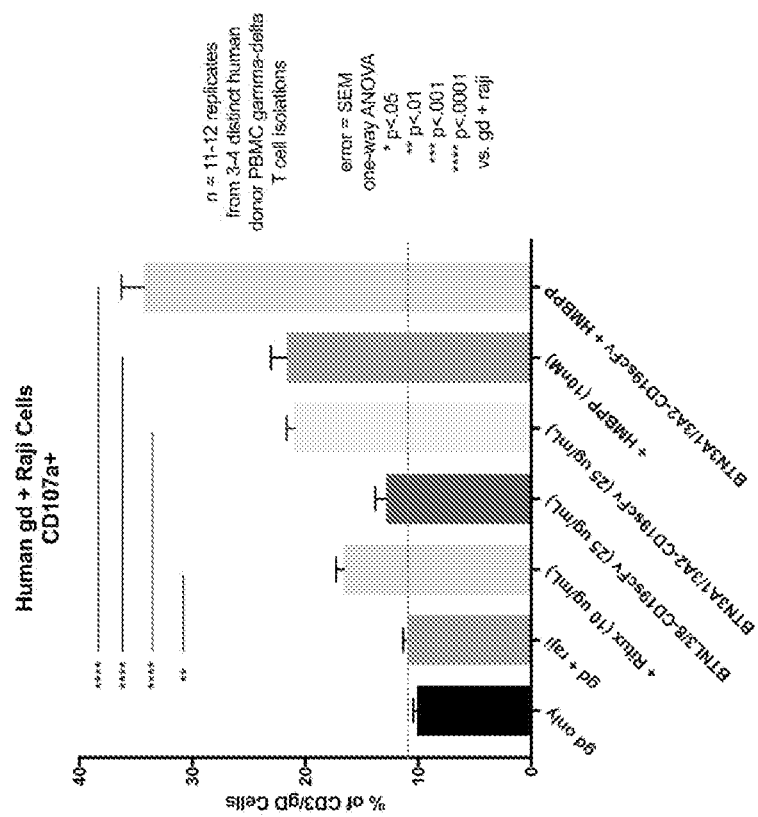

As shown in FIG. 18A, the frequency of CD107a+ human gamma delta T cells significantly increased following the co-culture with CD20 antibody (Rituximab), BTNL3/8-CD19scFv, BTN3A1/3A2-CD19scFv, HMBPP (positive control) or BTN3A1/3A2-CD19scFv in addition to HMBPP, compared to a combination human gamma delta T cells and Raji cells.

The assay for upregulation of CD69 was performed using the BTNL3/8-CD19 scFv GADLEN Protein and BTN3A1/3A2-CD19 scFv GADLEN protein in human Raji tumor cells (human Burkitt lymphoma cell line) from the same co-cultures as for the assay for upregulation of CD107a.

As shown in FIG. 18B, the proportion of human gamma delta T cells expressing the activation marker, significantly increased following the co-culture with CD20 antibody (Rituximab), BTNL3/8-CD19scFv, BTN3A1/3A2-CD19scFv, HMBPP (positive control) or BTN3A1/3A2-CD19scFv in addition to HMBPP, compared to a combination human gamma delta T cells and Raji cells. The data indicate that the BTNL3/8-CD19scFv and BTN3A1/3A2-CD19scFv GADLEN constructs both cause CD107a degranulation and CD69 expression in human gamma delta T cells, similar to what was observed in mouse gamma delta T cells using the species-specific construct. The increased activity of the BTN3A1/3A2 construct in this assay is likely a result of the higher proportion of Vγ9+gamma delta T cells in peripheral blood, which are the gamma delta T cell population that selectively respond to a BTN3A1/3A2 heterodimer. Gamma delta T cells isolated from human intestinal epithelium would be comparatively enriched for Vγ4+ gamma delta T cells, and therefore be selectively responsive to a BTNL3/8 GADLEN construct.

Figure 34A:
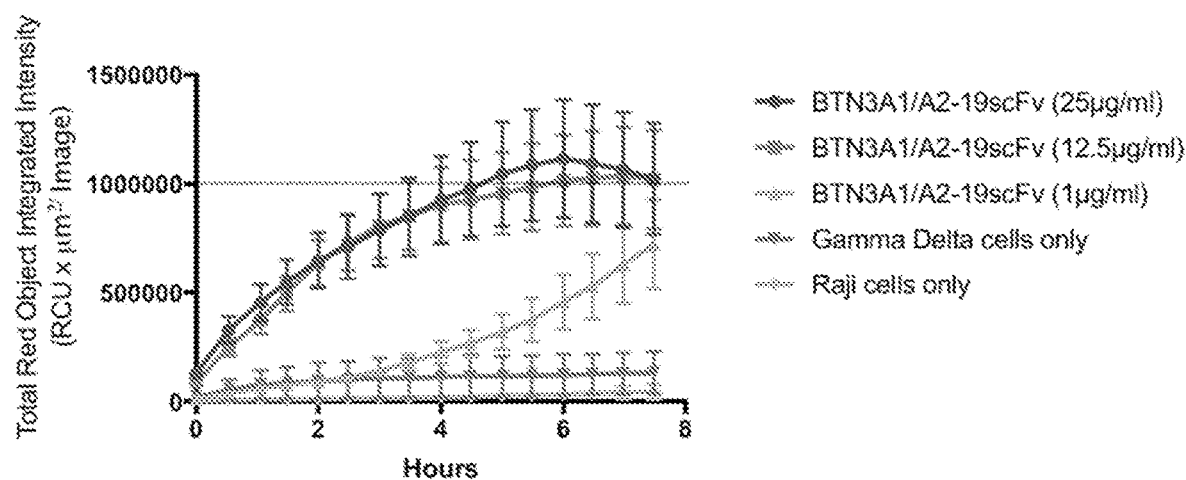
FIGS. 34A-34B show the representative results of a human gamma delta T cell/human tumor cell killing assay mediated by BTN3A1/A2-CD19scFv and BTNL3/8-Fc-CD19scFv heterodimer proteins. In these studies, purified human gamma delta T cells (isolated from human peripheral blood mononuclear cells) were co-cultured with human CD19+ Raji cells together with increasing concentrations (1-25 µg/ml) of BTN3A1/A2-CD19scFv or BTNL3/8-Fc-CD19scFv heterodimer proteins at a gamma delta T cells: Raji tumor cell ratio of 1:1, for 8 hours with live imaging every hour in an Incucyte imager. Raji cells alone (diamonds) and gamma delta T cells alone (inverted triangle) were included as negative controls. The Raji tumor cells were labeled with green fluorescence, and the assay included a red-fluorescent dye specific for Annexin-5, as an indicator of cell death. The y-axis in the figure indicates the integrated intensity of red fluorescence, which occurs when Raji tumor cells undergo cell death and stain positive for red-labeled Annexin-5.
Figure 34B:
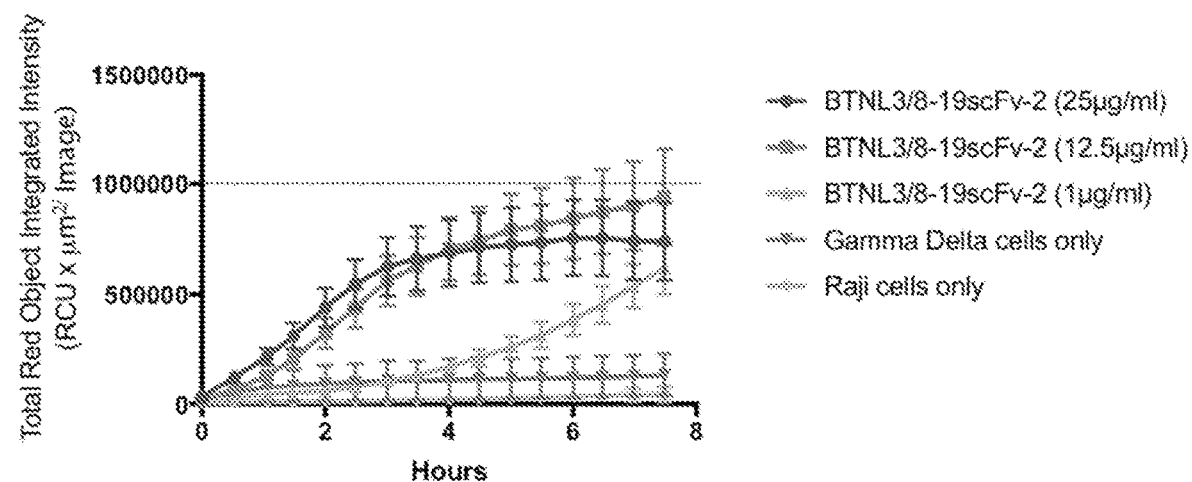

Whether BTNL3/8-CD19 scFv GADLEN protein and BTN3A1/3A2-CD19 scFv GADLEN protein can mediate killing of cancer cells was studied. In these studies, purified human gamma delta T cells (isolated from human peripheral blood mononuclear cells) were co-cultured with human CD19+ Raji cells together with increasing concentrations (1-25 µg/ml) of BTN3A1/A2-CD19scFv or BTNL3/8-Fc-CD19scFv heterodimer proteins at a gamma delta T cells: Raji tumor cell ratio of 1:1, for 8 hours with live imaging every hour in an Incucyte imager. The Raji tumor cells were labeled with green fluorescence, and the assay included a red-fluorescent dye specific for Annexin-5, as an indicator of cell death. Raji cells alone and gamma delta T cells alone were included as negative controls. The integrated intensity of red fluorescence, which occurs when Raji tumor cells undergo cell death and stain positive for red-labeled Annexin-5 was plotted as a function of time. As shown in FIG. 34A, BTN3A1/3A2-CD19 scFv GADLEN, in the repsence of gamma delta T cells, mediated increased killing of Raji cells (circles, squares and triangles) compared to Raji cells alone (diamonds) or gamma delta T cells alone (inverted triangle). 12.5 (squares) or 25 µg/ml BTN3A1/3A2-CD19 scFv GADLEN (circles) doses caused more efficient killing compared to 1 µg/ml (triangles) dose. Similarly, ss shown in FIG. 34A, BTNL3/8-CD19 scFv GADLEN protein, in the repsence of gamma delta T cells, mediated increased killing of Raji cells (circles, squares and triangles) compared to Raji cells alone (diamonds) or gamma delta T cells alone (inverted triangle). 12.5 (squares) or 25 µg/ml BTNL3/8-CD19 scFv GADLEN protein (circles) doses caused more efficient killing compared to 1 µg/ml (triangles) dose.

These results demonstrate that GADLEN proteins of the present technology induce contemporaneous activation and targeting of gamma delta T cells to tumor cells, causing efficient cancer cell killing. Accordingly, GADLEN proteins of the present technology are useful in the methods of modulating a patient's immune response disclosed herein.

Example 7: Various GADLEN Proteins of the Present Technology

Prepared in this example are heterodimeric proteins in which each polypeptide chain comprises a butyrophilin-like (BTNL) family protein linked by a charge polarized core domain to a portion of the extracellular domain of a Type I transmembrane protein Similar to the heterodimeric proteins shown in FIG. 1, these heterodimeric proteins each comprise two polypeptide chains; however, here, a first polypeptide chain (i.e., an alpha strand) comprises a portion of BTNL3 and a second polypeptide chain (i.e., a beta strand) comprises a portion of BTNL8.

Without wishing to be bound by theory, typically the immune system is roughly divided into 'innate' immunity and 'adaptive' immunity. Innate immune responses are akin to a front-line response system which can provide rapid, albeit incomplete, protection to a variety of threats through recognition of pathogen- or cell damage-associated molecular patterns. Adaptive immunity can be triggered by innate immunity, takes longer to become fully activated, tends to be significantly more potent, is generally antigen-specific and, importantly, includes long-lasting memory responses. Without wishing to be bound by theory, there is not a clean division of labor between innate and adaptive immune responses, and there are a growing number of phenotypically-described immune cell types and effector molecules which straddle the typical definition between innate and adaptive immunity.

Without wishing to be bound by theory, one of the cell types that straddles the interface between innate and adaptive immunity are a sub-population of T cells wherein the T cell receptor is derived through somatic gene rearrangement of V gamma and V delta genes as opposed to V alpha and V beta genes. This cell population, known as gamma delta T cells, is found at lower frequencies than alpha beta T cells, but is particularly abundant at epithelial surfaces including, without limitation, the gastrointestinal tract, the skin, and the uterus. Some gamma delta T cells are also found in the blood, and may be important for recognizing specific antigens including phosphor-antigens in the blood. Interestingly, across a range of thirty-nine human tumors and a dataset derived from ~39,000 human cancer patients, one of the most favorable prognostic factors uncovered was the proportion of gamma delta T cells found within biopsied tumors. This information suggests, inter alia, that manipulation of gamma delta T cells may have important consequences in the treatment of human cancers.

Recently, the molecular mechanisms by which the gamma delta T cell receptor identify cognate antigen have been better defined. Interestingly, without wishing to be bound by theory, one of the primary activation mechanisms for gamma delta T cells appears to be mediated through an evolutionarily conserved family of receptors known as butyrophilin-like (BTNL) proteins.

There are at least two btnl proteins in mice (btnl 1 and btnl 6) and at least 6 BTNL proteins in humans (including BTNL1, BTNL3, BTNL6, BTNL8, BTN3A1, BTN3A2, and BTN3A3). In humans, activation of gamma delta T cells by BTNL family proteins is dependent upon heterodimerization of different individual BTNL proteins. In gut epithelium, a heterodimer comprising BTNL1, BTNL3, BTNL6 and BTNL8 is required for efficient gamma delta T cell activation. In the blood, a heterodimer comprising BTN3A1 and BTN3A2 appears to be most important for recognition of phospho-antigens. Thus, heterodimerization of BTNL proteins appears to be an important mechanism for activation of gamma delta T cells in specific tissues, and distinct heterodimers of BTNL proteins may help guide immunity to specific antigens across a range of tissues. The specific domain of BTNL family proteins that interact with the gamma delta T cell receptor are derived from the V-domain of BTNL proteins.

Due to the requirement for BTNL protein heterodimerization, and the potentially important role for gamma delta T cells in cancer and other human diseases, therapeutic proteins which could provide functional BTNL heterodimers are useful for the treatment of human diseases, including cancer. Such heterodimeric proteins include those derived from fusion proteins (including Fc fusion proteins), or from therapeutic proteins derived from monoclonal antibody binding domains (including antibodies, bi-specific antibodies, tri-specific antibodies, quadra-specific antibodies, etc. and also including fusion partners between native protein binding domains (further including BTNL proteins) and antibodies or antibody fragments). In some instances, the therapeutic protein is derived from an Fc-containing fusion protein wherein the therapeutic protein was specifically designed to facilitate heterodimerization between two individual polypeptide chains, wherein one polypeptide chain includes one BTNL protein (BTNL1/BTNL3 for example) and the other polypeptide chain includes another BTNL protein (BTNL6/BTNL8 for example). In further instances, the BTNL1/6 containing heterodimer is further comprised of a second set of therapeutic proteins which may provide a dual-mechanism of action to the BTNL1/6 containing fusion protein. As an example, the second mechanism of action provides targeting of the BTNL1/6 heterodimer to a specific tissue or tumor antigen, and in another example the second mechanism of action provides a second co-stimulatory signal to immune cells, and in yet another example the second mechanism of action may provide a mechanism to block immune inhibitory signals including so-called "checkpoint" molecules in human cancers.

In further instances, the BTNL3/8 containing heterodimer is further comprised of a second set of therapeutic proteins which may provide a dual-mechanism of action to the BTNL3/8 containing fusion protein. As an example, the second mechanism of action provides targeting of the BTNL3/8 heterodimer to a specific tissue or tumor antigen, and in another example the second mechanism of action provides a second co-stimulatory signal to immune cells, and in yet another example the second mechanism of action may provide a mechanism to block immune inhibitory signals including so-called "checkpoint" molecules in human cancers.

Heterodimeric proteins relevant to this non-limiting example include the following specific combinations of alpha strands and beta strands:

(1) an alpha strand comprising a V-set domain of BTNL3 linked by a charge polarized core domain to a portion of the extracellular domain of T cell immunoreceptor with Ig and ITIM domains (TIGIT) and a beta strand comprising a V-set domain of BTNL8 linked by a charge polarized core domain to a portion of the extracellular domain of TIGIT. Illustrative alpha and beta strands have the following amino acid sequences:

BTNL3-Alpha-vTIGIT
(SEQ ID NO: 24)
CCGCCACCMEFGLSWVFLVAIIKGVQCQWQVTGPGKFVQALVGEDAVFSCS

LFPETSAEAMEVRFFRNQFHAVVHLYRDGEDWESKQMPQYRGRTEFVKDSI

AGGRVSLRLKNITPSDIGLYGCWFSSQIYDEEATWELRVAALGSLPLISIV

GYVDGGIQLLCLSSGWFPQPTAKWKGPQGQDLSSDSRANADGYSLYDVEIS

IIVQENAGSILCSIHLAEQSHEVESKVLIGETFFQPSPWRLASGSGSRKGG

KRGSKYGPPCPPCPAPEFLGGPSVFLFPPKPKDQLMISRTPEVTCVVVDVS

QEDPEVQFNWYVDGVEVHNAKTKPREEQFNSTYRVVSVLTVLHQDWLSGKE

YKCKVSSKGLPSSIEKTISNATGQPREPQVYTLPPSQEEMTKNQVSLTCLV

KGFYPSDIAVEWESNGQPENNYKTTPPVLDSDGSFFLYSRLTVDKSRWQEG

NVFSCSVLHEALHNHYTQKSLSLSLGKDEGGEDGSGSMMTGTIETTGNISA

EKGGSIILQCHLSSTTAQVTQVNWEQQDQLLAICNADLGWHISPSFKDRVA

PGPGLGLTLQSLTVNDTGEYFCIYHTYPDGTYTGRIFL

BTIVL8-Beta-vTIGIT
(SEQ ID NO: 25)
QWQVFGPDKPVQALVGEDAAFSCFLSPKTNAEAMEVRFFRGQFSSVVHLYR

DGKDQPFMQMPQYQGRTKLVKDSIAEGRISLRLENITVLDAGLYGCRISSQ

SYYQKAIWELQVSALGSVPLISITGYVDRDIQLLCQSSGWFPRPTAKWKGP

QGQDLSTDSRTNRDMHGLFDVEISLTVQENAGSISCSMRHAHLSREVESRV

QIGDTFFEPISWHLATKGSGSDEGGEDGSKYGPPCPPCPAPEFLGGPSVFL

FPPKPKDQLMISRTPEVTCVVVDVSQEDPEVQFNWYVDGVEVHNAKTKPRE

EQFNSTYRVVSVLTVLHQDWLSGKEYKCKVSSKGLPSSIEKTISNATGQPR

EPQVYTLPPSQEEMTKNQVSLTCLVKGFYPSDIAVEWESNGQPENNYKTTP

PVLDSDGSFFLYSRLTVDKSRWQEGNVFSCSVLHEALHNHYTQKSLSLSLG

KRKGGKRGSGSMMTGTIETTGNISAEKGGSIILQCHLSSTTAQVTQVNWEQ

QDQLLAICNADLGWHISPSFKDRVAPGPGLGLTLQSLTVNDTGEYFCIYHT

YPDGTYTGRIFL (2) an alpha strand comprising a V-set domain of BTNL3 linked by a charge polarized core domain to a portion of the extracellular domain of lymphocyte-activation gene 3 (LAG-3) and a beta strand comprising a V-set domain of BTNL8 linked by a charge polarized core domain to a portion of the extracellular domain of LAG-3. Illustrative alpha and beta strands have the following amino acid sequences:

BTNL3-Alpha-vLAG3
(SEQ ID NO: 26)
QWQVTGPGKFVQALVGEDAVFSCSLFPETSAEAMEVRFFRNQFHAVVHLYR
DGEDWESKQMPQYRGRTEFVKDSIAGGRVSLRLKNITPSDIGLYGCWFSSQ
IYDEEATWELRVAALGSLPLISIVGYVDGGIQLLCLSSGWFPQPTAKWKGP
QGQDLSSDSRANADGYSLYDVEISIIVQENAGSILCSIHLAEQSHEVESKV
LIGETFFQPSPWRLASGSGSRKGGKRGSKYGPPCPPCPAPEFLGGPSVFLF
PPKPKDQLMISRTPEVTCVVVDVSQEDPEVQFNWYVDGVEVHNAKTKPREE
QFNSTYRVVSVLTVLHQDWLSGKEYKCKVSSKGLPSSIEKTISNATGQPRE
PQVYTLPPSQEEMTKNQVSLTCLVKGFYPSDIAVEWESNGQPENNYKTTPP
VLDSDGSFFLYSRLTVDKSRWQEGNVFSCSVLHEALHNHYTQKSLSLSLGK
DEGGEDGSGSGAPAQLPCSPTIPLQDLSLLRRAGVTWQHQPDSGPPAAAPG
HPLAPGPHPAAPSSWGPRPRRYTVLSVGPGGLRSGRLPLQPRVQLDERGRQ
RGDFSLWLRPARRADAGEYRAAVHLRDRALSCRLRLRLG BTNL8-Beta-vLAG3
(SEQ ID NO: 27)
QWQVFGPDKPVQALVGEDAAFSCFLSPKTNAEAMEVRFFRGQFSSVVHLYR
DGKDQPFMQMPQYQGRTKLVKDSIAEGRISLRLENITVLDAGLYGCRISSQ
SYYQKAIWELQVSALGSVPLISITGYVDRDIQLLCQSSGWFPRPTAKWKGP
QGQDLSTDSRTNRDMHGLFDVEISLTVQENAGSISCSMRHAHLSREVESRV
QIGDTFFEPISWHLATKGSGSDEGGEDGSKYGPPCPPCPAPEFLGGPSVFL
FPPKPKDQLMISRTPEVTCVVVDVSQEDPEVQFNWYVDGVEVHNAKTKPRE
EQFNSTYRVVSVLTVLHQDWLSGKEYKCKVSSKGLPSSIEKTISNATGQPR
EPQVYTLPPSQEEMTKNQVSLTCLVKGFYPSDIAVEWESNGQPENNYKTTP
PVLDSDGSFFLYSRLTVDKSRWQEGNVFSCSVLHEALHNHYTQKSLSLSLG
KRKGGKRGSGSGAPAQLPCSPTIPLQDLSLLRRAGVTWQHQPDSGPPAAAP
GHPLAPGPHPAAPSSWGPRPRRYTVLSVGPGGLRSGRLPLQPRVQLDERGR
QRGDFSLWLRPARRADAGEYRAAVHLRDRALSCRLRLRLG (3) an alpha strand comprising a portion of the extracellular domain of TIGIT linked by a charge polarized core domain to a V-set domain of BTNL3 and a beta strand comprising a portion of the extracellular domain of TIGIT linked by a charge polarized core domain to a V-set domain of BTNL8. Illustrative alpha and beta strands have the following amino acid sequences:

TIGIT-Alpha-vBTIVL3
(SEQ ID NO: 28)
MMTGTIETTGNISAEKGGSIILQCHLSSTTAQVTQVNWEQQDQLLAICNAD
LGWHISPSFKDRVAPGPGLGLTLQSLTVNDTGEYFCIYHTYPDGTYTGRIF
LEVLESSVAEHGARFQIPGSGSRKGGKRGSKYGPPCPPCPAPEFLGGPSVF
LFPPKPKDQLMISRTPEVTCVVVDVSQEDPEVQFNWYVDGVEVHNAKTKPR
EEQFNSTYRVVSVLTVLHQDWLSGKEYKCKVSSKGLPSSIEKTISNATGQP
REPQVYTLPPSQEEMTKNQVSLTCLVKGFYPSDIAVEWESNGQPENNYKTT
PPVLDSDGSFFLYSRLTVDKSRWQEGNVFSCSVLHEALHNHYTQKSLSLSL
GKDEGGEDGSGSPLISIVGYVDGGIQLLCLSSGWFPQPTAKWKGPQGQDLS
SDSRANADGYSLYDVEISIIVQENAGSILCSIHLAEQSHEVE TIGIT-Beta-vBTIVL8
(SEQ ID NO: 29)
MMTGTIETTGNISAEKGGSIILQCHLSSTTAQVTQVNWEQQDQLLAICNAD
LGWHISPSFKDRVAPGPGLGLTLQSLTVNDTGEYFCIYHTYPDGTYTGRIF
LEVLESSVAEHGARFQIPGSGSDEGGEDGSKYGPPCPPCPAPEFLGGPSVF
LFPPKPKDQLMISRTPEVTCVVVDVSQEDPEVQFNWYVDGVEVHNAKTKPR
EEQFNSTYRVVSVLTVLHQDWLSGKEYKCKVSSKGLPSSIEKTISNATGQP
REPQVYTLPPSQEEMTKNQVSLTCLVKGFYPSDIAVEWESNGQPENNYKTT
PPVLDSDGSFFLYSRLTVDKSRWQEGNVFSCSVLHEALHNHYTQKSLSLSL
GKRKGGKRGSGSALGSVPLISITGYVDRDIQLLCQSSGWFPRPTAKWKGPQ
GQDLSTDSRTNRDMHGLFDVEISLTVQENAGSISCSMRHAHLSREVESRVQ (4) an alpha strand comprising a portion of the extracellular domain of LAG-3 linked by a charge polarized core domain to a V-set domain of BTNL3 and a beta strand comprising a portion of the extracellular domain of LAG-3 linked by a charge polarized core domain to a V-set domain of BTNL8. Illustrative alpha and beta strands have the following amino acid sequences:

LAG3-Alpha-vBTnL3
(SEQ ID NO: 30)
VPVVWAQEGAPAQLPCSPTIPLQDLSLLRRAGVTWQHQPDSGPPAAAPGHP
LAPGPHPAAPSSWGPRPRRYTVLSVGPGGLRSGRLPLQPRVQLDERGRQRG
DFSLWLRPARRADAGEYRAAVHLRDRALSCRLRLRLGQASMTASPPGSLRA
SDWVILNCSFSRPDRPASVHWFRNRGQGRVPVRESPHHHLAESFLFLPQVS
PMDSGPWGCILTYRDGFNVSIMYNLTVLGLEPPTPLTVYAGAGSRVGLPCR
LPAGVGTRSFLTAKWTPPGGGPDLLVTGDNGDFTLRLEDVSQAQAGTYTCH
IHLQEQQLNATVTLAIITVTPKSFGSPGSLGKLLCEVTPVSGQERFVWSSL
DTPSQRSFSGPWLEAQEAQLLSQPWQCQLYQGERLLGAAVYFTELSSPGAQ
RSGRAPGALPAGHLGSGSRKGGKRGSKYGPPCPPCPAPEFLGGPSVFLFPP
KPKDQLMISRTPEVTCVVVDVSQEDPEVQFNWYVDGVEVHNAKTKPREEQF
NSTYRVVSVLTVLHQDWLSGKEYKCKVSSKGLPSSIEKTISNATGQPREPQ
VYTLPPSQEEMTKNQVSLTCLVKGFYPSDIAVEWESNGQPENNYKTTPPVL
DSDGSFFLYSRLTVDKSRWQEGNVFSCSVLHEALHNHYTQKSLSLSLGKDE
GGEDGSGSPLISIVGYVDGGIQLLCLSSGWFPQPTAKWKGPQGQDLSSDSR
ANADGYSLYDVEISIIVQENAGSILCSIHLAEQSHEVE LAG3-Beta-vBTNL8

(SEQ ID NO: 31)
VPVVWAQEGAPAQLPCSPTIPLQDLSLLRRAGVTWQHQPDSGPPAAAPGHP
LAPGPHPAAPSSWGPRPRRYTVLSVGPGGLRSGRLPLQPRVQLDERGRQRG
DFSLWLRPARRADAGEYRAAVHLRDRALSCRLRLRLGQASMTASPPGSLRA
SDWVILNCSFSRPDRPASVHWFRNRGQGRVPVRESPHHHLAESFLFLPQVS
PMDSGPWGCILTYRDGFNVSIMYNLTVLGLEPPTPLTVYAGAGSRVGLPCR
LPAGVGTRSFLTAKWTPPGGGPDLLVTGDNGDFTLRLEDVSQAQAGTYTCH

IHLQEQQLNATVTLAIITVTPKSFGSPGSLGKLLCEVTPVSGQERFVWSSL
DTPSQRSFSGPWLEAQEAQLLSQPWQCQLYQGERLLGAAVYFTELSSPGAQ
RSGRAPGALPAGHLGSGSDEGGEDGSKYGPPCPPCPAPEFLGGPSVFLFPP
KPKDQLMISRTPEVTCVVVDVSQEDPEVQFNWYVDGVEVHNAKTKPREEQF
NSTYRVVSVLTVLHQDWLSGKEYKCKVSSKGLPSSIEKTISNATGQPREPQ
VYTLPPSQEEMTKNQVSLTCLVKGFYPSDIAVEWESNGQPENNYKTTPPVL
DSDGSFFLYSRLTVDKSRWQEGNVFSCSVLHEALHNHYTQKSLSLSLGKRK
GGKRGSGSALGSVPLISITGYVDRDIQLLCQSSGWFPRPTAKWKGPQGQDL
STDSRTNRDMHGLFDVEISLTVQENAGSISCSMRHAHLSREVESRVQ (5) an alpha strand comprising a portion of the extracellular domain of programmed cell death protein 1 (PD-1) linked by a charge polarized core domain to a V-set domain of BTNL3 and a beta strand comprising a portion of the extracellular domain of PD-1 linked by a charge polarized core domain to a V-set domain of BTNL8. Illustrative alpha and beta strands have the following amino acid sequences:

PD1-Alpha-vBTNL3

(SEQ ID NO: 32)

PGWFLDSPDRPWNPPTFSPALLVVTEGDNATFTCSFSNTSESFVLNWYRMS

PSNQTDKLAAFPEDRSQPGQDCRFRVTQLPNGRDFHMSVVRARRNDSGTYL

CGAISLAPKAQIKESLRAELRVTERRAEVPTAHPSPSPRPAGQFQTLVGSG

SRKGGKRGSKYGPPCPPCPAPEFLGGPSVFLFPPKPKDQLMISRTPEVTCV

VVDVSQEDPEVQFNWYVDGVEVHNAKTKPREEQFNSTYRVVSVLTVLHQDW

-continued

LSGKEYKCKVSSKGLPSSIEKTISNATGQPREPQVYTLPPSQEEMTKNQVS

LTCLVKGFYPSDIAVEWESNGQPENNYKTTPPVLDSDGSFFLYSRLTVDKS

RWQEGNVFSCSVLHEALHNHYTQKSLSLSLGKDEGGEDGSGSPLISIVGYV

DGGIQLLCLSSGWFPQPTAKWKGPQGQDLSSDSRANADGYSLYDVEISIIV

QENAGSILCSIHLAEQSHEVE

PD1-Beta-vBTNL8

(SEQ ID NO: 33)

PGWFLDSPDRPWNPPTFSPALLVVTEGDNATFTCSFSNTSESFVLNWYRMS

PSNQTDKLAAFPEDRSQPGQDCRFRVTQLPNGRDFHMSVVRARRNDSGTYL

CGAISLAPKAQIKESLRAELRVTERRAEVPTAHPSPSPRPAGQFQTLVGSG

SDEGGEDGSKYGPPCPPCPAPEFLGGPSVFLFPPKPKDQLMISRTPEVTCV

VVDVSQEDPEVQFNWYVDGVEVHNAKTKPREEQFNSTYRVVSVLTVLHQDW

LSGKEYKCKVSSKGLPSSIEKTISNATGQPREPQVYTLPPSQEEMTKNQVS

LTCLVKGFYPSDIAVEWESNGQPENNYKTTPPVLDSDGSFFLYSRLTVDKS

RWQEGNVFSCSVLHEALHNHYTQKSLSLSLGKRKGGKRGSGSALGSVPLIS

ITGYVDRDIQLLCQSSGWFPRPTAKWKGPQGQDLSTDSRTNRDMHGLFDVE

ISLTVQENAGSISCSMRHAHLSREVESRVQ (6) an alpha strand comprising a V-set domain of BTNL3 linked by a charge polarized core domain to a portion of the extracellular domain of alpha CD19 (αCD19) and a beta strand comprising a V-set domain of BTNL8 linked by a charge polarized core domain to a portion of the antibody binding domain directed to CD19. Illustrative alpha and beta strands have the following amino acid sequences:

Alpha Strand (SEQ ID NO: 35)

QWQVTGPGKFVQALVGEDAVFSCSLFPETSAEAMEVRFFRNQFHAVVHLYRDGED

WESKQMPQYRGRTEFVKDSIAGGRVSLRLKNITPSDIGLYGCWFSSQIYDEEATWEL

RVAALGSLPLISIVGYVDGGIQLLCLSSGWFPQPTAKWKGPQGQDLSSDSRANADGY

SLYDVEISIIVQENAGSILCSIHLAEQSHEVESKVLIGETFFQPSPWRLASGSGSRKGGK

RGSKYGPPCPPCPAPEFLGGPSVFLFPPKPKDQLMISRTPEVTCVVVDVSQEDPEVQF

NWYVDGVEVHNAKTKPREEQFNSTYRVVSVLTVLHQDWLSGKEYKCKVSSKGLPS

SIEKTISNATGQPREPQVYTLPPSQEEMTKNQVSLTCLVKGFYPSDIAVEWESNGQPE

NNYKTTPPVLDSDGSFFLYSRLTVDKSRWQEGNVFSCSVLHEALHNHYTQKSLSLSL

GKDEGGEDGSGSDIQLTQSPASLAVSLGQRATISCKASQSVDYDGDSYLNWYQQIPG

QPPKLLIYDASNLVSGIPPRFSGSGSGTDFTLNIHPVEKVDAATYHCQQSTEDPWTFG

GGTKLEIK*.

Beta Strand (SEQ ID NO: 36)

QWQVFGPDKPVQALVGEDAAFSCFLSPKTNAEAMEVRFFRGQFSSVVHLYRDGKDQ

PFMQMPQYQGRTKLVKDSIAEGRISLRLENITVLDAGLYGCRISSQSYYQKAIWELQV

SALGSVPLISITGYVDRDIQLLCQSSGWFPRPTAKWKGPQGQDLSTDSRTNRDMHGL

FDVEISLTVQENAGSISCSMRHAHLSREVESRVQIGDTFFEPISWHLATKGSGSDEGGE

DGSKYGPPCPPCPAPEFLGGPSVFLFPPKPKDQLMISRTPEVTCVVVDVSQEDPEVQF

NWYVDGVEVHNAKTKPREEQFNSTYRVVSVLTVLHQDWLSGKEYKCKVSSKGLPS

-continued

SIEKTISNATGQPREPQVYTLPPSQEEMTKNQVSLTCLVKGFYPSDIAVEWESNGQPE

NNYKTTPPVLDSDGSFFLYSRLTVDKSRWQEGNVFSCSVLHEALHNHYTQKSLSLSL

GKRKGGKRGSGSGSIQLTQSPAIMSASPGEKVTMTCRASSSVSYMNWYQQKSGTSPKR

WIYDTSKVASGVPYRFSGSGSGTSYSLTISSMEAEDAATYYCQQWSSNPLTFGAGTK

LELK **.

(7) an alpha strand comprising a V-set domain of BTNL3 linked by a charge polarized core domain to a portion of an antibody derived binding domain directed to PSMA (αPSMA) and a beta strand comprising a V-set domain of BTNL8 linked by a charge polarized core domain to an antibody-derived binding domain directed to PSMA. Illustrative alpha and beta strands have the following amino acid sequences:

AlphaStrand (SEQ ID NO: 37)

QWQVTGPGKFVQALVGEDAVFSCSLFPETSAEAMEVRFFRNQFHAVVHLYRDGED

WESKQMPQYRGRTEFVKDSIAGGRVSLRLKNITPSDIGLYGCWFSSQIYDEEATWEL

RVAALGSLPLISIVGYVDGGIQLLCLSSGWFPQPTAKWKGPQGQDLSSDSRANADGY

SLYDVEISIIVQENAGSILCSIHLAEQSHEVESKVLIGETFFQPSPWRLASGSGSRKGGK

RGSKYGPPCPPCPAPEFLGGPSVFLFPPKPKDQLMISRTPEVTCVVVDVSQEDPEVQF

NWYVDGVEVHNAKTKPREEQFNSTYRVVSVLTVLHQDWLSGKEYKCKVSSKGLPS

SIEKTISNATGQPREPQVYTLPPSQEEMTKNQVSLTCLVKGFYPSDIAVEWESNGQPE

NNYKTTPPVLDSDGSFFLYSRLTVDKSRWQEGNVFSCSVLHEALHNHYTQKSLSLSL

GKDEGGEDGSGSGEVQLVESGGGLVQPGGSLTLSCAASRFMISEYHMHWVRQAPGK

GLEWVSTINPAGTTDYAESVKGRFTISRDNAKNTLYLQMNSLKPEDTAVYYCDSYG

YRGQGTQVTV*

Beta Strand (SEQ ID NO: 38)

QWQVFGPDKPVQALVGEDAAFSCFLSPKTNAEAMEVRFFRGQFSSVVHLYRDGKDQ

PFMQMPQYQGRTKLVKDSIAVSRISLRLENITVLDAGLYGCRISSQSYYQKAIWELQV

SALGSVPLISITGYVDRDIQLLCQSSGWFPRPTAKWKGPQGQDLSTDSRTNRDMHGL

FDVEISLTVQENAGSISCSMRHAHLSREVESRVQIGDTFFEPISWHLATKGSGSDVSGE

DGSKYGPPCPPCPAPEFLGGPSVFLFPPKPKDQLMISRTPEVTCVVVDVSQEDPEVQF

NWYVDGVEVHNAKTKPREEQFNSTYRVVSVLTVLHQDWLSGKEYKCKVSSKGLPS

SIEKTISNATGQPREPQVYTLPPSQEEMTKNQVSLTCLVKGFYPSDIAVEWESNGQPE

NNYKTTPPVLDSDGSFFLYSRLTVDKSRWQEGNVFSCSVLHEALHNHYTQKSLSLSL

GKRKGGKRGSGSGSGQTVVTQEPSLTVSPGGTVTLTCASSTGAVTSGNYPNWVQQKPG

QAPRGLIGGTKFLVPGTPARFSGSLLGGKAALTLSGVQPEDEAEYYCTLWYSNRWVF

GGGTKLTVL*.

(8) an alpha strand comprising a V-set domain of BTNL3 linked by a charge polarized core domain to a portion of the extracellular domain of alpha CD19 (αCD19) and a beta strand comprising a V-set domain of BTNL8 linked by a charge polarized core domain to a portion of the antibody binding domain directed to CD19. Illustrative alpha and beta strands have the following amino acid sequences:

Alpha Strand (SEQ ID NO: 39)

CCGCCACCMEFGLSWVFLVAIIKGVQCQWQVTGPGKFVQALVGEDAVFSCS

LFPETSAEAMEVRFFRNQFHAVVHLYRDGEDWESKQMPQYRGRTEFVKDSI

AGGRVSLRLKNITPSDIGLYGCWFSSQIYDEEATWELRVAALGSLPLISIV

GYVDGGIQLLCLSSGWFPQPTAKWKGPQGQDLSSDSRANADGYSLYDVEIS

-continued

IIVQENAGSILCSIHLAEQSHEVESKVLIGETFFQPSPWRLASGSGSRKGG

KRGSKYGPPCPPCPAPEFLGGPSVFLFPPKPKDQLMISRTPEVTCVVVDVS

QEDPEVQFNWYVDGVEVHNAKTKPREEQFNSTYRVVSVLTVLHQDWLSGKE

YKCKVSSKGLPSSIEKTISNATGQPREPQVYTLPPSQEEMTKNQVSLTCLV

KGFYPSDIAVEWESNGQPENNYKTTPPVLDSDGSFFLYSRLTVDKSRWQEG

NVFSCSVLHEALHNHYTQKSLSLSLGKDEGGEDGSQVQLQQSGAELVRPGS

SVKISCKASGYAFSSYWMNWVKQRPGQGLEWIGQIWPGDGDTNYNGKFKGK

ATLTADESSSTAYMQLSSLASEDSAVYFCARRETTTVGRYYYAMDYWGQGT

TVTVSSGGGGSGGGGSGGGGSDIQLTQSPASLAVSLGQRATISCKASQSVD

YDGDSYLNWYQQIPGQPPKLLIYDASNLVSGIPPRFSGSGSGTDFTLNIHP

VEKVDAATYHCQQSTEDPWTFGGGTKLEIK.

Beta Strand (SEQ ID NO: 40)

<u>CCGCCACCMEFGLSWVFLVAIIKGVQC</u>QWQVFGPDKPVQALVGEDAAFSCF

LSPKTNAEAMEVRFFRGQFSSVVHLYRDGKDQPFMQMPQYQGRTKLVKDSI

AEGRISLRLENITVLDAGLYGCRISSQSYYQKAIWELQVSALGSVPLISIT

GYVDRDIQLLCQSSGWFPRPTAKWKGPQGQDLSTDSRTNRDMHGLFDVEIS

LTVQENAGSISCSMRHAHLSREVESRVQIGDTFFEPISWHLATKGSGSDEG

GEDGSKYGPPCPPCPAPEFLGGPSVFLFPPKPKDQLMISRTPEVTCVVVDV

SQEDPEVQFNWYVDGVEVHNAKTKPREEQFNSTYRVVSVLTVLHQDWLSGK

EYKCKVSSKGLPSSIEKTISNATGQPREPQVYTLPPSQEEMTKNQVSLTCL

VKGFYPSDIAVEWESNGQPENNYKTTPPVLDSDGSFFLYSRLTVDKSRWQE

GNVFSCSVLHEALHNHYTQKSLSLSLGKRKGGKRGSGSQVQLQQSGAELVR

PGSSVKISCKASGYAFSSYWMNWVKQRPGQGLEWIGQIWPGDGDTNYNGKF

KGKATLTADESSSTAYMQLSSLASEDSAVYFCARRETTTVGRYYYAMDYWG

QGTTVTVSSGGGGSGGGGSGGGGSDIQLTQSPASLAVSLGQRATISCKASQ

SVDYDGDSYLNWYQQIPGQPPKWYDASNLVSGIPPRFSGSGSGTDFTLNIH

PVEKVDAATYHCQQSTEDPWTFGGGTKLEIK.

(9) an alpha strand comprising a V-set domain of BTNL3 linked by a charge polarized core domain to a portion of the extracellular domain of alpha CD19 (αCD19) and a beta strand comprising a V-set domain of BTNL8 linked by a charge polarized core domain to a portion of the antibody binding domain directed to CD19. Illustrative alpha and beta strands have the following amino acid sequences:

Alpha Strand (SEQ ID NO: 41)

<u>CCGCCACCMEFGLSWVFLVAIIKGVQC</u>QWQVTGPGKFVQALVGEDAVFSCS

LFPETSAEAMEVRFFRNQFHAVVHLYRDGEDWESKQMPQYRGRTEFVKDSI

AGGRVSLRLKNITPSDIGLYGCWFSSQIYDEEATWELRVAALGSLPLISIV

GYVDGGIQLLCLSSGWFPQPTAKWKGPQGQDLSSDSRANADGYSLYDVEIS

IIVQENAGSILCSIHLAEQSHEVESKVLIGETFFQPSPWRLAS<u>EPKSCDKT</u>

<u>HTCPPCPAPELLGGPSVFLFPPKPKDTLMISRTPEVTCVVVDVSHEDPEVK</u>

<u>FNWYVDGVEVHNAKTKPREEQYNSTYRVVSVLTVLHQDWLNGKEYKCKVSN</u>

<u>KALPAPIEKTISKAKGQPREPQVYTLPPSRDELTKNQVSLYCLVKGFYPSD</u>

<u>IAVEWESNGQPENNYKTTPPVLDSDGSFFLYSKLTVDKSRWQQGNVFSCSV</u>

<u>MHEALHNHYTQKSLSLSPGK</u>GGGSQVQLQQSGAELVRPGSSVKISCKASGY

AFSSYWMNWVKQRPGQGLEWIGQIWPGDGDTNYNGKFKGKATLTADESSST

AYMQLSSLASEDSAVYFCARRETTTVGRYYYAMDYWGQGTTVTVSSGGGGS

GGGGSGGGGSDIQLTQSPASLAVSLGQRATISCKASQSVDYDGDSYLNWYQ

QIPGQPPKLLIYDASNLVSGIPPRFSGSGSGTDFTLNIHPVEKVDAATYHC

QQSTEDPWTFGGGTKLEIK.

Beta Strand (SEQ ID NO: 42)

<u>CCGCCACCMEFGLSWVFLVAIIKGVQC</u>QWQVFGPDKPVQALVGEDAAFSCF

LSPKTNAEAMEVRFFRGQFSSVVHLYRDGKDQPFMQMPQYQGRTKLVKDSI

AEGRISLRLENITVLDAGLYGCRISSQSYYQKAIWELQVSALGSVPLISIT

GYVDRDIQLLCQSSGWFPRPTAKWKGPQGQDLSTDSRTNRDMHGLFDVEIS

LTVQENAGSISCSMRHAHLSREVESRVQIGDTFFEPISWHLATK<u>EPKSCDK</u>

<u>THTCPPCPAPELLGGPSVFLFPPKPKDTLMISRTPEVTCVVVDVSHEDPEV</u>

<u>KFNWYVDGVEVHNAKTKPREEQYNSTYRVVSVLTVLHQDWLNGKEYKCKVS</u>

<u>NKALPAPIEKTISKAKGQPREPQVYTLPPSRDELTKNQVSLTCLVKGFYPS</u>

<u>DIAVEWESNGQPENNYKTTPPVLDSDGSFFLTSKLTVDKSRWQQGNVFSCS</u>

<u>VMHEALHNHYTQKSLSLSPGK</u>GGGSQVQLQQSGAELVRPGSSVKISCKASG

YAFSSYWMNWVKQRPGQGLEWIGQIWPGDGDTNYNGKFKGKATLTADESSS

TAYMQLSSLASEDSAVYFCARRETTTVGRYYYAMDYWGQGTTVTVSSGGGG

SGGGGSGGGGSDIQLTQSPASLAVSLGQRATISCKASQSVDYDGDSYLNWY

QQIPGQPPKLLIYDASNLVSGIPPRFSGSGSGTDFTLNIHPVEKVDAATYH

CQQSTEDPWTFGGGTKLEIK.

(10) an alpha strand comprising a V-set domain of mBTNL1 linked by a charge polarized core domain to a portion of the extracellular domain of alpha CD19 (αCD19) and a beta strand comprising a V-set domain of mBTNL6 linked by a charge polarized core domain to a portion of the antibody binding domain directed to CD19. Illustrative alpha and beta strands have the following amino acid sequences:

Alpha Strand (SEQ ID NO: 43)

<u>CCGCCACC</u><u>MEFGLSWVFLVAIIKGVQC</u>EVSWFSVKGPAEPITVLLGTEATLPCQLSPE

QSAARMHIRWYRAQPTPAVLVFHNGQEQGEVQMPEYRGRTQMVRQAIDMGSVALQ

IQQVQASDDGLYHCQFTDGFTSQEVSMELRVIGLGSAPLVHMTGPENDGIRVLCSSS

GWFPKPKVQWRDTSGNMLLSSSELQTQDREGLFQVEVSLLVTDRAIGNVICSIQNPM

YDQEKSKAILLPEPFFPKTCPWKGSGSDEGGEDG<u>VPKDCGCKPCICTVPEVSSVPISPP</u>

-continued

```
FPKDVLTITLTPKVTCVVVDISKDDPEVQFSWFVDDVEVHTAQTQPREDYNSTFRSV
SELPIMHQDWLNGKEFKCRVNSAAFPAPIEKTISKTKGRPKAPQVTTIPPPKEQMAKD
KVSLTCMITDFFPEDITVEWQWNGQPAENYKNTQPIMDTDGSYFVYSKLNVQKSNW
EAGNTFTCSVLHEGLHNHHTEKSLSHSPGK
```
RKGGKRGSGSEVQLQQSGAELVRPGTS
VKLSCKVSGDTITFYYMHFVKQRPGQGLEWIGRIDPEDESTKYSEKFKNKATLTADT
SSNTAYLKLSSLTSEDTATYFCIYGGYYFDYWGQGVMVTVSSGGGGSGGGGSGGGG
SDIQMTQSPASLSTSLGETVTIQCQASEDIYSGLAWYQQKPGKSPQLLIYGASDLQDG
VPSRFSGSGSGTQYSLKITSMQTEDEGVYFCQQGLTYPRTFGGGTKLELK.

Beta Strand (SEQ ID NO: 44)
<u>CCGCCACC</u><u>MEFGLSWVFLVAIIKGVQC</u>EQLPEYSQRTSLVKEQFHQGTAAVRILNVQ
APDSGIYICHFKQGVFYEEAILELKVAAMGSVPEVYIKGPEDGGVCVVCITSGWYPEP
QVHWKDSRGEKLTASLEIHSEDAQGLFRTETSLVVRDSSVRNVTCSTFNPILGQEKA
MAMFLPEPFFPKVSPWKPGSGSDEGGEDG
```
VPRDCGCKPCICTVPEVSSVFIFPPNFKD
VLTITLTPKVTCVVVDISKDDPEVQFSWFVDDVEVHTAQTQPREDQFNSTFRSVSELPI
MHQDWLNGKEFKCRVNSAAFPAPIEKTISKTKGRPKAPQVTTIPPPKEQMAKDKVSL
TCMITDFFPEDITVEWQWNGQPAENYKNTQPIMDTDGSYFVYSKLNVQKSNWEAGN
TFTCSVLHEGLHNHHTEKSLSHSPGK
```
RKGGKRGSGSEVQLQQSGAELVRPGTSVKLSC
KVSGDTITFYYMHFVKQRPGQGLEWIGRIDPEDESTKYSEKFKNKATLTADTSSNTA
YLKLSSLTSEDTATYFCIYGGYYFDYWGQGVMVTVSSGGGGSGGGGSGGGGSDIQM
TQSPASLSTSLGETVTIQCQASEDIYSGLAWYQQKPGKSPQLLIYGASDLQDGVPSRFS
GSGSGTQYSLKITSMQTEDEGVYFCQQGLTYPRTFGGGTKLELK.

(11) an alpha strand comprising a V-set domain of mBTNL1 linked by a charge polarized core domain to a portion of the extracellular domain of alpha CD19 (αCD19) and a beta strand comprising a V-set domain of mBTNL6 linked by a charge polarized core domain to a portion of the antibody binding domain directed to CD19. Illustrative alpha and beta strands have the following amino acid sequences:

Alpha Strand (SEQ ID NO: 45)
<u>CCGCCACC</u><u>MEFGLSWVFLVAIIKGVQC</u>EVSWFSVKGPAEPITVLLGTEATLPCQLSPE
QSAARMHIRWYRAQPTPAVLVFHNGQEQGEVQMPEYRGRTQMVRQAIDMGSVALQ
IQQVQASDDGLYHCQFTDGFTSQEVSMELRVIGLGSAPLVHMTGPENDGIRVLCSSS
GWFPKPKVQWRDTSGNMLLSSSELQTQDREGLFQVEVSLLVTDRAIGNVICSIQNPM
YDQEKSKAILLPEPFFPKTCPWKGSGSDEGGEDG
```
VPRDCGCKPCICTVPEVSSVFIFPP
KPKDVLTITLTPKVTCVVVDISKDDPEVQFSWFVDDVEVHTAQTQPREEQFNSTFRSV
SELPIMHQDWLNGKEFKCRVNSAAFPAPIEKTISKTKGRPKAPQVYTIFPPKEQMAKD
KVSLTCMITDFFPEDITVEWQWNGQPAENYKNTQPIMDTDGSYFVYSKLNVQKSNW
EAGNTFTCSVLHEGLHNHHTEKSLSHSPGK
```
RKGGKRGSGSDIQMTQSPASLSTSLGET
VTIQCQASEDIYSGLAWYQQKPGKSPQLLIYGASDLQDGVPSRFSGSGSGTQYSLKIT
SMQTEDEGVYFCQQGLTYPRTFGGGTKLELKGGGGSGGGGSGGGGSEVQLQQSGAE
LVRPGTSVKLSCKVSGDTITFYYMHFVKQRPGQGLEWIGRIDPEDESTKYSEKFKNK
ATLTADTSSNTAYLKLSSLTSEDTATYFCIYGGYYFDYWGQGVMVTVSS.

Beta Strand (SEQ ID NO: 46)
<u>CCGCCACC</u><u>MEFGLSWVFLVAIIKGVQC</u>EQLPEYSQRTSLVKEQFHQGTAAVRILNVQ
APDSGIYICHFKQGVFYEEAILELKVAAMGSVPEVYIKGPEDGGVCVVCITSGWYPEP -continued

QVHWKDSRGEKLTASLEIHSEDAQGLFRTETSLVVRDSSVRNVTCSTFNPILGQEKA

MAMFLPEPFFPKVSPWKPGSGSDEGGEDGVPRDCGCKPCICTVPEVSSVFIFPPKPKD

VLTITLTPKVTCVVVDISKDDPEVQFSWFVDDVEVHTAQTQPREEQFNSTFRSVSELPI

MHQDWLNGKEFKCRVNSAAFPAPIEKTISKTKGRPKAPQVYTIPPPKEQMAKDKVSL

TCMITDFFPEDITVEWQWNGQPAENYKNTQPIMDTDGSYFVYSKLNVQKSNWEAGN

TFTCSVLHEGLHNHHTEKSLSHSPGIRKGGKRGSGSDIQMTQSPASLSTSLGETVTIQC

QASEDIYSGLAWYQQKPGKSPQLLIYGASDLQDGVPSRFSGSGSGTQYSLKITSMQTE

DEGVYFCQQGLTYPRTFGGGTKLELKGGGGSGGGGSGGGGSEVQLQQSGAELVRPG

TSVKLSCKVSGDTITFYYMHFVKQRPGQGLEWIGRIDPEDESTKYSEKFKNKATLTA

DTSSNTAYLKLSSLTSEDTATYFCIYGGYYFDYWGQGVMVTVSS.

In embodiments, the charge polarized core domain of the above-mentioned illustrative strands (i.e., BTNL1-αCD19, BTNL3-αCD19, BTNL6-αCD19, BTNL8-αCD19, BTNL3-αPSMA, and BTNL8-αPSMA) comprises a polypeptide linker, optionally selected from a flexible amino acid sequence, IgG hinge region, or antibody sequence. In embodiments, the linker is a synthetic linker, optionally PEG. In embodiments, the linker comprises the hinge-CH2-CH3 Fc domain derived from IgG1, optionally human IgG1. In embodiments, the linker comprises the hinge-CH2-CH3 Fc domain derived from IgG4, optionally human IgG4.

In embodiments, each of the above-mentioned illustrative strands (i.e., BTNL3-Alpha-vTIGIT, BTNL8-Beta-vTIGIT, BTNL3-Alpha-vLAG3, BTNL8-Beta-vLAG3, TIGIT-Alpha-vBTNL3, TIGIT-Beta-vBTNL8, LAG3-Alpha-vBTNL3, LAG3-Beta-vBTNL8, PD 1-Alpha-vBTNL3, PD1-Beta-vBTNL8, BTNL3-αCD19, BTNL8-αCD19, BTNL3-αPSMA, and BTNL8-αPSMA) comprises an illustrative core domain having the following amino acid sequence:

(SEQ ID NO: 34)

SKYGPPCPPCPAPEFLGGPSVFLFPPKPKDQLMISRTPEVTCVVVDVSQED

PEVQFNWYVDGVEVHNAKTKPREEQFNSTYRVVSVLTVLHQDWLSGKEYKC

KVSSKGLPSSIEKTISNATGQPREPQVYTLPPSQEEMTKNQVSLTCLVKGF

YPSDIAVEWESNGQPENNYKTTPPVLDSDGSFFLYSRLTVDKSRWQEGNVF

SCSVLHEALHNHYTQKSLSLSLGK

Since one end of each strand comprises a targeting sequence (e.g., the portion of the extracellular domain of TIGIT, LAG-3, and PD-1 which is capable of binding to its ligand/receptor on the surface of a cancer cell), the heterochimeric proteins of this Example are particularly useful in the treatment of cancers. Here, the targeting sequence localizes the BTNL3/8 heterodimer to the surface of a cancer cell.

Figure 19:
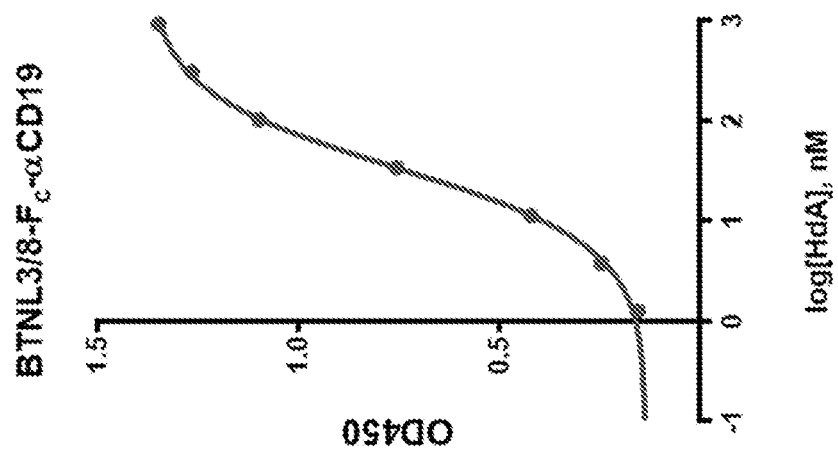
FIG. 19 shows an ELISA assay that was developed to demonstrate specific detection of the BTNL3/8-Fc-αCD19 heterodimer protein.
Figure 20:
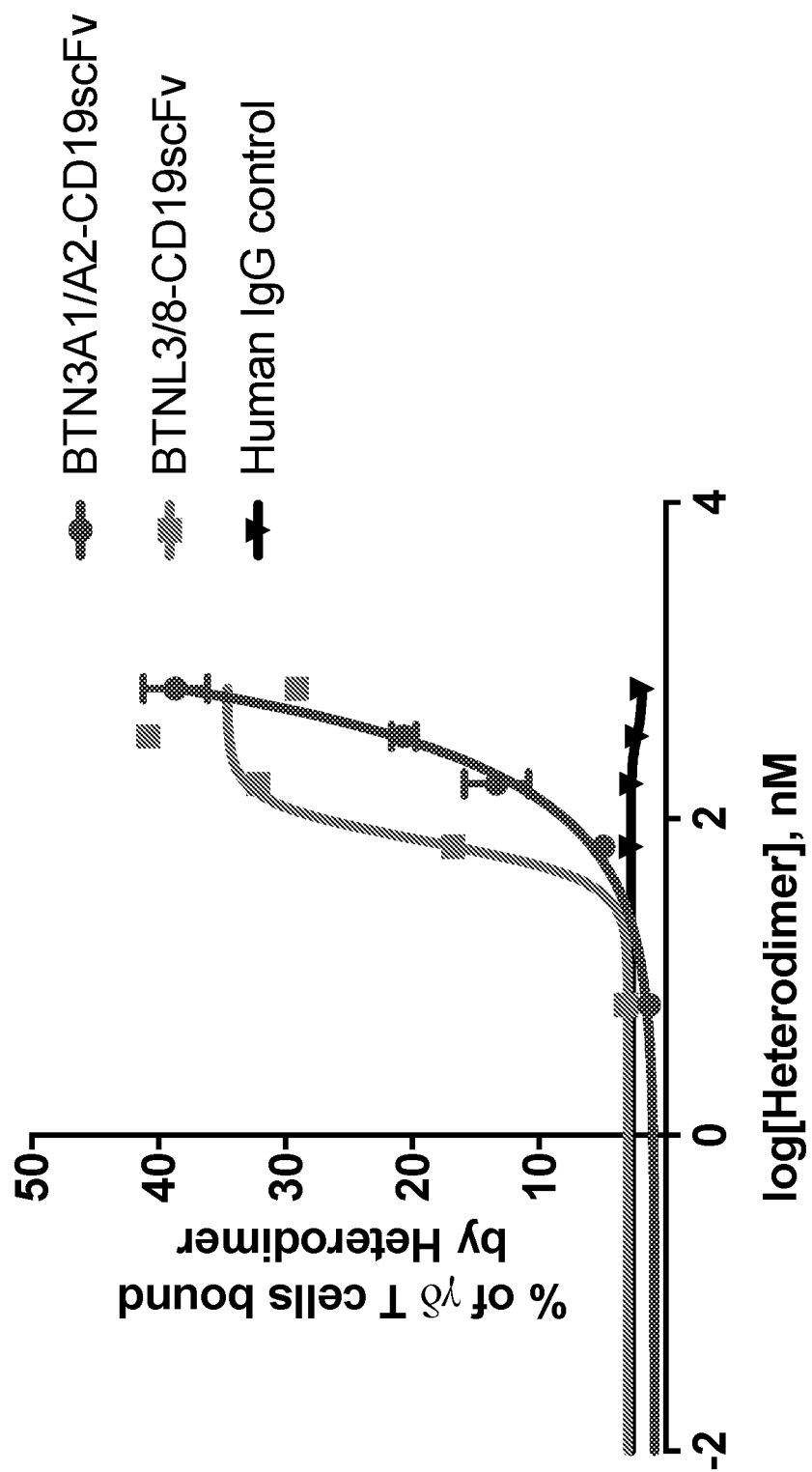
FIG. 20 is a graph showing the percentage of binding of the BTNL3/8-Fc-αCD19scFv and BTN3A1/A2-CD19scFv heterodimer proteins to isolated human γδTCR T cells.

In this example, several heterodimeric proteins were generated based on the methods disclosed herein. For example, the following heterodimeric proteins were constructed: (1) a heterodimeric protein comprising BTNL3/8 linked by a charge polarized core domain to αCD19; (2) a heterodimeric protein comprising BTNL3/8 linked by a charge polarized core domain to αPSMA; (3) a heterodimeric protein comprising BTNL3/8 linked by a charge polarized core domain to vTIGIT; (4) a heterodimeric protein comprising BTNL3/8 linked by a charge polarized core domain to vLAG3; (5) a heterodimeric protein comprising LAG3 linked by a charge polarized core domain to vBTNL3/8, (6) a heterodimeric protein comprising PD1 linked by a charge polarized core domain to vBTNL3/8, (7) a heterodimeric protein comprising BTNL1/6 linked by a charge polarized core domain to αCD19; and (8) a heterodimeric protein comprising mBTNL1/6 linked by a charge polarized core domain to αCD19.

Several assays were performed to characterize the generated heterodimers and demonstrate their utility in the treatment of cancers.

FIG. 16 shows an ELISA assay that was developed to demonstrate specific detection of the BTNL3/8-Fc-αCD19 heterodimer protein. Microtiter plates were coated overnight with decreasing concentrations of the BTNL3/8-Fc-αCD19 heterodimeric protein (heterodimeric protein; HdA), and then blocked and incubated with CD19-His recombinant protein. An HRP-conjugated anti-His monoclonal antibody was used for detection of the HdA-protein complex. As shown in FIG. 16, the presence of the BTNL3/8-Fc-αCD19 heterodimer was observed through capture with CD19-His recombinant protein, and detection with an HRP-conjugated anti-His monoclonal antibody. FIG. 17 is a graph showing the percentage of binding of the BTNL3/8-Fc-αCD19 heterodimer protein to isolated human γδTCR T cells. Increasing amounts of the BTNL3/8-Fc-αCD19 heterodimer protein were co-incubated with $10^6$ human γδTCR T cells freshly isolated from a healthy donor, followed by counter staining with a cocktail of antibodies, including anti-BTNL3/8. Graphed data is pre-gated on γδTCR+ T cells. The results of FIG. 17 show that the BTNL3/8-Fc-αCD19 heterodimer protein binds to human γδTCR T cells. FIG. 18 are graphs showing binding of the BTNL3/8-Fc-αCD19 heterodimer protein to B-cell lines. B-cell lines with and without CD19 expression were co-incubated with increasing amounts of the BTNL3/8-Fc-αCD19 heterodimer protein, then stained with a cocktail of antibodies for Flow Cytometry analysis. As shown in FIG. 18, the BTNL3/8-Fc-αCD19 heterodimer protein binds to Toledo cells (e.g., at about 10 μg/ml). Minimal binding was observed to Raji and SR cells. The results of this experiment demonstrate the BTNL3/8-Fc-αCD19 heterodimer protein binds to B-cells in a site specific manner FIG. 19 is a graph showing the ability of the BTNL3/8-Fc-αCD19 heterodimer protein to tether γδ T-cells to Raji cells. In these experiments, γδ T-cells were labeled with green cell tracker dye, and Raji tumor cells were labeled with deep red cell tracker dye, and then the labeled γδ T-cells and Raji tumor cells were co-cultured in the presence of the BTNL3/8-Fc-CD19. Flow cytometry was used to assess the ability of the BTNL3/8-Fc-αCD19 heterodimer protein to tether γδ T-cells to Raji cells. As shown in FIG. 19, the BTNL3/8-Fc-αCD19 heterodimer protein tethered the γδ T-cells to Raji cells. FIG. 20 is a graph showing the ability of the BTNL3/8-Fc-αCD19 heterodimer protein to tether γδ T-cells to Toledo cells. In these experiments, γδ T-cells were labeled with αCD3(PE-Cy7) antibody, and Toledo tumor cells were labeled with αCD20 (BV650) antibody. The cells were then co-cultured in the presence of the BTNL3/8-Fc-αCD19 heterodimer protein or control proteins (i.e., Igg4, BTNL3-Fc), and then analyzed using flow cytometry. As shown in FIG. 20, the BTNL3/8-Fc-αCD19 heterodimer protein tethered the γδ T-cells to Toledo cells.

Figure 21:
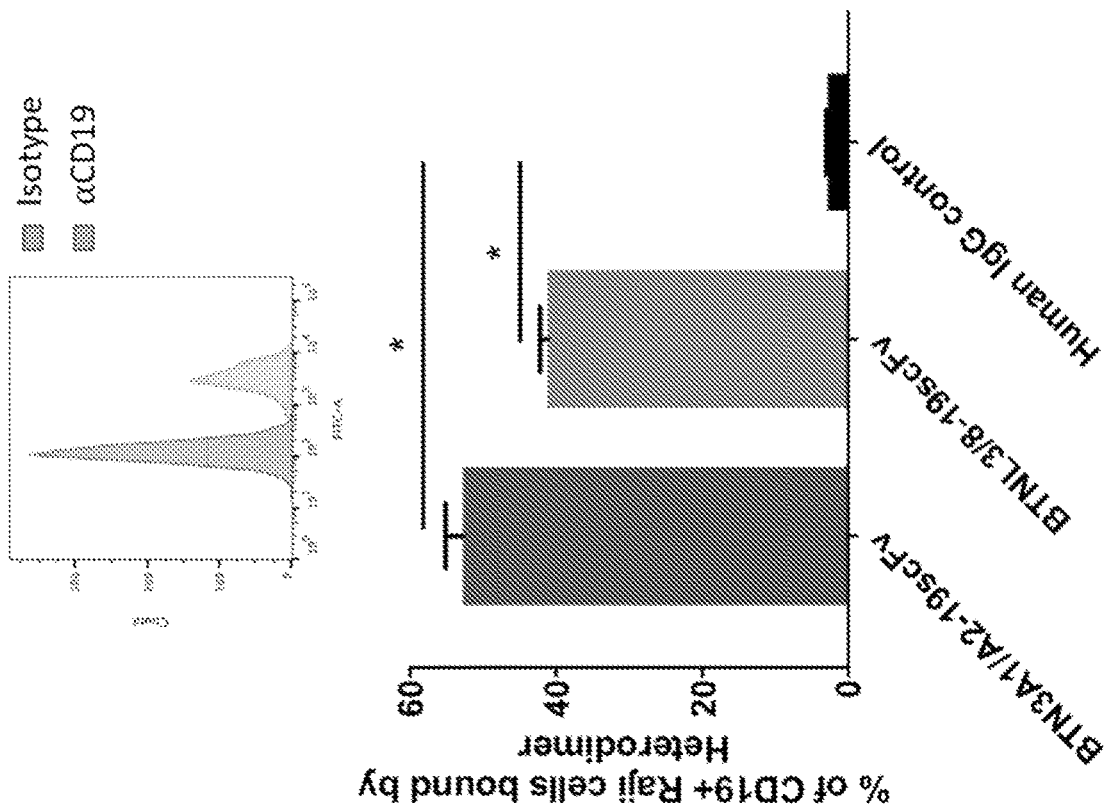
FIG. 21 shows graphs illustrating the binding of the BTNL3/8-Fc-CD19scFv and BTN3A1/A2-CD19scFv heterodimer proteins BTNL3/8-Fc-αCD19 heterodimer protein to CD19+ Raji B-cells.
Figure 22:
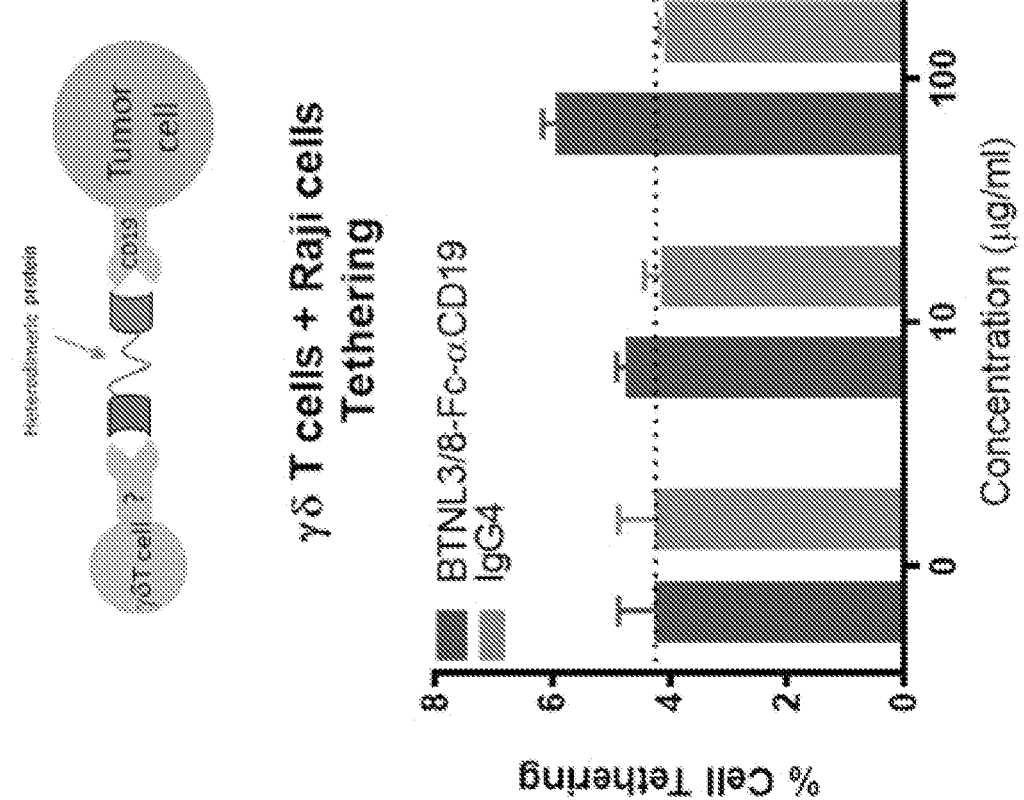
FIG. 22 is a graph showing the ability of the BTNL3/8-Fc-αCD19 heterodimer protein to tether γδ T-cells to CD19+ Raji cells.
Figure 23:
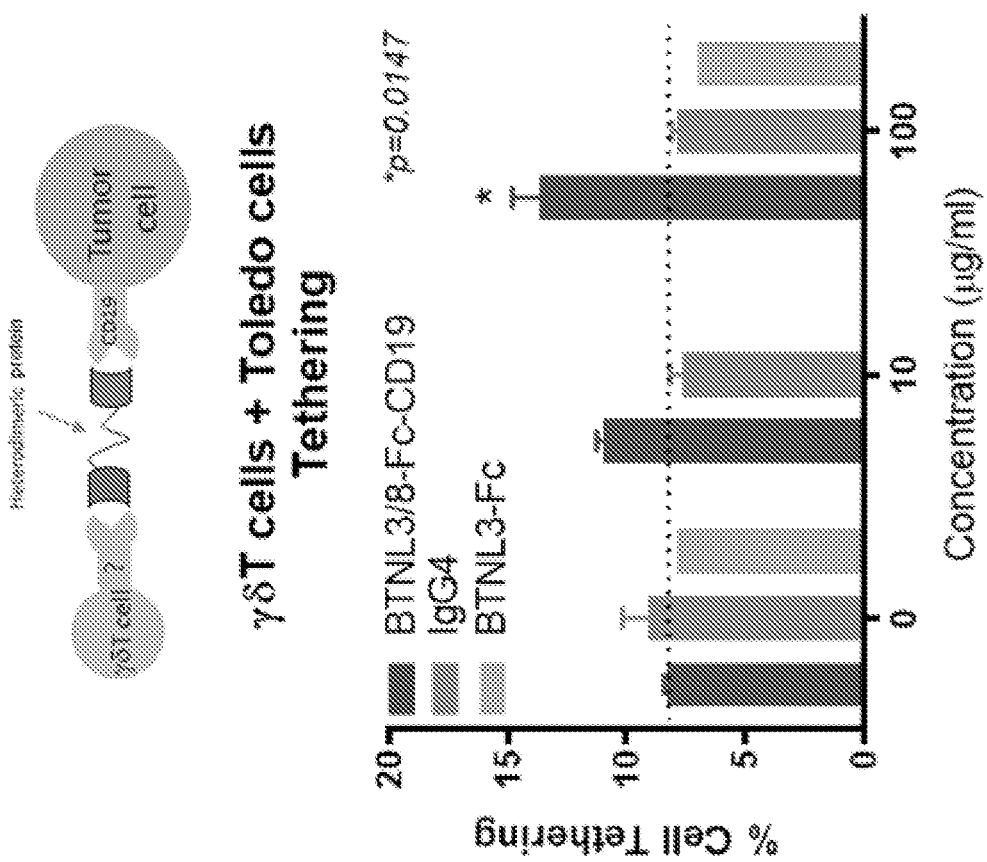
FIG. 23 is a graph showing the ability of the BTNL3/8-Fc-αCD19 heterodimer protein to tether γδ T-cells to CD19+ Toledo cells.

FIG. 21 shows an ELISA assay that was developed to demonstrate specific detection of the BTNL3/8-Fc-αPSMA heterodimer protein. In these experiments, microtiter plates were coated overnight with decreasing concentrations of the BTNL3/8-Fc-αPSMA heterodimer protein (heterodimeric protein HdA), and then blocked, and incubated with a PSMA-His recombinant protein. An HRP-conjugated anti-His monoclonal antibody was used for detection of the HdA-protein complex. As shown in FIG. 21, the presence of the BTNL3/8-Fc-αPSMA heterodimer was observed through capture with the PSMA-His recombinant protein, and detection with an HRP-conjugated anti-His monoclonal antibody. FIG. 22 is a graph showing the percentage of binding of the BTNL3/8-Fc-αPSMA heterodimer protein to isolated human γδTCR T cells. Increasing amounts of the BTNL3/8-Fc-αPSMA heterodimer protein were co-incubated with $10^6$ human γδTCR T cells freshly isolated from a healthy donor, followed by counter staining with a cocktail of antibodies, including anti-BTNL3/8. Graphed data is pre-gated on γδTCR+ T cells. The results of FIG. 22 show that the BTNL3/8-Fc-αPSMA heterodimer protein binds to human γδTCR T cells. FIG. 23 are graphs showing binding of the BTNL3/8-Fc-αPSMA heterodimer protein to prostate cancer cell lines. Prostate cancer cell lines with (i.e., LNCap) and without (PC3) PSMA expression were co-incubated with increasing amounts of the BTNL3/8-Fc-αPSMA heterodimer protein, then stained with a cocktail of antibodies for flow cytometry analysis. As shown in FIG. 23, the BTNL3/8-Fc-αPSMA heterodimer protein binds to LNCap cells that express PSMA in a dose dependent manner but not to PC3 cells, demonstrating the utility of the heterodimeric proteins disclosed herein in the treatment of cancers.

Figure 24:
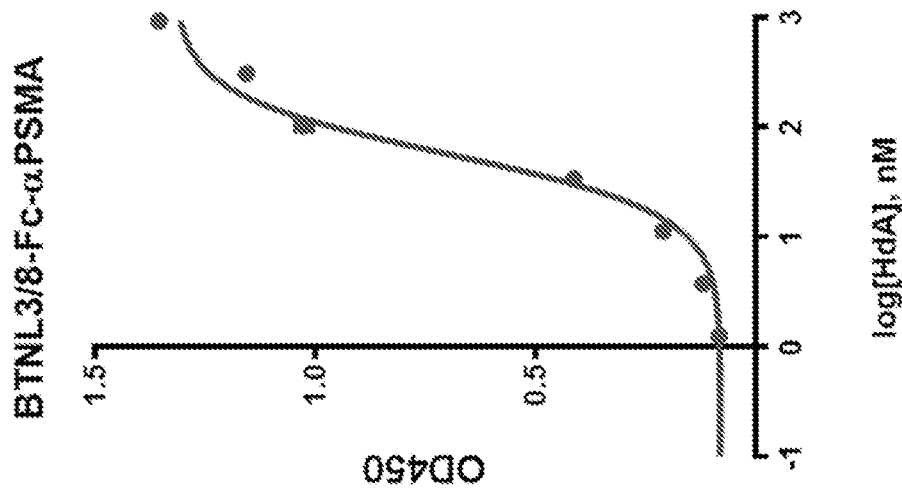
FIG. 24 shows an ELISA assay that was developed to demonstrate specific detection of the BTNL3/8-Fc-αPSMA heterodimer protein.

FIG. 24 are graphs showing binding of the BTNL3/8-Fc-vTIGIT heterodimer protein to isolated human γδTCR T cells. The BTNL3/8-Fc-vTIGIT heterodimer protein was co-incubated with $10^6$ human γδTCR T cells freshly isolated from a healthy donor, and counter stained with a cocktail of antibodies, including an anti-BTNL3/8 antibody. The results show that the BTNL3/8-Fc-vTIGIT heterodimer protein binds to γδTCR T cells.

Figure 25:
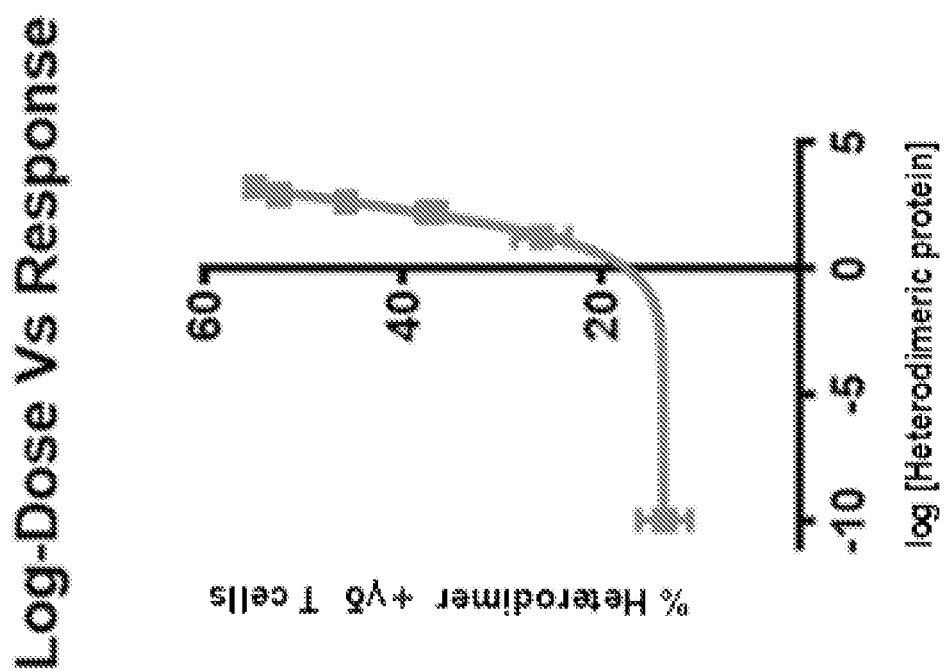
FIG. 25 is a graph showing the percentage of binding of the BTNL3/8-Fc-αPSMA heterodimer protein to isolated human γδTCR T cells.

FIG. 25 are graphs showing binding of the BTNL3/8-Fc-vLAG3 heterodimer protein to isolated human γδTCR T cells. The BTNL3/8-Fc-vLAG3 heterodimer protein was co-incubated with $10^6$ human γδTCR T cells freshly isolated from a healthy donor, and counter stained with a cocktail of antibodies, including an anti-BTNL3/8 antibody. The results show that the BTNL3/8-Fc-vLAG3 heterodimer protein binds to γδTCR T cells.

Figure 26:
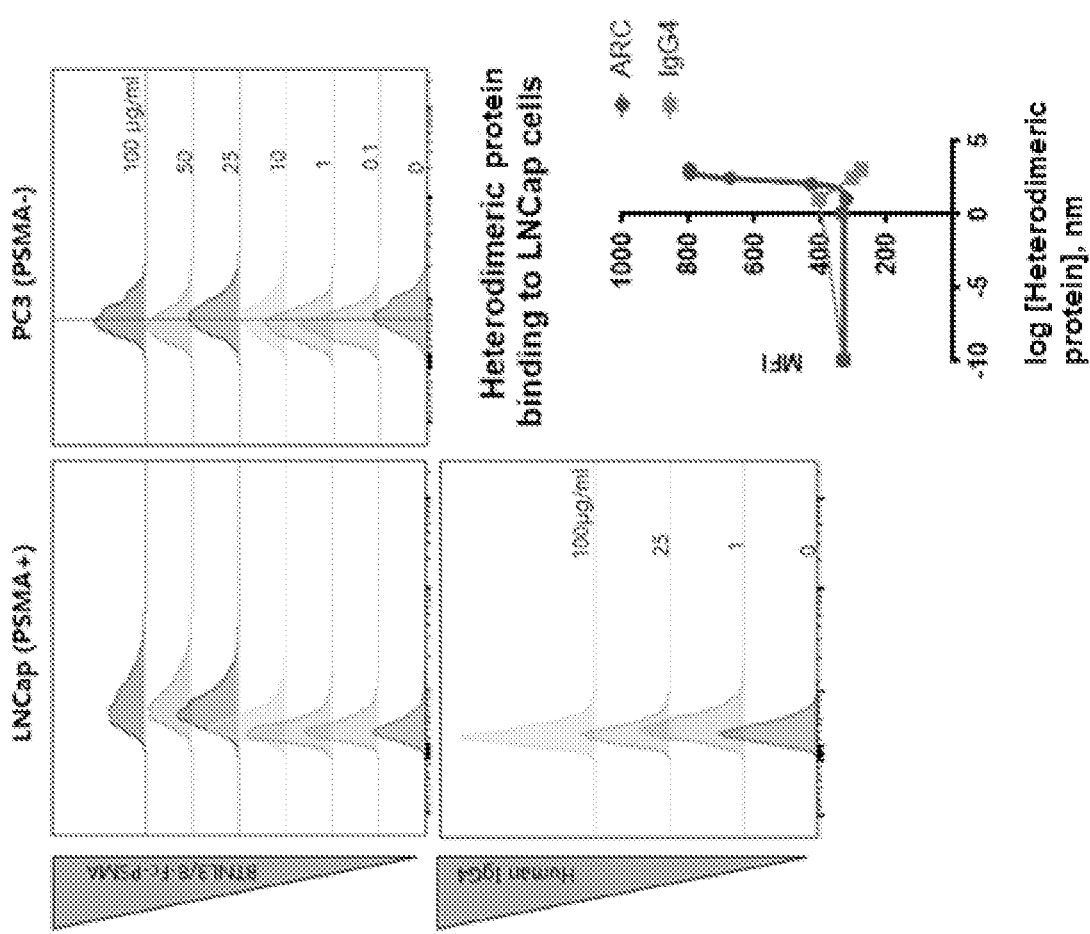
FIG. 26 shows the flow cytometry profiles and graphs illustrating the binding of the BTNL3/8-Fc-αPSMA heterodimer protein to prostate cancer cell lines.
Figure 27:
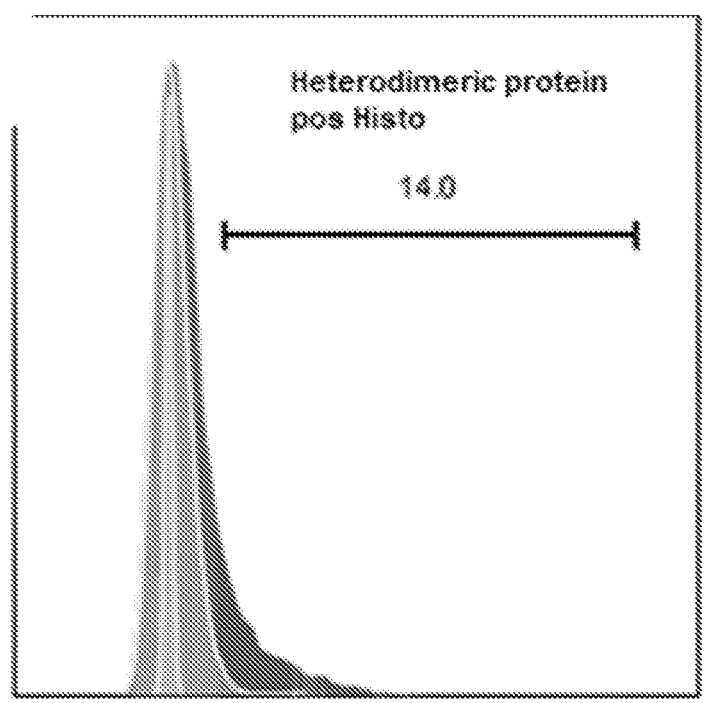
FIG. 27 shows the flow cytometry profiles and graphs illustrating the binding of the BTNL3/8-Fc-vTIGIT heterodimer protein to isolated human γδTCR T cells.
Figure 27:
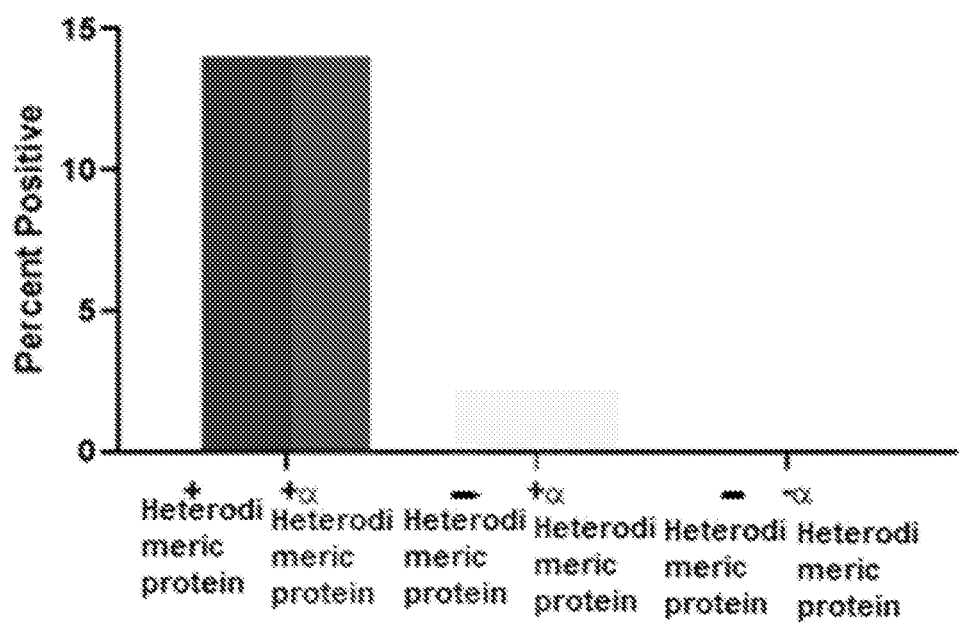

FIG. 26 is a Western blot showing detection of the TIGIT-Fc-vBTNL3/8 heterodimer protein under different conditions using anti-human TIGIT antibody (left), anti-human Fc antibody (middle), or anti-human BTNL8 antibody (right). FIG. 27 are graphs showing binding of the TIGIT-Fc-vBTNL3/8 heterodimer protein to isolated human γδTCR T cells. The TIGIT-Fc-vBTNL3/8 heterodimer protein was co-incubated with $10^6$ human γδTCR T cells freshly isolated from a healthy donor, and counter stained with a cocktail of antibodies, including an anti-TIGIT antibody. The results show that the TIGIT-Fc-vBTNL3/8 heterodimer protein binds to γδTCR T cells.

Figure 28:
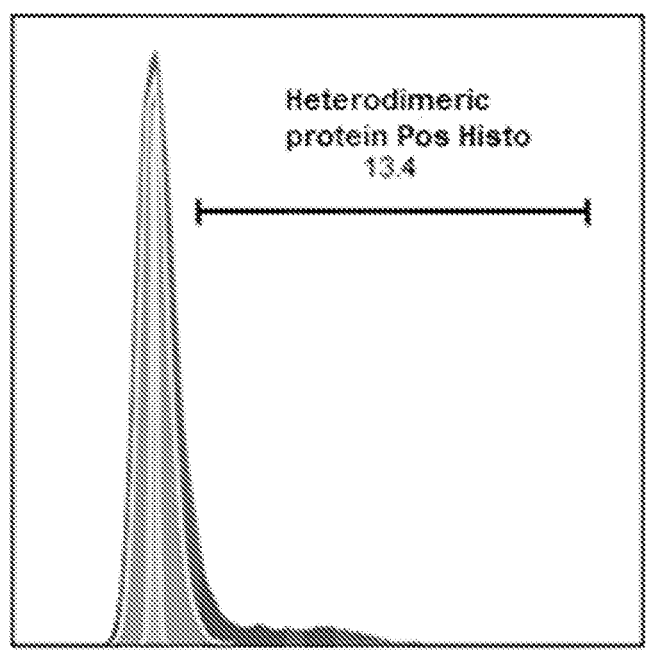
FIG. 28 are graphs showing binding of the BTNL3/8-Fc-vLAG3 heterodimer proteinto isolated human γδTCR T cells.
Figure 28:
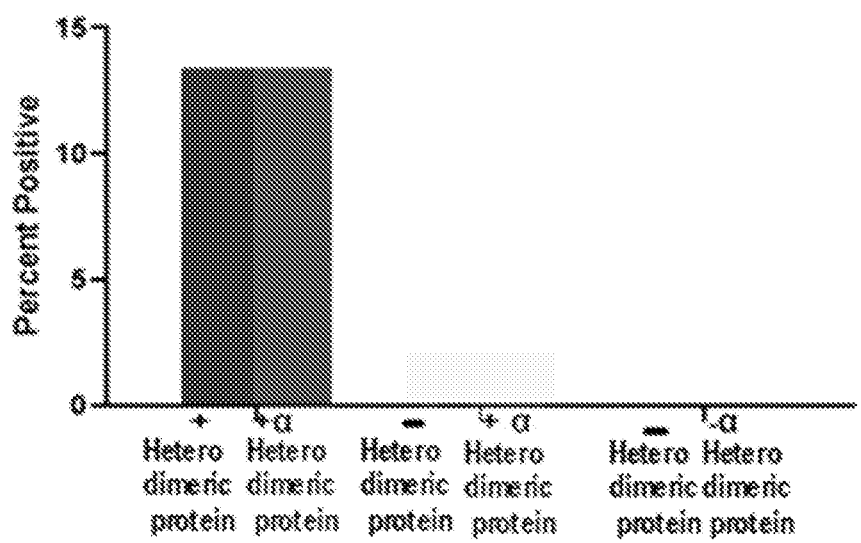
Figure 29:
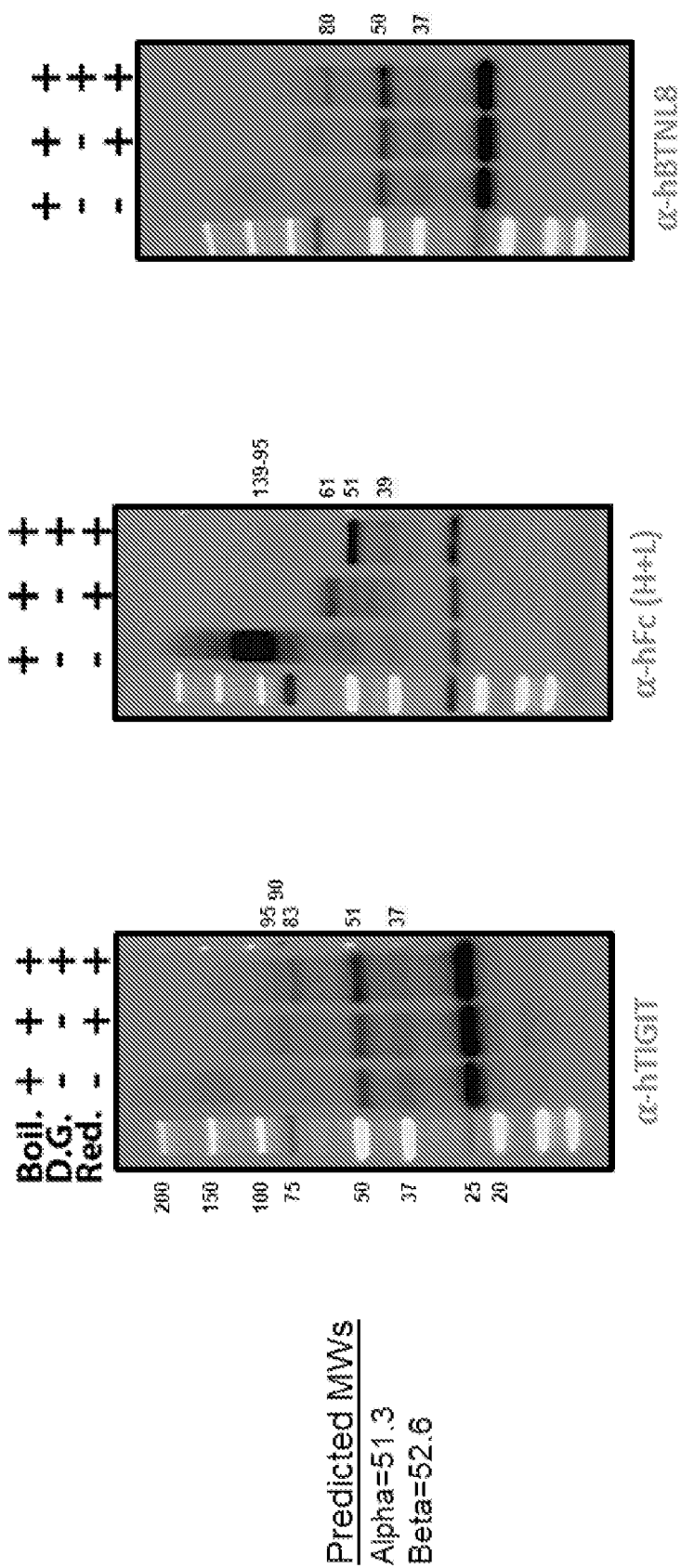
FIG. 29 shows Western blots illustrating detection of the TIGIT-Fc-vBTNL3/8 heterodimer protein under different conditions using anti-human TIGIT antibody (left), anti-human Fc antibody (middle), or anti-human BTNL8 antibody (right). "Biol" is boiled, is "DG" is de-glycosylated and "Red" is reducing conditions.
Figure 30:
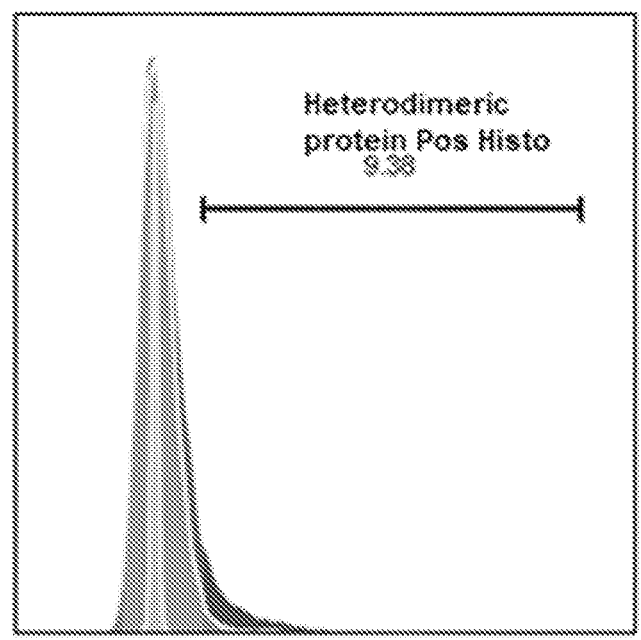
FIG. 30 shows the flow cytometry profiles and graphs illustrating the binding of the TIGIT-Fc-vBTNL3/8 heterodimer protein to isolated human γδTCR T cells.
Figure 30:
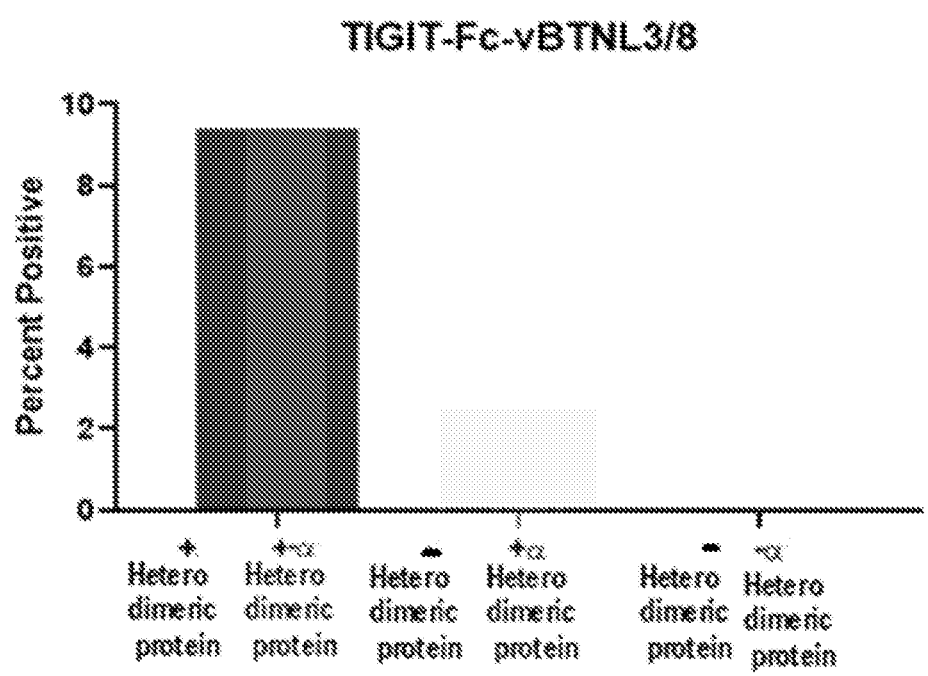
Figure 31:
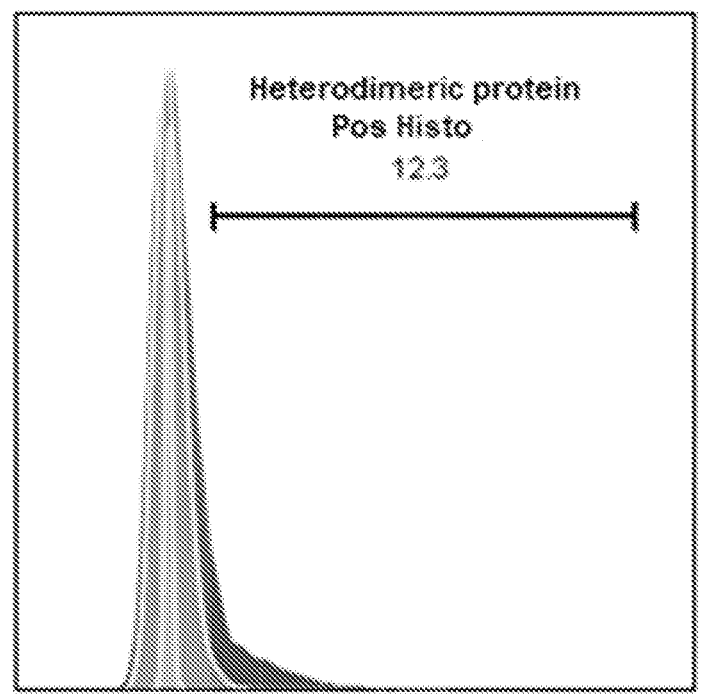
FIG. 31 shows the flow cytometry profiles and graphs illustrating the binding of the LAG3-Fc-vBTNL3/8 heterodimer protein to isolated human γδTCR T cells.
Figure 31:
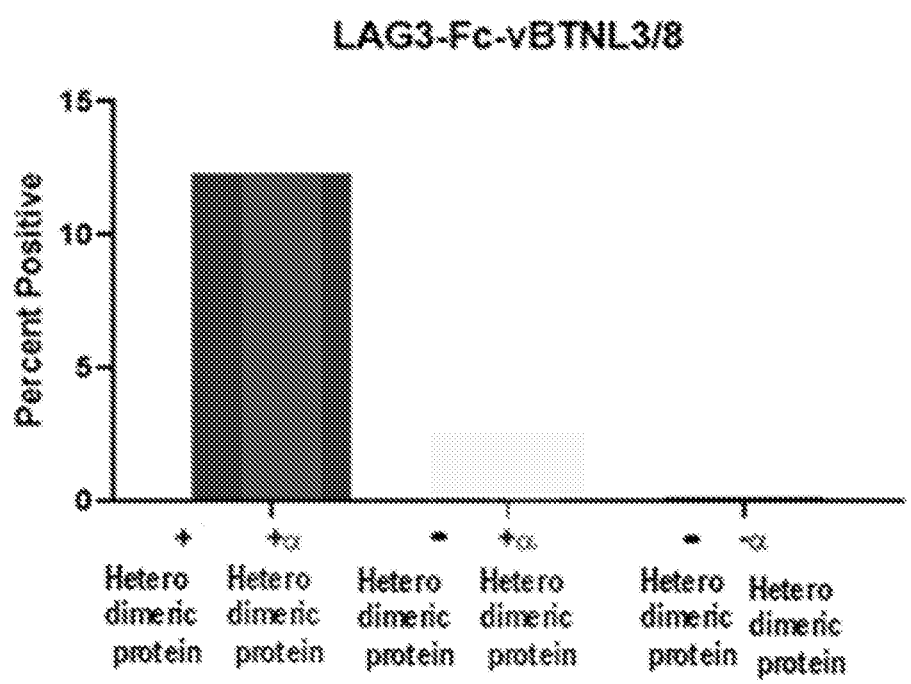

FIG. 28 are graphs showing binding of the LAG3-Fc-vBTNL3/8 heterodimer protein to isolated human γδTCR T cells. The LAG3-Fc-vBTNL3/8 heterodimer protein was co-incubated with $10^6$ human γδTCR T cells freshly isolated from a healthy donor, and counter stained with a cocktail of antibodies, including an anti-LAG3 antibody. The results show that the LAG3-Fc-vBTNL3/8 heterodimer protein binds to γδTCR T cells.

The experiments in this example demonstrate, inter alia, the utility of the heterodimeric proteins disclosed herein to treat cancer in a subject.

Sequences of other heterodimer proteins of the current technology are as follows:

The sequence of an illustrative core domain is provided below:

```
                                            (SEQ ID NO: 15)
SKYGPPCPPCPAPEFLGGPSVFLFPPKPKDQLMISRTPEVTCVVVDVSQED

PEVQFNWYVDGVEVHNAKTKPREEQFNSTYRVVSVLTVLHQDWLSGKEYKC

KVSSKGLPSSIEKTISNATGQPREPQVYTLPPSQEEMTKNQVSLTCLVKGF

YPSDIAVEWESNGQPENNYKTTPPVLDSDGSFFLYSRLTVDKSRWQEGNVF

SCSVLHEALHNHYTQKSLSLSLGKIEGRMD
```

The sequence of an illustrative charge polarized core domain (positive-negative) is provided below:

```
                                            (SEQ ID NO: 16)
GSGSRKGGKRGSKYGPPCPPCPAPEFLGGPSVFLFPPKPKDQLMIS

RTPEVTCVVVDVSQEDPEVQFNWYVDGVEVHNAKTKPREE

QFNSTYRVVSVLTVLHQDWLSGKEYKCKVSSKGLPSSIEKTIS

NATGQPREPQVYTIPPSQEEMTKNQVSLTCLVKGFYPSDIAVE

WESNGQPENNYKTTPPVLDSDGSFFLYSRLTVDKSRWQEGNV

FSCSVLHEALHNHYTQKSLSLSLGKDEGGEDGSGS
```

The sequence of an illustrative charge polarized core domain (negative-positive) is provided below:

```
                                            (SEQ ID NO: 17)
GSGSDEGGEDGSKYGPPCPPCPAPEFLGGPSVFLFPPKPKDQLMI

SRTPEVTCVVVDVSQEDPEVQFNWYVDGVEVHNAKTKP

REEQFNSTYRVVSVLTVLHQDWLSGKEYKCKVSSKGLPSSIEKTI

SNATGQPREPQVYTLPPSQEEMTKNQVSLTCLVKGFYPSDIAVE

WESNGQPENNYKTTPPVLDSDGSFFLYSRLTVDKSRWQEG

NVFSCSVLHEALHNHYTQKSLSLSLGKRKGGKRGSGS
```

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present technology is not entitled to antedate such publication by virtue of prior invention.

As used herein, all headings are simply for organization and are not intended to limit the disclosure in any manner. The content of any individual section may be equally applicable to all sections.

What is claimed is:

1. A heterodimeric protein comprising:
   (a) a first domain comprising one or more butyrophilin family proteins selected from BTN3A1, BTN3A2, BTN2A1, BTNL3, and BTNL8, or fragments thereof that comprise the extracellular domain of the butyrophilin family proteins;
   (b) a second domain comprising a targeting domain, wherein the targeting domain is capable of binding to CD19 and selected from an antibody and a single-chain antibody (scFv); and
   (c) a linker that adjoins the first and second domain, the linker comprises:
      a peptide comprising negatively charged amino acid residues comprising the sequence DEGGED (SEQ ID NO: 13) or GSGSDEGGEDGS (SEQ ID NO: 14), and/or
      a peptide comprising positively charged amino acid residues comprising the sequence RKGGKR (SEQ ID NO: 11) or GSGSRKGGKRGS (SEQ ID NO: 12).

2. The heterodimeric protein of claim 1, wherein the heterodimeric protein comprises an alpha chain and a beta chain wherein the alpha chain and the beta chain each independently comprise (a) a first domain comprising the one or more butyrophilin family proteins, or fragments thereof that comprise the extracellular domain of the butyrophilin family proteins;
   (b) a second domain comprising the targeting domain; and
   (c) a linker that adjoins the first and second domain comprising:
      a peptide comprising negatively charged amino acid residues comprising the sequence DEGGED (SEQ ID NO: 13) or GSGSDEGGEDGS (SEQ ID NO: 14), and/or
      a peptide comprising positively charged amino acid residues comprising the sequence RKGGKR (SEQ ID NO: 11) or GSGSRKGGKRGS (SEQ ID NO: 12).

3. The heterodimeric protein of claim 2, wherein the alpha chain and the beta chain self-associate to form the heterodimer.

4. The heterodimeric protein of claim 2, wherein the first domain of the alpha chain and the beta chain comprise:
   (a) human BTNL3 and human BTNL8, respectively; or human BTNL8 and human BTNL3, respectively;
   (b) human BTN2A1 and human BTN3A1, respectively; or human BTN3A1 and human BTN2A1, respectively; or
   (c) human BTN3A1 and human BTN3A2, respectively; or human BTN3A2 and human BTN3A1, respectively.

5. The heterodimeric protein of claim 2, wherein the linker comprises:
   (a) a first charge polarized core domain adjoined to the first domain of alpha chain, optionally at the carboxy terminus, and
   (b) a second charge polarized core domain adjoined to the first domain of beta chain, optionally at the carboxy terminus.

6. The heterodimeric protein of claim 5, wherein the linker comprises the hinge-CH2-CH3 Fc domain derived from IgG1 or the hinge-CH2-CH3 Fc domain derived from IgG4.

7. The heterodimeric protein of claim 1, wherein the targeting domain is an antibody.

8. The heterodimeric protein of claim 1, wherein the targeting domain is a single-chain antibody (scFv).

9. The heterodimeric protein of claim 1, wherein the targeting domain is capable of binding a cancer cell.

10. The heterodimeric protein of claim 1, wherein the targeting domain comprises a polypeptide having an amino acid sequence of a polypeptide selected from SEQ ID NOs: 53, 54, 56 or 59.

11. The heterodimeric protein of claim 1, wherein the first domain comprises a polypeptide having at least 95% identity with the polypeptide selected from SEQ ID NOs: 49-52 or 102.

12. The heterodimeric protein of claim 1, wherein the peptide comprising positively charged amino acid residues comprises the sequence RKGGKR (SEQ ID NO: 11) or GSGSRKGGKRGS (SEQ ID NO: 12).

13. The heterodimeric protein of claim 1, wherein the peptide comprising negatively charged amino acid residues comprises the sequence DEGGED (SEQ ID NO: 13) or GSGSDEGGEDGS (SEQ ID NO: 14).

14. The heterodimeric protein of claim 1, wherein the heterodimeric protein is capable of forming a synapse between a gamma delta T cell and a tumor cell and/or the heterodimeric protein is capable of contemporaneous activation and targeting of gamma delta T cells to tumor cells.

15. A pharmaceutical composition, comprising the heterodimeric protein of claim 1.

16. The heterodimeric protein of claim 1, wherein the first domain and/or the heterodimeric protein modulates or is capable of modulating a gamma delta T cell.

17. The heterodimeric protein of claim 16, wherein the gamma delta T cell is selected from a cell expressing Vγ4, Vγ9δ2, or Vγ7δ4.

18. The heterodimeric protein of claim 16, wherein the modulation of a gamma delta T cell is activation of a gamma delta T cell.

* * * * *